US010538781B2

(12) United States Patent
Abad et al.

(10) Patent No.: US 10,538,781 B2
(45) Date of Patent: Jan. 21, 2020

(54) MATE FAMILY GENES AND USES FOR PLANT IMPROVEMENT

(71) Applicant: Monsanto Technology LLC, St. Louis, MO (US)

(72) Inventors: Mark Scott Abad, Webster Groves, MO (US); Marie Coffin, Cary, NC (US); Barry S. Goldman, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 15/732,280

(22) Filed: Oct. 17, 2017

(65) Prior Publication Data

US 2018/0119167 A1 May 3, 2018

Related U.S. Application Data

(63) Continuation of application No. 14/544,259, filed on Dec. 12, 2014, now abandoned, which is a continuation of application No. 13/694,398, filed on Nov. 28, 2012, now abandoned, which is a continuation of application No. 12/459,621, filed on Jul. 2, 2009, now Pat. No. 8,343,764, which is a continuation of application No. 11/431,855, filed on May 10, 2006, now abandoned.

(60) Provisional application No. 60/723,596, filed on Oct. 4, 2005, provisional application No. 60/679,917, filed on May 10, 2005.

(51) Int. Cl.
*C12N 15/82* (2006.01)
*C07K 14/415* (2006.01)

(52) U.S. Cl.
CPC ........ *C12N 15/8273* (2013.01); *C07K 14/415* (2013.01); *C12N 15/8241* (2013.01); *C12N 15/8243* (2013.01); *C12N 15/8247* (2013.01); *C12N 15/8251* (2013.01); *C12N 15/8261* (2013.01); *Y02A 40/146* (2018.01)

(58) Field of Classification Search
None
See application file for complete search history.

(56) References Cited

U.S. PATENT DOCUMENTS

| 4,329,371 A | 5/1982 | Hart |
| 5,188,642 A | 2/1993 | Shah et al. |
| 5,728,925 A | 3/1998 | Herrera-Estrella et al. |
| 6,107,547 A | 8/2000 | Coruzzi et al. |
| 6,559,358 B1 | 5/2003 | Murray |
| 6,914,176 B1 | 7/2005 | Nagel |
| 7,189,891 B2 * | 3/2007 | Guerinot ............. C07K 14/415 800/278 |
| 7,569,389 B2 | 8/2009 | Feldmann et al. |
| 7,968,768 B2 | 6/2011 | Anderson et al. |
| 8,343,764 B2 | 1/2013 | Abad et al. |
| 2004/0025202 A1 | 2/2004 | Laurie et al. |
| 2004/0031072 A1 | 2/2004 | La Rosa et al. |
| 2004/0154056 A1 | 8/2004 | Guerinot et al. |
| 2006/0150283 A1 | 7/2006 | Alexandrov et al. |
| 2007/0124833 A1 | 5/2007 | Abad et al. |
| 2013/0152224 A1 | 6/2013 | Abad et al. |
| 2015/0184189 A1 | 7/2015 | Abad et al. |

FOREIGN PATENT DOCUMENTS

| EP | 1086128 B | 12/1999 |
| WO | WO-0009727 A2 | 2/2000 |
| WO | WO-2005065339 A2 | 7/2005 |
| WO | WO-2005065339 A3 | 7/2005 |
| WO | WO-2006076423 A2 | 7/2006 |
| WO | WO-2006076423 A3 | 7/2006 |
| WO | WO-06138005 A2 | 12/2006 |
| WO | WO-2006138005 A3 | 12/2006 |

OTHER PUBLICATIONS

Sjolander. Phylogenomic inference of protein molecular function: advances and challenges. Bioinformatics. Jan. 22, 2004;20(2):1709. (Year: 2004).*
GenBank Accession No. BAB10551, (Feb. 14, 2004).
"U.S. Appl. No. 11/431,855, Final Office Action dated Apr. 7, 2009", 13 pgs.
"U.S. Appl. No. 11/431,855, Non-Final Office Action dated Sep. 30, 2008", 11 pgs.
"U.S. Appl. No. 11/431,855, Response filed Jul. 7, 2008 to Restriction Requirement dated Mar. 5, 2008", 2 pgs.
"U.S. Appl. No. 11/431,855, Response filed Dec. 29, 2008 to Non-Final Office Action dated Sep. 30, 2008", 16 pgs.
"U.S. Appl. No. 11/431,855, Restriction Requirement dated Mar. 5, 2008", 12 pgs.
"U.S. Appl. No. 12/459,621, Non Final Office Action dated Dec. 28, 2011", 11 pgs.
"U.S. Appl. No. 12/459,621, Notice of Allowance dated Aug. 2, 2012", 9 pgs.
"U.S. Appl. No. 12/459,621, Preliminary Amendment filed Jul. 2, 2009", 8 pgs.
"U.S. Appl. No. 12/459,621, Response filed Mar. 28, 2012 to Non Final Office Action dated Dec. 28, 2011", 7 pgs.
"U.S. Appl. No. 12/459,621, Response filed Sep. 26, 2011 to Restriction Requirement dated Jul. 26, 2011", 8 pgs.
"U.S. Appl. No. 13/694,398, Non Final Office Action dated Sep. 12, 2014", 18 pgs.

(Continued)

*Primary Examiner* — Cynthia E Collins
(74) *Attorney, Agent, or Firm* — Schwegman Lundberg & Woessner, P.A.

(57) ABSTRACT

Transgenic seed having a recombinant MATE family gene for crops with improved traits are provided by trait-improving recombinant DNA in the nucleus of cells of the seed where plants grown from such transgenic seed exhibit one or more improved traits as compared to a control plant. Of particular interest are transgenic plants that have increased yield. The present invention also provides recombinant DNA molecules for expression of a protein, and recombinant DNA molecules for suppression of a protein.

8 Claims, 3 Drawing Sheets

Specification includes a Sequence Listing.

(56) References Cited

OTHER PUBLICATIONS

"U.S. Appl. No. 13/694,398, Preliminary Amendment filed Feb. 18, 2013", 8 pgs.
"U.S. Appl. No. 13/694,398, Response filed May 21, 2014 to Restriction Requirement dated Mar. 21, 2014", 8 pgs.
"U.S. Appl. No. 13/694,398, Restriction Requirement dated Mar. 21, 2014", 11 pgs.
"U.S. Appl. No. 14/544,259, Advisory Action dated Sep. 26, 2017", 3 pgs.
"U.S. Appl. No. 14/544,259, Final Office Action dated May 17, 2017", 21 pgs.
"U.S. Appl. No. 14/544,259, Non Final Office Action dated Nov. 4, 2016", 32 pgs.
"U.S. Appl. No. 14/544,259, Preliminary Amendment filed Mar. 3, 2015", 9 pgs.
"U.S. Appl. No. 14/544,259, Response filed Feb. 2, 2017 to Non Final Office Action dated Nov. 4, 2016", 16 pgs.
"U.S. Appl. No. 14/544,259, Response filed Jul. 5, 2016 to Restriction Requirement dated May 5, 2016", 11 pgs.
"U.S. Appl. No. 14/544,259, Response filed Aug. 16, 2017 to Final Office Action dated May 17, 2017", 9 pgs.
"U.S. Appl. No. 14/544,259, Restriction Requirement dated May 5, 2016", 13 pgs.
"U.S. Appl. No. 12/459,621, Restriction Requirement dated Jul. 26, 2011", 10 pgs.
"*Arabidopsis thaliana* aberrant lateral root formation 5 (ALF5) mRNA, complete cds", GenBank Accession No. AF337954.1, (Mar. 20, 2001), 2 pgs.
"Chinese Application Serial No. 200680025272.0, First Office Action dated Feb. 24, 2011", (w/ English Translation), 10 pgs.
"Chinese Application Serial No. 200680025272.0, Office Action dated Jan. 6, 2012", w/ English Translation, 7 pgs.
"Chinese Application Serial No. 200680025272.0, Office Action dated Jul. 18, 2012", 7 pgs.
"Chinese Application Serial No. 200680025272.0, Office Action dated Oct. 31, 2012", (w/ English Translation), 10 pgs.
"Chinese Application Serial No. 200680025272.0, Office Action dated Jun. 18, 2012", 7 pgs.
"Chinese Application Serial No. 200680025272.0, Office Action Response filed Jan. 16, 2012", 5 pgs.
"Chinese Application Serial No. 200680025272.0, Response filed May 2, 2012", (w/ English Translation of Claim 1), 4 pgs.
"Chinese Application Serial No. 200680025272.0, Response filed Jul. 11, 2011 to Office Action dated Feb. 24, 2011", (w/ English Translation of Claims), 26 pgs.
"Chinese Application Serial No. 200680025272.0, Response filed Aug. 31, 2012 to Office Action dated Jul. 18, 2012", (w/ English Translation of Claim), 4 pgs.
"Chinese Application Serial No. 200680025272.0, Second Office Action dated Aug. 30, 2011", (English Translation), 6 pgs.
"Chinese Application Serial No. 200680025272.0, Office Action dated Feb. 24, 2011", (w/ English Translation), 10 pgs.
"European Application Serial No. 06799914.4, Amended Claims filed Jan. 16, 2009", 6 pgs.
"European Application Serial No. 06799914.4, Communication dated Jun. 23, 2009", 3 pgs.
"European Application Serial No. 06799914.4, Communication pursuant to Rules 161 and 162 dated Dec. 20, 2007", 2 pgs.
"European Application Serial No. 06799914.4, Office Action dated May 4, 2010", 4 pgs.
"European Application Serial No. 06799914.4, Office Action dated Aug. 16, 2011", 3 pgs.
"European Application Serial No. 06799914.4, Office Action Response Filed-Sep. 8, 2010", 4 pgs.
"European Application Serial No. 06799914.4, Response filed Jan. 14, 2008 to Communication pursuant to Rules 161 and 162 EPC", 7 pgs.
"European Application Serial No. 06799914.4, Response filed Aug. 25, 2009 to Communication dated Jun. 23, 2009", 2 pgs.
"European Application Serial No. 06799914.4, Supplementary European Search Report dated Jun. 4, 2009", 6 pgs.
"European Application Serial No. 12156516.2, European Search Report dated Jun. 26, 2012", 5 pgs.
"GenBank Accession No. AAN70749 glutamine synthetase, putative [Pseudomonas putida KT2440]", (Nov. 5, 2001), 1 pg.
"GenBank Accession No. AAO58736 glutamine synthetase [*Pseudomonas syringae* pv. tomato str. DC3000]", (Mar. 3, 2003), 2 pgs.
"GenBank Accession No. P42753 Cyclin-D3-1 (G1/S-specific cyclin-D3-1) (CycD3;1) (Cyclin-delta-3)(Cyclin-d3)", (May 20, 2008), 5 pgs.
"International Application Serial No. PCT/US2006/018535, International Search Report dated Oct. 21, 2008", 5 pgs.
"International Application Serial No. PCT/US2006/018535, International Written Opinion dated Oct. 21, 2008", 4 pgs.
"Pfam alignment for GenBank Accession No. P42753", Wellcome Trust, Sanger Institute, (Sep. 26, 008), 2 pgs.
"Pfam alignment for the amino acid sequence encoded by SEQ ID No. 31 of Murray", Wellcome Trust, Sanger Institute, (Sep. 26, 2008), 2 pgs.
"Unknown protein [*Arabidopsis thaliana*]", GenBank Accession No. AAL32589.1, (Nov. 25, 2001), 2 pgs.
"Unnamed protein product [*Arabidopsis thaliana*]", GenBank Accession No. BAB02774.1, (Feb. 14, 2004), 2 pgs.
Bouche, N., et al., "*Arabidopsis* gene knockout: phenotypes wanted", Curr Opin Plant Biol., 4(2), (2001), 111-117.
Bray, Elizabeth, "Genes commonly regulated by water-deficit stress in *Arabidopsis thaliana*", Journal of Experimental Botany, 55(407), doi:10.1093/jxb/erh270, (Sep. 24, 2004), 2331-2341.
Cebolla, et al., "The mitotic inhibitor ccs52 is required for endoreduplication and ploidy-dependent cell enlargement in plants", The EMBO Journal, 18, (1999), 4476-4484.
Hoshida, Hisashi, et al., "Enhanced tolerance to salt stress in transgenic rice that overexpresses chloroplast glutamine synthetase", Plant Mol. Bio, (May 2000), 9 pgs.
Ishida, Y., et al., "High efficiency transformation of maize (*Zea mays* L.) mediated by Agrobacterium tumefaciens", Nature Biotechnology, 14(6), (1996), 745-750.
Kim, H J, et al., "A genetic link between cold responses and flowering time through FVE in *Arabidopsis thaliana*", Nat Genet. Feb. 2004, 36(2), (2004), 167-71.
Riou-Khamlichi, Catherine, et al., "Cytokinin activation of *Arabidopsis* cell division through a D-type cyclin", Science, vol. 283, (Mar. 5, 1999), 1541-1544.
Sakamoto, A, et al., "Unnamed Protein Product [*Oryza sativa*]", GenBank Accession CAA32462, (Apr. 18, 2005), 2 pgs.
Shuai, Bin, et al., "The lateral organ boundaries gene defines a novel, plant-specific gene family.", Journal of Plant Physiology, 129(2), (Jun. 1, 2002), 747-761.
Skandalis, A., et al., "Abstract: Enzymatic properties of rat DNA polymerase beta mutants obtained by randomized mutagenesis", Nucleic Acids Res. Jun. 1, 2001;29(11):2418-26, (Jun. 1, 2001), 1 pg.
Stoop, A. A., et al., "Abstract: High-density mutagenesis by combined DNA shuffling and phage display to assign essential amino acid residues in protein-protein interactions: application to study structure-function of plasminogen activation inhibitor 1 (PAI-I)", J Mol Biol. Sep. 1, 2000;301(5):1135-47, (Sep. 1, 2000), 1 pg.
Tamura, T, et al., "Osmotic stress tolerance of transgenic tobacco expressing a gene encoding a membrane-located receptor-like protein from tobacco plants", Plant Physiol, (Feb. 2003), 454-62.
Tingey, S. V, et al., "Glutamine Synthetase (chloroplast GS2) (EC 6.3.1.2) [Pisum sativum]", GenBank Accession AAA33653, (Apr. 27, 1993), 1 pg.
Tingey, S. V, et al., "Glutamine Synthetase (chloroplast GS2) (EC 6.3.1.2) [Pisum sativum]", GenBank Accession AAA33669, (Apr. 27, 1993), 1 pg.
Tingey, S. V, et al., "Unnamed Protein Product [Pisum sativum]", GenBank Accession CAA28456, (Apr. 18, 2005), 1 pg.
Whisstock, J. C, et al., "Prediction of protein function from protein sequence and structure", Q Rev Biophys, (Aug. 2003), 307-40.

(56) References Cited

OTHER PUBLICATIONS

Yeh, T. C., et al., "Abstract: A dual role for the kinase-like domain of the tyrosine kinase Tyk2 in interferon-alpha signaling", Proc Natl Acad Sci USA. Aug. 1, 2000;97(16):8991-6, (Aug. 1, 2000), 1 pg.
Zhou, et al., "The plant cyclin-dependent kinase inhibitor ICK1 has distinct functional domains for in vivo kinase inhibition", protein instability and nuclear localization. Plant J, (Aug. 2003), 476-89.
Diener, Andrew C., et al., "*Arabidopsis* ALF5, a Multidrug Efflux Transporter Gene Family Member, Confers Resistance to Toxins", The Plant Cell, vol. 13, (Jul. 2001), 1625-1637.
Eckardt, Nancy A., "Move It on Out with MATEs", The Plant Cell, vol. 13, (Jul. 2001), 1477-1480.
The 1001 Genomes Consortium, "1,135 Genomes Reveal the Global Pattern of Polymorphism in *Arabidopsis thaliana*", Cell 166, (Jul. 14, 2016), 481-491.
Weigel, Detlef, et al., "The 1001 Genomes Project for *Arabidopsis thaliana*", Genome Biology 2009, vol. 10, Issue 5, Article 107, (May 27, 2009), 107.1-107.5.

\* cited by examiner

Figure 1. Consensus sequence of SEQ ID NO:601 and its homologs

SEQ ID NO

```
601        --------MDITVRISGLKSSNLIRITPRFS--SSSRFRCSNNEPPRKGNESNAGGGGDK
32524      --------MDITVRISGLKSSNLIRITPRFS--SSSRFRCSNNEPPRKGNESNGGGG-DK
3404       MQMDVYTHISLPSFISHRFSSSRFQCSSLSS-YSPFKLVCSNRDSKESQRNDDNNNKGDK
2616       ---MQMDIVYTPSFISHRFSSSRHQCPSLSSSYSPFKLFCSNRDFKESQRNDDNNNKGDK
8168       --------------------MDVLLGSGRFLARRPP-LALVPRCSRGSPDKSG-SDKGET
8488       --------------------MDVLLGSGRFLARRPP-LALVPRCSRGSPDKSG-SDKGET
8557       --------------------MDVLLGSGRFLARRPP-LALVPRCSRGSPDKSG-SDKGET
7495       --------------------MDVLLGSGRFLARRPP-LALVPRCSRGSPDKSG-SDKGET
8625       --------------------MDILLGSGRFLARRTP-LMLVPRCSRGSRDRSG-SDKGET
8626       --------------------MDILLGSGRFLARRTP-LMLVPRCSRGSRDRSG-SDKGET
4535       --------------------MDILLGSGRFLARRLPPLALVPRCSRGSPDKSG-SDKGET
6255       --------------------MGILLVSGRFLARRPP-LALAPRCSRGSPDKRG-RDEGDT
4458       --------------------MDTLLGSGRFLARRPP-LALAPRCSRGSPEKGGGSDKGDT
5207       ------------------------------------------------------MISSDT
6640       ------------------------------------------------------------
consensuss ------------------xxxxxxxxrfxxxxxxxxlxxxxrxxxxsxxxxxxxxxgxx ASTDWDKAWKNFKKQSKKSLFSQFNVDKYVTWNPPRSEFDLSEEVDPIKRT-ERSNLMLW
ASTDWDKAWKNFKKQSKKSLFSQFNVDKYVTWNPPRSEFDLSEEVDPIKRT-ERSNLMLW
SSTDWDKAWSKFKKQGGKKPFSKF-SDKYVSWNPKRSEFPLSEEVDPIKRT-ERSNLSFW
SSTDWDKAWSKFKKQGGKKPFSKF-SDKYVSWNPRRSEFPLSEEVDPIKRT-ERSNLSFW
S-ADWDKAWSAFKKKGKRTLFSDFSPDKYVTWNPRRSEYPLSEEVDPIKRS-ERSNLMLW
S-ADWDKAWSAFKKKGKRTLFSDFSPDKYVIWNPRRSEYPLSEEVDPIKRS-ERSNLMLW
S-ADWDKAWSAFKKKGKRTLFSDFSPDKYVTWNPRRSEYPLSEEVDPIKRT-ERSNLMLW
S-ADWDKAWSAFKKKGKRTLFSDFSPDKYVTWNPRRSEYPLSEEVDPIKRT-ERSNLMLW
S-ADWDKAWAKFKKKGKRTLFSDFSPDKYVTWNPRRSEYPLSEEVDPIKRTERSN-LMLW
S-ADWDKAWAKFKKKGKRTLFSDFSPDKYVTWNPRRSEYPLSEEVDPIKSQLKDLNLMRC
S-TDWDKAWASFKNKGKRTLFSDFSPNKYVTWNPRRSEYPLSEEVDPIKRT-ERSNLMLW
SSTDWDKAWSTFKKKGKKTLFSEFSPNKYVTWNPRRSEYPLSEEVDPIKRA-ERSNLMLW
SSTDWDKAWSTFKKKGKKTLFSEFSPNKYVSWNPRRSEYPLSEEVDPIRRT-ERSNLMLW
SSTEWDKAWSSLRKKGKKTLFSEFSPNKYVTCNPRRIEYPLSGRSRSIXRAXRSNLML--
----------FHTTKLTSSLFHDFSRIKLVTCNPWPTQNPLPQQVDPIKRS-QTSQLXLW
sxxdwdkawxxfkkkgkxxlFsxFsxxKyVtwNPrrsexpLseevdpIkrx-ersnlmlw TSPRFTLVGAIVIVSFLLLYTILAPVK---------------------------*
TSPRFTLVGAIVIVSFLLLYTILAPVK---------------------------*
NSPTFTLGGAIIIVLFLLLYTILAPIK---------------------------*
NSPTFTLGGAIIIVTFLLLYTILAPIK---------------------------*
TSPQFTLVGAIIIVLTLLIYTLVVPPPK--------------------------*
TSPQFTLVGAIIIVLTLLIYTLVVPPPK--------------------------*
TSPQFTLVGAIIIVLTLLIYTLVVPPPK--------------------------*
TSPQFTLVGAIII-----------------------------------------*
TSPQFTLVGAIIIVLTLLIYTLVVPPK---------------------------*
TSPQFRWVRRSSSSCHN-------------------------------------*
TSPQFTLVGAIIIVLTLLIYTLVVPPPK--------------------------*
TSPRFTLVGAIIIVSALLIYTLVVPPK---------------------------*
TSPKFTLVMAIVIVSTLLIYTIVVPPK---------------------------*
------------------------------------------------------*
TSPQFPLDGAIIIVSPPLINTQVVPPPKKLHRSQPPPPLTCNLAEKKKSSLHCTFST*
tspxftlvgaixivxxllxytxxxpxxx--------------------------*
```

MATE FAMILY GENES AND USES FOR PLANT IMPROVEMENT

CROSS REFERENCE TO RELATED APPLICATIONS

This application is a continuation of and claims the benefit under 35 U.S.C. § 120 to U.S. application Ser. No. 14/544,259, filed Dec. 12, 2014, which is a continuation of and claims the benefit under 35 U.S.C. § 120 to U.S. application Ser. No. 13/694,398, filed Nov. 28, 2012, which is a continuation of and claims the benefit of priority under 35 U.S.C. § 120 to U.S. application Ser. No. 12/459,621, filed on Jul. 2, 2009, which is a continuation of U.S. application Ser. No. 11/431,855 filed on May 10, 2006, which claims benefit under 35 USC § 119(e) of U.S. provisional application Ser. No. 60/679,917, filed May 10, 2005, and U.S. provisional application Ser. No. 60/723,596, filed Oct. 4, 2005, the benefit of priority of which are claimed hereby, and all of which are incorporated herein by reference in their entirety.

INCORPORATION OF SEQUENCE LISTING

Two copies of the sequence listing (COPY 1 REPLACEMENT May 11, 2018 and COPY 2 REPLACEMENT May 11, 2018) and a computer readable form (CRF REPLACEMENT May 11, 2018) of the sequence listing, all on CD-R's, each containing the file named "3126.020US5.TXT", which is 97,937,408 bytes (measured in MS-WINDOWS®) and recorded on May 11, 2018, are incorporated herein by reference in their entirety.

INCORPORATION OF TABLES

Two copies of Table 2 (COPY 1 REPLACEMENT May 11, 2018 and COPY 2 REPLACEMENT May 11, 2018) and a computer readable form (CRF REPLACEMENT May 11, 2018), all on CD-R's, each containing the file named "table.TXT", which is 331,776 bytes when measured in MS-WINDOWS® operating system, was recorded on May 11, 2018, are incorporated herein by reference in their entirety.

INCORPORATION OF COMPUTER PROGRAM LISTING

A Computer Program Listing (COPY 1 REPLACEMENT May 11, 2018 and COPY 2 REPLACEMENT May 11, 2018) with folders "hmmer-2.3.2" and "288pfamDir" are contained on a CD-R and are incorporated herein by reference in their entirety. Folder hmmer-2.3.2 contains the source code and other associated file for implementing the HMMer software for Pfam analysis. Folder 288pfamDir contains 288 Pfam Hidden Markov Models. Both folders were recorded on the disk on May 11, 2018, having a total size of 23,205,888 bytes when measured in MS-WINDOWS® operating system.

FIELD OF THE INVENTION

Disclosed herein are transgenic plant cells, plants and seeds comprising recombinant DNA and methods of making and using such plant cells, plants and seeds.

BACKGROUND OF THE INVENTION

Transgenic plants with improved traits such as improved yield, environmental stress tolerance, pest resistance, herbicide tolerance, modified seed compositions, and the like are desired by both farmers and consumers. Although considerable efforts in plant breeding have provided significant gains in desired traits, the ability to introduce specific DNA into plant genomes provides further opportunities for generation of plants with improved and/or unique traits. The ability to develop transgenic plants with improved traits depends in part on the identification of useful recombinant DNA for production of transformed plants with improved properties, e.g. by actually selecting a transgenic plant from a screen for such improved property.

SUMMARY OF THE INVENTION

This invention provides plant cell nuclei with recombinant that imparts enhanced agronomic traits in transgenic plants having the nuclei in their cells. Recombinant DNA in this invention is provided in a construct comprising a promoter that is functional in plant cells and that is operably linked to DNA that encodes a protein having at least one amino acid domain in a sequence that exceeds the Pfam gathering cutoff for amino acid sequence alignment with a protein domain family identified by a Pfam name in the group of Pfam domain names identified in Table 17. In more specific embodiments of the invention plant cells are provided which express a protein having amino acid sequence with at least 90% identity to a consensus amino acid sequence in the group of consensus amino acid sequences consisting of the consensus amino acid sequence constructed for SEQ ID NO: 426 and homologs thereof listed in Table 2 through the consensus amino acid sequence constructed for SEQ ID NO: 850 and homologs thereof listed in Table 2. Amino acid sequences of homologs are SEQ ID NO: 851 through 33634. In even more specific embodiments of the invention the protein expressed in plant cells is a protein selected from the group of proteins identified in Table 1 by annotation to a related protein in Genbank and alternatively identified in Table 16 by identification of protein domain family.

LENGTHY TABLES

The patent contains a lengthy table section. A copy of the table is available in electronic form from the USPTO web site (http://seqdata.uspto.gov/?pageRequest=docDetail&DocID=US10538781B2). An electronic copy of the table will also be available from the USPTO upon request and payment of the fee set forth in 37 CFR 1.19(b)(3).

Other aspects of the invention are specifically directed to transgenic plant cells, and transgenic plants comprising a plurality of plant cells with such nuclei, progeny transgenic seed, embryo and transgenic pollen from such plants. Such plant cell nuclei are selected from a population of transgenic plants regenerated from plant cells with a nucleus transformed with recombinant DNA by screening the transgenic plants in the population for an enhanced trait as compared to control plants that do not have the recombinant DNA in their nucleus, where the enhanced trait is enhanced water use efficiency, enhanced cold tolerance, enhanced heat tolerance, enhanced shade tolerance, enhanced tolerance to salt exposure, increased yield, enhanced nitrogen use efficiency, enhanced seed protein and enhanced seed oil. In some aspects of the invention the recombinant DNA expresses a protein that imparts the enhanced trait; in other aspects of the invention the recombinant DNA expresses RNA for suppressing the level of an endogenous protein. In yet another aspect of the invention the nucleus of plant cells in plants, seeds, embryo and pollen further comprise DNA expressing a protein that provides tolerance from exposure to an herbicide applied at levels that are lethal to a wild type of said plant cell. Such tolerance is especially useful not only as an advantageous trait in such plants but is also useful in a selection step in the methods of the invention. In aspects of the invention the agent of such herbicide is a glyphosate, dicamba, or glufosinate compound.

Yet other aspects of the invention provide nuclei is cells of transgenic plants which are homozygous for the recombinant DNA and transgenic seed of the invention from corn, soybean, cotton, canola, alfalfa, wheat or rice plants. In other important embodiments for practice of various aspects of the invention in Argentina the recombinant DNA in the nucleus is provided in plant cells derived from corn lines that that are and maintain resistance to a virus such as the Mal de Rio Cuarto virus or a fungus such as the *Puccina sorghi* fungus or to both.

This invention also provides methods for manufacturing non-natural, transgenic seed that can be used to produce a crop of transgenic plants with an enhanced trait resulting from expression of stably-integrated, recombinant DNA in the nucleus of the plant cells. In some aspects of the invention the recombinant DNA can express a protein having at least one domain of amino acids in a sequence that exceeds the Pfam gathering cutoff for amino acid sequence alignment with a protein domain family identified by a Pfam name in the group of Pfam names identified in Table 17; in other aspects the recombinant DNA suppresses the level of a such a protein More specifically the method comprises (a) screening a population of plants for an enhanced trait and recombinant DNA, where individual plants in the population can exhibit the trait at a level less than, essentially the same as or greater than the level that the trait is exhibited in control plants which do not express the recombinant DNA; (b) selecting from the population one or more plants that exhibit the trait at a level greater than the level that said trait is exhibited in control plants; (c) verifying that the recombinant DNA is stably integrated in said selected plants; (d) analyzing tissue of a selected plant to determine the production of a protein having the function of a protein encoded by nucleotides in a sequence of one of SEQ ID NO:1-425; and (e) collecting seed from a selected plant. In one aspect of the invention the plants in the population further comprise DNA expressing a protein that provides tolerance to exposure to an herbicide applied at levels that are lethal to wild type plant cells and where the selecting is effected by treating the population with the herbicide, e.g. a glyphosate, dicamba, or glufosinate compound. In another aspect of the invention the plants are selected by identifying plants with the enhanced trait. The methods are especially useful for manufacturing corn, soybean, cotton, alfalfa, wheat or rice seed selected as having one of the enhanced traits described above.

Another aspect of the invention provides a method of producing hybrid corn seed comprising acquiring hybrid corn seed from a herbicide tolerant corn plant which also has a nucleus of this invention with stably-integrated, recombinant DNA The method further comprises producing corn plants from said hybrid corn seed, where a fraction of the plants produced from said hybrid corn seed is homozygous for said recombinant DNA, a fraction of the plants produced from said hybrid corn seed is hemizygous for said recombinant DNA, and a fraction of the plants produced from said hybrid corn seed has none of said recombinant DNA; selecting corn plants which are homozygous and hemizygous for said recombinant DNA by treating with an herbicide; collecting seed from herbicide-treated-surviving corn plants and planting said seed to produce further progeny corn plants; repeating the selecting and collecting steps at least once to produce an inbred corn line; and crossing the inbred corn line with a second corn line to produce hybrid seed.

Another aspect of the invention provides a method of selecting a plant comprising a nucleus of this invention in its plant cells by using an immunoreactive antibody to detect the presence of protein expressed by recombinant DNA in seed or plant tissue. Another aspect of the invention provides anti-counterfeit milled seed having, as an indication of origin, a nucleus of this invention with unique recombinant DNA.

Aspects of the invention relating to nucleus in plant cells having recombinant DNA for suppressing the expression of a protein are identified in Table 1 and Table 16. More specific aspects of the invention provide plant cells having recombinant DNA for suppressing the expression of a protein having the function in a plant of the protein with amino acid sequence of SEQ ID NO: 426, 428, 429, 430, 524, 525, 541, 601, 602, 650, 651, 654, 655, 657, 660, 694, 698, 772, 801 or the corresponding Pfam identified in Table 16, i.e. Histone, WD40, NPH3, FHA, PB1, ADH_zinc_N, NAPRTase, ADK_lid, p450, B56, DUF231, C2, DUF568, WD40, F-box, Pkinase, Terpene_synth, respectively. Such suppression can be effected by any of a number of ways known in the art, e.g. anti-sense suppression, RNAi or mutation knockout and the like.

Another aspect of this invention relates to growing transgenic plants with enhanced water use efficiency or enhanced nitrogen use efficiency. For instance, this invention provides methods of growing a corn, cotton or soybean crop without irrigation water comprising planting seed having plant cells of the invention which are selected for enhanced water use efficiency. Alternatively methods comprise applying reduced irrigation water, e.g. providing up to 300 millimeters of ground water during the production of a corn crop. This invention also provides methods of growing a corn, cotton or soybean crop without added nitrogen fertilizer comprising planting seed having plant cells of the invention which are selected for enhanced nitrogen use efficiency. Alternatively methods comprise applying reduced amount of nitrogen input as compared to the conventional input during the production of a corn crop.

The various aspects of this invention are especially useful for transgenic plant cells in seeds and transgenic plants having any of the above-described enhanced traits in crop plants such as corn (maize), soybean, cotton, canola (rape), wheat, sunflower, sorghum, alfalfa, barley, millet, rice, tobacco, fruit and vegetable crops, and turfgrass.

The invention also provides recombinant DNA constructs comprising the DNA useful in the nuclei in plant cells for imparting enhanced traits in plants having those cells.

BRIEF DESCRIPTION OF THE DRAWINGS

FIG. 1 is a consensus amino acid sequence of SEQ ID NO: 601 and homologs.

DETAILED DESCRIPTION OF THE INVENTION

Figure 2:
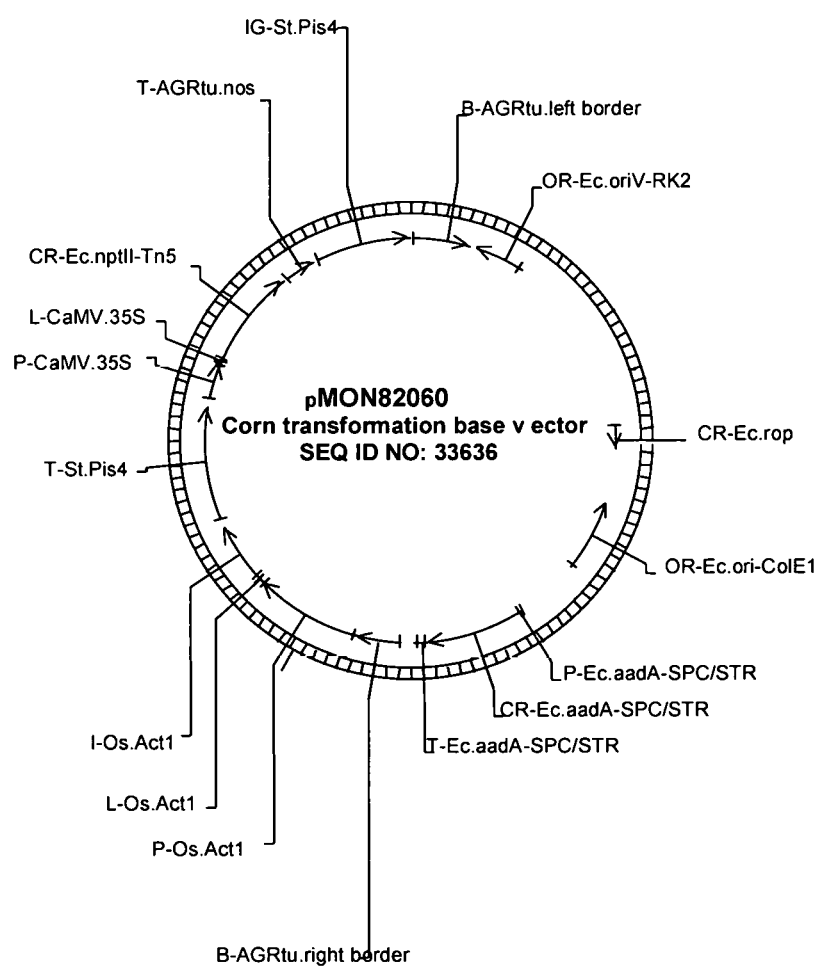
FIGS. 2 and 3 are plasmid maps.

In the attached sequence listing:

SEQ ID NO:1-425 are nucleotide sequences of the coding strand of DNA for "genes" used in the recombinant DNA imparting an enhanced trait in plant cells, i.e. each represents a coding sequence for a protein;

SEQ ID NO:426-850 are amino acid sequences of the cognate protein of the "genes" with nucleotide coding sequence 1-425;

SEQ ID NO:851-33634 are amino acid sequences of homologous proteins;

SEQ ID NO:33635 is a consensus amino acid sequence.

SEQ ID NO:33636 is a nucleotide sequence of a plasmid base vector useful for corn transformation; and SEQ ID NO:33637 is a DNA sequence of a plasmid base vector useful for soybean transformation.

The nuclei of this invention are identified by screening transgenic plants for one or more traits including improved drought stress tolerance, improved heat stress tolerance, improved cold stress tolerance, improved high salinity stress tolerance, improved low nitrogen availability stress tolerance, improved shade stress tolerance, improved plant growth and development at the stages of seed imbibition through early vegetative phase, and improved plant growth and development at the stages of leaf development, flower production and seed maturity.

"Gene" refers to chromosomal DNA, plasmid DNA, cDNA, synthetic DNA, or other DNA that encodes a peptide, polypeptide, protein, or RNA molecule, and regions flanking the coding sequences involved in the regulation of expression. In aspects of the invention where an improved trait is provided by expression of a protein, "gene" refers at least to coding nucleotide sequence for a protein or a function polypeptide fragment of a protein that imparts the trait. In aspects of the invention where an improved trait is provided by suppression of expression of an endogenous protein, "gene" refers to any part of the gene that can be a target for suppression.

"Transgenic seed" means a plant seed whose nucleus has been altered by the incorporation of recombinant DNA, e.g., by transformation as described herein. The term "transgenic plant" is used to refer to the plant produced from an original transformation event, or progeny from later generations or crosses of a plant to a transformed plant, so long as the progeny contains a nucleus with the recombinant DNA in its genome.

"Recombinant DNA" a polynucleotide having a genetically engineered modification introduced through combination of endogenous and/or exogenous elements in a transcription unit, manipulation via mutagenesis, restriction enzymes, and the like or simply by inserting multiple copies of a native transcription unit. Recombinant DNA may comprise DNA segments obtained from different sources, or DNA segments obtained from the same source, but which have been manipulated to join DNA segments which do not naturally exist in the joined form. A recombinant polynucleotide may exist outside of the cell, for example as a PCR fragment, or integrated into a genome, such as a plant genome.

"Trait" means a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g., by measuring uptake of carbon dioxide, or by the observation of the expression level of a gene or genes, e.g., by employing Northern analysis, RT-PCR, microarray gene expression assays, or reporter gene expression systems, or by agricultural observations such as stress tolerance, yield, or pathogen tolerance.

A "control plant" is a plant without trait-improving recombinant DNA in its nucleus. A control plant is used to measure and compare trait improvement in a transgenic plant with such trait-improving recombinant DNA. A suitable control plant may be a non-transgenic plant of the parental line used to generate a transgenic plant herein. Alternatively, a control plant may be a transgenic plant that comprises an empty vector or marker gene, but does not contain the recombinant DNA that produces the trait improvement. A control plant may also be a negative segregant progeny of hemizygous transgenic plant. In certain demonstrations of trait improvement, the use of a limited number of control plants can cause a wide variation in the control dataset. To minimize the effect of the variation within the control dataset, a "reference" is used. As use herein a "reference" is a trimmed mean of all data from both transgenic and control plants grown under the same conditions and at the same developmental stage. The trimmed mean is calculated by eliminating a specific percentage, i.e., 20%, of the smallest and largest observation from the data set and then calculating the average of the remaining observation.

"Trait improvement" means a detectable and desirable difference in a characteristic in a transgenic plant relative to a control plant or a reference. In some cases, the trait improvement can be measured quantitatively. For example, the trait improvement can entail at least a 2% desirable difference in an observed trait, at least a 5% desirable difference, at least about a 10% desirable difference, at least about a 20% desirable difference, at least about a 30% desirable difference, at least about a 50% desirable difference, at least about a 70% desirable difference, or at least about a 100% difference, or an even greater desirable difference. In other cases, the trait improvement is only measured qualitatively. It is known that there can be a natural variation in a trait. Therefore, the trait improvement observed entails a change of the normal distribution of the trait in the transgenic plant compared with the trait distribution observed in a control plant or a reference, which is evaluated by statistical methods provided herein. Trait improvement includes, but is not limited to, yield increase, including increased yield under non-stress conditions and increased yield under environmental stress conditions. Stress conditions may include, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density.

Many agronomic traits can affect "yield", including without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Other traits that can affect yield include, efficiency of germination (including germination in stressed conditions), growth rate (including growth rate in stressed conditions), ear number, seed number per ear, seed size, composition of seed (starch, oil, protein) and characteristics of seed fill. Also of interest is the generation of transgenic plants that demonstrate desirable phenotypic properties that may or may not confer an increase in overall plant yield. Such properties include enhanced plant morphology, plant physiology or improved components of the mature seed harvested from the transgenic plant.

"Yield-limiting environment" means the condition under which a plant would have the limitation on yield including environmental stress conditions.

"Stress condition" means a condition unfavorable for a plant, which adversely affect plant metabolism, growth and/or development. A plant under the stress condition typically shows reduced germination rate, retarded growth and development, reduced photosynthesis rate, and eventually leading to reduction in yield. Specifically, "water deficit stress" used herein preferably refers to the sub-optimal conditions for water and humidity needed for normal growth of natural plants. Relative water content (RWC) can be used as a physiological measure of plant water deficit. It measures the effect of osmotic adjustment in plant water status, when a plant is under stressed conditions. Conditions which may result in water deficit stress include heat, drought, high salinity and PEG induced osmotic stress.

"Cold stress" means the exposure of a plant to a temperatures below (two or more degrees Celsius below) those normal for a particular species or particular strain of plant. "Nitrogen nutrient" means any one or any mix of the nitrate salts commonly used as plant nitrogen fertilizer, including, but not limited to, potassium nitrate, calcium nitrate, sodium nitrate, ammonium nitrate. The term ammonium as used herein means any one or any mix of the ammonium salts commonly used as plant nitrogen fertilizer, e.g., ammonium nitrate, ammonium chloride, ammonium sulfate, etc.

"Low nitrogen availability stress" means a plant growth condition that does not contain sufficient nitrogen nutrient to maintain a healthy plant growth and/or for a plant to reach its typical yield under a sufficient nitrogen growth condition. For example, a limiting nitrogen condition can refers to a growth condition with 50% or less of the conventional nitrogen inputs. "Sufficient nitrogen growth condition" means a growth condition where the soil or growth medium contains or receives optimal amounts of nitrogen nutrient to sustain a healthy plant growth and/or for a plant to reach its typical yield for a particular plant species or a particular strain. One skilled in the art would recognize what constitute such soil, media and fertilizer inputs for most plant species.

"Shade stress" means a growth condition that has limited light availability that triggers the shade avoidance response in plant. Plants are subject to shade stress when localized at lower part of the canopy, or in close proximity of neighboring vegetation. Shade stress may become exacerbated when the planting density exceeds the average prevailing density for a particular plant species. The average prevailing densities per acre of a few examples of crop plants in the USA in the year 2000 were: wheat 1,000,000-1,500,000; rice 650,000-900,000; soybean 150,000-200,000, canola 260,000-350,000, sunflower 17,000-23,000 and cotton 28,000-55,000 plants per acre (Cheikh, e.g., (2003) U.S. Patent Application No. 20030101479).

"Increased yield" of a transgenic plant of the present invention is evidenced and measured in a number of ways, including test weight, seed number per plant, seed weight, seed number per unit area (i.e., seeds, or weight of seeds, per acre), bushels per acre, tons per acre, tons per acre, kilo per hectare. For example, maize yield can be measured as production of shelled corn kernels per unit of production area, e.g., in bushels per acre or metric tons per hectare, often reported on a moisture adjusted basis, e.g., at 15.5% moisture. Increased yield can result from improved utilization of key biochemical compounds, such as nitrogen, phosphorous and carbohydrate, or from improved tolerance to environmental stresses, such as cold, heat, drought, salt, and attack by pests or pathogens. Trait-improving recombinant DNA can also be used to provide transgenic plants having improved growth and development, and ultimately increased yield, as the result of modified expression of plant growth regulators or modification of cell cycle or photosynthesis pathways.

"Expression" means transcription of DNA to produce RNA. The resulting RNA may be without limitation mRNA encoding a protein, antisense RNA, or a double-stranded RNA for use in RNAi technology. Expression also refers to production of encoded protein from mRNA.

A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells such *Agrobacterium* or *Rhizobium*. Examples of promoters under developmental control include promoters that preferentially initiate transcription in certain tissues, such as leaves, roots, or seeds. Such promoters are referred to as "tissue preferred". Promoters which initiate transcription only in certain tissues are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions, or certain chemicals, or the presence of light. Tissue specific, tissue preferred, cell type specific, and inducible promoters constitute the class of "non-constitutive" promoters. A "constitutive" promoter is a promoter which is active under most conditions. As used herein, "antisense orientation" includes reference to a polynucleotide sequence that is operably linked to a promoter in an orientation where the antisense strand is transcribed. The antisense strand is sufficiently complementary to an endogenous transcription product such that translation of the endogenous transcription product is often inhibited.

As used herein, "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

A "consensus sequence" refers to an artificial, amino acid sequence of conserved parts of the proteins encoded by homologous genes, e.g., as determined by a CLUSTALW alignment of amino acid sequence of homolog proteins.

Homologous genes are genes which encode proteins with the same or similar biological function to the protein encoded by the second gene. Homologous genes may be generated by the event of speciation (see ortholog) or by the event of genetic duplication (see paralog). "Orthologs" refer to a set of homologous genes in different species that evolved from a common ancestral gene by specification. Normally, orthologs retain the same function in the course of evolution; and "paralogs" refer to a set of homologous genes in the same species that have diverged from each other as a consequence of genetic duplication. Thus, homologous genes can be from the same or a different organism. As used herein, "homolog" means a protein that performs the same biological function as a second protein including those identified by sequence identity search.

Percent identity refers to the extent to which two optimally aligned DNA or protein segments are invariant throughout a window of alignment of components, e.g., nucleotide sequence or amino acid sequence. An "identity fraction" for aligned segments of a test sequence and a reference sequence is the number of identical components which are shared by sequences of the two aligned segments divided by the total number of sequence components in the reference segment over a window of alignment which is the smaller of the full test sequence or the full reference sequence. "Percent identity" ("% identity") is the identity fraction times 100. "% identity to a consensus amino acid sequence" is 100 times the identity fraction in a window of alignment of an amino acid sequence of a test protein optimally aligned to consensus amino acid sequence of this invention.

"*Arabidopsis*" means plants of *Arabidopsis thaliana*.

"Pfam" refers to a large collection of multiple sequence alignments and hidden Markov models covering many common protein families, e.g. Pfam version 18.0 (August 2005) contains alignments and models for 7973 protein families and is based on the Swissprot 47.0 and SP-TREMBL 30.0 protein sequence databases. See S. R. Eddy, "Profile Hidden Markov Models", *Bioinformatics* 14:755-763, 1998. Pfam is currently maintained and updated by a Pfam Consortium. The alignments represent some evolutionary conserved structure that has implications for the protein's function. Profile hidden Markov models (profile HMMs) built from the Pfam alignments are useful for automatically recognizing that a new protein belongs to an existing protein family even if the homology by alignment appears to be low. Once one DNA is identified as encoding a protein which imparts an enhanced trait when expressed in transgenic plants, other DNA encoding proteins in the same protein family are identified by querying the amino acid sequence of protein encoded by candidate DNA against the Hidden Markov Model which characterizes the Pfam domain using HMMER software, a current version of which is provided in the appended computer listing. Candidate proteins meeting the gathering cutoff for the alignment of a particular Pfam are in the protein family and have cognate DNA that is useful in constructing recombinant DNA for the use in the plant cells of this invention. Hidden Markov Model databases for use with HMMER software in identifying DNA expressing protein in a common Pfam for recombinant DNA in the plant cells of this invention are also included in the appended computer listing. The HMMER software and Pfam databases are version 18.0 and were used to identify known domains in the proteins corresponding to amino acid sequence of SEQ ID NO: 426 through SEQ ID NO: 850. All DNA encoding proteins that have scores higher than the gathering cutoff disclosed in Table 17 by Pfam analysis disclosed herein can be used in recombinant DNA of the plant cells of this invention, e.g. for selecting transgenic plants having enhanced agronomic traits. The relevant Pfams for use in this invention, as more specifically disclosed below, are Mito_carr, 6PGD, UBX, iPGM_N, WD40, Fer4, Enolase_C, DUF1639, PBP, PLAC8, Acyl-CoA_dh_1, Isoamylase_N, Acyl-CoA_dh_2, PC4, Sugar_tr, UCH, Enolase_N, HATPase_c, PRA-PH, Pkinase, SBP56, PEP-utilizers, SIS, PCI, DUF1644, Terpene_synth, Acyl-CoA_dh_M, Acyl-CoA_dh_N, Glutaminase, Lectin_legB, Dehydrin, MatE, Ank, 2-Hacid_dh_C, Chal_sti_synt_C, DUF1070, ATP-grasp_2, Arginase, HABP4_PAI-RBP1, ABC2_membrane, DUF1723, Glyco_hydro_1, MFS_1, ARD, PDT, HMA, Pro_isomerase, Ferric_reduct, PRA-CH, Aa_trans, ACT, LisH, PGM_PMM_II, Spermine_synth, zf-MYND, LRRNT_2, Ribul_P_3_epim, PGM_PMM_IV, NPH3, DapB_C, TPR_1, TPR_2, FAE1_CUT1_RppA, K_trans, F-box, Cyclin_C, ADK, NUDIX, NIR_SIR, PEP-CK_ATP, La, DapB_N, MtN3_slv, FMO-like, TIM, FKBP_C, PMEI, Peptidase_C12, Cyclin_N, DUF568, Methyltransf_11, Methyltransf_12, DUF1677, DnaJ_C, BRAP2, IF2_N, Carboxyl_trans, mTERF, Glyoxalase, TMEM14, Mlo, Beta_elim_lyase, Pyr_redox_dim, Glyco_transf_8, Nicastrin, Flavodoxin_1, Epimerase, PTPA, Lipase_3, Pyr_redox_2, GSHPx, ELM2, PGI, Aminotran_1_2, ABC_tran, GRP, PGK, Oleosin, Sulfotransfer_1, EXS, DUF1325, AMP-binding, Arm, NTP_transferase, LSM, Metalloenzyme, Molybdop_Fe4S4, MFAP1_C, Aminotran_3, PHD, B56, DUF588, PSI_PsaF, zf-CCCH, HEAT, PALP, FH2, SapB_1, Ammonium_transp, MannoseP_isomer, NOP5NT, SapB_2, Pyr_redox, Pollen_allerg_1, Asp, DUF662, FHA, YjeF_N, COX5C, GTP_EFTU_D2, Ion_trans_2, PK, DUF231, FAD_binding_1, Hrf1, FAD_binding_4, FAD_binding_6, FAD_binding_8, CBS, Smr, aPHC, DUF241, Brix, Ras, Acetyltransf_1, NAF, SPX, Na_Ca_ex, C2, p450, PP2C, Histone, 2-Hacid_dh, SBF, CCT, BCNT, PK_C, Miro, CH, PfkB, ACP_syn_III_C, Sterol_desat, ADH_zinc_N, CS, Cys_Met_Meta_PP, Lactamase_B, Bromodomain, CDI, Linker_histone, DAO, Dicty_CAR, Aldo_ket_red, zf-AN1, Methyltransf_6, DUF1005, LEA_2, NIR_SIR Jeff, DUF260, Oxidored_FMN, DUF26, Lectin_C, Pec_lyase_C, Nop, TB2_DP1_HVA22, ADH_N, YGGT, NAPRTase, NAD_binding_1, DUF914, PGM_PMM_I, NAD_binding_2, AICARFT_IMPCHas, Auxin_inducible, NAD_binding_6, Anti-silence, RuBisCO_large, Response_reg, FeThRed_A, Di19, SNARE, PGM_PMM_III, Molydop_binding, efhand, zf-CCHC, GTP_EFTU, ARID, adh_short, Fibrillarin, RuBisCO_large_N, WWE, AA_permease, PABP, OMPdecase, RRM_1, U-box, OPT, TBC, MGS, DUF786, 3Beta_HSD, zf-UBP, zf-A20, DPBB_1, GDPD, PI-PLC-X, SEP, PI-PLC-Y, NOSIC, Glycolytic, SET, ADK_lid, Alpha-amylase, EB1, PGAM, Abhydrolase_1, Glyco_hydro_14, Lung_7-TM R, Abhydrolase 3, TCTP, GATase_2, Gln-synt_C, 20G-FeII_Oxy, Pribosyltran, MIF, CoA_trans, RCC1, Pkinase_Tyr, MIP, DnaJ, HSCB_C, Trehalose_PPase, LRR_1, Cupin_2, LRR_2, Glyco_hydro_28, Yip1, Trp_syntA, Sedlin_N, SGS, Aldedh, CK_II_beta, zf-C3HC4, GIDA, PB1, IMPDH, Carb_kinase, PurA, Molybdopterin, Nodulin-like, Tim17, Xan_ur_permease, Hist_deacetyl, RNA_pol_Rpb8, Agenet, Myb_DNA-binding, Glyoxal_oxid_N, Ribophorin_I, and FAE_3-kCoA_syn1.

Recombinant DNA Constructs

The present invention provides recombinant DNA constructs comprising one or more polynucleotides disclosed herein for imparting one or more improved traits to transgenic plant when incorporated into the nucleus of the plant cells. Such constructs also typically comprise a promoter operatively linked to said polynucleotide to provide for expression in the plant cells. Other construct components may include additional regulatory elements, such as 5' or 3' untranslated regions (such as polyadenylation sites), intron regions, and transit or signal peptides. Such recombinant DNA constructs can be assembled using methods known to those of ordinary skill in the art.

In a preferred embodiment, a polynucleotide of the present invention is operatively linked in a recombinant DNA construct to a promoter functional in a plant to provide for expression of the polynucleotide in the sense orientation such that a desired protein or polypeptide fragment of a protein is produced. Also provided are embodiments wherein a polynucleotide is operatively linked to a promoter functional in a plant to provide for expression of gene suppression RNA to suppress the level of an endogenous protein.

Recombinant constructs prepared in accordance with the present invention also generally include a 3' untranslated DNA region (UTR) that typically contains a polyadenylation sequence following the polynucleotide coding region. Examples of useful 3' UTRs include those from the nopaline synthase gene of *Agrobacterium tumefaciens* (nos), a gene encoding the small subunit of a ribulose-1,5-bisphosphate carboxylase-oxygenase (rbcS), and the T7 transcript of *Agrobacterium tumefaciens*. Constructs and vectors may also include a transit peptide for targeting of a gene target to a plant organelle, particularly to a chloroplast, leucoplast or other plastid organelle. For descriptions of the use of chloroplast transit peptides, see U.S. Pat. Nos. 5,188,642 and 5,728,925, incorporated herein by reference.

Table 1 provides a list of genes that provide recombinant DNA that was used in a model plant to discover associated improved traits and that can be used with homologs to define a consensus amino acid sequence for characterizing recombinant DNA for use in the nuclei of this invention. An understanding of Table 1 is facilitated by the following description of the headings:

"NUC SEQ ID NO" refers to a SEQ ID NO. for particular DNA sequence in the Sequence Listing.

"PEP SEQ ID NO" refers to a SEQ ID NO. in the Sequence Listing for the amino acid sequence of a protein cognate to a particular DNA "construct_id" refers to an arbitrary number used to identify a particular recombinant DNA construct comprising the particular DNA.

"Gene ID" refers to an arbitrary name used to identify the particular DNA. "orientation" refers to the orientation of the particular DNA in a recombinant DNA construct relative to the promoter.

TABLE 1

| NUC SEQ ID NO | PEP SEQ IDNO | Gene ID | Construct ID | orientation |
|---|---|---|---|---|
| 1 | 426 | CGPG699 | 10919 | ANTI-SENSE |
| 2 | 427 | CGPG567 | 11142 | SENSE |
| 3 | 428 | CGPG267 | 11310 | ANTI-SENSE |
| 4 | 429 | CGPG1179 | 11866 | ANTI-SENSE |
| 5 | 430 | CGPG959 | 11937 | ANTI-SENSE |
| 6 | 431 | CGPG2158 | 16218 | SENSE |
| 7 | 432 | CGPG2446 | 17410 | SENSE |
| 8 | 433 | CGPG1862 | 18401 | SENSE |
| 9 | 434 | CGPG3014 | 18665 | SENSE |
| 10 | 435 | CGPG1674 | 19141 | SENSE |
| 11 | 436 | CGPG2680 | 19156 | SENSE |
| 12 | 437 | CGPG3577 | 19621 | SENSE |
| 13 | 438 | CGPG4065 | 19760 | SENSE |
| 14 | 439 | CGPG3929 | 19857 | SENSE |
| 15 | 440 | CGPG2488 | 70510 | SENSE |
| 16 | 441 | CGPG3012 | 70605 | SENSE |
| 17 | 442 | CGPG3162 | 70607 | SENSE |
| 18 | 443 | CGPG607 | 70812 | SENSE |
| 19 | 444 | CGPG4084 | 70933 | SENSE |
| 20 | 445 | CGPG3917 | 70939 | SENSE |
| 21 | 446 | CGPG4414 | 71319 | SENSE |
| 22 | 447 | CGPG185 | 71446 | SENSE |
| 23 | 448 | CGPG1679 | 71609 | SENSE |
| 24 | 449 | CGPG271 | 71649 | SENSE |
| 25 | 450 | CGPG4434 | 71814 | SENSE |
| 26 | 451 | CGPG2198 | 71945 | SENSE |
| 27 | 452 | CGPG5253 | 72005 | SENSE |
| 28 | 453 | CGPG5231 | 72026 | SENSE |
| 29 | 454 | CGPG4815 | 72533 | SENSE |
| 30 | 455 | CGPG4859 | 72637 | SENSE |
| 31 | 456 | CGPG1589 | 72782 | SENSE |
| 32 | 457 | CGPG1826 | 72794 | SENSE |
| 33 | 458 | CGPG3899 | 72919 | SENSE |
| 34 | 459 | CGPG5610 | 72983 | SENSE |
| 35 | 460 | CGPG5665 | 73025 | SENSE |
| 36 | 461 | CGPG5697 | 73050 | SENSE |
| 37 | 462 | CGPG5695 | 73092 | SENSE |
| 38 | 463 | CGPG4862 | 73338 | SENSE |
| 39 | 464 | CGPG4910 | 73344 | SENSE |
| 40 | 465 | CGPG6541 | 73536 | SENSE |
| 41 | 466 | CGPG1756 | 73644 | SENSE |
| 42 | 467 | CGPG4927 | 73662 | SENSE |
| 43 | 468 | CGPG5106 | 73672 | SENSE |
| 44 | 469 | CGPG5167 | 73733 | SENSE |
| 45 | 470 | CGPG1924 | 73846 | SENSE |
| 46 | 471 | CGPG5201 | 73863 | SENSE |
| 47 | 472 | CGPG1884 | 74059 | SENSE |
| 48 | 473 | CGPG5089 | 74205 | SENSE |
| 49 | 474 | CGPG5870 | 74321 | SENSE |
| 50 | 475 | CGPG5888 | 74337 | SENSE |
| 51 | 476 | CGPG1461 | 74388 | SENSE |
| 52 | 477 | CGPG6743 | 74412 | SENSE |
| 53 | 478 | CGPG6722 | 74445 | SENSE |
| 54 | 479 | CGPG82 | 74522 | SENSE |
| 55 | 480 | CGPG6761 | 74526 | SENSE |
| 56 | 481 | CGPG6781 | 74576 | SENSE |
| 57 | 482 | CGPG4914 | 74707 | SENSE |
| 58 | 483 | CGPG5840 | 74743 | SENSE |
| 59 | 484 | CGPG5980 | 74755 | SENSE |
| 60 | 485 | CGPG1743 | 75202 | SENSE |
| 61 | 486 | CGPG5434 | 75220 | SENSE |
| 62 | 487 | CGPG5824 | 75226 | SENSE |
| 63 | 488 | CGPG5879 | 75231 | SENSE |
| 64 | 489 | CGPG5949 | 75239 | SENSE |
| 65 | 490 | CGPG6096 | 75258 | SENSE |
| 66 | 491 | CGPG6218 | 75270 | SENSE |
| 67 | 492 | CGPG6226 | 75271 | SENSE |
| 68 | 493 | CGPG7518 | 75355 | SENSE |
| 69 | 494 | CGPG7654 | 75460 | SENSE |
| 70 | 495 | CGPG6875 | 75847 | SENSE |
| 71 | 496 | CGPG8259 | 75907 | SENSE |
| 72 | 497 | CGPG8229 | 75927 | SENSE |
| 73 | 498 | CGPG8224 | 75962 | SENSE |
| 74 | 499 | CGPG1927 | 75984 | SENSE |
| 75 | 500 | CGPG5962 | 76119 | SENSE |
| 76 | 501 | CGPG5375 | 76209 | SENSE |
| 77 | 502 | CGPG8949 | 76323 | SENSE |
| 78 | 503 | CGPG8943 | 76346 | SENSE |
| 79 | 504 | CGPG8896 | 76352 | SENSE |

TABLE 1-continued

| NUC SEQ ID NO | PEP SEQ IDNO | Gene ID | Construct ID | orientation |
|---|---|---|---|---|
| 80 | 505 | CGPG8960 | 76360 | SENSE |
| 81 | 506 | CGPG5891 | 76512 | SENSE |
| 82 | 507 | CGPG7260 | 76575 | SENSE |
| 83 | 508 | CGPG2647 | 76733 | SENSE |
| 84 | 509 | CGPG6995 | 76741 | SENSE |
| 85 | 510 | CGPG9046 | 76845 | SENSE |
| 86 | 511 | CGPG9047 | 76857 | SENSE |
| 87 | 512 | CGPG9083 | 76902 | SENSE |
| 88 | 513 | CGPG9076 | 76913 | SENSE |
| 89 | 514 | CGPG9108 | 76917 | SENSE |
| 90 | 515 | CGPG9109 | 76929 | SENSE |
| 91 | 516 | CGPG5933 | 77009 | SENSE |
| 92 | 517 | CGPG6335 | 77022 | SENSE |
| 93 | 518 | CGPG9174 | 77108 | SENSE |
| 94 | 519 | CGPG9120 | 77125 | SENSE |
| 95 | 520 | CGPG9200 | 77135 | SENSE |
| 96 | 521 | CGPG9263 | 77219 | SENSE |
| 97 | 522 | CGPG8087 | 77351 | SENSE |
| 98 | 523 | CGPG385 | 14810 | SENSE |
| 99 | 524 | CGPG1857 | 14835 | ANTI-SENSE |
| 100 | 525 | CGPG1788 | 15419 | ANTI-SENSE |
| 101 | 526 | CGPG1966 | 16223 | SENSE |
| 102 | 527 | CGPG1908 | 17903 | SENSE |
| 103 | 528 | CGPG3545 | 18279 | SENSE |
| 104 | 529 | CGPG3557 | 18284 | SENSE |
| 105 | 530 | CGPG3340 | 18332 | SENSE |
| 106 | 531 | CGPG3431 | 18349 | SENSE |
| 107 | 532 | CGPG3530 | 18623 | SENSE |
| 108 | 533 | CGPG3119 | 19551 | SENSE |
| 109 | 534 | CGPG3594 | 19627 | SENSE |
| 110 | 535 | CGPG4031 | 19785 | SENSE |
| 111 | 536 | CGPG4036 | 19944 | SENSE |
| 112 | 537 | CGPG2384 | 70125 | SENSE |
| 113 | 538 | CGPG1598 | 70504 | SENSE |
| 114 | 539 | CGPG560 | 70830 | SENSE |
| 115 | 540 | CGPG4002 | 70943 | SENSE |
| 116 | 541 | CGPG1422 | 71711 | ANTI-SENSE |
| 117 | 542 | CGPG4429 | 71962 | SENSE |
| 118 | 543 | CGPG862 | 72352 | SENSE |
| 119 | 544 | CGPG2251 | 72413 | SENSE |
| 120 | 545 | CGPG646 | 72603 | SENSE |
| 121 | 546 | CGPG2569 | 72676 | SENSE |
| 122 | 547 | CGPG5507 | 72737 | SENSE |
| 123 | 548 | CGPG5547 | 72742 | SENSE |
| 124 | 549 | CGPG5517 | 72762 | SENSE |
| 125 | 550 | CGPG5792 | 72993 | SENSE |
| 126 | 551 | CGPG5766 | 73031 | SENSE |
| 127 | 552 | CGPG5775 | 73091 | SENSE |
| 128 | 553 | CGPG4809 | 73224 | SENSE |
| 129 | 554 | CGPG4872 | 73340 | SENSE |
| 130 | 555 | CGPG6420 | 73420 | SENSE |
| 131 | 556 | CGPG6402 | 73489 | SENSE |
| 132 | 557 | CGPG5073 | 73750 | SENSE |
| 133 | 558 | CGPG5091 | 73751 | SENSE |
| 134 | 559 | CGPG3570 | 73814 | SENSE |
| 135 | 560 | CGPG4342 | 73855 | SENSE |
| 136 | 561 | CGPG4483 | 73856 | SENSE |
| 137 | 562 | CGPG1527 | 73929 | SENSE |
| 138 | 563 | CGPG4351 | 74063 | SENSE |
| 139 | 564 | CGPG4753 | 74072 | SENSE |
| 140 | 565 | CGPG4757 | 74073 | SENSE |
| 141 | 566 | CGPG4805 | 74075 | SENSE |
| 142 | 567 | CGPG6624 | 74135 | SENSE |
| 143 | 568 | CGPG3161 | 74313 | SENSE |
| 144 | 569 | CGPG3770 | 74315 | SENSE |
| 145 | 570 | CGPG6673 | 74427 | SENSE |
| 146 | 571 | CGPG6702 | 74490 | SENSE |
| 147 | 572 | CGPG21 | 74511 | SENSE |
| 148 | 573 | CGPG6801 | 74531 | SENSE |
| 149 | 574 | CGPG154 | 74532 | SENSE |
| 150 | 575 | CGPG6762 | 74538 | SENSE |
| 151 | 576 | CGPG6763 | 74550 | SENSE |
| 152 | 577 | CGPG1467 | 74579 | SENSE |
| 153 | 578 | CGPG6160 | 74644 | SENSE |
| 154 | 579 | CGPG15 | 74703 | SENSE |
| 155 | 580 | CGPG5825 | 74733 | SENSE |
| 156 | 581 | CGPG5936 | 74749 | SENSE |
| 157 | 582 | CGPG5974 | 74752 | SENSE |
| 158 | 583 | CGPG1366 | 74773 | SENSE |
| 159 | 584 | CGPG7390 | 74896 | SENSE |
| 160 | 585 | CGPG7421 | 74976 | SENSE |
| 161 | 586 | CGPG7446 | 74991 | SENSE |
| 162 | 587 | CGPG6295 | 75289 | SENSE |
| 163 | 588 | CGPG1476 | 76003 | SENSE |
| 164 | 589 | CGPG1821 | 76074 | SENSE |
| 165 | 590 | CGPG6975 | 76137 | SENSE |
| 166 | 591 | CGPG6189 | 76220 | SENSE |
| 167 | 592 | CGPG8868 | 76301 | SENSE |
| 168 | 593 | CGPG8909 | 76318 | SENSE |
| 169 | 594 | CGPG8951 | 76347 | SENSE |
| 170 | 595 | CGPG5892 | 76513 | SENSE |
| 171 | 596 | CGPG7171 | 76566 | SENSE |
| 172 | 597 | CGPG6142 | 76719 | SENSE |
| 173 | 598 | CGPG7212 | 76757 | SENSE |
| 174 | 599 | CGPG9034 | 76891 | SENSE |
| 175 | 600 | CGPG9270 | 77208 | SENSE |
| 176 | 601 | CGPG1112 | 12116 | ANTI-SENSE |
| 177 | 602 | CGPG1284 | 13053 | ANTI-SENSE |
| 178 | 603 | CGPG1640 | 14733 | SENSE |
| 179 | 604 | CGPG2136 | 16132 | SENSE |
| 180 | 605 | CGPG3542 | 18276 | SENSE |
| 181 | 606 | CGPG1691 | 70851 | SENSE |
| 182 | 607 | CGPG4067 | 70941 | SENSE |
| 183 | 608 | CGPG5335 | 72134 | SENSE |
| 184 | 609 | CGPG27 | 72326 | SENSE |
| 185 | 610 | CGPG3441 | 72978 | SENSE |
| 186 | 611 | CGPG4375 | 73619 | SENSE |
| 187 | 612 | CGPG5176 | 73737 | SENSE |
| 188 | 613 | CGPG6637 | 74196 | SENSE |
| 189 | 614 | CGPG661 | 74546 | SENSE |
| 190 | 615 | CGPG869 | 74558 | SENSE |
| 191 | 616 | CGPG6159 | 74643 | SENSE |
| 192 | 617 | CGPG5931 | 75234 | SENSE |
| 193 | 618 | CGPG6282 | 75278 | SENSE |
| 194 | 619 | CGPG7671 | 75585 | SENSE |
| 195 | 620 | CGPG1574 | 76063 | SENSE |
| 196 | 621 | CGPG9294 | 77401 | SENSE |
| 197 | 622 | CGPG2435 | 17808 | SENSE |
| 198 | 623 | CGPG3336 | 18330 | SENSE |
| 199 | 624 | CGPG3613 | 18409 | SENSE |
| 200 | 625 | CGPG4168 | 19813 | SENSE |
| 201 | 626 | CGPG6517 | 73580 | SENSE |
| 202 | 627 | CGPG993 | 73935 | SENSE |
| 203 | 628 | CGPG6631 | 74124 | SENSE |
| 204 | 629 | CGPG5393 | 74725 | SENSE |
| 205 | 630 | CGPG1313 | 76403 | SENSE |
| 206 | 631 | CGPG8150 | 77366 | SENSE |
| 207 | 632 | CGPG1661 | 72414 | SENSE |
| 208 | 633 | CGPG6427 | 73409 | SENSE |
| 209 | 634 | CGPG4906 | 73723 | SENSE |
| 210 | 635 | CGPG5092 | 73747 | SENSE |
| 211 | 636 | CGPG6146 | 74634 | SENSE |
| 212 | 637 | CGPG6022 | 74769 | SENSE |
| 213 | 638 | CGPG5883 | 75232 | SENSE |
| 214 | 639 | CGPG7596 | 75429 | SENSE |
| 215 | 640 | CGPG8248 | 75965 | SENSE |
| 216 | 641 | CGPG8233 | 75975 | SENSE |
| 217 | 642 | CGPG1573 | 76061 | SENSE |
| 218 | 643 | CGPG7141 | 76155 | SENSE |
| 219 | 644 | CGPG8941 | 76322 | SENSE |
| 220 | 645 | CGPG6337 | 76440 | SENSE |
| 221 | 646 | CGPG9005 | 76828 | SENSE |
| 222 | 647 | CGPG9208 | 77136 | SENSE |
| 223 | 648 | CGPG4348 | 77303 | SENSE |
| 224 | 649 | CGPG8099 | 77352 | SENSE |
| 225 | 650 | CGPG618 | 10913 | ANTI-SENSE |
| 226 | 651 | CGPG251 | 10925 | ANTI-SENSE |
| 227 | 652 | CGPG636 | 11357 | SENSE |
| 228 | 653 | CGPG639 | 11358 | SENSE |
| 229 | 654 | CGPG287 | 11432 | ANTI-SENSE |
| 230 | 655 | CGPG893 | 11927 | ANTI-SENSE |
| 231 | 656 | CGPG1122 | 12050 | SENSE |
| 232 | 657 | CGPG657 | 12358 | ANTI-SENSE |
| 233 | 658 | CGPG1489 | 13809 | SENSE |

TABLE 1-continued

| NUC SEQ ID NO | PEP SEQ IDNO | Gene ID | Construct ID | orientation |
|---|---|---|---|---|
| 234 | 659 | CGPG2122 | 16877 | SENSE |
| 235 | 660 | CGPG1683 | 18117 | ANTI-SENSE |
| 236 | 661 | CGPG4685 | 71651 | SENSE |
| 237 | 662 | CGPG4729 | 72449 | SENSE |
| 238 | 663 | CGPG4880 | 72649 | SENSE |
| 239 | 664 | CGPG5680 | 73107 | SENSE |
| 240 | 665 | CGPG7317 | 74875 | SENSE |
| 241 | 666 | CGPG4902 | 75079 | SENSE |
| 242 | 667 | CGPG6720 | 75180 | SENSE |
| 243 | 668 | CGPG5850 | 75228 | SENSE |
| 244 | 669 | CGPG6010 | 75246 | SENSE |
| 245 | 670 | CGPG7488 | 75375 | SENSE |
| 246 | 671 | CGPG7592 | 75476 | SENSE |
| 247 | 672 | CGPG7672 | 75502 | SENSE |
| 248 | 673 | CGPG6923 | 75857 | SENSE |
| 249 | 674 | CGPG6988 | 75873 | SENSE |
| 250 | 675 | CGPG1357 | 75970 | SENSE |
| 251 | 676 | CGPG5918 | 76115 | SENSE |
| 252 | 677 | CGPG6020 | 76217 | SENSE |
| 253 | 678 | CGPG7032 | 76287 | SENSE |
| 254 | 679 | CGPG7069 | 76294 | SENSE |
| 255 | 680 | CGPG8900 | 76305 | SENSE |
| 256 | 681 | CGPG8923 | 76391 | SENSE |
| 257 | 682 | CGPG6296 | 76438 | SENSE |
| 258 | 683 | CGPG7053 | 76452 | SENSE |
| 259 | 684 | CGPG7134 | 76563 | SENSE |
| 260 | 685 | CGPG6951 | 77055 | SENSE |
| 261 | 686 | CGPG6994 | 77059 | SENSE |
| 262 | 687 | CGPG7019 | 77062 | SENSE |
| 263 | 688 | CGPG7024 | 77063 | SENSE |
| 264 | 689 | CGPG9255 | 77218 | SENSE |
| 265 | 690 | CGPG9274 | 77256 | SENSE |
| 266 | 691 | CGPG6130 | 77314 | SENSE |
| 267 | 692 | CGPG8074 | 77344 | SENSE |
| 268 | 693 | CGPG8081 | 77348 | SENSE |
| 269 | 694 | CGPG172 | 10443 | ANTI-SENSE |
| 270 | 695 | CGPG2482 | 17814 | SENSE |
| 271 | 696 | CGPG3222 | 18537 | SENSE |
| 272 | 697 | CGPG3259 | 18831 | SENSE |
| 273 | 698 | CGPG1900 | 19044 | ANTI-SENSE |
| 274 | 699 | CGPG4128 | 19950 | SENSE |
| 275 | 700 | CGPG20 | 70221 | SENSE |
| 276 | 701 | CGPG201 | 71110 | SENSE |
| 277 | 702 | CGPG3420 | 71718 | SENSE |
| 278 | 703 | CGPG4308 | 71838 | SENSE |
| 279 | 704 | CGPG5244 | 72087 | SENSE |
| 280 | 705 | CGPG5538 | 72729 | SENSE |
| 281 | 706 | CGPG3738 | 73302 | SENSE |
| 282 | 707 | CGPG6454 | 73484 | SENSE |
| 283 | 708 | CGPG6530 | 73594 | SENSE |
| 284 | 709 | CGPG5175 | 73736 | SENSE |
| 285 | 710 | CGPG5756 | 74016 | SENSE |
| 286 | 711 | CGPG5361 | 74266 | SENSE |
| 287 | 712 | CGPG6709 | 74479 | SENSE |
| 288 | 713 | CGPG6755 | 74549 | SENSE |
| 289 | 714 | CGPG6765 | 74574 | SENSE |
| 290 | 715 | CGPG6039 | 74607 | SENSE |
| 291 | 716 | CGPG6158 | 74642 | SENSE |
| 292 | 717 | CGPG3578 | 75015 | SENSE |
| 293 | 718 | CGPG7528 | 75380 | SENSE |
| 294 | 719 | CGPG7756 | 75560 | SENSE |
| 295 | 720 | CGPG7663 | 75765 | SENSE |
| 296 | 721 | CGPG8249 | 75977 | SENSE |
| 297 | 722 | CGPG2232 | 76052 | SENSE |
| 298 | 723 | CGPG5494 | 76109 | SENSE |
| 299 | 724 | CGPG5947 | 76116 | SENSE |
| 300 | 725 | CGPG7160 | 76158 | SENSE |
| 301 | 726 | CGPG6262 | 76232 | SENSE |
| 302 | 727 | CGPG6909 | 76269 | SENSE |
| 303 | 728 | CGPG8884 | 76303 | SENSE |
| 304 | 729 | CGPG8965 | 76474 | SENSE |
| 305 | 730 | CGPG5861 | 76529 | SENSE |
| 306 | 731 | CGPG7138 | 76625 | SENSE |
| 307 | 732 | CGPG7246 | 76759 | SENSE |
| 308 | 733 | CGPG5378 | 77026 | SENSE |
| 309 | 734 | CGPG9168 | 77131 | SENSE |
| 310 | 735 | CGPG1505 | 14944 | SENSE |
| 311 | 736 | CGPG3614 | 18410 | SENSE |
| 312 | 737 | CGPG3220 | 18536 | SENSE |
| 313 | 738 | CGPG3062 | 19540 | SENSE |
| 314 | 739 | CGPG3580 | 19624 | SENSE |
| 315 | 740 | CGPG3725 | 70353 | SENSE |
| 316 | 741 | CGPG592 | 71215 | SENSE |
| 317 | 742 | CGPG4417 | 71320 | SENSE |
| 318 | 743 | CGPG2276 | 73076 | SENSE |
| 319 | 744 | CGPG4975 | 73666 | SENSE |
| 320 | 745 | CGPG2790 | 73852 | SENSE |
| 321 | 746 | CGPG4972 | 74080 | SENSE |
| 322 | 747 | CGPG5140 | 74211 | SENSE |
| 323 | 748 | CGPG19 | 74510 | SENSE |
| 324 | 749 | CGPG6769 | 74527 | SENSE |
| 325 | 750 | CGPG6770 | 74539 | SENSE |
| 326 | 751 | CGPG737 | 74556 | SENSE |
| 327 | 752 | CGPG6789 | 74577 | SENSE |
| 328 | 753 | CGPG5374 | 74729 | SENSE |
| 329 | 754 | CGPG5978 | 74753 | SENSE |
| 330 | 755 | CGPG5979 | 74754 | SENSE |
| 331 | 756 | CGPG7447 | 74908 | SENSE |
| 332 | 757 | CGPG948 | 75107 | SENSE |
| 333 | 758 | CGPG6052 | 75254 | SENSE |
| 334 | 759 | CGPG7661 | 75741 | SENSE |
| 335 | 760 | CGPG8261 | 75931 | SENSE |
| 336 | 761 | CGPG5447 | 76207 | SENSE |
| 337 | 762 | CGPG7068 | 76293 | SENSE |
| 338 | 763 | CGPG5938 | 76517 | SENSE |
| 339 | 764 | CGPG7100 | 76559 | SENSE |
| 340 | 765 | CGPG9003 | 76804 | SENSE |
| 341 | 766 | CGPG6299 | 77018 | SENSE |
| 342 | 767 | CGPG9135 | 77115 | SENSE |
| 343 | 768 | CGPG9144 | 77128 | SENSE |
| 344 | 769 | CGPG9194 | 77158 | SENSE |
| 345 | 770 | CGPG9202 | 77159 | SENSE |
| 346 | 771 | CGPG9139 | 77163 | SENSE |
| 347 | 772 | CGPG414 | 10923 | ANTI-SENSE |
| 348 | 773 | CGPG1072 | 14836 | SENSE |
| 349 | 774 | CGPG1986 | 15130 | SENSE |
| 350 | 775 | CGPG2916 | 18214 | SENSE |
| 351 | 776 | CGPG111 | 70236 | SENSE |
| 352 | 777 | CGPG4317 | 70639 | SENSE |
| 353 | 778 | CGPG4387 | 70668 | SENSE |
| 354 | 779 | CGPG4492 | 70674 | SENSE |
| 355 | 780 | CGPG597 | 70804 | SENSE |
| 356 | 781 | CGPG345 | 70821 | SENSE |
| 357 | 782 | CGPG4786 | 72505 | SENSE |
| 358 | 783 | CGPG4998 | 72824 | SENSE |
| 359 | 784 | CGPG5076 | 73283 | SENSE |
| 360 | 785 | CGPG5104 | 73292 | SENSE |
| 361 | 786 | CGPG6502 | 73578 | SENSE |
| 362 | 787 | CGPG6630 | 74112 | SENSE |
| 363 | 788 | CGPG5484 | 74249 | SENSE |
| 364 | 789 | CGPG5394 | 74278 | SENSE |
| 365 | 790 | CGPG6058 | 74359 | SENSE |
| 366 | 791 | CGPG2090 | 74393 | SENSE |
| 367 | 792 | CGPG6664 | 74414 | SENSE |
| 368 | 793 | CGPG7706 | 75530 | SENSE |
| 369 | 794 | CGPG7884 | 75752 | SENSE |
| 370 | 795 | CGPG6965 | 75867 | SENSE |
| 371 | 796 | CGPG1256 | 75910 | SENSE |
| 372 | 797 | CGPG2297 | 76101 | SENSE |
| 373 | 798 | CGPG6246 | 76431 | SENSE |
| 374 | 799 | CGPG9037 | 76832 | SENSE |
| 375 | 800 | CGPG1941 | 16023 | SENSE |
| 376 | 801 | CGPG2055 | 16424 | ANTI-SENSE |
| 377 | 802 | CGPG2427 | 17807 | SENSE |
| 378 | 803 | CGPG386 | 70802 | SENSE |
| 379 | 804 | CGPG393 | 70817 | SENSE |
| 380 | 805 | CGPG609 | 70819 | SENSE |
| 381 | 806 | CGPG4022 | 70908 | SENSE |
| 382 | 807 | CGPG942 | 72351 | SENSE |
| 383 | 808 | CGPG1800 | 73087 | SENSE |
| 384 | 809 | CGPG4783 | 73223 | SENSE |
| 385 | 810 | CGPG3257 | 73709 | SENSE |
| 386 | 811 | CGPG1696 | 73804 | SENSE |
| 387 | 812 | CGPG1982 | 73819 | SENSE |

TABLE 1-continued

| NUC SEQ ID NO | PEP SEQ IDNO | Gene ID | Construct ID | orientation |
|---|---|---|---|---|
| 388 | 813 | CGPG3780 | 73851 | SENSE |
| 389 | 814 | CGPG6602 | 74156 | SENSE |
| 390 | 815 | CGPG6621 | 74194 | SENSE |
| 391 | 816 | CGPG5493 | 74252 | SENSE |
| 392 | 817 | CGPG5811 | 74317 | SENSE |
| 393 | 818 | CGPG5902 | 74328 | SENSE |
| 394 | 819 | CGPG6791 | 74506 | SENSE |
| 395 | 820 | CGPG6778 | 74540 | SENSE |
| 396 | 821 | CGPG6166 | 74650 | SENSE |
| 397 | 822 | CGPG3735 | 74718 | SENSE |
| 398 | 823 | CGPG5854 | 74745 | SENSE |
| 399 | 824 | CGPG7451 | 74956 | SENSE |
| 400 | 825 | CGPG5024 | 75076 | SENSE |
| 401 | 826 | CGPG6054 | 75255 | SENSE |
| 402 | 827 | CGPG6207 | 75269 | SENSE |
| 403 | 828 | CGPG7620 | 75432 | SENSE |
| 404 | 829 | CGPG7623 | 75468 | SENSE |
| 405 | 830 | CGPG7775 | 75686 | SENSE |
| 406 | 831 | CGPG73 | 75911 | SENSE |
| 407 | 832 | CGPG2100 | 76064 | SENSE |
| 408 | 833 | CGPG6026 | 76121 | SENSE |
| 409 | 834 | CGPG7269 | 76193 | SENSE |
| 410 | 835 | CGPG6361 | 76237 | SENSE |
| 411 | 836 | CGPG6993 | 76281 | SENSE |
| 412 | 837 | CGPG8899 | 76388 | SENSE |
| 413 | 838 | CGPG6926 | 76557 | SENSE |
| 414 | 839 | CGPG7172 | 76567 | SENSE |
| 415 | 840 | CGPG7129 | 76624 | SENSE |
| 416 | 841 | CGPG7276 | 76764 | SENSE |
| 417 | 842 | CGPG9031 | 76855 | SENSE |
| 418 | 843 | CGPG9105 | 76976 | SENSE |
| 419 | 844 | CGPG9082 | 76985 | SENSE |
| 420 | 845 | CGPG6212 | 77014 | SENSE |
| 421 | 846 | CGPG9206 | 77112 | SENSE |
| 422 | 847 | CGPG9151 | 77117 | SENSE |
| 423 | 848 | CGPG9129 | 77138 | SENSE |
| 424 | 849 | CGPG9224 | 77226 | SENSE |
| 425 | 850 | CGPG9358 | 77418 | SENSE |

Recombinant DNA

DNA for use in the present invention to improve traits in plants have a nucleotide sequence of SEQ ID NO:1 through SEQ ID NO:425, as well as the homologs of such DNA molecules. A subset of the DNA for gene suppression aspects of the invention includes fragments of the disclosed full polynucleotides consisting of oligonucleotides of 21 or more consecutive nucleotides. Oligonucleotides the larger molecules having a sequence selected from the group consisting of SEQ ID NO:1 through SEQ ID NO:425 are useful as probes and primers for detection of the polynucleotides used in the invention. Also useful in this invention are variants of the DNA. Such variants may be naturally occurring, including DNA from homologous genes from the same or a different species, or may be non-natural variants, for example DNA synthesized using chemical synthesis methods, or generated using recombinant DNA techniques. Degeneracy of the genetic code provides the possibility to substitute at least one base of the protein encoding sequence of a gene with a different base without causing the amino acid sequence of the polypeptide produced from the gene to be changed. Hence, a DNA useful in the present invention may have any base sequence that has been changed from the sequences provided herein by substitution in accordance with degeneracy of the genetic code.

Homologs of the genes providing DNA demonstrated as useful in improving traits in model plants disclosed herein will generally have significant identity with the DNA disclosed herein. DNA is substantially identical to a reference DNA if, when the sequences of the polynucleotides are optimally aligned there is about 60% nucleotide equivalence; more preferably 70%; more preferably 80% equivalence; more preferably 85% equivalence; more preferably 90%; more preferably 95%; and/or more preferably 98% or 99% equivalence over a comparison window. A comparison window is preferably at least 50-100 nucleotides, and more preferably is the entire length of the polynucleotide provided herein. Optimal alignment of sequences for aligning a comparison window may be conducted by algorithms; preferably by computerized implementations of these algorithms (for example, the Wisconsin Genetics Software Package Release 7.0-10.0, Genetics Computer Group, 575 Science Dr., Madison, Wis.). The reference polynucleotide may be a full-length molecule or a portion of a longer molecule. Preferentially, the window of comparison for determining polynucleotide identity of protein encoding sequences is the entire coding region.

Proteins useful for imparting improved traits are entire proteins or at least a sufficient portion of the entire protein to impart the relevant biological activity of the protein. Proteins useful for generation of transgenic plants having improved traits include the proteins with an amino acid sequence provided herein as SEQ ID NO: 426 through SEQ ID NO: 850, as well as homologs of such proteins.

Homologs of the proteins useful in the invention are identified by comparison of the amino acid sequence of the protein to amino acid sequences of proteins from the same or different plant sources, e.g., manually or by using known homology-based search algorithms such as those commonly known and referred to as BLAST, FASTA, and Smith-Waterman. As used herein, a homolog is a protein from the same or a different organism that performs the same biological function as the polypeptide to which it is compared. An orthologous relation between two organisms is not necessarily manifest as a one-to-one correspondence between two genes, because a gene can be duplicated or deleted after organism phylogenetic separation, such as speciation. For a given protein, there may be no ortholog or more than one ortholog. Other complicating factors include alternatively spliced transcripts from the same gene, limited gene identification, redundant copies of the same gene with different sequence lengths or corrected sequence. A local sequence alignment program, e.g., BLAST, can be used to search a database of sequences to find similar sequences, and the summary Expectation value (E-value) used to measure the sequence base similarity. As a protein hit with the best E-value for a particular organism may not necessarily be an ortholog or the only ortholog, a reciprocal BLAST search is used in the present invention to filter hit sequences with significant E-values for ortholog identification. The reciprocal BLAST entails search of the significant hits against a database of amino acid sequences from the base organism that are similar to the sequence of the query protein. A hit is a likely ortholog, when the reciprocal BLAST's best hit is the query protein itself or a protein encoded by a duplicated gene after speciation. Thus, homolog is used herein to describe proteins that are assumed to have functional similarity by inference from sequence base similarity. The relationship of homologs with amino acid sequences of SEQ ID NO: 851 to SEQ ID NO: 33634 to the proteins with amino acid sequences of SEQ ID NO: to 426 to SEQ ID NO: 850 is found in the listing of Table 2.

Other functional homolog proteins differ in one or more amino acids from those of a trait-improving protein disclosed herein as the result of one or more of the well-known conservative amino acid substitutions, e.g., valine is a conservative substitute for alanine and threonine is a conservative substitute for serine. Conservative substitutions for an amino acid within the native sequence can be selected from other members of a class to which the naturally occurring amino acid belongs. Representative amino acids within these various classes include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; and (4) neutral nonpolar (hydrophobic) amino acids such as alanine, leucine, isoleucine, valine, proline, phenylalanine, tryptophan, and methionine. Conserved substitutes for an amino acid within a native amino acid sequence can be selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Naturally conservative amino acids substitution groups are: valine-leucine, valine-isoleucine, phenylalanine-tyrosine, lysine-arginine, alanine-valine, aspartic acid-glutamic acid, and asparagine-glutamine. A further aspect of the invention comprises proteins that differ in one or more amino acids from those of a described protein sequence as the result of deletion or insertion of one or more amino acids in a native sequence.

Homologs of the trait-improving proteins disclosed provided herein will generally demonstrate significant sequence identity. Of particular interest are proteins having at least 50% sequence identity, more preferably at least about 70% sequence identity or higher, e.g., at least about 80% sequence identity with an amino acid sequence of SEQ ID NO: 426 through SEQ ID NO: 850. Of course useful proteins also include those with higher identity, e.g., 90% to 99% identity. Identity of protein homologs is determined by optimally aligning the amino acid sequence of a putative protein homolog with a defined amino acid sequence and by calculating the percentage of identical and conservatively substituted amino acids over the window of comparison. The window of comparison for determining identity can be the entire amino acid sequence disclosed herein, e.g., the full sequence of any of SEQ ID NO: 426 through SEQ ID NO: 850.

Genes that are homologous to each other can be grouped into families and included in multiple sequence alignments. Then a consensus sequence for each group can be derived. This analysis enables the derivation of conserved and class-(family) specific residues or motifs that are functionally important. These conserved residues and motifs can be further validated with 3D protein structure if available. The consensus sequence can be used to define the full scope of the invention, e.g., to identify proteins with a homolog relationship. Thus, the present invention contemplates that protein homologs include proteins with an amino acid sequence that has at least 90% identity to such a consensus amino acid sequence sequences.

Promoters

Numerous promoters that are active in plant cells have been described in the literature. These include promoters present in plant genomes as well as promoters from other sources, including nopaline synthase (NOS) promoter and octopine synthase (OCS) promoters carried on tumor-inducing plasmids of *Agrobacterium tumefaciens*, caulimovirus promoters such as the cauliflower mosaic virus or Figwort mosaic virus promoters. For instance, see U.S. Pat. Nos. 5,858,742 and 5,322,938 which disclose versions of the constitutive promoter derived from cauliflower mosaic virus (CaMV35S), U.S. Pat. No. 5,378,619 which discloses a Figwort Mosaic Virus (FMV) 35S promoter, U.S. Pat. No. 6,437,217 which discloses a maize RS81 promoter, U.S. Pat. No. 5,641,876 which discloses a rice actin promoter, U.S. Pat. No. 6,426,446 which discloses a maize RS324 promoter, U.S. Pat. No. 6,429,362 which discloses a maize PR-1 promoter, U.S. Pat. No. 6,232,526 which discloses a maize A3 promoter, U.S. Pat. No. 6,177,611 which discloses constitutive maize promoters, U.S. Pat. No. 6,433,252 which discloses a maize L3 oleosin promoter, U.S. Pat. No. 6,429,357 which discloses a rice actin 2 promoter and intron, U.S. Pat. No. 5,837,848 which discloses a root specific promoter, U.S. Pat. No. 6,084,089 which discloses cold inducible promoters, U.S. Pat. No. 6,294,714 which discloses light inducible promoters, U.S. Pat. No. 6,140,078 which discloses salt inducible promoters, U.S. Pat. No. 6,252,138 which discloses pathogen inducible promoters, U.S. Pat. No. 6,175,060 which discloses phosphorus deficiency inducible promoters, U.S. Patent Application Publication 2002/0192813A1 which discloses 5', 3' and intron elements useful in the design of effective plant expression vectors, U.S. patent application Ser. No. 09/078,972 which discloses a coixin promoter, U.S. patent application Ser. No. 09/757,089 which discloses a maize chloroplast aldolase promoter, and U.S. patent application Ser. No. 10/739,565 which discloses water-deficit inducible promoters, all of which are incorporated herein by reference. These and numerous other promoters that function in plant cells are known to those skilled in the art and available for use in recombinant polynucleotides of the present invention to provide for expression of desired genes in transgenic plant cells.

Furthermore, the promoters can include multiple "enhancer sequences" to assist in elevating gene expression. Such enhancers are known in the art. By including an enhancer sequence with such constructs, the expression of the selected protein may be enhanced. These enhancers often are found 5' to the start of transcription in a promoter that functions in eukaryotic cells, but can often be inserted in the forward or reverse orientation 5' or 3' to the coding sequence. In some instances, these 5' enhancing elements are introns. Deemed to be particularly useful as enhancers are the 5' introns of the rice actin 1 and rice actin 2 genes. Examples of other enhancers that can be used in accordance with the invention include elements from the CaMV 35S promoter, octopine synthase genes, the maize alcohol dehydrogenase gene, the maize shrunken 1 gene and promoters from non-plant eukaryotes.

In some aspects of the invention it is preferred that the promoter element in the DNA construct be capable of causing sufficient expression to result in the production of an effective amount of a polypeptide in water deficit conditions. Such promoters can be identified and isolated from the regulatory region of plant genes that are over expressed in water deficit conditions. Specific water-deficit-inducible promoters for use in this invention are derived from the 5' regulatory region of genes identified as a heat shock protein 17.5 gene (HSP17.5), an HVA22 gene (HVA22), a Rab17 gene and a cinnamic acid 4-hydroxylase (CA4H) gene (CA4H) of *Zea maize*. Such water-deficit-inducible promoters are disclosed in U.S. application Ser. No. 10/739,565, incorporated herein by reference.

In some aspects of the invention, sufficient expression in plant seed tissues is desired to effect improvements in seed composition. Exemplary promoters for use for seed composition modification include promoters from seed genes such as napin (U.S. Pat. No. 5,420,034), *maize* L3 oleosin (U.S. Pat. No. 6,433,252), zein Z27 (Russell et al., (1997) *Transgenic Res.* 6(2):157-166), globulin 1 (Belanger et al., (1991) *Genetics* 129:863-872), glutelin 1 (Russell (1997) supra), and peroxiredoxin antioxidant (Per1) (Stacy et al., (1996) *Plant Mol Biol.* 31(6):1205-1216).

In some aspects of the invention, preferential expression in plant green tissues is desired. Promoters of interest for such uses include those from genes such as SSU (Fischhoff, et al., (1992) *Plant Mol Biol.* 20:81-93), aldolase and pyruvate orthophosphate dikinase (PPDK) (Taniguchi, et al., (2000) *Plant Cell Physiol.* 41(1):42-48).

Gene suppression includes any of the well-known methods for suppressing transcription of a gene or the accumulation of the mRNA corresponding to that gene thereby preventing translation of the transcript into protein. Post-transcriptional gene suppression is mediated by transcription of RNA that forms double-stranded RNA (dsRNA) having homology to a gene targeted for suppression. Suppression can also be achieved by insertion mutations created by transposable elements may also prevent gene function. For example, in many dicot plants, transformation with the T-DNA of *Agrobacterium* may be readily achieved and large numbers of transformants can be rapidly obtained. Also, some species have lines with active transposable elements that can efficiently be used for the generation of large numbers of insertion mutations, while some other species lack such options. Mutant plants produced by *Agrobacterium* or transposon mutagenesis and having altered expression of a polypeptide of interest can be identified using the polynucleotides of the present invention. For example, a large population of mutated plants may be screened with polynucleotides encoding the polypeptide of interest to detect mutated plants having an insertion in the gene encoding the polypeptide of interest.

Gene Stacking

The present invention also contemplates that the trait-improving recombinant DNA provided herein can be used in combination with other recombinant DNA to create plants with a multiple desired traits. The combinations generated can include multiple copies of any one or more of the recombinant DNA constructs. These stacked combinations can be created by any method, including but not limited to cross breeding of transgenic plants, or multiple genetic transformation.

Transformation Methods

Numerous methods for producing plant cell nuclei with recombinant DNA are known in the art and may be used in the present invention. Two commonly used methods for plant transformation are *Agrobacterium*-mediated transformation and microprojectile bombardment. Microprojectile bombardment methods are illustrated in U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn) and U.S. Pat. No. 6,153,812 (wheat) and *Agrobacterium*-mediated transformation is described in U.S. Pat. No. 5,159,135 (cotton); U.S. Pat. No. 5,824,877 (soybean); U.S. Pat. No. 5,591,616 (corn); and U.S. Pat. No. 6,384,301 (soybean), all of which are incorporated herein by reference. For *Agrobacterium tumefaciens* based plant transformation system, additional elements present on transformation constructs will include T-DNA left and right border sequences to facilitate incorporation of the recombinant polynucleotide into the plant genome.

In general it is preferred to introduce heterologous DNA randomly, i.e., at a non-specific location, in the genome of a target plant line. In special cases it may be useful to target heterologous DNA insertion in order to achieve site-specific integration, e.g., to replace an existing gene in the genome, to use an existing promoter in the plant genome, or to insert a recombinant polynucleotide at a predetermined site known to be active for gene expression. Several site specific recombination systems exist which are known to function implants include cre-lox as disclosed in U.S. Pat. No. 4,959,317 and FLP-FRT as disclosed in U.S. Pat. No. 5,527,695, both incorporated herein by reference.

Transformation methods of this invention are preferably practiced in tissue culture on media and in a controlled environment. "Media" refers to the numerous nutrient mixtures that are used to grow cells in vitro, that is, outside of the intact living organism. Recipient cell targets include, but are not limited to, meristem cells, callus, immature embryos and gametic cells such as microspores, pollen, sperm and egg cells. It is contemplated that any cell from which a fertile plant may be regenerated is useful as a recipient cell. Callus may be initiated from tissue sources including, but not limited to, immature embryos, seedling apical meristems, microspores and the like. Cells capable of proliferating as callus are also recipient cells for genetic transformation. Practical transformation methods and materials for making transgenic plants of this invention, e.g., various media and recipient target cells, transformation of immature embryos and subsequent regeneration of fertile transgenic plants are disclosed in U.S. Pat. Nos. 6,194,636 and 6,232,526 and U.S. patent application Ser. No. 09/757,089, which are incorporated herein by reference.

In practice DNA is introduced into only a small percentage of target cell nuclei in any one experiment. Marker genes are used to provide an efficient system for identification of those cells with nuclei that are stably transformed by receiving and integrating a transgenic DNA construct into their genomes. Preferred marker genes provide selective markers that confer resistance to a selective agent, such as an antibiotic or herbicide. Potentially transformed cells with a nucleus of the invention are exposed to the selective agent. In the population of surviving cells will be those cells where, generally, the resistance-conferring gene has been integrated and expressed at sufficient levels to permit cell survival. Cells may be tested further to confirm stable integration of the exogenous DNA in the nucleus. Useful selective marker genes include those conferring resistance to antibiotics such as kanamycin (nptII), hygromycin B (aph IV) and gentamycin (aac3 and aacC4) or resistance to herbicides such as glufosinate (bar or pat) and glyphosate (EPSPS). Examples of such selectable are illustrated in U.S. Pat. Nos. 5,550,318; 5,633,435; 5,780,708 and 6,118,047, all of which are incorporated herein by reference. Screenable markers which provide an ability to visually identify transformants can also be employed, e.g., a gene expressing a colored or fluorescent protein such as a luciferase or green fluorescent protein (GFP) or a gene expressing a beta-glucuronidase or uidA gene (GUS) for which various chromogenic substrates are known. It is also contemplated that combinations of screenable and selectable markers will be useful for identification of transformed cells. See PCT publication WO 99/61129 which discloses use of a gene fusion between a selectable marker gene and a screenable marker gene, e.g., an NPTII gene and a GFP gene.

Cells that survive exposure to the selective agent, or cells that have been scored positive in a screening assay, may be cultured in regeneration media and allowed to mature into plants. Developing plantlets can be transferred to soil less plant growth mix, and hardened off, e.g., in an environmentally controlled chamber at about 85% relative humidity, 600 ppm $CO_2$, and 25-250 microeinsteins $m^{-2}s^{-1}$ of light, prior to transfer to a greenhouse or growth chamber for maturation. Plants are preferably matured either in a growth chamber or greenhouse. Plants are regenerated from about 6 wk to 10 months after a transformant is identified, depending on the initial tissue. During regeneration, cells are grown to plants on solid media at about 19 to 28° C. After regenerating plants have reached the stage of shoot and root development, they may be transferred to a greenhouse for further growth and testing. Plants may be pollinated using conventional plant breeding methods known to those of skill in the art and seed produced.

Progeny may be recovered from transformed plants and tested for expression of the exogenous recombinant polynucleotide. Useful assays include, for example, "molecular biological" assays, such as Southern and Northern blotting and PCR; "biochemical" assays, such as detecting the presence of RNA, e.g., double stranded RNA, or a protein product, e.g., by immunological means (ELISAs and Western blots) or by enzymatic function; plant part assays, such as leaf or root assays; and also, by analyzing the phenotype of the whole regenerated plant.

Discovery of Trait-Improving Recombinant DNA

To identify nuclei with recombinant DNA that confer improved traits to plants, *Arabidopsis thaliana* was transformed with a candidate recombinant DNA construct and screened for an improved trait.

*Arabidopsis thaliana* is used a model for genetics and metabolism in plants. *Arabidopsis* has a small genome, and well-documented studies are available. It is easy to grow in large numbers and mutants defining important genetically controlled mechanisms are either available, or can readily be obtained. Various methods to introduce and express isolated homologous genes are available (see Koncz, e.g., Methods in *Arabidopsis* Research e.g., (1992), World Scientific, New Jersey, New Jersey, in "Preface").

A two-step screening process was employed which comprised two passes of trait characterization to ensure that the trait modification was dependent on expression of the recombinant DNA, but not due to the chromosomal location of the integration of the transgene. Twelve independent transgenic lines for each recombinant DNA construct were established and assayed for the transgene expression levels. Five transgenic lines with high transgene expression levels were used in the first pass screen to evaluate the transgene's function in T2 transgenic plants. Subsequently, three transgenic events, which had been shown to have one or more improved traits, were further evaluated in the second pass screen to confirm the transgene's ability to impart an improved trait. The following Table 3 summarizes the improved traits that have been confirmed as provided by a recombinant DNA construct.

In particular, Table 3 reports:

"PEP SEQ ID" which is the amino acid sequence of the protein cognate to the DNA in the recombinant DNA construct corresponding to a protein sequence of a SEQ ID NO. in the Sequence Listing.

"construct id" is an arbitrary name for the recombinant DNA describe more particularly in Table 1.

"annotation" refers to a description of the top hit protein obtained from an amino acid sequence query of each PEP SEQ ID NO to GenBank database of the National Center for Biotechnology Information (ncbi). More particularly, "gi" is the GenBank ID number for the top BLAST hit.

"description" refers to the description of the top BLAST hit.

"e-value" provides the expectation value for the BLAST hit.

"identity" refers to the percentage of identically matched amino acid residues along the length of the portion of the sequences which is aligned by BLAST between the sequence of interest provided herein and the hit sequence in GenBank.

"traits" identify by two letter codes the confirmed improvement in a transgenic plant provided by the recombinant DNA. The codes for improved traits are:

"CK" which indicates cold tolerance improvement identified under a cold shock tolerance screen;

"CS" which indicates cold tolerance improvement identified by a cold germination tolerance screen;

"DS" which indicates drought tolerance improvement identified by a soil drought stress tolerance screen;

"PEG" which indicates osmotic stress tolerance improvement identified by a PEG induced osmotic stress tolerance screen;

"HS" which indicates heat stress tolerance improvement identified by a heat stress tolerance screen;

"SS" which indicates high salinity stress tolerance improvement identified by a salt stress tolerance screen;

"LN" which indicates nitrogen use efficiency improvement identified by a limited nitrogen tolerance screen;

"LL" which indicates attenuated shade avoidance response identified by a shade tolerance screen under a low light condition;

"PP" which indicates improved growth and development at early stages identified by an early plant growth and development screen;

"SP" which indicates improved growth and development at late stages identified by a late plant growth and development screen provided herein.

TABLE 3

| PEP SEQ ID NO | e value | % identity | annotation | | trait |
| --- | --- | --- | --- | --- | --- |
| | | | GenBank id | description | |
| 426 | 1.00E−35 | 100 | gi\|21553646\| | histone H2A | CK |
| 427 | 6.00E−59 | 100 | gi\|7327824\| | ref\|NP_195785.1\| macrophage migration inhibitory factor family protein/MIF family protein [*Arabidopsis thaliana*] | CK |

TABLE 3-continued

| PEP SEQ ID NO | e value | % identity | GenBank id | description | trait | | | | |
|---|---|---|---|---|---|---|---|---|---|
| 428 | 0 | 99 | gi|28416663| | ref|NP_180648.1| transducin family protein/ WD-40 repeat family protein | CK | | | | |
| 429 | 2.00E−78 | 100 | gi|23198326| | gb|AAN15690.1|unknown protein [Arabidopsis thaliana] | CK | | | | |
| 430 | 0 | 100 | gi|23297810| | ref|NP_194910.2| phototropic-responsive NPH3 family protein | CK | LN | | | |
| 431 | 8.00E−48 | 100 | gi|12248017| | ref|NP_173542.1| small nuclear ribonucleoprotein, putative/snRNP, putative/ Sm protein, putative | CK | | | | |
| 432 | 1.00E−126 | 100 | gi|16323514| | ref|NP_187673.1| diadenosine 5',5'''-P1,P4-tetraphosphate hydrolase, putative [Arabidopsis thaliana] | CK | CS | PP | HS | |
| 433 | 0 | 100 | gi|30679613| | ref|NP_172113.1| DNA-binding bromodomain-containing protein Contains similarity to a Ring3 protein | CK | SS | PEG | | |
| 434 | 2.00E−48 | 100 | gi|52354271| | gb|AAC17827.1| similar to late embryogenesis abundant proteins | CK | PP | | | |
| 435 | 0 | 100 | gi|20466169| | ref|NP_564623.2| sodium/calcium exchanger family protein/calcium-binding EF hand family protein | CK | | | | |
| 436 | 2.00E−87 | 100 | gi|19310829| | ref|NP_179396.1| histone H1-3 (HIS1-3) | CK | | | | |
| 437 | 1.00E−99 | 100 | gi|21593872| | ref|NP_563973.1| family protein lactoylglutathione lyase family protein/glyoxalase I | CK | | | | |
| 438 | 1.00E−159 | 66 | gi|15220367| | ref|NP_176890.1|F-box family protein [Arabidopsis thaliana] | CK | CS | HS | | |
| 439 | 0 | 78 | gi|9757954| | ref|NP_199024.1| expressed protein [Arabidopsis thaliana] | CK | | | | |
| 440 | 5.00E−51 | 100 | gi|21618078| | ref|NP_176371.1| postsynaptic protein-related [Arabidopsis thaliana] | CK | HS | SS | | |
| 441 | 0 | 100 | gi|24030234| | ref|NP_027420.1| zinc finger (CCCH-type) family protein [Arabidopsis thaliana] | CK | CS | SS | LL | PEG |
| 442 | 0 | 100 | gi|21618116| | ref|NP_567671.1| bile acid: sodium symporter family protein | CK | | | | |
| 443 | 1.00E−168 | 100 | gi|16930405| | ref|NP_850182.1| PUR alpha-1 protein [Arabidopsis thaliana] | CK | PP | HS | SS | |
| 444 | 0 | 83 | gi|23397029| | ref|NP_567709.1| 26S proteasome regulatory subunit, putative (RPN7) | CK | CS | PP | | |
| 445 | 0 | 83 | gi|30349498| | ref|NP_850094.1| CBL-interacting protein kinase 3 (CIPK3) | CK | SS | PEG | | |
| 446 | 0 | 100 | gi|9294291| | dbj|BAB02193.1|cytochrome p450 | CK | PP | | | |
| 447 | 0 | 100 | gi|7270365| | emb|CAB80133.1|cyclin delta-3 | CK | PP | HS | SS | PEG |
| 448 | 0 | 100 | gi|31580811| | gb|AAP51420.1|ferric-chelate reductase [Arabidopsis thaliana] | CK | | | | |
| 449 | 0 | 99 | gi|8439909| | ref|NP_563791.1| protein phosphatase 2C family protein/PP2C family protein | CK | | | | |
| 450 | 0 | 100 | gi|15238701| | ref|NP_197894.1|cytochrome P450 family protein [Arabidopsis thaliana] | CK | DS | | | |

TABLE 3-continued

| PEP SEQ ID NO | e value | % identity | GenBank id | description | trait | | | |
|---|---|---|---|---|---|---|---|---|
| 451 | 1.00E−178 | 100 | gi|21553567| | gb|AAM62660.1|unknown [*Arabidopsis thaliana*] | CK | | | |
| 452 | 0 | 100 | gi|23198354| | ref|NP_193140.1| selenium-binding protein, putative [*Arabidopsis thaliana*] | CK | HS | | |
| 453 | 0 | 100 | gi|22655117| | ref|NP_565411.2| calcium-dependent protein kinase isoform 6 (CPK6) | CK | CS | HS | SS | LL |
| 454 | 4.00E−83 | 100 | gi|21537110| | ref|NP_197849.1| expressed protein [*Arabidopsis thaliana*] | CK | LN | | |
| 455 | 1.00E−122 | 100 | gi|23397082| | ref|NP_174418.1| photosystem I reaction center subunit III family protein | CK | PEG | | |
| 456 | 0 | 100 | gi|30680112| | ref|NP_179369.2| expressed protein [*Arabidopsis thaliana*] | CK | | | |
| 457 | 0 | 100 | gi|4678321| | ref|NP_190390.1| expressed protein [*Arabidopsis thaliana*] | CK | | | |
| 458 | 0 | 100 | gi|3169180| | ref|NP_179889.1| casein kinase II alpha chain, putative [*Arabidopsis thaliana*] | CK | | | |
| 459 | 0 | 100 | gi|30725494| | ref|NP_851182.1| protein kinase family protein [*Arabidopsis thaliana*] | CK | SS | | |
| 460 | 0 | 100 | gi|26986957| | ref|NP_742382.1|4-aminobutyrate aminotransferase [*Pseudomonas putida* KT2440] | CK | DS | | |
| 461 | 0 | 91 | gi|37526249| | ref|NP_929593.1|4-aminobutyrate aminotransferase (gamma-amino-N-butyrate transaminase) (GABA transaminase) | CK | | | |
| 462 | 0 | 83 | gi|37527865| | ref|NP_931210.1|glutamate synthase [NADPH] small chain (glutamate synthase beta subunit) (NADPH-GOGAT) (GLTS beta chain) | CK | | | |
| 463 | 0 | 100 | gi|23308229| | ref|NP_175649.1| glycosyl hydrolase family 1 protein/beta-glucosidase, putative a | CK | PP | | |
| 464 | 0 | 100 | gi|30685484| | ref|NP_849681.1|serine/threonine protein phosphatase 2A (PP2A) 55 kDa regulatory subunit B [*Arabidopsis thaliana*] | CK | LL | LN | |
| 465 | 0 | 99 | gi|16080446| | ref|NP_391273.1|phospho-glycerate kinase [*Bacillus subtilis* subsp. *subtilis* str. 168] | CK | PP | | |
| 466 | 0 | 100 | gi|6729016| | gb|AAF27012.1|putative SAR DNA-binding protein-1 [*Arabidopsis thaliana*] | CK | | | |
| 467 | 0 | 100 | gi|42569691| | ref|NP_181253.2|transducin family protein/WD-40 repeat family protein | CK | HS | | |
| 468 | 5.00E−96 | 100 | gi|38603990| | ref|NP_177237.1| C2 domain-containing protein | CK | | | |
| 469 | 0 | 100 | gi|22136622| | ref|NP_193273.1| cytochrome P450 family protein [*Arabidopsis thaliana*] | CK | PP | | |
| 470 | 0 | 100 | gi|22331742| | ref|NP_190771.2|F-box family protein/WD-40 repeat family protein [*Arabidopsis thaliana*] | CK | | | |
| 471 | 1.00E−162 | 100 | gi|7021738| | ref|NP_566517.1| expressed protein [*Arabidopsis thaliana*] | CK | CS | SS | |

TABLE 3-continued

| PEP SEQ ID NO | e value | % identity | GenBank id | description | annotation | | | | trait |
|---|---|---|---|---|---|---|---|---|---|
| 472 | 0 | 98 | gi\|10176804\| | dbj\|BAB09992.1\|serine/threonine protein kinase-like [*Arabidopsis thaliana*] | CK | SS | LL | | |
| 473 | 0 | 100 | gi\|28827534\| | ref\|NP_568971.1\| leucine-rich repeat transmembrane protein kinase, putative | CK | | | | |
| 474 | 0 | 100 | gi\|12321664\| | gb\|AAG50866.1\|protein kinase, putative [*Arabidopsis thaliana*] | CK | | | | |
| 475 | 1.00E−177 | 100 | gi\|2651299\| | ref\|NP_181590.1\| protein kinase family protein | CK | | | | |
| 476 | 0 | 100 | gi\|56381947\| | ref\|NP_564161.1\| phosphoglycerate/bisphosphoglycerate mutase family protein | CK | SS | | | |
| 477 | 0 | 100 | gi\|15075789\| | ref\|NP_386871.1\| PROBABLE PHOSPHOGLYCERATE KINASE PROTEIN | CK | | | | |
| 478 | 0 | 96 | gi\|28872422\| | ref\|NP_795041.1\|glutamine synthetase | CK | CS | | | |
| 479 | 0 | 100 | gi\|21595073\| | ref\|NP_192046.1\| mitogen-activated protein kinase, putative/MAPK, putative (MPK4) | CK | SS | PEG | | |
| 480 | 0 | 100 | gi\|10174347\| | ref\|NP_242595.1\| glutamate synthase (small subunit) | CK | | | | |
| 481 | 0 | 100 | gi\|16081086\| | ref\|NP_391914.1\|ornithine aminotransferase | CK | PP | | | |
| 482 | 0 | 100 | gi\|18400003\| | ref\|NP_564469.1\|WD-40 repeat family protein [*Arabidopsis thaliana*] | CK | HS | SS | LL | PEG |
| 483 | 0 | 100 | gi\|4559336\| | ref\|NP_181783.1\| protein kinase family protein [*Arabidopsis thaliana*] | CK | | | | |
| 484 | 0 | 100 | gi\|11994319\| | ref\|NP_188976.1\| casein kinase, putative [*Arabidopsis thaliana*] | CK | CS | PP | SS | PEG |
| 485 | 0 | 100 | gi\|23507789\| | ref\|NP_176390.1\| mitochondrial transcription termination factor-related/mTERF-related [*Arabidopsis thaliana*] | CK | LN | | | |
| 486 | 1.00E−120 | 100 | gi\|10177463\| | dbj\|BAB10854.1\|unnamed protein product [*Arabidopsis thaliana*] | CK | LL | | | |
| 487 | 0 | 100 | gi\|15221219\| | ref\|NP_177573.1\|protein kinase, putative [*Arabidopsis thaliana*] | CK | LL | | | |
| 488 | 0 | 100 | gi\|15218854\| | ref\|NP_174217.1\|CBL-interacting protein kinase 18 (CIPK18) | CK | CS | LL | PEG | |
| 489 | 0 | 100 | gi\|22136780\| | ref\|NP_189420.1\| monodehydroascorbate reductase, putative [*Arabidopsis thaliana*] | CK | PP | LL | | |
| 490 | 1.00E−132 | 100 | gi\|17104619\| | gb\|AAL34198.1\|putative glutathione peroxidase [*Arabidopsis thaliana*] | CK | | | | |
| 491 | 0 | 100 | gi\|7268589\| | ref\|NP_192114.1\| sugar transporter, putative [*Arabidopsis thaliana*] | CK | | | | |
| 492 | 0 | 100 | gi\|56381949\| | ref\|NP_200733.2\| sugar transporter family protein [*Arabidopsis thaliana*] | CK | | | | |
| 493 | 7.00E−60 | 83 | gi\|31433365\| | ref\|NP_922597.1\| unknown protein | CK | SS | LL | | |
| 494 | 1.00E−171 | 79 | gi\|34910712\| | ref\|NP_916703.1\|putative nuclear RNA binding protein A [*Oryza sativa*] | CK | | | | |
| 495 | 1.00E−139 | 100 | gi\|51536564\| | ref\|NP_189139.1\| zinc finger (C3HC4-type RING finger) family protein | CK | PP | | | |
| 496 | 1.00E−136 | 98 | gi\|22995109\| | ref\|ZP_00039591.1\|COG0149: Triosephosphate isomerase | CK | PEG | | | |

TABLE 3-continued

| PEP SEQ ID NO | e value | % identity | GenBank id | description | trait | | |
|---|---|---|---|---|---|---|---|
| 497 | 0 | 74 | gi\|32488446\| | ref\|XP_473139.1\| OSJNBa0004N05.3 [*Oryza sativa* (*japonica* cultivar-group)] | CK | | |
| 498 | 0 | 100 | gi\|23126040\| | ref\|ZP_00107950.1\|COG0155: Sulfite reductase, beta subunit (hemoprotein) [*Nostoc punctiforme* PCC 73102] | CK | | |
| 499 | 0 | 100 | gi\|7287983\| | ref\|NP_191594.1\| armadillo/beta-catenin repeat family protein/F-box family protein [*Arabidopsis thaliana*] | CK | PEG | |
| 500 | 0 | 100 | gi\|9758604\| | dbj\|BAB09237.1\|beta-amylase [*Arabidopsis thaliana*] | CK | | |
| 501 | 0 | 100 | gi\|23463051\| | ref\|NP_178065.1\| inosine-5'-monophosphate dehydrogenase [*Arabidopsis thaliana*] | CK | | |
| 502 | 1.00E−100 | 77 | gi\|55168250\| | gb\|AAV44116.1\|unknown protein [*Oryza sativa* (*japonica* cultivar-group)] | CK | | |
| 503 | 0 | 83 | gi\|50942175\| | ref\|XP_480615.1\|putative aminoimidazolecarboximide ribonucleotide transformylase | CK | | |
| 504 | 1.00E−159 | 100 | gi\|10177927\| | ref\|NP_199602.1\| respiratory burst oxidase protein D (RbohD)/ NADPH oxidase | CK | | |
| 505 | 1.00E−172 | 86 | gi\|57899142\| | dbj\|BAD87004.1\|unknown protein [*Oryza sativa* (*japonica* cultivar-group)] | CK | | |
| 506 | 0 | 100 | gi\|15223469\| | ref\|NP_171679.1\|protein kinase family protein [*Arabidopsis thaliana*] | CK | | |
| 507 | 0 | 100 | gi\|3482918\| | ref\|NP_172414.1\| ATP-citrate synthase (ATP-citrate (pro-S-)-lyase/citrate cleavage enzyme), putative | CK | SS | |
| 508 | 0 | 100 | gi\|23297150\| | ref\|NP_567724.1\| fibrillarin 2 (FIB2) [*Arabidopsis thaliana*] | CK | | |
| 509 | 0 | 100 | gi\|7268631\| | ref\|NP_193573.1\|F-box family protein [*Arabidopsis thaliana*] | CK | LL | PEG |
| 510 | 6.00E−87 | 79 | gi\|21553981\| | ref\|NP_564267.1\| peptidyl-prolyl cis-trans isomerase cyclophilin-type family protein [*Arabidopsis thaliana*] | CK | | |
| 511 | 1.00E−151 | 68 | gi\|34913784\| | ref\|NP_918239.1\| pectate lyase-like protein | CK | | |
| 512 | 4.00E−91 | 75 | gi\|53793523\| | dbj\|BAD54684.1\|unknown protein [*Oryza sativa* (*japonica* cultivar-group)] | CK | | |
| 513 | 1.00E−41 | 63 | gi\|50948309\| | ref\|XP_483682.1\|putative auxin induced protein | CK | LL | |
| 514 | 1.00E−53 | 58 | gi\|56202166\| | dbj\|BAD73644.1\|60S ribosomal protein L18A-like | CK | CS | PEG |
| 515 | 7.00E−85 | 93 | gi\|34910948\| | dbj\|BAB84492.1\| nuclear movement protein-like | CK | | |
| 516 | 0 | 100 | gi\|6513938\| | ref\|NP_566157.1\| nodulin family protein [*Arabidopsis thaliana*] | CK | | |
| 517 | 1.00E−171 | 100 | gi\|6957722\| | ref\|NP_186908.1\| delta 7-sterol-C5-desaturase, putative [*Arabidopsis thaliana*] | CK | LL | |
| 518 | 0 | 100 | gi\|17132051\| | ref\|NP_486997.1\| hypothetical protein alr2957 [*Nostoc sp.* PCC 7120] | CK | PP | |
| 519 | 0 | 71 | gi\|34911116\| | ref\|NP916905.1\|putative glyoxal oxidase | CK | | |

TABLE 3-continued

| PEP SEQ ID NO | e value | % identity | GenBank id | description | annotation | trait | | |
|---|---|---|---|---|---|---|---|---|
| 520 | 6.00E−24 | 42 | gi|4803925| | ref|NP_565499.1| expressed protein [*Arabidopsis thaliana*] | CK | SS | | |
| 521 | 0 | 81 | gi|50934555| | ref|XP_476805.1|unknown protein | CK | SS | LN | PEG |
| 522 | 8.00E−94 | 100 | gi|26453028| | ref|NP_197956.1| expressed protein | CK | PP | SS | PEG |
| 523 | 1.00E−167 | 100 | gi|9795142| | emb|CAB67657.2|splicing factor-like protein [*Arabidopsis thaliana*] ref|NP_190918.3| zinc knuckle (CCHC-type) family protein [*Arabidopsis thaliana*] | CS | PP | | |
| 524 | 1.00E−146 | 100 | gi|6642639| | ref|NP_187382.1| forkhead-associated domain-containing protein/FHA domain-containing protein | CS | PEG | | |
| 525 | 0 | 100 | gi|9279657| | ref|NP_188451.1| octicosapeptide/Phox/Bem1 p (PB1) domain-containing protein [*Arabidopsis thaliana*] | CS | PP | HS | LN |
| 526 | 0 | 100 | gi|9759010| | dbj|BAB09537.1|unnamed protein product [*Arabidopsis thaliana*] | CS | | | |
| 527 | 0 | 100 | gi|18390671| | ref|NP_563769.1|F-box family protein | CS | PP | HS | SS |
| 528 | 0 | 100 | gi|12248033| | ref|NP_172880.1| phytochrome kinase, putative [*Arabidopsis thaliana*] | CS | | | |
| 529 | 0 | 100 | gi|21554404| | ref|NP_179646.1| DNAJ heat shock family protein [*Arabidopsis thaliana*] | CS | PP | SS | |
| 530 | 1.00E−111 | 100 | gi|10177521| | ref|NP_201441.1| dehydrin (RAB18) rab18 protein-*Arabidopsis thaliana* sp|P30185|DHR18_ARATH Dehydrin Rab18 | CS | PEG | | |
| 531 | 0 | 100 | gi|20260458| | dbj|BAB70612.1| anthocyanin-related membrane protein 1 | CS | SS | | |
| 532 | 0 | 100 | gi|21553568| | ref|NP_849480.1| expressed protein | CS | PP | PEG | |
| 533 | 0 | 100 | gi|21553616| | ref|NP_568089.1| expressed protein | CS | | | |
| 534 | 1.00E−158 | 100 | gi|21554409| | ref|NP_174469.1| histidine biosynthesis bifunctional protein (HISIE) [*Arabidopsis thaliana*] pir||T51812 phosphoribosyl-AMP cyclohydrolase (EC 3.5.4.19) | CS | | | |
| 535 | 1.00E−156 | 68 | gi|50949063| | ref|XP_493889.1|putative protein kinase [*Oryza sativa*] | CS | | | |
| 536 | 0 | 76 | gi|31455393| | emb|CAD92450.1|amino acid permease 6 [*Brassica napus*] | CS | SS | | |
| 537 | 0 | 100 | gi|6324421| | sp|Q12068|GRE2_YEAST NADPH-dependent methylglyoxal reductase GRE2 (Genes de respuesta a estres protein 2) | CS | | | |
| 538 | 0 | 99 | gi|18401915| | ref|NP_566612.1|histone deacetylase family protein [*Arabidopsis thaliana*] | CS | | | |
| 539 | 0 | 100 | gi|30685903| | ref|NP_851041.1|zinc finger (CCCH-type) family protein [*Arabidopsis thaliana*] | CS | PEG | | |
| 540 | 1.00E−134 | 68 | gi|31432120| | ref|NP_921503.1| putative polyprotein [*Oryza sativa* (*japonica* cultivar-group)] | CS | PP | | |

TABLE 3-continued

| PEP SEQ ID NO | e value | % identity | GenBank id | description | trait | | | |
|---|---|---|---|---|---|---|---|---|
| 541 | 0 | 100 | gi\|22136556\| | emb\|CAB80464.1\| cinnamyl-alcohol dehydrogenase ELI3-2 [*Arabidopsis thaliana*] | CS | | | |
| 542 | 0 | 100 | gi\|7413528\| | ref\|NP_196086.1\| cytochrome P450, putative [*Arabidopsis thaliana*] | CS | | | |
| 543 | 0 | 99 | gi\|42568440\| | ref\|NP_199845.2\|DNA repair protein-related [*Arabidopsis thaliana*] | CS | PEG | | |
| 544 | 0 | 100 | gi\|30102478\| | ref\|NP_195917.1\| hydrolase, alpha/beta fold family protein [*Arabidopsis thaliana*] | CS | PEG | | |
| 545 | 0 | 100 | gi\|21280881\| | ref\|NP_176968.1\| glycerate dehydrogenase/NADH-dependent hydroxypyruvate reductase | CS | HS | SS | PEG |
| 546 | 0 | 100 | gi\|10177967\| | ref\|NP_198904.1\| WD-40 repeat Family protein/zfwd3 protein (ZFWD3) [*Arabidopsis thaliana*] | CS | PEG | | |
| 547 | 0 | 100 | gi\|7269306\| | ref\|NP_567705.1\| ubiquitin-specific protease 16, putative (UBP16) | CS | | | |
| 548 | 0 | 99 | gi\|6324066\| | sp\|P53845\|YN03_YEAST Hypothetical 35.5 kDa protein in PIK1-POL2 intergenic region | CS | | | |
| 549 | 0 | 99 | gi\|6323074\| | ref\|NP_013146.1\|Microtubule-associated protein (MAP) of the XMAP215/Dis1 family; regulates microtubule dynamics during spindle orientation and metaphase chromosome alignment; interacts with spindle pole body component Spc72p [*Saccharomyces cerevisiae*] | CS | | | |
| 550 | 0 | 100 | gi\|6324990\| | ref\|NP_015058.1\|Dicarboxylic amino acid permease, mediates high-affinity and high-capacity transport of L-glutamate and L-aspartate; also a transporter for Gln, Asn, Ser, Ala, and Gly [*Saccharomyces cerevisiae*] | CS | PP | | |
| 551 | 0 | 100 | gi\|51013603\| | sp\|P50947\|YNJ7_YEAST Hypothetical 37.0 kDa Protein in RAS2-RPS7B intergenic region | CS | PEG | | |
| 552 | 0 | 100 | gi\|6319413\| | ref\|NP_009495.1\|Shp1p [*Saccharomyces cerevisiae*] emb\|CAA80789.1\| YBLO515 [*Saccharomyces cerevisiae*] emb\|CAA84878.1\| SHP1 | CS | | | |
| 553 | 0 | 100 | gi\|22136824\| | ref\|NP_197455.1\| expressed protein [*Arabidopsis thaliana*] | CS | PP | | |
| 554 | 0 | 100 | gi\|22655036\| | ref\|NP_566453.1\| WD-40 repeat family protein [*Arabidopsis thaliana*] | CS | | | |
| 555 | 0 | 100 | gi\|48771699\| | ref\|ZP_00276041.1\|COG1062: Zn-dependent alcohol dehydrogenases, class III [*Ralstonia metallidurans* CH34] | CS | | | |
| 556 | 0 | 100 | gi\|49176169\| | ref\|NP_416429.3\|D-cysteine desulfhydrase, PLP-dependent enzyme cysteine desulfhydrase, PLP-dependent enzyme | CS | | | |

TABLE 3-continued

| PEP SEQ ID NO | e value | % identity | GenBank id | description | annotation | | trait | |
|---|---|---|---|---|---|---|---|---|
| 557 | 0 | 100 | gi|9294512| | gb|AAK21273.1| aberrant lateral root formation 5 [*Arabidopsis thaliana*] ref|NP_566730.1| MATE efflux family protein [*Arabidopsis thaliana*] | CS | PP | SS |
| 558 | 0 | 100 | gi|31711972| | ref|NP_175641.1| protein kinase family protein/C-type lectin domain-containing protein | CS | SS | |
| 559 | 8.00E−61 | 100 | gi|21592962| | ref|NP_564579.1| expressed protein [*Arabidopsis thaliana*] | CS | SS | |
| 560 | 0 | 100 | gi|30102452| | ref|NP_195770.1| mitochondrial substrate carrier family protein [*Arabidopsis thaliana*] | CS | LL | |
| 561 | 0 | 100 | gi|6056406| | gb|AAF02870.1|Hypothetical protein [*Arabidopsis thaliana*] | CS | | |
| 562 | 1.00E−143 | 100 | gi|21689635| | emb|CAB78986.1| lectin like protein [*Arabidopsis thaliana*] | CS | SS | |
| 563 | 0 | 100 | gi|22135769| | ref|NP_188127.1| oxidoreductase, zinc-binding dehydrogenase family protein | CS | | |
| 564 | 6.00E−91 | 100 | gi|21553433| | ref|NP_199669.1| FK506-binding protein 2-2 (FKBP15-2)/immunophilin/peptidyl-prolyl cis-trans isomerase/rotamase | CS | PEG | |
| 565 | 1.00E−151 | 100 | gi|21592742| | ref|NP_195534.1| expansin, putative (EXP20) | CS | PP | |
| 566 | 8.00E−64 | 100 | gi|21537125| | ref|NP_196975.1| expressed protein [*Arabidopsis thaliana*] | CS | | |
| 567 | 1.00E−49 | 100 | gi|16331623| | ref|NP442351.1|hypothetical protein ssl0353 [*Synechocystis* sp. PCC 6803] | CS | LN | |
| 568 | 0 | 100 | gi|21618054| | ref|NP_564383.1| ABC transporter family protein [*Arabidopsis thaliana*] | CS | | |
| 569 | 0 | 100 | gi|7321037| | ref|NP192879.1| ARID/BRIGHT DNA-binding domain-containing protein/ELM2 domain-containing protein/Myb-like DNA-binding domain-containing protein | CS | PP | SS |
| 570 | 1.00E−44 | 100 | gi|58299| | emb|CAA48415.1|unnamed protein product [synthetic construct] | CS | | |
| 571 | 0 | 99 | gi|10172815| | dbj|BAB03922.1|glycine betaine aldehyde dehydrogenase [*Bacillus halodurans* C-125] | CS | PEG | |
| 572 | 1.00E−165 | 100 | gi|3928103| | ref|NP_181434.1| aquaporin, putative [*Arabidopsis thaliana*] | CS | PP | |
| 573 | 0 | 91 | gi|37524126| | ref|NP_927470.1|phosphoenol-pyruvate carboxykinase [ATP] [*Photorhabdus luminescens* subsp. *laumondii* TTO1] | CS | | |
| 574 | 0 | 100 | gi|9293860| | ref|NP_564217.1| lysine and histidine specific transporter, putative [*Arabidopsis thaliana*] | CS | | |
| 575 | 0 | 100 | gi|10175358| | ref|NP_243603.1| 1-pyrroline-5-carboxylate dehydrogenase [*Bacillus halodurans* C-125] | CS | | |

TABLE 3-continued

| PEP SEQ ID NO | e value | % identity | GenBank id | description | annotation | | trait | |
|---|---|---|---|---|---|---|---|---|
| 576 | 0 | 100 | gi|10175785| | ref|NP_244029.1| pyruvate kinase [*Bacillus halodurans* C-125] | CS | PP | | |
| 577 | 8.00E-45 | 100 | gi|9758890| | dbj|BAB09466.1|auxin-induced protein-like [*Arabidopsis thaliana*] | CS | | | |
| 578 | 1.00E-108 | 100 | gi|17104761| | ref|NP_193699.1| Ras-related GTP-binding protein, putative [*Arabidopsis thaliana*] | CS | LN | | |
| 579 | 0 | 100 | gi|5915859| | sp|O22203|C98A3_ARATH Cytochrome P450 98A3 | CS | | | |
| 580 | 0 | 100 | gi|6729015| | ref|NP_187156.1| protein kinase family protein [*Arabidopsis thaliana*] | CS | SS | PEG | |
| 581 | 0 | 100 | gi|21689671| | ref|NP_195397.1| transporter-related [*Arabidopsis thaliana*] | CS | PP | SS | |
| 582 | 0 | 100 | gi|20148451| | ref|NP_564797.1| flavin-containing monooxygenase family protein/FMO family protein | CS | SS | PEG | |
| 583 | 0 | 100 | gi|21280977| | gb|AAM45011.1|putative protein kinase [*Arabidopsis thaliana*] | CS | | | |
| 584 | 1.00E-116 | 82 | gi|27452901| | gb|AAO15285.1|Putative dihydrodipicolinate reductase-like protein [*Oryza sativa (japonica* cultivar-group)] | CS | | | |
| 585 | 1.00E-123 | 99 | gi|23113896| | ref|ZP_00099233.1|COG0036: Pentose-5-phosphate-3-epimerase [*Desulfitobacterium hafniense* DCB-2] | CS | | | |
| 586 | 8.00E-95 | 99 | gi|16330731| | |YCF3_SYNY3 Photosystem I assembly protein ycf3 | CS | | | |
| 587 | 0 | 100 | gi|21700831| | ref|NP_191332.2| protein kinase, putative [*Arabidopsis thaliana*] | CS | DS | SS | PEG |
| 588 | 0 | 100 | gi|4415911| | gb|AAD20142.1|putative poly(A) binding protein [*Arabidopsis thaliana*] | CS | | | |
| 589 | 0 | 100 | gi|5733869| | gb|AAD49757.1|Contains F-box domain PF|00646. [*Arabidopsis thaliana*] | CS | | | |
| 590 | 1.00E-149 | 100 | gi|29824243| | ref|NP_192170.1| tryptophan synthase, alpha subunit, putative [*Arabidopsis thaliana*] | CS | | | |
| 591 | 0 | 100 | gi|26449849| | ref|NP_198924.1| glycerophosphoryl diester phosphodiesterase family protein | CS | HS | | |
| 592 | 0 | 78 | gi|56783874| | dbj|BAD81286.1|putative dual specificity kinase 1 | CS | | | |
| 593 | 0 | 100 | gi|6321857| | ref|NP011933.1|Ssf1p [*Saccharomyces cerevisiae*] sp|P38789|SSF1_YEAST Ribosome biogenesis protein SSF1 | CS | DS | | |
| 594 | 1.00E-180 | 89 | gi|50906987| | ref|XP_464982.1|lipase class 3-like [*Oryza sativa (japonica* cultivar-group)] dbj|BAD21500.1| lipase class 3-like [*Oryza sativa (japonica* cultivar-group)] | CS | | | |
| 595 | 0 | 100 | gi|2558659| | gb|AAB81672.1|putative protein kinase [*Arabidopsis thaliana*] | CS | HS | PEG | |
| 596 | 0 | 100 | gi|9758547| | ref|NP_201503.1| expressed protein [*Arabidopsis thaliana*] | CS | | | |

TABLE 3-continued

| PEP SEQ ID NO | e value | % identity | GenBank id | description | trait | | | |
|---|---|---|---|---|---|---|---|---|
| 597 | 0 | 100 | gi\|4678335\| | ref\|NP_190376.1\| L-galactono-1,4-lactone dehydrogenase, putative | CS | SS | | |
| 598 | 1.00E-173 | 100 | gi\|21553608\| | ref\|NP_564800.1\| expressed protein [Arabidopsis thaliana] | CS | | | |
| 599 | 0 | 79 | gi\|50912531\| | ref\|XP_467673.1\|putative nicastrin [Oryza sativa (japonica cultivar-group)] | CS | DS | SS | PEG |
| 600 | 0 | 80 | gi\|50898642\| | ref\|XP_450109.1\|nodulation receptor kinase-like protein | CS | PP | SS | |
| 601 | 5.00E-74 | 100 | gi\|30693828\| | ref\|NP_850693.1\|expressed protein [Arabidopsis thaliana] | DS | | | |
| 602 | 0 | 100 | gi\|25054896\| | ref\|NP_179923.2\| nicotinate phosphoribosyltransferase family protein/NAPRTase family protein [Arabidopsis thaliana] | DS | | | |
| 603 | 1.00E-121 | 100 | gi\|6006854\| | gb\|AAF00630.1\|hypothetical protein [Arabidopsis thaliana] | DS | LN | | |
| 604 | 0 | 100 | gi\|6862917\| | ref\|NP_566273.1\| heavy-metal-associated domain-containing protein | DS | | | |
| 605 | 0 | 100 | gi\|56382003\| | ref\|NP_177794.1\| 12-oxophytodienoate reductase (OPR1) [Arabidopsis thaliana] | DS | | | |
| 606 | 0 | 100 | gi\|21280825\| | gb\|AAM45040.1\|putative AtMlo-h1 protein [Arabidopsis thaliana] | DS | | | |
| 607 | 0 | 61 | gi\|22136432\| | ref\|NP_191438.2\| glycosyl transferase family 8 protein [Arabidopsis thaliana] | DS | SS | | |
| 608 | 0 | 69 | gi\|22136270\| | ref\|NP_190235.1\| armadillo/beta-catenin repeat family protein/U-box domain-containing family protein | DS | | | |
| 609 | 0 | 100 | gi\|4678377\| | ref\|NP_193087.1\| ammonium transporter 1, member 1 (AMT1.1) | DS | | | |
| 610 | 1.00E-143 | 99 | gi\|27754217\| | ref\|NP_187413.1\| expressed protein [Arabidopsis thaliana] | DS | LN | PEG | |
| 611 | 1.00E-123 | 100 | gi\|21554344\| | ref\|NP_198627.1\| ASF1-like anti-silencing family protein [Arabidopsis thaliana] | DS | PP | HS | |
| 612 | 0 | 77 | gi\|25402857\| | pir\|\|A86318protein F15H18.11 [imported] - Arabidopsis thaliana gb\|AAF25996.1\| F15H18.11 | DS | PP | | |
| 613 | 1.00E-139 | 99 | gi\|16329950\| | ref\|NP440678.1\|hypothetical protein slr1900 [Synechocystis sp. PCC 6803] | DS | | | |
| 614 | 0 | 100 | gi\|30725526\| | gb\|AAP37785.1\|At4g24520 [Arabidopsis thaliana] emb\|CAB79362.1\| NADPH-ferrihemoprotein reductase ATR1 | DS | SS | | |
| 615 | 0 | 98 | gi\|3335345\| | gb\|AAC27147.1\|Contains similarity to ABC transporter gb\|1651790 from Synechocystis sp. | DS | LL | PEG | |
| 616 | 1.00E-120 | 100 | gi\|38603932\| | ref\|NP_193578.1\| Ras-related GTP-binding protein, putative [Arabidopsis thaliana] | DS | | | |
| 617 | 0 | 100 | gi\|15810337\| | ref\|NP_565310.1\| expressed protein [Arabidopsis thaliana] | DS | PEG | | |

TABLE 3-continued

| PEP SEQ ID NO | e value | % identity | GenBank id | description | trait | | |
|---|---|---|---|---|---|---|---|
| 618 | 0 | 100 | gi|8978074| | ref|NP_199518.1| protein kinase, putative [*Arabidopsis thaliana*] | DS | | |
| 619 | 0 | 75 | gi|9294678| | dbj|BAB03027.1|glutamine-fructose-6-phosphate transaminase 2 [*Arabidopsis thaliana*] | DS | | |
| 620 | 0 | 100 | gi|42567142| | ref|NP_194265.2|EXS family protein/ ERD1/XPR1/SYG1 family protein [*Arabidopsis thaliana*] gb|AAR99486.1| PHO1-like protein [*Arabidopsis thaliana*] | DS | | |
| 621 | 1.00E-151 | 89 | gi|50938765| | ref|XP_478910.1|serine/ threonine protein kinase PKPA-like protein [*Oryza sativa*] | DS | SS | PEG |
| 622 | 0 | 100 | gi|16323410| | gb|AAD49980.1| Similar to gb|AF110333 PrMC3 protein from *Pinus radiata* and is a member of PF|00135 Carboxylesterases family. | HS | | |
| 623 | 7.00E-86 | 100 | gi|23397128| | ref|NP_178620.1| glycine-rich protein (GRP) [*Arabidopsis thaliana*] | HS | SS | |
| 624 | 1.00E-104 | 100 | gi|24417354| | ref|NP_564833.1| expressed protein [*Arabidopsis thaliana*] | HS | | |
| 625 | 1.00E-48 | 57 | gi|21553397| | ref|NP_180326.1| zinc finger (AN1-like) family protein [*Arabidopsis thaliana*] | HS | | |
| 626 | 0 | 100 | gi|16130575| | ref|NP_417147.1|succinate-semialdehyde dehydrogenase I, NADP-dependent [*Escherichia coli* K12] | HS | | |
| 627 | 0 | 100 | gi|15218645| | ref|NP_176713.1|cytochrome P450, putative [*Arabidopsis thaliana*] | HS | PEG | |
| 628 | 0 | 100 | gi|16329269| | ref|NP_439997.1|hypothetical protein slr0731 [*Synechocystis* sp. PCC 6803] | HS | | |
| 629 | 0 | 99 | gi|12322845| | gb|AAG51407.1|putative cysteine synthase; 39489-37437 [*Arabidopsis thaliana*] | HS | | |
| 630 | 1.00E-126 | 100 | gi|28827686| | gb|AAO50687.1|unknown protein [*Arabidopsis thaliana*] | HS | PEG | |
| 631 | 1.00E-143 | 100 | gi|23197714| | ref|NP_196259.2| DNAJ heat shock N-terminal domain-containing protein | HS | SS | LL |
| 632 | 0 | 100 | gi|21554091| | gb|AAM63172.1|putative integral membrane protein [*Arabidopsis thaliana*] | LL | | |
| 633 | 0 | 100 | gi|16329756| | ref|NP_440484.1|formaldehyde dehydrogenase (glutathione) | LL | | |
| 634 | 0 | 100 | gi|26450489| | ref|NP_190148.1| transducin family protein/ WD-40 repeat family protein | LL | | |
| 635 | 0 | 100 | gi|3980410| | ref|NP_180485.1| lectin protein kinase, putative [*Arabidopsis thaliana*] | LL | LN | |
| 636 | 1.00E-153 | 100 | gi|6572061| | ref|NP_190708.1| expressed protein [*Arabidopsis thaliana*] | LL | LN | |
| 637 | 1.00E-141 | 100 | gi|22328141| | ref|NP_201402.2|hetero-geneous nuclear ribonucleoprotein, putative/ hnRNP, putative | LL | LN | |
| 638 | 0 | 100 | gi|15219657| | ref|NP_176819.1|protein kinase family protein [*Arabidopsis thaliana*] | LL | | |

TABLE 3-continued

| PEP SEQ ID NO | e value | % identity | GenBank id | description | trait | |
|---|---|---|---|---|---|---|
| 639 | 5.00E−53 | 55 | gi\|34906632\| | ref\|NP_914663.1\|P0431G06.11 [*Oryza sativa (japonica* cultivar-group)] | LL | |
| 640 | 1.00E−169 | 100 | gi\|21674686\| | ref\|NP_662751.1\|6-phosphogluconate dehydrogenase, decarboxylating, putative [*Chlorobium tepidum* TLS] | LL | |
| 641 | 1.00E−69 | 96 | gi\|32490260\| | ref\|XP_473078.1\| OSJNBa0014K14.9 [*Oryza sativa (japonica* cultivar-group)] | LL | PEG |
| 642 | 0 | 100 | gi\|52354393\| | gb\|AAU44517.1\|hypothetical protein AT4G22980 [*Arabidopsis thaliana*] | LL | PEG |
| 643 | 2.00E−90 | 100 | gi\|9758347\| | ref\|NP_200586.1\| expressed protein [*Arabidopsis thaliana*] | LL | LN |
| 644 | 0 | 82 | gi\|50946759\| | ref\|XP_482907.1\|putative glycoprotein 3-alpha-L-fucosyltransferase | LL | LN |
| 645 | 1.00E−131 | 83 | gi\|7269121\| | emb\|CAB79230.1\|predicted protein [*Arabidopsis thaliana*] | LL | |
| 646 | 1.00E−130 | 88 | gi\|50929089\| | ref\|XP_474072.1\|OSJNBb0079B02.14 [*Oryza sativa (japonica* cultivar-group)] | LL | LN |
| 647 | 0 | 100 | gi\|10176523\| | ref\|NP_244766.1\| acetyl-CoA: acetoacetyl-CoA transferase [*Bacillus halodurans* C-125] | LL | |
| 648 | 0 | 100 | gi\|34365735\| | ref\|NP_566384.1\| xanthine/uracil permease family protein [*Arabidopsis thaliana*] | LL | |
| 649 | 1.00E−84 | 100 | gi\|10177539\| | ref\|NP_201459.1\| expressed protein [*Arabidopsis thaliana*] | LL | |
| 650 | 1.00E−137 | 100 | gi\|21537398\| | ref\|NP_201145.1\| adenylate kinase [*Arabidopsis thaliana*] | LN | |
| 651 | 0 | 100 | gi\|10177005\| | ref\|NP_851136.1\| cytochrome P450 family protein [*Arabidopsis thaliana*] | LN | |
| 652 | 0 | 99 | gi\|9758597\| | ref\|NP_851196.1\| outward rectifying potassium channel (KCO1) [*Arabidopsis thaliana*] | LN | |
| 653 | 1.00E−126 | 100 | gi\|20453405\| | ref\|NP_180901.1\| plastid developmental protein DAG, putative [*Arabidopsis thaliana*] | LN | |
| 654 | 0 | 100 | gi\|7378631\| | ref\|NP_195967.1\| serine/threonine protein phosphatase 2A (PP2A) regulatory subunit B' (B'alpha) | LN | |
| 655 | 0 | 100 | gi\|50058955\| | gb\|AAT69222.1\|hypothetical protein At2g30900 [*Arabidopsis thaliana*] | LN | |
| 656 | 3.00E−36 | 100 | gi\|26453058\| | ] ref\|NP_191804.1\| expressed protein [*Arabidopsis thaliana*] | LN | |
| 657 | 0 | 100 | gi\|28973131\| | ref\|NP_190313.1\| phosphoinositide-specific phospholipase C family protein | LN | |
| 658 | 0 | 100 | gi\|23297411\| | gb\|AAN12963.1\|enolase (2-phospho-D-glycerate hydroylase) [*Arabidopsis thaliana*] | LN | |
| 659 | 1.00E−157 | 100 | gi\|22136938\| | ref\|NP_566528.1\| expressed protein [*Arabidopsis thaliana*] | LN | |

TABLE 3-continued

| PEP SEQ ID NO | e value | % identity | GenBank id | description | trait |
|---|---|---|---|---|---|
| 660 | 0 | 100 | gi\|9294186\| | ref\|NP_566763.1\| auxin-responsive family protein [*Arabidopsis thaliana*] | LN |
| 661 | 0 | 100 | gi\|7269372\| | ref\|NP_194252.1\| transporter, putative [*Arabidopsis thaliana*] | LN |
| 662 | 3.00E−93 | 100 | gi\|28393887\| | ref\|NP182046.1\| auxin-responsive protein-related [*Arabidopsis thaliana*] | LN |
| 663 | 0 | 100 | gi\|4725942\| | ref\|NP_192980.1\| trehalose-6-phosphate phosphatase, putative | LN |
| 664 | 0 | 100 | gi\|15074657\| | ref\|NP_385829.1\| PROBABLE AMINOTRANSFERASE PROTEIN | LN |
| 665 | 1.00E−179 | 81 | gi\|35215000\| | ref\|NP_927371.1\| glutathione dependent formaldehyde dehydrogenase | LN |
| 666 | 1.00E−142 | 100 | gi\|23507799\| | ref\|NP_565973.1\| LOB domain protein 16/lateral organ boundaries domain protein 16 | LN |
| 667 | 0 | 99 | gi\|48731145\| | ref\|ZP_00264891.1\|COG1012: NAD-dependent aldehyde dehydrogenases [*Pseudomonas fluorescens* PfO-1] | LN |
| 668 | 0 | 99 | gi\|15223033\| | ref\|NP_177763.1\|protein kinase, putative [*Arabidopsis thaliana*] | LN |
| 669 | 0 | 100 | gi\|22137136\| | ref\|NP_181639.1\| RNA recognition motif (RRM)-containing protein | LN |
| 670 | 0 | 100 | gi\|50904773\| | ref\|XP_463875.1\|putative iron-phytosiderophore transporter protein yellow stripe 1 | LN |
| 671 | 5.00E−40 | 48 | gi\|15232064\| | ref\|NP_189339.1\|expressed protein [*Arabidopsis thaliana*] | LN |
| 672 | 0 | 88 | gi\|51535369\| | dbj\|BAD37240.1\|putative phosphotyrosyl phosphatase activator [*Oryza sativa* (*japonica* cultivar-group)] | LN |
| 673 | 8.00E−93 | 100 | gi\|21555349\| | ref\|NP_190798.1\| ATP synthase D chain-related [*Arabidopsis thaliana*] | LN |
| 674 | 0 | 100 | gi\|9795597\| | ref\|NP_173294.1\| sulfotransferase family protein [*Arabidopsis thaliana*] | LN |
| 675 | 0 | 100 | gi\|42567054\| | ref\|NP_194058.2\|protein kinase family protein [*Arabidopsis thaliana*] | LN |
| 676 | 0 | 100 | gi\|31711846\| | ref\|NP_177412.1\| cinnamyl-alcohol dehydrogenase, putative | LN |
| 677 | 0 | 100 | gi\|23308375\| | ref\|NP_851141.1\| RNA recognition motif (RRM)-containing protein | LN |
| 678 | 0 | 100 | gi\|7329658\| | emb\|CAB82755.1\|protein kinase ATN1-like protein [*Arabidopsis thaliana*] | LN |
| 679 | 0 | 100 | gi\|22655386\| | ref\|NP_197288.1\| cation exchanger, putative (CAX7) [*Arabidopsis thaliana*] | LN |
| 680 | 1.00E−162 | 100 | gi\|20197230\| | gb\|AAM14984.1\|high affinity K+ transporter (AtKUP1 AtKT1p) [*Arabidopsis thaliana*] | LN |
| 681 | 0 | 100 | gi\|15219169\| | ref\|NP_175713.1\|protein kinase family protein [*Arabidopsis thaliana*] | LN |

TABLE 3-continued

| PEP SEQ ID NO | e value | % identity | GenBank id | description | trait | |
|---|---|---|---|---|---|---|
| 682 | 0 | 100 | gi|9758951| | ref|NP_568809.2| protein kinase family protein [*Arabidopsis thaliana*] | LN | |
| 683 | 0 | 100 | gi|7573368| | ref|NP_196762.1| expressed protein [*Arabidopsis thaliana*] | LN | |
| 684 | 0 | 100 | gi|20259017| | ref|NP_200323.1| expressed protein [*Arabidopsis thaliana*] | LN | |
| 685 | 6.00E−80 | 100 | gi|30793811| | ref|NP_191519.1| DNA-directed RNA polymerase I, II, and III, putative | LN | PEG |
| 686 | 0 | 100 | gi|7268609| | ref|NP_193550.1| outward rectifying potassium channel, putative (KCO6) | LN | |
| 687 | 1.00E−111 | 71 | gi|7270315| | ref|NP_195093.1| L-galactose dehydrogenase (L-GalDH) [*Arabidopsis thaliana*] | LN | |
| 688 | 5.00E−98 | 100 | gi|29824277| | ref|NP_568016.1| expressed protein [*Arabidopsis thaliana*] | LN | |
| 689 | 1.00E−170 | 69 | gi|7269325| | emb|CAB79384.1|protein kinase (AFC2) [*Arabidopsis thaliana*] | LN | |
| 690 | 3.00E−96 | 79 | gi|57899263| | dbj|BAD87508.1|putative calcyclin-binding protein [*Oryza sativa (japonica cultivar-group)*] | LN | |
| 691 | 1.00E−164 | 100 | gi|11994637| | emb|CAD44270.1| monomeric G-protein [*Arabidopsis thaliana*] | LN | |
| 692 | 1.00E−109 | 100 | gi|7269377| | ref|NP_194256.1| invertase/pectin methylesterase inhibitor family protein | LN | |
| 693 | 1.00E−57 | 100 | gi|7340686| | ref|NP_195832.1| thylakoid membrane one helix protein (OHP) [*Arabidopsis thaliana*] | LN | |
| 694 | 0 | 100 | gi|21689839| | gb|AAM67563.1|putative protein transport protein SEC12p [*Arabidopsis thaliana*] | PEG | |
| 695 | 1.00E−36 | 100 | gi|10177015| | ref|NP_199045.1| ubiquitin family protein [*Arabidopsis thaliana*] | PEG | |
| 696 | 1.00E−106 | 100 | gi|20466087| | ref|NP_179457.1| zinc finger (C3HC4-type RING finger) family protein | PEG | |
| 697 | 0 | 100 | gi|7267203| | ref|NP_192355.1| aspartyl protease family protein [*Arabidopsis thaliana*] | PEG | |
| 698 | 0 | 100 | gi|46931342| | ref|NP_850347.1| F-box family protein [*Arabidopsis thaliana*] | PEG | |
| 699 | 0 | 60 | gi|46931354| | gb|AAT06481.1|At3g23540 [*Arabidopsis thaliana*] | PEG | |
| 700 | 1.00E−161 | 100 | gi|21594556| | gb|AAM66021.1|plasma membrane intrinsic protein SIMIP [*Arabidopsis thaliana*] | PEG | |
| 701 | 0 | 100 | gi|902923| | dbj|BAA07547.1|phosphoinositide specific phospholipase C [*Arabidopsis thaliana*] | PEG | |
| 702 | 0 | 100 | gi|26449713| | ref|NP_195154.2| transducin family protein/WD-40 repeat family protein | PEG | |
| 703 | 0 | 94 | gi|15232616| | ref|NP_188176.1|phototropic-responsive NPH3 family protein [*Arabidopsis thaliana*] | PEG | |

TABLE 3-continued

| PEP SEQ ID NO | e value | % identity | GenBank id | description | trait |
|---|---|---|---|---|---|
| 704 | 0 | 100 | gi\|23296692\| | ref\|NP_189177.1\| formin homology 2 domain-containing protein/FH2 domain-containing protein [*Arabidopsis thaliana*] | PEG |
| 705 | 0 | 100 | gi\|51013899\| | ref\|NP_015238.1\| Ydc1p [*Saccharomyces cerevisiae*] gb\|AAB68212.1\| Lpg21p gb\|AAG22594.1\| alkaline ceramidase Ydc1p | PEG |
| 706 | 0 | 100 | gi\|23297093\| | ref\|NP_565508.1\| fructose-bisphosphate aldolase, putative [*Arabidopsis thaliana*] | PEG |
| 707 | 0 | 99 | gi\|6322722\| | ref\|NP 012795.1\|Pgm1p [*Saccharomyces cerevisiae*] emb\|CAA50895.1\| phosphoglucomutase | PEG |
| 708 | 0 | 99 | gi\|10175338\| | ref\|NP_243583.1\| glutaminase [*Bacillus halodurans* C-125] | PEG |
| 709 | 0 | 94 | gi\|7268277\| | ref\|NP_193265.1\| cytochrome P450 family protein [*Arabidopsis thaliana*] | PEG |
| 710 | 0 | 100 | gi\|6322296\| | sp\|P38970\|HAL5_YEAST Serine/threonine-protein kinase HAL5 | PEG |
| 711 | 0 | 100 | gi\|17104779\| | ref\|NP_564866.1\| U-box domain-containing protein | PEG |
| 712 | 0 | 99 | gi\|16080934\| | ref\|NP_391762.1\|aldehyde dehydrogenase [*Bacillus subtilis* subsp. *subtilis* str. 168] | PEG |
| 713 | 0 | 87 | gi\|37524894\| | ref\|NP_928238.1\|glutamate-1-semialdehyde 2,1-aminomutase [*Photorhabdus luminescens* subsp. *laumondii* TTO1] | PEG |
| 714 | 0 | 100 | gi\|16077848\| | ref\|NP_388662.1\|trehalose-6-phosphate hydrolase [*Bacillus subtilis* subsp. *subtilis* str. 168] | PEG |
| 715 | 1.00E-81 | 100 | gi\|1922244\| | ref\|NP_171654.1\| late embryogenesis abundant protein, putative/LEA protein, putative | PEG |
| 716 | 1.00E-112 | 100 | gi\|7268505\| | ref\|NP 193486.1\| Ras-related GTP-binding protein, putative [*Arabidopsis thaliana*] | PEG |
| 717 | 3.00E-44 | 100 | gi\|21592597\| | ref\|NP_563987.1\| expressed protein [*Arabidopsis thaliana*] gb\|AAF18498.1\| Identical to gb\|Y10291 GAG1 protein | PEG |
| 718 | 3.00E-97 | 44 | gi\|52353666\| | gb\|AAU44232.1\|hypothetical protein [*Oryza sativa* (*japonica* cultivar-group)] | PEG |
| 719 | 1.00E-175 | 63 | gi\|53850529\| | gb\|AAC31235.1\| hypothetical protein [*Arabidopsis thaliana*] gb\|AAT71954.1\| | PEG |
| 720 | 1.00E-131 | 99 | gi\|16330417\| | ref\|NP_441145.1\|hypothetical protein sll1162 [*Synechocystis* sp. PCC 6803] | PEG |
| 721 | 0 | 100 | gi\|17129862\| | ref\|NP_484561.1\| fructokinase [*Nostoc* sp. PCC 7120] | PEG |

TABLE 3-continued

| PEP SEQ ID NO | e value | % identity | GenBank id | description | trait | | |
|---|---|---|---|---|---|---|---|
| 722 | 0 | 100 | gi\|15293245\| | ref\|NP_567109.1\| COP9 signalosome complex subunit 1/CSN complex subunit 1 (CSN1)/COP11 protein (COP11)/FUSCA protein (FUS6) [*Arabidopsis thaliana*] | PEG | | |
| 723 | 0 | 100 | gi\|20259583\| | ref\|NP_180431.1\| beta-ketoacyl-CoA synthase family protein [*Arabidopsis thaliana*] | PEG | | |
| 724 | 0 | 100 | gi\|20465963\| | ref\|NP_189034.1\| beta-amylase, putative/1,4-alpha-D-glucan maltohydrolase, putative [*Arabidopsis thaliana*] | PEG | | |
| 725 | 4.00E−72 | 100 | gi\|32815911\| | ref\|NP_201100.1\| expressed protein [*Arabidopsis thaliana*] | PEG | | |
| 726 | 1.00E−179 | 100 | gi\|8953402\| | ref\|NP_196701.1\| protein kinase-related [*Arabidopsis thaliana*] | PEG | | |
| 727 | 0 | 100 | gi\|6522600\| | emb\|CAB61965.1\|1-aminocyclopropane-1-carboxylic acid oxidase-like protein | PEG | | |
| 728 | 1.00E−145 | 85 | gi\|57899179\| | dbj\|BAD87231.1\|membrane protein-like [*Oryza sativa* (*japonica* cultivar-group)] | PEG | | |
| 729 | 0 | 87 | gi\|50909427\| | ref\|XP_466202.1\|putative DNA J domain protein [*Oryza sativa* (*japonica* cultivar-group)] | PEG | | |
| 730 | 0 | 100 | gi\|53828613\| | ref\|NP_179479.1\| protein kinase family protein [*Arabidopsis thaliana*] | PEG | | |
| 731 | 1.00E−93 | 100 | gi\|23306374\| | ref\|NP_200428.1\| expressed protein [*Arabidopsis thaliana*] | PEG | | |
| 732 | 1.00E−172 | 100 | gi\|56121884\| | ref\|NP_178191.1\| major intrinsic family protein/ MIP family protein | PEG | | |
| 733 | 0 | 98 | gi\|24762199\| | gb\|AAN64166.1\|unknown protein [*Arabidopsis thaliana*] | PEG | | |
| 734 | 0 | 100 | gi\|21230100\| | ref\|NP_636017.1\|phosphomannose isomerase/GDP-mannose pyrophosphorylase | PEG | | |
| 735 | 0 | 100 | gi\|10177277\| | dbj\|BAB10630.1\|glucose-6-phosphate isomerase, cytosolic [*Arabidopsis thaliana*] | PP | | |
| 736 | 3.00E−61 | 100 | gi\|21537079\| | ref\|NP_564835.1\| expressed protein [*Arabidopsis thaliana*] | PP | HS | |
| 737 | 3.00E−91 | 100 | gi\|26452507\| | ref\|NP_197149.1\| dimethylmenaquinone methyltransferase family protein | PP | PEG | |
| 738 | 0 | 100 | gi\|5734730\| | ref\|NP_172592.1\| glucose transporter (STP1) [*Arabidopsis thaliana*] | PP | | |
| 739 | 1.00E−113 | 100 | gi\|5734748\| | ref\|NP_564017.1\| integral membrane family protein [*Arabidopsis thaliana*] | PP | SS | PEG |
| 740 | 1.00E−153 | 100 | gi\|30693623\| | ref\|NP_198871.2\|expressed protein [*Arabidopsis thaliana*] | PP | | |
| 741 | 0 | 100 | gi\|56381993\| | ref\|NP_177188.1\| spermidine synthase 2 (SPDSYN2)/putrescine aminopropyltransferase 2 | PP | SS | PEG |
| 742 | 0 | 100 | gi\|4678359\| | emb\|CAB41169.1\|cytochrome P450-like protein [*Arabidopsis thaliana*] | PP | | |

TABLE 3-continued

| PEP SEQ ID NO | e value | % identity | GenBank id | description | annotation | | | trait | | |
|---|---|---|---|---|---|---|---|---|---|---|
| 743 | 0 | 100 | gi\|15220055\| | ref\|NP_173165.1\|translation initiation factor IF-2, chloroplast, putative [*Arabidopsis thaliana*] | PP | | | | | |
| 744 | 1.00E−168 | 100 | gi\|21593654\| | ref\|NP_181996.1\| casein kinase II beta chain, putative [*Arabidopsis thaliana*] | PP | LL | LN | PEG | | |
| 745 | 0 | 100 | gi\|9758987\| | dbj\|BAB09497.1\|chloroplast nucleoid DNA-binding protein-like [*Arabidopsis thaliana*] ref\|NP_199325.1\| aspartyl protease family protein [*Arabidopsis thaliana*] | PP | | | | | |
| 746 | 0 | 100 | gi\|12642918\| | ref\|NP_180133.1\| protein phosphatase 2C, putative/ PP2C, putative | PP | SS | | | | |
| 747 | 0 | 100 | gi\|7270935\| | ref\|NP_195661.1\| cytochrome P450 family protein [*Arabidopsis thaliana*] | PP | | | | | |
| 748 | 1.00E−138 | 100 | gi\|21554052\| | gb\|AAM63133.1\|delta tonoplast integral protein delta-TIP [*Arabidopsis thaliana*] | PP | | | | | |
| 749 | 0 | 85 | gi\|28872439\| | ref\|NP_795058.1\|phospho-glycerate mutase, 2,3-bisphosphoglycerate-independent | PP | | | | | |
| 750 | 0 | 100 | gi\|25284116\| | pir\|\|95262probable formate dehydrogenase (EC 1.2.1.2) alpha chain FdoG [imported] - *SinoRhizobium meliloti* (strain 1021) magaplasmid pSymA | PP | PEG | | | | |
| 751 | 1.00E−55 | 100 | gi\|7629997\| | ref\|NP_190945.1\| late embryogenesis abundant protein-related/LEA protein-related | PP | SS | PEG | | | |
| 752 | 0 | 100 | gi\|23126243\| | ref\|ZP_00108145.1\|COG1523: Type II secretory pathway, pullulanase PulA and related glycosidases [*Nostoc punctiforme* PCC 73102] | PP | SS | | | | |
| 753 | 0 | 100 | gi\|42563087\| | ref\|NP_564975.2\|CBS domain-containing protein [*Arabidopsis thaliana*] | PP | | | | | |
| 754 | 0 | 100 | gi\|17104597\| | ref\|NP_566716.1\| protein kinase, putative [*Arabidopsis thaliana*] | PP | SS | LL | | | |
| 755 | 0 | 100 | gi\|15810541\| | ref\|NP_566876.3\| protein kinase family protein [*Arabidopsis thaliana*] | PP | SS | | | | |
| 756 | 3.00E−84 | 99 | gi\|16331120\| | ref\|NP_441848.1\|hypothetical protein sll0359 [*Synechocystis* sp. PCC 6803] | PP | | | | | |
| 757 | 0 | 99 | gi\|4835235\| | emb\|CAB42913.1\|putative protein [*Arabidopsis thaliana*] pir\|\|T08405 hypothetical protein F18B3.120 - *Arabidopsis thaliana* | PP | | | | | |
| 758 | 0 | 100 | gi\|18394553\| | ref\|NP_564042.1\|expressed protein [*Arabidopsis thaliana*] | PP | | | | | |
| 759 | 0 | 99 | gi\|49176911\| | ref\|NP_858035.1\| mercuric reductase [uncultured bacterium] | PP | | | | | |
| 760 | 0 | 100 | gi\|53794956\| | ref\|ZP_00356067.1\|COG4992: Ornithine/acetylornithine aminotransferase [*Chloroflexus aurantiacus*] | PP | SS | | | | |

TABLE 3-continued

| PEP SEQ ID NO | e value | % identity | GenBank id | description | annotation | | | | trait |
|---|---|---|---|---|---|---|---|---|---|
| 761 | 0 | 100 | gi|6714476| | ref|NP_186761.1| cystathionine gamma-synthase, chloroplast/O-succinylhomoserine (Thiol)-lyase (CGS) | PP | LL | | | |
| 762 | 0 | 100 | gi|9755789| | ref|NP_197266.1| expressed protein [*Arabidopsis thaliana*] | PP | SS | LL | LN | PEG |
| 763 | 0 | 100 | gi|15810649| | pir||T48630 high affinity nitrate transporter-like protein - *Arabidopsis thaliana* | PP | | | | |
| 764 | 1.00E-129 | 100 | gi|26451800| | ref|NP_850901.1| expressed protein [*Arabidopsis thaliana*] | PP | | | | |
| 765 | 4.00E-58 | 91 | gi|50948565| | ref|XP_483810.1|putative Bet1/Sft1-related SNARE (AtBS14a) [*Oryza sativa*] | PP | PEG | | | |
| 766 | 0 | 100 | gi|7630064| | emb|CAB88286.1|serine/threonine-specific protein kinase-like protein | PP | | | | |
| 767 | 0 | 92 | gi|50932239| | ref|XP_475647.1|putative glutaryl-CoA dehydrogenase | PP | HS | PEG | | |
| 768 | 1.00E-104 | 50 | gi|30684716| | ref|NP_196906.2|expressed protein [*Arabidopsis thaliana*] | PP | SS | | | |
| 769 | 2.00E-87 | 89 | gi|50912633| | ref|XP_467724.1|unknown protein [*Oryza sativa* (*japonica* cultivar-group)] | PP | PEG | | | |
| 770 | 9.00E-13 | 94 | gi|6682226| | gb|AAF23278.1|unknown protein [*Arabidopsis thaliana*] | PP | HS | SS | PEG | |
| 771 | 2.00E-90 | 49 | gi|31430516| | ref|NP_920131.1| putative *Magnaporthe grisea* pathogenicity protein | PP | | | | |
| 772 | 0 | 100 | gi|23297753| | ref|NP_192381.1| calcium-dependent protein kinase, putative/CDPK, putative | SP | HS | PEG | | |
| 773 | 3.00E-54 | 100 | gi|4417292| | ref|NP_179791.1| expressed protein [*Arabidopsis thaliana*] | SP | CK | PP | PEG | |
| 774 | 0 | 100 | gi|20148423| | ref|NP_177550.1| sulfotransferase family protein [*Arabidopsis thaliana*] | SP | | | | |
| 775 | 4.00E-88 | 100 | gi|21554027| | ref|NP_192830.1| transcriptional coactivator p15 (PC4) family protein (KELP) | SP | SS | | | |
| 776 | 1.00E-100 | 100 | gi|22136806| | ref|NP_176726.1| flowering locus T protein (FT) [*Arabidopsis thaliana*] | SP | SS | PEG | | |
| 777 | 6.00E-93 | 100 | gi|21592464| | ref|NP_565844.1| zinc finger (AN1-like) family protein [*Arabidopsis thaliana*] | SP | LN | | | |
| 778 | 1.00E-101 | 100 | gi|8778645| | gb|AAF79653.1|F5O11.17 [*Arabidopsis thaliana*] | SP | LN | | | |
| 779 | 2.00E-80 | 100 | gi|28973123| | ref|NP_196373.1| glycine-rich protein (GRP20) [*Arabidopsis thaliana*] | SP | CK | | | |
| 780 | 0 | 100 | gi|11994377| | ref|NP_188020.1| exopolygalacturonase/galacturan 1,4-alpha-galacturonidase/pectinase | SP | PP | PEG | | |
| 781 | 0 | 100 | gi|20465689| | ref|NP_200440.1| peroxisomal targeting signal type 1 receptor (PEX5) | SP | CK | | | |
| 782 | 8.00E-51 | 100 | gi|21536923| | ref|NP_194774.1| glycine-rich protein [*Arabidopsis thaliana*] | SP | CK | | | |
| 783 | 1.00E-124 | 100 | gi|30023686| | ref|NP_197608.1| leucine-rich repeat protein, putative [*Arabidopsis thaliana*] | SP | DS | PEG | | |

TABLE 3-continued

| PEP SEQ ID NO | e value | % identity | GenBank id | annotation description | | trait | | |
|---|---|---|---|---|---|---|---|---|
| 784 | 3.00E−76 | 100 | gi|26453292| | ref|NP_563653.2| NPR1/NIM1-interacting protein 1 (NIMIN-1) [*Arabidopsis thaliana*] | SP | SS | LN | |
| 785 | 1.00E−90 | 100 | gi|15220022| | ref|NP_173727.1|C2 domain-containing protein [*Arabidopsis thaliana*] | SP | CS | PEG | |
| 786 | 2.00E−97 | 100 | gi|56479608| | ref|NP_706078.2|hypoxanthine phosphoribosyltransferase [*Shigella flexneri* 2a str. 301] EDL933] | SP | SS | PEG | |
| 787 | 1.00E−130 | 99 | gi|16331548| | ref|NP_442276.1|hypothetical protein slr0630 [*Synechocystis* sp. PCC 6803] | SP | SS | | |
| 788 | 0 | 100 | gi|20259167| | ref|NP_568786.1| protein phosphatase 2C, putative/ PP2C, putative | SP | | | |
| 789 | 0 | 100 | gi|6466946| | ref|NP_974249.1| prephenate dehydratase family protein [*Arabidopsis thaliana*] | SP | PEG | | |
| 790 | 1.00E−130 | 100 | gi|20465721| | ref|NP_174536.1| plastid developmental protein DAG, putative | SP | CS | PEG | |
| 791 | 1.00E−63 | 84 | gi|10177620| | dbj|BAB10767.1|unnamed protein product [*Arabidopsis thaliana*] | SP | SS | | |
| 792 | 1.00E−44 | 100 | gi|58299| | emb|CAA48415.1|unnamed protein product [synthetic construct] | SP | CK | PEG | |
| 793 | 1.00E−108 | 54 | gi|3150411| | ref|NP_180570.1| GCN5-related N-acetyltransferase (GNAT) family protein | SP | CS | | |
| 794 | 0 | 100 | gi|16331766| | ref|NP_442494.1|aldehyde dehydrogenase [*Synechocystis* sp. PCC 6803] | SP | SS | PEG | |
| 795 | 1.00E−30 | 100 | gi|7340711| | emb|CAB82954.1|cytochrome c oxidase subunit 5c-like protein [*Arabidopsis thaliana*] | SP | CK | CS | PEG |
| 796 | 1.00E−137 | 100 | gi|5430750| | ref|NP_175374.2| expressed protein [*Arabidopsis thaliana*] | SP | CS | HS | PEG |
| 797 | 1.00E−93 | 100 | gi|19310667| | ref|NP_188286.1| translationally controlled tumor family protein [*Arabidopsis thaliana*] | SP | PP | SS | |
| 798 | 0 | 100 | gi|15293235| | ref|NP_194825.1| CBL-interacting protein kinase 6 (CIPK6) [*Arabidopsis thaliana*] | SP | LN | | |
| 799 | 1.00E−165 | 62 | gi|4220476| | gb|AAD12699.1|putative ribophorin I [*Arabidopsis thaliana*] | SP | | | |
| 800 | 0 | 100 | gi|20908080| | ref|NP_200169.1| RabGAP/TBC domain-containing protein [*Arabidopsis thaliana*] | SS | | | |
| 801 | 1.00E−68 | 99 | gi|51449987| | ref|NP_189210.2| myrcene/ocimene synthase, putative [*Arabidopsis thaliana*] | SS | PEG | | |
| 802 | 2.00E−94 | 100 | gi|21592517| | ref|NP_564266.1| expressed protein [*Arabidopsis thaliana*] | SS | | | |
| 803 | 0 | 100 | gi|42572237| | ref|NP_974213.1|ankyrin repeat family protein/ regulator of chromosome condensation (RCC1) family protein [*Arabidopsis thaliana*] | SS | PEG | | |

TABLE 3-continued

| PEP SEQ ID NO | e value | % identity | GenBank id | description | | trait | |
|---|---|---|---|---|---|---|---|
| 804 | 1.00E-115 | 100 | gi|21593862| | ref|NP_190632.1| kip-related protein 2 (KRP2)/ cyclin-dependent kinase inhibitor 2 (ICK2)/cdc2a-interacting protein [*Arabidopsis thaliana*] | SS | |
| 805 | 0 | 100 | gi|8843792| | ref|NP_200680.1| PRLI-interacting factor, putative [*Arabidopsis thaliana*] | SS | LN |
| 806 | 0 | 90 | gi|21586474| | gb|AAM55306.1|auxin influx carrier protein [*Medicago truncatula*] | SS | |
| 807 | 0 | 99 | gi|20799715| | gb|Aref|NP_190468.1| AMP-dependent synthetase and ligase family protein | SS | |
| 808 | 0 | 100 | gi|15293255| | ref|NP_564424.1| PHD finger family protein [*Arabidopsis thaliana*] | SS | |
| 809 | 0 | 100 | gi|24030409| | ref|NP_194207.1| expressed protein [*Arabidopsis thaliana*] | SS | LN |
| 810 | 0 | 100 | gi|6728973| | ref|NP_186938.1| leucine-rich repeat transmembrane protein kinase, putative | SS | PEG |
| 811 | 1.00E-133 | 100 | gi|27754697| | gb|AAO22792.1|putative cytochrome c oxidoreductase [*Arabidopsis thaliana*] | SS | PEG |
| 812 | 0 | 91 | gi|4539445| | ref|NP_192805.1| transcription elongation factor-related [*Arabidopsis thaliana*] | SS | |
| 813 | 0 | 100 | gi|23296600| | ref|NP_568107.1| pseudo-response regulator 7 (APRR7) [*Arabidopsis thaliana*] sp|Q93WK5|APRR7_ARATH Two-component response regulator-like APRR7 (Pseudo-response regulator 7) | SS | |
| 814 | 0 | 99 | gi|16331392| | ref|NP_442120.1|ribulose bisphosphate carboxylase large subunit | SS | |
| 815 | 0 | 99 | gi|16329673| | ref|NP_440401.1|mercuric reductase [*Synechocystis* sp. PCC 6803] | SS | |
| 816 | 0 | 100 | gi|23506207| | gb|AAN31115.1|At2g26250/ T1D16.11 [*Arabidopsis thaliana*] gb|AAG60062.1| putative beta-ketoacyl-CoA synthase FIDDLEHEAD | SS | |
| 817 | 0 | 99 | gi|6016708| | ref|NP_186798.1| protein kinase, putative [*Arabidopsis thaliana*] | SS | |
| 818 | 0 | 100 | gi|21593811| | gb|AAM65778.1|putative NADPH quinone oxidoreductase [*Arabidopsis thaliana*] | SS | |
| 819 | 0 | 100 | gi|23125809| | ref|ZP_00107727.1|COG0166: Glucose-6-phosphate isomerase [*Nostoc punctiforme* PCC 73102] | SS | |
| 820 | 0 | 100 | gi|16077353| | ref|NP_388166.1|hypothetical protein BSU02840 [*Bacillus subtilis* subsp. *subtilis* str. 168] | SS | PEG |
| 821 | 1.00E-117 | 100 | gi|7269793| | ref|NP194624.1| Rac-like GTP-binding protein (ARAC7) [*Arabidopsis thaliana*] | SS | |
| 822 | 1.00E-128 | 96 | gi|27808548| | gb|AAO24554.1|At1g61150 [*Arabidopsis thaliana*] | SS | PEG |
| 823 | 0 | 97 | gi|30684071| | ref|NP_850128.1|protein kinase family protein [*Arabidopsis thaliana*] | SS | |

TABLE 3-continued

| PEP SEQ ID NO | e value | % identity | GenBank id | description | | trait | |
|---|---|---|---|---|---|---|---|
| 824 | 2.00E−77 | 99 | gi\|16330866\| | ref\|NP_441594.1\|hypothetical protein slr1273 [*Synechocystis* sp. PCC 6803] | SS | LL | |
| 825 | 1.00E−177 | 100 | gi\|23297050\| | ref\|NP_194073.2\| short-chain dehydrogenase/reductase (SDR) family protein | SS | | |
| 826 | 1.00E−109 | 100 | gi\|12083284\| | ref\|NP_173437.1\| Rac-like GTP-binding protein (ARAC4)/Rho-like GTP-binding protein (ROP2) | SS | | |
| 827 | 0 | 100 | gi\|20465939\| | ref\|NP_850393.1\| sugar transporter family protein [*Arabidopsis thaliana*] | SS | | |
| 828 | 0 | 98 | gi\|2661128\| | gb\|AAC04613.1\|arginase [*Glycine max*] pir\|T06222 probable arginase (EC 3.5.3.1) - soybean sp\|O49046\|ARGI_SOYBN Arginase | SS | | |
| 829 | 0 | 64 | gi\|40539114\| | gb\|AAR87370.1\|expressed protein [*Oryza sativa* (*japonica* cultivar-group)] | SS | | |
| 830 | 0 | 91 | gi\|52137615\| | emb\|CAH40838.1\|protein-O-fucosyltransferase 1 [*Saccharum officinarum*] | SS | | |
| 831 | 0 | 100 | gi\|5733881\| | ref\|NP_175261.1\| G protein coupled receptor-related [*Arabidopsis thaliana*] | SS | | |
| 832 | 8.00E−88 | 100 | gi\|15217930\| | ref\|NP_176128.1\|hypothetical protein [*Arabidopsis thaliana*] | SS | | |
| 833 | 1.00E−29 | 75 | gi\|20465895\| | ref\|NP_974937.1\| RNA recognition motif (RRM)-containing protein | SS | LN | |
| 834 | 5.00E−79 | 100 | gi\|3927837\| | ref\|NP_180456.1\| mitochondrial import inner membrane translocase subunit Tim17/Tim22/Tim23 family protein [*Arabidopsis thaliana*] | SS | | |
| 835 | 1.00E−115 | 100 | gi\|21554015\| | ref\|N13_565766.1\| glycolipid transfer protein-related [*Arabidopsis thaliana*] | SS | | |
| 836 | 1.00E−131 | 100 | gi\|26452816\| | ref\|NP_193484.1\| ubiquitin carboxyl-terminal hydrolase | SS | | |
| 837 | 1.00E−102 | 99 | gi\|10177705\| | ref\|NP_199436.1\| inward rectifying potassium channel (KAT1) | SS | LN | |
| 838 | 1.00E−144 | 100 | gi\|7669950\| | ref\|NP_190844.1\| integral membrane Yip1 family protein [*Arabidopsis thaliana*] | SS | PEG | |
| 839 | 0 | 100 | gi\|10177595\| | ref\|NP_201509.1\| protein kinase family protein [*Arabidopsis thaliana*] | SS | LN | |
| 840 | 4.00E−27 | 100 | gi\|38566508\| | ref\|NP_200137.1\| arabinogalactan-protein, putative (AGP22) [*Arabidopsis thaliana*] | SS | | |
| 841 | 0 | 100 | gi\|18391117\| | ref\|NP_563862.1\|expressed protein [*Arabidopsis thaliana*] | SS | PEG | |
| 842 | 0 | 92 | gi\|50251322\| | dbj\|BAD28194.1\|putative MFAP1 protein [*Oryza sativa* (*japonica* cultivar-group)] | SS | | |
| 843 | 1.00E−112 | 95 | gi\|3201969\| | gb\|AAC19375.1\|submergence induced protein 2A [*Oryza sativa*] | SS | | |
| 844 | 1.00E−74 | 88 | gi\|29371519\| | gb\|AAO72703.1\|unknown [*Oryza sativa* (*japonica* cultivar-group)] | SS | | |

TABLE 3-continued

| PEP SEQ ID NO | e value | % identity | GenBank id | description | annotation | | trait |
|---|---|---|---|---|---|---|---|
| 845 | 0 | 100 | gi\|28416475\| | ref\|NP_187911.1\| transporter-related [*Arabidopsis thaliana*] | | SS | PEG |
| 846 | 0 | 100 | gi\|21323473\| | ref\|NP_599939.1\| detergent sensitivity rescuer dtsR2 [*Corynebacterium glutamicum* ATCC 13032] | | SS | LN |
| 847 | 0 | 82 | gi\|50928705\| | gb\|AAQ14479.1\| putative aminotransferase [*Oryza sativa*] | | SS | |
| 848 | 0 | 99 | gi\|3695005\| | gb\|AAC63962.1\|pyruvate dehydrogenase kinase isoform 2; PDK2 [*Zea mays*] | | SS | |
| 849 | 0 | 100 | gi\|10175838\| | ref\|NP_244081.1\| hypothetical protein BH3215 [*Bacillus halodurans* C-125] | | SS | PEG |
| 850 | 0 | 100 | gi\|33589668\| | ref\|NP_564285.1\| calmodulin-binding protein [*Arabidopsis thaliana*] | | SS | PEG |

Trait Improvement Screens

DS-Improvement of Drought Tolerance Identified by a Soil Drought Stress Tolerance Screen:

Drought or water deficit conditions impose mainly osmotic stress on plants. Plants are particularly vulnerable to drought during the flowering stage. The drought condition in the screening process disclosed in Example 1B started from the flowering time and was sustained to the end of harvesting. The present invention provides recombinant DNA that can improve the plant survival rate under such sustained drought condition. Exemplary recombinant DNA for conferring such drought tolerance are identified as such in Table 3. Such recombinant DNA may find particular use in generating transgenic plants that are tolerant to the drought condition imposed during flowering time and in other stages of the plant life cycle. As demonstrated from the model plant screen, in some embodiments of transgenic plants with trait-improving recombinant DNA grown under such sustained drought condition can also have increased total seed weight per plant in addition to the increased survival rate within a transgenic population, providing a higher yield potential as compared to control plants.

PEG-Improvement of Drought Tolerance Identified by PEG Induced Osmotic Stress Tolerance Screen:

Various drought levels can be artificially induced by using various concentrations of polyethylene glycol (PEG) to produce different osmotic potentials (Pilon-Smits e.g., (1995) Plant Physiol. 107:125-130). Several physiological characteristics have been reported as being reliable indications for selection of plants possessing drought tolerance. These characteristics include the rate of seed germination and seedling growth. The traits can be assayed relatively easily by measuring the growth rate of seedling in PEG solution. Thus, a PEG-induced osmotic stress tolerance screen is a useful surrogate for drought tolerance screen. As demonstrated from the model plant screen, embodiments of transgenic plants with trait-improving recombinant DNA identified in the PEG-induced osmotic stress tolerance screen can survive better drought conditions providing a higher yield potential as compared to control plants.

SS-Improvement of Drought Tolerance Identified by High Salinity Stress Tolerance Screen:

Three different factors are responsible for salt damages: (1) osmotic effects, (2) disturbances in the mineralization process, (3) toxic effects caused by the salt ions, e.g., inactivation of enzymes. While the first factor of salt stress results in the wilting of the plants that is similar to drought effect, the ionic aspect of salt stress is clearly distinct from drought. The present invention provides genes that help plants to maintain biomass, root growth, and/or plant development in high salinity conditions, which are identified as such in Table 3. Since osmotic effect is one of the major components of salt stress, which is common to the drought stress, trait-improving recombinant DNA identified in a high salinity stress tolerance screen can also provide transgenic crops with improved drought tolerance. As demonstrated from the model plant screen, embodiments of transgenic plants with trait-improving recombinant DNA identified in a high salinity stress tolerance screen can survive better drought conditions and/or high salinity conditions providing a higher yield potential as compared to control plants.

HS-Improvement of Drought Tolerance Identified by Heat Stress Tolerance Screen:

Heat and drought stress often occur simultaneously, limiting plant growth. Heat stress can cause the reduction in photosynthesis rate, inhibition of leaf growth and osmotic potential in plants. Thus, genes identified by the present invention as heat stress tolerance conferring genes may also impart improved drought tolerance to plants. As demonstrated from the model plant screen, embodiments of transgenic plants with trait-improving recombinant DNA identified in a heat stress tolerance screen can survive better heat stress conditions and/or drought conditions providing a higher yield potential as compared to control plants.

CK and CS-Improvement of Tolerance to Cold Stress:

Low temperature may immediately result in mechanical constraints, changes in activities of macromolecules, and reduced osmotic potential. In the present invention, two screening conditions, i.e., cold shock tolerance screen (CK) and cold germination tolerance screen (CS), were set up to look for transgenic plants that display visual growth advantage at lower temperature. In cold germination tolerance screen, the transgenic *Arabidopsis* plants were exposed to a constant temperature of 8° C. from planting until day 28 post plating. The trait-improving recombinant DNA identified by such screen are particular useful for the production of transgenic plant that can germinate more robustly in a cold temperature as compared to the wild type plants. In cold shock tolerance screen, the transgenic plants were first grown under the normal growth temperature of 22° C. until day 8 post plating, and subsequently were placed under 8° C. until day 28 post plating. As demonstrated from the model plant screen, embodiments of transgenic plants with trait-improving recombinant DNA identified in a cold shock stress tolerance screen and/or a cold germination stress tolerance screen can survive better cold conditions providing a higher yield potential as compared to control plants.

Improvement of Tolerance to Multiple Stresses:

Different kinds of stresses often lead to identical or similar reaction in the plants. Genes that are activated or inactivated as a reaction to stress can either act directly in a way the genetic product reduces a specific stress, or they can act indirectly by activating other specific stress genes. By manipulating the activity of such regulatory genes, i.e., multiple stress tolerance genes, the plant can be enabled to react to different kinds of stresses. For examples, PEP SEQ ID NO: 459 can be used to improve both salt stress tolerance and cold stress tolerance in plants. Of particular interest, plants transformed with PEP SEQ ID NO: 440 can resist heat stress, salt stress and cold stress. In addition to these multiple stress tolerance genes, the stress tolerance conferring genes provided by the present invention may be used in combinations to generate transgenic plants that can resist multiple stress conditions.

PP-Improvement of Early Plant Growth and Development:

It has been known in the art that to minimize the impact of disease on crop profitability, it is important to start the season with healthy vigorous plants. This means avoiding seed and seedling diseases, leading to increased nutrient uptake and increased yield potential. Traditionally early planting and applying fertilizer are the methods used for promoting early seedling vigor. In early development stage, plant embryos establish only the basic root-shoot axis, a cotyledon storage organ(s), and stem cell populations, called the root and shoot apical meristems, that continuously generate new organs throughout post-embryonic development. "Early growth and development" used herein encompasses the stages of seed imbibition through the early vegetative phase. The present invention provides genes that are useful to produce transgenic plants that have advantages in one or more processes including, but not limited to, germination, seedling vigor, root growth and root morphology under non-stressed conditions. The transgenic plants starting from a more robust seedling are less susceptible to the fungal and bacterial pathogens that attach germinating seeds and seedling. Furthermore, seedlings with advantage in root growth are more resistant to drought stress due to extensive and deeper root architecture. Therefore, it can be recognized by those skilled in the art that genes conferring the growth advantage in early stages to plants may also be used to generate transgenic plants that are more resistant to various stress conditions due to improved early plant development. The present invention provides such exemplary recombinant DNA that confer both the stress tolerance and growth advantages to plants, identified as such in Table 3, e.g., PEP SEQ ID NO: 529 which can improve the plant early growth and development, and impart salt and cold tolerance to plants. As demonstrated from the model plant screen, embodiments of transgenic plants with trait-improving recombinant DNA identified in the early plant development screen can grow better under non-stress conditions and/or stress conditions providing a higher yield potential as compared to control plants.

SP-Improvement of Late Plant Growth and Development:

"Late growth and development" used herein encompasses the stages of leaf development, flower production, and seed maturity. In certain embodiments, transgenic plants produced using genes that confer growth advantages to plants provided by the present invention, identified as such in Table 3, exhibit at least one phenotypic characteristics including, but not limited to, increased rosette radius, increased rosette dry weight, seed dry weight, silique dry weight, and silique length. On one hand, the rosette radius and rosette dry weight are used as the indexes of photosynthesis capacity, and thereby plant source strength and yield potential of a plant. On the other hand, the seed dry weight, silique dry weight and silique length are used as the indexes for plant sink strength, which are considered as the direct determinants of yield. As demonstrated from the model plant screen, embodiments of transgenic plants with trait-improving recombinant DNA identified in the late development screen can grow better and/or have improved development during leaf development and seed maturation providing a higher yield potential as compared to control plants.

LL-Improvement of Tolerance to Shade Stress Identified in a Low Light Screen:

The effects of light on plant development are especially prominent at the seedling stage. Under normal light conditions with unobstructed direct light, a plant seeding develops according to a characteristic photomorphogenic pattern, in which plants have open and expanded cotyledons and short hypocotyls. Then the plant's energy is devoted to cotyledon and leaf development while longitudinal extension growth is minimized. Under low light condition where light quality and intensity are reduced by shading, obstruction or high population density, a seedling displays a shade-avoidance pattern, in which the seedling displays a reduced cotyledon expansion, and hypocotyls extension is greatly increased. As the result, a plant under low light condition increases significantly its stem length at the expanse of leaf, seed or fruit and storage organ development, thereby adversely affecting of yield. The present invention provides recombinant DNA that enable plants to have an attenuated shade avoidance response so that the source of plant can be contributed to reproductive growth efficiently, resulting higher yield as compared to the wild type plants. As demonstrated from the model plant screen, embodiments of transgenic plants with trait-improving recombinant DNA identified in a shade stress tolerance screen can have attenuated shade response under shade conditions providing a higher yield potential as compared to control plants. The transgenic plants generated by the present invention may be suitable for a higher density planting, thereby resulting increased yield per unit area.

LN-Improvement of Tolerance to Low Nitrogen Availability Stress

Nitrogen is a key factor in plant growth and crop yield. The metabolism, growth and development of plants are profoundly affected by their nitrogen supply. Restricted nitrogen supply alters shoot to root ratio, root development, activity of enzymes of primary metabolism and the rate of senescence (death) of older leaves. All field crops have a fundamental dependence on inorganic nitrogenous fertilizer. Since fertilizer is rapidly depleted from most soil types, it must be supplied to growing crops two or three times during the growing season. Enhanced nitrogen use efficiency by plants should enable crops cultivated under low nitrogen availability stress condition resulted from low fertilizer input or poor soil quality.

According to the present invention, transgenic plants generated using the recombinant nucleotides, which confer enhanced nitrogen use efficiency, identified as such in Table 3, exhibit one or more desirable traits including, but not limited to, increased seedling weight, greener leaves, increased number of rosette leaves, increased or decreased root length. One skilled in the art may recognize that the transgenic plants provided by the present invention with enhanced nitrogen use efficiency may also have altered amino acid or protein compositions, increased yield and/or better seed quality. The transgenic plants of the present invention may be productively cultivated under low nitrogen growth conditions, i.e., nitrogen-poor soils and low nitrogen fertilizer inputs, which would cause the growth of wild type plants to cease or to be so diminished as to make the wild type plants practically useless. The transgenic plants also may be advantageously used to achieve earlier maturing, faster growing, and/or higher yielding crops and/or produce more nutritious foods and animal feedstocks when cultivated using nitrogen non-limiting growth conditions.

Stacked Traits:

The present invention also encompasses transgenic plants with stacked engineered traits, e.g., a crop having an improved phenotype resulting from expression of a trait-improving recombinant DNA, in combination with herbicide and/or pest resistance traits. For example, genes of the current invention can be stacked with other traits of agronomic interest, such as a trait providing herbicide resistance, for example a RoundUp Ready® trait, or insect resistance, such as using a gene from *Bacillus thuringensis* to provide resistance against lepidopteran, coliopteran, homopteran, hemiopteran, and other insects. Herbicides for which resistance is useful in a plant include glyphosate herbicides, phosphinothricin herbicides, oxynil herbicides, imidazolinone herbicides, dinitroaniline herbicides, pyridine herbicides, sulfonylurea herbicides, bialaphos herbicides, sulfonamide herbicides and gluphosinate herbicides. To illustrate that the production of transgenic plants with herbicide resistance is a capability of those of ordinary skill in the art, reference is made to U.S. patent application publications 2003/0106096A1 and 2002/0112260A1 and U.S. Pat. Nos. 5,034,322; 5,776,760, 6,107,549 and 6,376,754, all of which are incorporated herein by reference. To illustrate that the production of transgenic plants with pest resistance is a capability of those of ordinary skill in the art reference is made to U.S. Pat. Nos. 5,250,515 and 5,880,275 which disclose plants expressing an endotoxin of *Bacillus thuringiensis* bacteria, to U.S. Pat. No. 6,506,599 which discloses control of invertebrates which feed on transgenic plants which express dsRNA for suppressing a target gene in the invertebrate, to U.S. Pat. No. 5,986,175 which discloses the control of viral pests by transgenic plants which express viral replicase, and to U.S. Patent Application Publication 2003/0150017 A1 which discloses control of pests by a transgenic plant which express a dsRNA targeted to suppressing a gene in the pest, all of which are incorporated herein by reference.

Once one recombinant DNA has been identified as conferring an improved trait of interest in transgenic *Arabidopsis* plants, several methods are available for using the sequence of that recombinant DNA and knowledge about the protein it encodes to identify homologs of that sequence from the same plant or different plant species or other organisms, e.g., bacteria and yeast. Thus, in one aspect, the invention provides methods for identifying a homologous gene with a DNA sequence homologous to any of SEQ ID NO: 1 through SEQ ID NO: 425, or a homologous protein with an amino acid sequence homologous to any of SEQ ID NO: 426 through SEQ ID NO: 850. In another aspect, the present invention provides the protein sequences of identified homologs for a sequence listed as SEQ ID NO: 851 through SEQ ID NO: 33634. In yet another aspect, the present invention also includes linking or associating one or more desired traits, or gene function with a homolog sequence provided herein.

The trait-improving recombinant DNA and methods of using such trait-improving recombinant DNA for generating transgenic plants with improved traits provided by the present invention are not limited to any particular plant species. Indeed, the plants according to the present invention may be of any plant species, i.e., may be monocotyledonous or dicotyledonous. Preferably, they will be agricultural useful plants, i.e., plants cultivated by man for purposes of food production or technical, particularly industrial applications. Of particular interest in the present invention are corn and soybean plants. The recombinant DNA constructs optimized for soybean transformation and recombinant DNA constructs optimized for corn transformation are provided by the present invention. Other plants of interest in the present invention for production of transgenic plants having improved traits include, without limitation, cotton, canola, wheat, sunflower, sorghum, alfalfa, barley, millet, rice, tobacco, fruit and vegetable crops, and turfgrass.

In certain embodiments, the present invention contemplates to use an orthologous gene in generating the transgenic plants with similarly improved traits as the transgenic *Arabidopsis* counterpart. Improved physiological properties in transgenic plants of the present invention may be confirmed in responses to stress conditions, for example in assays using imposed stress conditions to detect improved responses to drought stress, nitrogen deficiency, cold growing conditions, or alternatively, under naturally present stress conditions, for example under field conditions. Biomass measures may be made on greenhouse or field grown plants and may include such measurements as plant height, stem diameter, root and shoot dry weights, and, for corn plants, ear length and diameter.

Trait data on morphological changes may be collected by visual observation during the process of plant regeneration as well as in regenerated plants transferred to soil. Such trait data includes characteristics such as normal plants, bushy plants, taller plants, thicker stalks, narrow leaves, striped leaves, knotted phenotype, chlorosis, albino, anthocyanin production, or altered tassels, ears or roots. Other enhanced traits may be identified by measurements taken under field conditions, such as days to pollen shed, days to silking, leaf extension rate, chlorophyll content, leaf temperature, stand, seedling vigor, internode length, plant height, leaf number, leaf area, tillering, brace roots, stay green, stalk lodging, root lodging, plant health, barreness/prolificacy, green snap, and pest resistance. In addition, trait characteristics of harvested grain may be confirmed, including number of kernels per row on the ear, number of rows of kernels on the ear, kernel abortion, kernel weight, kernel size, kernel density and physical grain quality.

To confirm hybrid yield in transgenic corn plants expressing genes of the present invention, it may be desirable to test hybrids over multiple years at multiple locations in a geographical location where *maize* is conventionally grown, e.g., in Iowa, Illinois or other locations in the midwestern United States, under "normal" field conditions as well as under stress conditions, e.g., under drought or population density stress.

Transgenic plants can be used to provide plant parts according to the invention for regeneration or tissue culture of cells or tissues containing the constructs described herein.

Plant parts for these purposes can include leaves, stems, roots, flowers, tissues, epicotyl, meristems, hypocotyls, cotyledons, pollen, ovaries, cells and protoplasts, or any other portion of the plant which can be used to regenerate additional transgenic plants, cells, protoplasts or tissue culture. Seeds of transgenic plants are provided by this invention can be used to propagate more plants containing the trait-improving recombinant DNA constructs of this invention. These descendants are intended to be included in the scope of this invention if they contain a trait-improving recombinant DNA construct of this invention, whether or not these plants are selfed or crossed with different varieties of plants.

The various aspects of the invention are illustrated by means of the following examples which are in no way intended to limit the full breath and scope of claims.

EXAMPLES

Example 1. Identification of Recombinant DNA that Confers Improved Trait(s) to Plants A. Expression Constructs for *Arabidopsis* Plant Transformation Each gene of interest was amplified from a genomic or cDNA library using primers specific to sequences upstream and downstream of the coding region. Transformation vectors were prepared to constitutively transcribe DNA in either sense orientation (for enhanced protein expression) or antisense orientation (for endogenous gene suppression) under the control of an enhanced Cauliflower Mosaic Virus 35S promoter (U.S. Pat. No. 5,359,142) directly or indirectly (Moore, e.g., PNAS 95:376-381, 1998; Guyer, e.g., Genetics 149: 633-639, 1998; International patent application NO. PCT/EP98/07577). The transformation vectors also contain a bar gene as a selectable marker for resistance to glufosinate herbicide. The transformation of *Arabidopsis* plants was carried out using the vacuum infiltration method known in the art (Bethtold, e.g., Methods Mol. Biol. 82:259-66, 1998). Seeds harvested from the plants, named as T1 seeds, were subsequently grown in a glufosinate-containing selective medium to select for plants which were actually transformed and which produced T2 transgenic seed.

B. Soil Drought Tolerance Screen

This example describes a soil drought tolerance screen to identify *Arabidopsis* plants transformed with recombinant DNA that wilt less rapidly and/or produce higher seed yield when grown in soil under drought conditions T2 seeds were sown in flats filled with Metro/Mix® 200 (The Scotts® Company, USA). Humidity domes were added to each flat and flats were assigned locations and placed in climate-controlled growth chambers. Plants were grown under a temperature regime of 22° C. at day and 20° C. at night, with a photoperiod of 16 hours and average light intensity of 170 μmol/m$^2$/s. After the first true leaves appeared, humidity domes were removed. The plants were sprayed with glufosinate herbicide and put back in the growth chamber for 3 additional days. Flats were watered for 1 hour the week following the herbicide treatment. Watering was continued every seven days until the flower bud primordia became apparent, at which time plants were watered for the last time.

To identify drought tolerant plants, plants were evaluated for wilting response and seed yield. Beginning ten days after the last watering, plants were examined daily until 4 plants/line had wilted. In the next six days, plants were monitored for wilting response. Five drought scores were assigned according to the visual inspection of the phenotypes: 1 for healthy, 2 for dark green, 3 for wilting, 4 severe wilting, and 5 for dead. A score of 3 or higher was considered as wilted.

At the end of this assay, seed yield measured as seed weight per plant under the drought condition was characterized for the transgenic plants and their controls and analyzed as a quantitative response according to example 1M.

Two approaches were used for statistical analysis on the wilting response. First, the risk score was analyzed for wilting phenotype and treated as a qualitative response according to the example 1L. Alternatively, the survival analysis was carried out in which the proportions of wilted and non-wilted transgenic and control plants were compared over each of the six days under scoring and an overall log rank test was performed to compare the two survival curves using S-PLUS statistical software (S-PLUS 6, Guide to statistics, Insightful, Seattle, Wash., USA). Table 4 provides a list of recombinant DNA constructs that improve drought tolerance in transgenic plants.

TABLE 4

| PEP SEQ ID NO | Construct ID | Nomination ID | Orientation | Drought score Delta mean | P-value | Seed yield Delta mean | P-value | Time to wilting Risk score mean | P-value |
|---|---|---|---|---|---|---|---|---|---|
| 601 | 12116 | CGPG1112 | ANTI-SENSE | 0.119 | 0.496 | 0.736 | 0.014 | −0.026 | 1.000 |
| 602 | 13053 | CGPG1284 | ANTI-SENSE | 0.122 | 0.532 | 0.785 | 0.028 | −0.122 | 1.000 |
| 603 | 14733 | CGPG1640 | SENSE | 0.469 | 0.016 | −0.225 | 0.363 | 0.263 | 1.000 |
| 604 | 16132 | CGPG2136 | SENSE | 0.149 | 0.529 | 0.472 | 0.046 | / | / |
| 605 | 18276 | CGPG3542 | SENSE | 0.320 | 0.088 | 0.433 | 0.264 | 0.362 | 1.000 |
| 606 | 70851 | CGPG1691 | SENSE | 0.267 | 0.065 | 0.427 | 0.017 | / | / |
| 607 | 70941 | CGPG4067 | SENSE | 0.254 | 0.056 | 0.533 | 0.006 | / | / |
| 450 | 71814 | CGPG4434 | SENSE | 0.241 | 0.186 | 0.719 | 0.020 | 0.348 | 1.000 |
| 609 | 72326 | CGPG27 | SENSE | 0.300 | 0.149 | 0.674 | 0.036 | 0.152 | 1.000 |
| 608 | 72134 | CGPG5335 | SENSE | 0.239 | 0.169 | 0.613 | 0.077 | 0.010 | 1.000 |
| 783 | 72824 | CGPG4998 | SENSE | 0.254 | 0.180 | 0.608 | 0.046 | / | / |
| 610 | 72978 | CGPG3441 | SENSE | 0.447 | 0.094 | −0.973 | 0.071 | / | / |
| 611 | 73619 | CGPG4375 | SENSE | 0.990 | 0.022 | −0.204 | 0.283 | 0.900 | 1.000 |
| 612 | 73737 | CGPG5176 | SENSE | 0.162 | 0.293 | 1.126 | 0.000 | 0.333 | 1.000 |
| 460 | 73025 | CGPG5665 | SENSE | 0.065 | 0.731 | 0.489 | 0.095 | / | / |
| 613 | 71196 | CGPG6637 | SENSE | 0.172 | 0.230 | 1.533 | 0.001 | / | / |
| 614 | 74546 | CGPG661 | SENSE | −0.052 | 0.727 | 0.777 | 0.030 | −0.226 | 1.000 |

TABLE 4-continued

| PEP SEQ ID NO | Construct ID | Nomination ID | Orientation | Drought score Delta mean | P-value | Seed yield Delta mean | P-value | Time to wilting Risk score mean | P-value |
|---|---|---|---|---|---|---|---|---|---|
| 615 | 74558 | CGPG869 | SENSE | 0.344 | 0.072 | −0.138 | 0.117 | 0.033 | 0.955 |
| 616 | 74643 | CGPG6159 | SENSE | 0.369 | 0.042 | −1.232 | 0.125 | 0.556 | 1.000 |
| 617 | 75234 | CGPG5931 | SENSE | 0.157 | 0.038 | −0.095 | 0.479 | 0.026 | 0.881 |
| 618 | 75278 | CGPG6282 | SENSE | 0.110 | 0.200 | 1.027 | 0.003 | 0.057 | 0.789 |
| 587 | 75289 | CGPG6295 | SENSE | 0.627 | 0.004 | −0.074 | 0.267 | 0.196 | 0.883 |
| 619 | 75585 | CGPG7671 | SENSE | 0.474 | 0.008 | −0.452 | 0.259 | / | / |
| 620 | 76063 | CGPG1574 | SENSE | 0.105 | 0.637 | 0.985 | 0.062 | 0.023 | 1.000 |
| 593 | 76318 | CGPG8909 | SENSE | 0.509 | 0.009 | 1.093 | 0.005 | 0.471 | 0.952 |
| 599 | 76891 | CGPG9034 | SENSE | 0.186 | 0.115 | 0.796 | 0.003 | 0.128 | 1.000 |
| 621 | 77401 | CGPG9294 | SENSE | −0.072 | 0.643 | 0.554 | 0.061 | −0.090 | 1.000 |

If p<0.05 and delta or risk score mean>0, the transgenic plants showed statistically significant trait improvement as compared to the reference (p value, of the delta of a quantitative response or of the risk score of a qualitative response, is the probability that the observed difference between the transgenic plants and the reference occur by chance) If p<0.2 and delta or risk score mean>0, the transgenic plants showed a trend of trait improvement as compared to the reference.

C. Heat Stress Tolerance Screen

Under high temperatures, *Arabidopsis* seedlings become chlorotic and root growth is inhibited. This example sets forth the heat stress tolerance screen to identify *Arabidopsis* plants transformed with the gene of interest that are more resistant to heat stress based on primarily their seedling weight and root growth under high temperature. T2 seeds were plated on ½×MS salts, 11% phytagel, with 10 µg/ml BASTA (7 per plate with 2 control seeds; 9 seeds total per plate). Plates were placed at 4° C. for 3 days to stratify seeds. Plates were then incubated at room temperature for 3 hours and then held vertically for 11 additional days at temperature of 34° C. at day and 20° C. at night. Photoperiod was 16 h. Average light intensity was ~140 µmol/m$^2$/s. After 14 days of growth, plants were scored for glufosinate resistance, root length, final growth stage, visual color, and seedling fresh weight. A photograph of the whole plate was taken on day 14.

The seedling weight and root length were analyzed as quantitative responses according to example 1M. The final grow stage at day 14 was scored as success if 50% of the plants had reached 3 rosette leaves and size of leaves are greater than 1 mm (Boyes, e.g., (2001) The Plant Cell 13, 1499-1510). The growth stage data was analyzed as a qualitative response according to example 1L. Table 5 provides a list of recombinant DNA constructs that improve heat tolerance in transgenic plants.

TABLE 5

| PEP seq id | Construct ID | Nomination ID | Orientation | Root length at day 14 | | Growth stage at day 14 | | Seedling weight at day 14 | |
|---|---|---|---|---|---|---|---|---|---|
| | | | | Delta mean | P-value | Risk score mean | P-value | Delta mean | P-value |
| 772 | 10923 | CGPG414 | ANTI-SENSE | 0.443 | 0.032 | / | / | / | / |
| 525 | 15419 | CGPG1788 | ANTI-SENSE | 0.385 | 0.040 | −0.070 | / | 0.416 | 0.076 |
| 527 | 17903 | CGPG1908 | SENSE | 0.125 | 0.091 | / | / | / | / |
| 623 | 18330 | CGPG3336 | SENSE | 0.274 | 0.174 | 1.014 | 0.310 | 1.279 | 0.012 |
| 624 | 18409 | CGPG3613 | SENSE | 0.181 | 0.098 | / | / | / | / |
| 736 | 18410 | CGPG3614 | SENSE | 0.398 | 0.094 | / | / | / | / |
| 432 | 17410 | CGPG2446 | SENSE | 0.199 | 0.067 | 0.241 | 0.304 | 0.828 | 0.271 |
| 622 | 17808 | CGPG2435 | SENSE | 0.266 | 0.040 | / | / | / | / |
| 438 | 19760 | CGPG4065 | SENSE | 0.015 | 0.771 | −0.111 | / | 1.611 | 0.005 |
| 625 | 19813 | CGPG4168 | SENSE | 0.183 | 0.088 | 0.643 | 0.344 | 0.807 | 0.038 |
| 440 | 70510 | CGPG2488 | SENSE | 0.607 | 0.056 | 0.171 | 0.184 | 0.863 | 0.021 |
| 443 | 70812 | CGPG607 | SENSE | 0.319 | 0.080 | 0.882 | 0.345 | 0.934 | 0.055 |
| 447 | 71446 | CGPG185 | SENSE | 0.427 | 0.110 | 0.184 | 0.160 | 0.470 | 0.068 |
| 452 | 72005 | CGPG5253 | SENSE | 0.209 | 0.098 | 0.331 | 0.586 | 1.178 | 0.122 |
| 545 | 72603 | CGPG646 | SENSE | 0.476 | 0.029 | −0.170 | 0.149 | 1.272 | 0.185 |
| 611 | 73619 | CGPG4375 | SENSE | 0.368 | 0.058 | 0.853 | 0.241 | 0.746 | 0.102 |
| 467 | 73662 | CGPG4927 | SENSE | 0.205 | 0.053 | / | / | / | / |
| 453 | 72026 | CGPG5231 | SENSE | 0.589 | 0.012 | / | / | / | / |
| 626 | 73580 | CGPG6517 | SENSE | −0.077 | 0.602 | −0.195 | / | 1.106 | 0.052 |
| 628 | 74124 | CGPG6631 | SENSE | 0.256 | 0.055 | 0.460 | 0.013 | 0.512 | 0.110 |
| 627 | 73935 | CGPG993 | SENSE | 0.284 | 0.089 | 1.102 | 0.262 | 1.098 | 0.115 |
| 482 | 74707 | CGPG4914 | SENSE | 0.077 | 0.680 | 0.099 | 0.745 | 0.773 | 0.058 |
| 629 | 74725 | CGPG5393 | SENSE | 0.351 | 0.038 | / | / | / | / |
| 591 | 76220 | CGPG6189 | SENSE | 0.381 | 0.039 | / | / | / | / |
| 796 | 75910 | CGPG1256 | SENSE | 0.514 | 0.081 | / | / | / | / |
| 630 | 76403 | CGPG1313 | SENSE | 0.158 | 0.075 | −0.033 | 0.864 | 0.252 | 0.581 |
| 595 | 76513 | CGPG5892 | SENSE | 0.281 | 0.051 | / | / | / | / |
| 631 | 77366 | CGPG8150 | SENSE | 0.259 | 0.044 | −0.116 | 0.058 | 0.354 | 0.369 |

TABLE 5-continued

| PEP seq id | Construct ID | Nomination ID | Orientation | Root length at day 14 Delta mean | P-value | Growth stage at day 14 Risk score mean | P-value | Seedling weight at day 14 Delta mean | P-value |
|---|---|---|---|---|---|---|---|---|---|
| 767 | 77115 | CGPG9135 | SENSE | 0.269 | 0.094 | / | / | / | / |
| 770 | 77159 | CGPG9202 | SENSE | 0.170 | 0.502 | −0.014 | 0.887 | 0.389 | 0.048 |

If $p<0.05$ and delta or risk score mean>0, the transgenic plants showed statistically significant trait improvement as compared to the reference. If $p<0.2$ and delta or risk score mean>0, the transgenic plants showed a trend of trait improvement as compared to the reference.

D. Salt Stress Tolerance Screen

This example sets forth the high salinity stress screen to identify *Arabidopsis* plants transformed with the gene of interest that are tolerant to high levels of salt based on their rate of development, root growth and chlorophyll accumulation under high salt conditions.

T2 seeds were plated on glufosinate selection plates containing 90 mM NaCl and grown under standard light and temperature conditions. All seedlings used in the experiment were grown at a temperature of 22° C. at day and 20° C. at night, a 16-hour photoperiod, an average light intensity of approximately 120 umol/m$^2$. On day 11, plants were measured for primary root length. After 3 more days of growth (day 14), plants were scored for transgenic status, primary root length, growth stage, visual color, and the seedlings were pooled for fresh weight measurement. A photograph of the whole plate was also taken on day 14.

The seedling weight and root length were analyzed as quantitative responses according to example 1M. The final growth stage at day 14 was scored as success if 50% of the plants reached 3 rosette leaves and size of leaves are greater than 1 mm (Boyes, D. C., et al., (2001), The Plant Cell 13, 1499/1510). The growth stage data was analyzed as a qualitative response according to example 1L. Table 6 provides a list of recombinant DNA constructs that improve high salinity tolerance in transgenic plants

TABLE 6

| PEP SEQ ID NO | Construct ID | Orientation | Root length at day 11 Delta mean | P-value | Root length at day 14 Delta mean | P-value | Growth stage at day 14 RS mean | P-value | Seedling weight at day 14 Delta mean | P-value |
|---|---|---|---|---|---|---|---|---|---|---|
| 800 | 16023 | SENSE | 0.333 | 0.007 | 0.308 | 0.005 | 0.400 | 0.311 | 0.469 | 0.033 |
| 801 | 16424 | ANTI-SENSE | 0.193 | 0.059 | 0.184 | 0.033 | 0.312 | 0.470 | 0.303 | 0.068 |
| 527 | 17903 | SENSE | 0.094 | 0.034 | 0.028 | 0.432 | 1.109 | 0.283 | 0.185 | 0.041 |
| 529 | 18284 | SENSE | 0.183 | 0.063 | 0.290 | 0.046 | −0.043 | 0.739 | 0.584 | 0.100 |
| 623 | 18330 | SENSE | 0.583 | 0.018 | 0.584 | 0.022 | 0.672 | 0.063 | 1.267 | 0.039 |
| 531 | 18349 | SENSE | 0.191 | 0.046 | 0.218 | 0.107 | −0.013 | 0.726 | 0.147 | 0.628 |
| 802 | 17807 | SENSE | 0.162 | 0.175 | 0.238 | 0.094 | 1.412 | 0.081 | 0.606 | 0.043 |
| 775 | 18214 | SENSE | 0.233 | 0.067 | 0.306 | 0.032 | 0.608 | 0.128 | 0.859 | 0.035 |
| 433 | 18401 | SENSE | 0.229 | 0.117 | 0.261 | 0.161 | 1.721 | 0.138 | 0.691 | 0.057 |
| 739 | 19624 | SENSE | 0.150 | 0.071 | 0.074 | 0.285 | 0.071 | 0.348 | 0.163 | 0.086 |
| 536 | 19944 | SENSE | 0.200 | 0.018 | 0.284 | 0.106 | 0.704 | 0.356 | 0.578 | 0.038 |
| 776 | 70236 | SENSE | 0.265 | 0.000 | 0.262 | 0.019 | 1.387 | 0.280 | 0.628 | 0.027 |
| 440 | 70510 | SENSE | 0.037 | 0.763 | 0.021 | 0.799 | 1.329 | 0.020 | 0.220 | 0.011 |
| 441 | 70605 | SENSE | 0.341 | 0.058 | 0.390 | 0.036 | 0.802 | 0.002 | 0.668 | 0.008 |
| 803 | 70802 | SENSE | 0.244 | 0.025 | 0.221 | 0.030 | 0.948 | 0.275 | 0.540 | 0.035 |
| 443 | 70812 | SENSE | 0.229 | 0.150 | 0.259 | 0.036 | 0.644 | 0.181 | 0.483 | 0.054 |
| 804 | 70817 | SENSE | 0.346 | 0.008 | 0.322 | 0.010 | 0.417 | 0.147 | 0.613 | 0.050 |
| 805 | 70819 | SENSE | 0.018 | 0.846 | 0.100 | 0.108 | −0.250 | 0.009 | 0.062 | 0.097 |
| 806 | 70908 | SENSE | 0.284 | 0.070 | 0.327 | 0.028 | 0.955 | 0.158 | 0.935 | 0.002 |
| 445 | 70939 | SENSE | 0.241 | 0.025 | 0.162 | 0.001 | 1.414 | 0.143 | 0.376 | 0.056 |
| 607 | 70941 | SENSE | 0.648 | 0.008 | 0.656 | 0.002 | 3.713 | 0.006 | 1.061 | 0.009 |
| 741 | 71215 | SENSE | 0.253 | 0.023 | 0.193 | 0.026 | 2.155 | 0.037 | 0.561 | 0.019 |
| 447 | 71446 | SENSE | 0.288 | 0.014 | 0.312 | 0.014 | 1.490 | 0.088 | 0.794 | 0.011 |
| 807 | 72351 | SENSE | 0.234 | 0.026 | 0.213 | 0.000 | 1.041 | 0.134 | 0.247 | 0.062 |
| 545 | 72603 | SENSE | 0.688 | 0.007 | 0.570 | 0.007 | 0.854 | 0.070 | 1.029 | 0.028 |
| 459 | 72983 | SENSE | 0.113 | 0.198 | 0.119 | 0.079 | 1.072 | 0.576 | 0.304 | 0.081 |
| 453 | 72026 | SENSE | 0.222 | 0.149 | 0.255 | 0.054 | 3.706 | 0.006 | 0.715 | 0.053 |
| 810 | 73709 | SENSE | 0.180 | 0.055 | 0.173 | 0.055 | 0.209 | 0.342 | 0.493 | 0.114 |
| 557 | 73750 | SENSE | 0.184 | 0.037 | 0.168 | 0.021 | 0.111 | 0.585 | 0.573 | 0.002 |
| 558 | 73751 | SENSE | 0.039 | 0.765 | 0.129 | 0.101 | 1.961 | 0.091 | 0.487 | 0.055 |
| 786 | 73578 | SENSE | 0.194 | 0.004 | 0.103 | 0.008 | 0.330 | 0.137 | −0.017 | 0.929 |
| 813 | 73851 | SENSE | 0.644 | 0.005 | 0.500 | 0.000 | 3.097 | 0.026 | 0.955 | 0.005 |
| 787 | 74112 | SENSE | 0.390 | 0.007 | 0.257 | 0.001 | 0.636 | 0.178 | 0.337 | 0.156 |
| 814 | 74156 | SENSE | 0.395 | 0.001 | 0.328 | 0.004 | 0.829 | 0.079 | 0.454 | 0.000 |
| 815 | 74194 | SENSE | 0.062 | 0.352 | 0.057 | 0.218 | 0.995 | 0.082 | 0.173 | 0.040 |
| 562 | 73929 | SENSE | 0.211 | 0.311 | 0.245 | 0.125 | 0.822 | 0.111 | 0.621 | 0.071 |
| 816 | 74252 | SENSE | 0.678 | 0.010 | 0.604 | 0.018 | 1.627 | 0.027 | 1.330 | 0.028 |

TABLE 6-continued

| PEP SEQ ID NO | Construct ID | Orientation | Root length at day 11 Delta mean | Root length at day 11 P-value | Root length at day 14 Delta mean | Root length at day 14 P-value | Growth stage at day 14 RS mean | Growth stage at day 14 P-value | Seedling weight at day 14 Delta mean | Seedling weight at day 14 P-value |
|---|---|---|---|---|---|---|---|---|---|---|
| 569 | 74315 | SENSE | −0.087 | 0.327 | −0.042 | 0.472 | 0.088 | 0.600 | 0.282 | 0.094 |
| 817 | 74317 | SENSE | 0.227 | 0.082 | 0.205 | 0.122 | 3.190 | 0.059 | 0.424 | 0.011 |
| 476 | 74388 | SENSE | 0.185 | 0.112 | 0.140 | 0.084 | 1.750 | 0.110 | 0.533 | 0.032 |
| 819 | 74506 | SENSE | 0.211 | 0.032 | 0.220 | 0.038 | 1.329 | 0.203 | 0.525 | 0.016 |
| 479 | 74522 | SENSE | 0.262 | 0.022 | 0.188 | 0.076 | 0.562 | 0.265 | 0.184 | 0.494 |
| 820 | 74540 | SENSE | 0.318 | 0.066 | 0.219 | 0.094 | 0.137 | 0.610 | 0.299 | 0.316 |
| 752 | 74577 | SENSE | 0.216 | 0.144 | 0.183 | 0.041 | 1.105 | 0.296 | 0.518 | 0.020 |
| 808 | 73087 | SENSE | 0.125 | 0.466 | 0.200 | 0.059 | 0.067 | 0.398 | 0.446 | 0.043 |
| 818 | 74328 | SENSE | 0.069 | 0.309 | 0.092 | 0.005 | 0.544 | 0.442 | 0.354 | 0.000 |
| 821 | 74650 | SENSE | 0.015 | 0.657 | 0.008 | 0.919 | 1.307 | 0.031 | 0.352 | 0.026 |
| 614 | 74546 | SENSE | 0.318 | 0.003 | 0.307 | 0.001 | 1.709 | 0.071 | 0.524 | 0.005 |
| 824 | 74956 | SENSE | 0.194 | 0.005 | 0.199 | 0.064 | 1.553 | 0.063 | 0.455 | 0.024 |
| 751 | 74556 | SENSE | 0.006 | 0.952 | 0.109 | 0.212 | 0.334 | 0.283 | 0.419 | 0.080 |
| 791 | 74393 | SENSE | 0.410 | 0.023 | 0.384 | 0.057 | 0.656 | 0.002 | 0.696 | 0.020 |
| 826 | 75255 | SENSE | −0.002 | 0.984 | 0.033 | 0.689 | 0.518 | 0.504 | 0.490 | 0.093 |
| 827 | 75269 | SENSE | 0.122 | 0.095 | 0.095 | 0.278 | 1.520 | 0.292 | 0.519 | 0.046 |
| 587 | 75289 | SENSE | 0.218 | 0.001 | 0.213 | 0.024 | 2.926 | 0.112 | 0.543 | 0.021 |
| 809 | 73223 | SENSE | 0.340 | 0.140 | 0.249 | 0.179 | 0.420 | 0.351 | 0.729 | 0.073 |
| 784 | 73283 | SENSE | 0.128 | 0.292 | 0.320 | 0.200 | −0.006 |  | 0.682 | 0.032 |
| 811 | 73804 | SENSE | 0.174 | 0.069 | 0.090 | 0.328 | 0.140 | 0.536 | 0.095 | 0.609 |
| 559 | 73814 | SENSE | 0.135 | 0.100 | 0.185 | 0.082 | 0.800 | 0.293 | 0.375 | 0.104 |
| 812 | 73819 | SENSE | 0.344 | 0.017 | 0.321 | 0.021 | 2.159 | 0.117 | 0.672 | 0.027 |
| 471 | 73863 | SENSE | 0.335 | 0.030 | 0.251 | 0.041 | 1.905 | 0.220 | 0.563 | 0.050 |
| 472 | 74059 | SENSE | 0.265 | 0.039 | 0.293 | 0.022 | −0.146 | 0.035 | 0.298 | 0.161 |
| 746 | 74080 | SENSE | 0.107 | 0.509 | 0.130 | 0.133 | 1.101 | 0.293 | 0.584 | 0.071 |
| 482 | 74707 | SENSE | 0.544 | 0.029 | 0.623 | 0.013 | 0.966 | 0.104 | 1.122 | 0.007 |
| 822 | 74718 | SENSE | 0.289 | 0.111 | 0.382 | 0.021 | 0.648 | 0.404 | 0.646 | 0.112 |
| 580 | 74733 | SENSE | 0.152 | 0.138 | 0.129 | 0.095 | 0.190 | 0.685 | 0.220 | 0.338 |
| 823 | 74745 | SENSE | 0.166 | 0.035 | 0.123 | 0.240 | 1.102 | 0.100 | 0.580 | 0.014 |
| 581 | 74749 | SENSE | 0.444 | 0.048 | 0.478 | 0.010 | 0.796 | 0.173 | 1.076 | 0.008 |
| 582 | 74752 | SENSE | 0.260 | 0.310 | 0.450 | 0.088 | 0.467 | 0.284 | 0.947 | 0.022 |
| 754 | 74753 | SENSE | −0.058 | 0.235 | 0.082 | 0.326 |  |  | 0.330 | 0.005 |
| 755 | 74754 | SENSE | 0.230 | 0.088 | 0.228 | 0.077 | 0.966 | 0.353 | 0.407 | 0.118 |
| 484 | 74755 | SENSE | 0.070 | 0.574 | −0.020 | 0.470 | 0.265 | 0.208 | 0.455 | 0.073 |
| 493 | 75355 | SENSE | 0.290 | 0.057 | 0.305 | 0.000 | 0.440 | 0.425 | 0.360 | 0.301 |
| 828 | 75432 | SENSE | 0.249 | 0.020 | 0.178 | 0.100 | 0.475 | 0.196 | 0.216 | 0.454 |
| 829 | 75468 | SENSE | 0.146 | 0.344 | 0.185 | 0.054 | 1.373 | 0.268 | 0.311 | 0.141 |
| 794 | 75752 | SENSE | 0.402 | 0.058 | 0.394 | 0.049 | 0.521 | 0.335 | 0.672 | 0.027 |
| 760 | 75931 | SENSE | 0.104 | 0.239 | 0.074 | 0.433 | 1.121 | 0.209 | 0.321 | 0.069 |
| 832 | 76064 | SENSE | 0.349 | 0.011 | 0.270 | 0.046 | 0.152 | 0.360 | 0.250 | 0.295 |
| 797 | 76101 | SENSE | 0.527 | 0.064 | 0.542 | 0.107 | 0.724 | 0.367 | 1.480 | 0.024 |
| 833 | 76121 | SENSE | −0.026 | 0.849 | 0.019 | 0.829 | 2.841 | 0.059 | 0.069 | 0.822 |
| 834 | 76193 | SENSE | 0.262 | 0.020 | 0.254 | 0.021 | 0.834 | 0.097 | 0.441 | 0.054 |
| 835 | 76237 | SENSE | 0.334 | 0.098 | 0.365 | 0.047 | 0.727 | 0.042 | 0.786 | 0.137 |
| 836 | 76281 | SENSE | 0.167 | 0.154 | 0.181 | 0.184 | 0.572 | 0.096 | 0.598 | 0.092 |
| 762 | 76293 | SENSE | 0.042 | 0.763 | −0.044 | 0.776 | 0.769 | 0.270 | 0.610 | 0.017 |
| 831 | 75911 | SENSE | 0.179 | 0.041 | 0.143 | 0.083 | 1.508 | 0.266 | 0.464 | 0.001 |
| 830 | 75686 | SENSE | 0.378 | 0.036 | 0.358 | 0.039 | 1.039 | 0.057 | 0.666 | 0.014 |
| 837 | 76388 | SENSE | 0.209 | 0.054 | 0.163 | 0.136 | 0.853 | 0.367 | 0.485 | 0.013 |
| 838 | 76557 | SENSE | 0.165 | 0.042 | 0.104 | 0.095 | 1.943 | 0.027 | 0.395 | 0.031 |
| 839 | 76567 | SENSE | −0.046 | 0.551 | 0.067 | 0.196 | 1.685 | 0.108 | 0.273 | 0.053 |
| 507 | 76575 | SENSE | 0.101 | 0.302 | 0.183 | 0.067 | 0.121 | 0.496 | 0.298 | 0.306 |
| 840 | 76624 | SENSE | 0.399 | 0.047 | 0.367 | 0.041 | 0.652 | 0.122 | 0.622 | 0.069 |
| 597 | 76719 | SENSE | 0.229 | 0.051 | 0.140 | 0.317 | 0.726 | 0.330 | 0.487 | 0.083 |
| 841 | 76764 | SENSE | 0.482 | 0.036 | 0.376 | 0.036 | 2.259 | 0.163 | 0.670 | 0.127 |
| 825 | 75076 | SENSE | 0.186 | 0.139 | 0.233 | 0.016 | 2.197 | 0.062 | 0.538 | 0.031 |
| 843 | 76976 | SENSE | 0.455 | 0.013 | 0.375 | 0.044 | 3.499 | 0.020 | 0.737 | 0.007 |
| 844 | 76985 | SENSE | 0.313 | 0.050 | 0.299 | 0.037 | 3.310 | 0.041 | 0.587 | 0.048 |
| 842 | 76855 | SENSE | 0.463 | 0.026 | 0.636 | 0.010 | 0.188 | 0.020 | 1.334 | 0.001 |
| 599 | 76891 | SENSE | 0.325 | 0.000 | 0.368 | 0.003 | 0.445 | 0.087 | 0.795 | 0.003 |
| 845 | 77014 | SENSE | 0.005 | 0.889 | −0.040 | 0.597 | 0.024 | 0.932 | 0.265 | 0.098 |
| 522 | 77351 | SENSE | 0.392 | 0.048 | 0.454 | 0.014 | 2.912 | 0.052 | 1.340 | 0.006 |
| 631 | 77366 | SENSE | 0.214 | 0.007 | 0.159 | 0.017 | 0.205 | 0.076 | 0.382 | 0.029 |
| 846 | 77112 | SENSE | −0.001 | 0.986 | 0.020 | 0.801 | 1.640 | 0.020 | 0.583 | 0.025 |
| 847 | 77117 | SENSE | 0.219 | 0.058 | 0.234 | 0.116 | 1.406 | 0.172 | 0.516 | 0.072 |
| 768 | 77128 | SENSE | 0.239 | 0.020 | 0.312 | 0.019 | 0.324 | 0.523 | 0.470 | 0.028 |
| 520 | 77135 | SENSE | 0.153 | 0.070 | 0.133 | 0.059 | 0.386 | 0.503 | 0.344 | 0.064 |
| 848 | 77138 | SENSE | 0.171 | 0.030 | 0.271 | 0.012 | 1.211 | 0.256 | 0.482 | 0.035 |
| 770 | 77159 | SENSE | 0.188 | 0.115 | 0.220 | 0.110 | 1.176 | 0.381 | 0.589 | 0.039 |
| 600 | 77208 | SENSE | 0.321 | 0.075 | 0.254 | 0.154 | 0.183 | 0.578 | 0.540 | 0.059 |
| 521 | 77219 | SENSE | 0.297 | 0.090 | 0.413 | 0.018 | 2.299 | 0.024 | 1.010 | 0.014 |
| 849 | 77226 | SENSE | 0.164 | 0.193 | 0.098 | 0.413 | 1.279 | 0.142 | 0.264 | 0.043 |

TABLE 6-continued

| PEP SEQ ID NO | Construct ID | Orientation | Root length at day 11 | | Root length at day 14 | | Growth stage at day 14 | | Seedling weight at day 14 | |
|---|---|---|---|---|---|---|---|---|---|---|
| | | | Delta mean | P-value | Delta mean | P-value | RS mean | P-value | Delta mean | P-value |
| 621 | 77401 | SENSE | 0.317 | 0.068 | 0.274 | 0.018 | 1.134 | 0.258 | 0.502 | 0.213 |
| 850 | 77418 | SENSE | 0.204 | 0.096 | 0.201 | 0.110 | 0.344 | 0.184 | 0.626 | 0.005 |

If $p<0.05$ and delta or risk score mean$>0$, the transgenic plants showed statistically significant trait improvement as compared to the reference. If $p<0.2$ and delta or risk score mean$>0$, the transgenic plants showed a trend of trait improvement as compared to the reference.

E. Polyethylene Glycol (PEG) Induced Osmotic Stress Tolerance Screen

There are numerous factors, which can influence seed germination and subsequent seedling growth, one being the availability of water. Genes, which can directly affect the success rate of germination and early seedling growth, are potentially useful agronomic traits for improving the germination and growth of crop plants under drought stress. In this assay, PEG was used to induce osmotic stress on germinating transgenic lines of *Arabidopsis thaliana* seeds in order to screen for osmotically resistant seed lines.

T2 seeds were plated on BASTA selection plates containing 3% PEG and grown under standard light and temperature conditions. Seeds were plated on each plate containing 3% PEG, ½×MS salts, 1% phytagel, and 10 μg/ml glufosinate. Plates were placed at 4° C. for 3 days to stratify seeds. On day 11, plants were measured for primary root length. After 3 more days of growth, i.e., at day 14, plants were scored for transgenic status, primary root length, growth stage, visual color, and the seedlings were pooled for fresh weight measurement. A photograph of the whole plate was taken on day 14.

Seedling weight and root length were analyzed as quantitative responses according to example 1M. The final growth stage at day 14 was scored as success or failure based on whether the plants reached 3 rosette leaves and size of leaves are greater than 1 mm. The growth stage data was analyzed as a qualitative response according to example 1L. Table 7 provides a list of recombinant DNA constructs that improve osmotic stress tolerance in transgenic plants.

TABLE 7

| PEP SEQ ID NO | Construct ID | Orientation | Root length at day 11 | | Root length at day 14 | | Growth stage at day 14 | | Seedling weight at day 14 | |
|---|---|---|---|---|---|---|---|---|---|---|
| | | | Delta mean | P-value | Delta mean | P-value | RS mean | P-value | Delta mean | P-value |
| 694 | 10443 | ANTI-SENSE | 0.162 | 0.251 | 0.127 | 0.118 | 3.475 | 0.022 | 0.547 | 0.157 |
| 772 | 10923 | ANTI-SENSE | 0.235 | 0.033 | 0.332 | 0.010 | 3.496 | 0.020 | 0.284 | 0.098 |
| 524 | 14835 | ANTI-SENSE | 0.195 | 0.134 | 0.126 | 0.173 | 1.477 | 0.362 | 0.300 | 0.050 |
| 773 | 14836 | SENSE | 0.210 | 0.159 | 0.037 | 0.707 | 2.867 | 0.040 | 0.205 | 0.332 |
| 801 | 16424 | ANTI-SENSE | 0.309 | 0.055 | 0.201 | 0.210 | 2.261 | 0.150 | 0.375 | 0.012 |
| 530 | 18332 | SENSE | 0.129 | 0.095 | 0.141 | 0.028 | 2.205 | 0.134 | 0.062 | 0.379 |
| 737 | 18536 | SENSE | 0.214 | 0.036 | 0.228 | 0.065 | 3.062 | 0.082 | 0.323 | 0.153 |
| 696 | 18537 | SENSE | 0.206 | 0.030 | 0.197 | 0.034 | 2.641 | 0.076 | 0.399 | 0.112 |
| 697 | 18831 | SENSE | 0.002 | 0.988 | 0.030 | 0.828 | 3.243 | 0.050 | −0.170 | 0.134 |
| 698 | 19044 | ANTI-SENSE | 0.300 | 0.082 | 0.220 | 0.006 | 2.465 | 0.113 | 0.284 | 0.113 |
| 695 | 17814 | SENSE | 0.215 | 0.056 | 0.057 | 0.542 | 4.000 | 0.000 | 0.573 | 0.004 |
| 433 | 18401 | SENSE | 0.229 | 0.017 | 0.143 | 0.252 | 1.670 | 0.065 | 0.503 | 0.004 |
| 532 | 18623 | SENSE | 0.246 | 0.028 | 0.205 | 0.050 | 1.836 | 0.002 | 0.356 | 0.009 |
| 739 | 19624 | SENSE | 0.088 | 0.232 | −0.011 | 0.867 | 1.317 | 0.075 | 0.458 | 0.135 |
| 699 | 19950 | SENSE | 0.225 | 0.119 | 0.214 | 0.072 | 3.393 | 0.030 | 0.335 | 0.078 |
| 700 | 70221 | SENSE | 0.148 | 0.179 | 0.076 | 0.152 | 3.183 | 0.060 | 0.351 | 0.088 |
| 776 | 70236 | SENSE | 0.094 | 0.489 | 0.115 | 0.414 | 2.368 | 0.033 | 0.116 | 0.179 |
| 441 | 70605 | SENSE | 0.423 | 0.020 | 0.355 | 0.042 | 3.087 | 0.021 | 0.588 | 0.075 |
| 803 | 70802 | SENSE | 0.182 | 0.345 | 0.089 | 0.596 | 3.228 | 0.053 | 0.183 | 0.477 |
| 780 | 70804 | SENSE | 0.244 | 0.053 | 0.108 | 0.207 | 2.514 | 0.233 | 0.434 | 0.011 |
| 539 | 70830 | SENSE | 0.226 | 0.030 | 0.064 | 0.387 | 0.914 | 0.354 | 0.272 | 0.028 |
| 445 | 70939 | SENSE | 0.086 | 0.396 | −0.040 | 0.508 | 3.390 | 0.031 | 0.335 | 0.058 |
| 701 | 71110 | SENSE | −0.206 | 0.153 | −0.164 | 0.212 | 1.410 | 0.018 | −0.318 | 0.079 |
| 741 | 71215 | SENSE | 0.337 | 0.025 | 0.152 | 0.047 | 2.979 | 0.000 | 0.566 | 0.032 |
| 447 | 71446 | SENSE | 0.263 | 0.003 | 0.129 | 0.155 | 2.672 | 0.057 | 0.500 | 0.011 |
| 702 | 71718 | SENSE | 0.197 | 0.031 | 0.257 | 0.036 | 3.310 | 0.041 | 0.189 | 0.137 |
| 703 | 71838 | SENSE | 0.234 | 0.039 | 0.260 | 0.016 | 3.164 | 0.063 | 0.079 | 0.583 |
| 704 | 72087 | SENSE | 0.242 | 0.052 | 0.216 | 0.060 | 4.000 | 0.000 | 0.299 | 0.177 |
| 543 | 72352 | SENSE | 0.194 | 0.185 | 0.259 | 0.053 | 1.666 | 0.069 | 0.227 | 0.080 |
| 544 | 72413 | SENSE | 0.082 | 0.241 | 0.158 | 0.024 | 3.196 | 0.058 | −0.040 | 0.748 |
| 545 | 72603 | SENSE | 0.178 | 0.197 | 0.180 | 0.208 | 3.093 | 0.076 | 0.127 | 0.489 |
| 455 | 72637 | SENSE | 0.247 | 0.002 | 0.197 | 0.017 | 3.274 | 0.046 | 0.348 | 0.041 |

TABLE 7-continued

| PEP SEQ ID NO | Construct ID | Orientation | Root length at day 11 Delta mean | P-value | Root length at day 14 Delta mean | P-value | Growth stage at day 14 RS mean | P-value | Seedling weight at day 14 Delta mean | P-value |
|---|---|---|---|---|---|---|---|---|---|---|
| 546 | 72676 | SENSE | 0.141 | 0.015 | 0.181 | 0.094 | 4.000 | 0.000 | 0.301 | 0.017 |
| 705 | 72729 | SENSE | 0.402 | 0.017 | 0.242 | 0.001 | 2.119 | 0.090 | 0.568 | 0.005 |
| 783 | 72824 | SENSE | 0.166 | 0.281 | 0.349 | 0.071 | 2.355 | 0.107 | 0.278 | 0.212 |
| 610 | 72978 | SENSE | 0.190 | 0.112 | 0.304 | 0.032 | 1.328 | 0.494 | −0.047 | 0.654 |
| 706 | 73302 | SENSE | 0.400 | 0.001 | 0.346 | 0.026 | 3.489 | 0.021 | 0.497 | 0.010 |
| 744 | 73666 | SENSE | 0.361 | 0.017 | 0.177 | 0.258 | 3.488 | 0.021 | 0.757 | 0.008 |
| 810 | 73709 | SENSE | 0.222 | 0.041 | 0.130 | 0.258 | 2.104 | 0.106 | 0.426 | 0.009 |
| 709 | 73736 | SENSE | 0.275 | 0.026 | 0.210 | 0.006 | 2.536 | 0.115 | 0.378 | 0.112 |
| 551 | 73031 | SENSE | 0.095 | 0.109 | 0.201 | 0.033 | 3.122 | 0.019 | 0.178 | 0.262 |
| 707 | 73484 | SENSE | 0.365 | 0.104 | 0.185 | 0.315 | 2.980 | 0.029 | 0.489 | 0.017 |
| 786 | 73578 | SENSE | 0.113 | 0.118 | 0.125 | 0.209 | 2.516 | 0.083 | 0.156 | 0.251 |
| 708 | 73594 | SENSE | 0.087 | 0.625 | 0.183 | 0.201 | 1.230 | 0.041 | 0.140 | 0.232 |
| 627 | 73935 | SENSE | 0.378 | 0.000 | 0.261 | 0.037 | 3.484 | 0.021 | 0.489 | 0.023 |
| 711 | 74266 | SENSE | −0.005 | 0.943 | −0.050 | 0.648 | 2.571 | 0.074 | 0.287 | 0.074 |
| 789 | 74278 | SENSE | 0.145 | 0.299 | 0.134 | 0.452 | 3.666 | 0.008 | 0.350 | 0.140 |
| 790 | 74359 | SENSE | 0.365 | 0.026 | 0.291 | 0.112 | 2.220 | 0.053 | 0.351 | 0.030 |
| 792 | 74414 | SENSE | 0.310 | 0.035 | 0.272 | 0.054 | 2.515 | 0.037 | 0.323 | 0.015 |
| 479 | 74522 | SENSE | 0.224 | 0.077 | 0.169 | 0.016 | 2.547 | 0.086 | 0.178 | 0.333 |
| 750 | 74539 | SENSE | 0.327 | 0.102 | 0.197 | 0.371 | 3.356 | 0.012 | 0.496 | 0.011 |
| 820 | 74540 | SENSE | 0.290 | 0.007 | 0.376 | 0.013 | 3.350 | 0.036 | 0.458 | 0.096 |
| 714 | 74574 | SENSE | 0.236 | 0.096 | 0.155 | 0.053 | 2.448 | 0.255 | 0.179 | 0.475 |
| 715 | 74607 | SENSE | 0.274 | 0.007 | 0.285 | 0.004 | 2.783 | 0.053 | 0.341 | 0.007 |
| 716 | 74642 | SENSE | 0.386 | 0.022 | 0.273 | 0.089 | 2.308 | 0.009 | 0.378 | 0.141 |
| 615 | 74558 | SENSE | 0.184 | 0.012 | 0.053 | 0.528 | 2.052 | 0.036 | 0.097 | 0.259 |
| 751 | 74556 | SENSE | 0.258 | 0.186 | 0.160 | 0.362 | 2.253 | 0.042 | 0.477 | 0.059 |
| 488 | 75231 | SENSE | 0.035 | 0.555 | 0.061 | 0.577 | 3.350 | 0.036 | 0.253 | 0.059 |
| 617 | 75234 | SENSE | 0.053 | 0.310 | 0.018 | 0.240 | 3.273 | 0.046 | 0.197 | 0.096 |
| 587 | 75289 | SENSE | 0.226 | 0.032 | 0.245 | 0.019 | 3.458 | 0.024 | 0.506 | 0.052 |
| 785 | 73292 | SENSE | −0.003 | 0.956 | 0.008 | 0.746 | 2.088 | 0.079 | 0.274 | 0.120 |
| 811 | 73804 | SENSE | 0.305 | 0.051 | 0.273 | 0.170 | 2.250 | 0.150 | 0.377 | 0.021 |
| 717 | 75015 | SENSE | −0.036 | 0.360 | −0.065 | 0.167 | 3.362 | 0.034 | 0.111 | 0.227 |
| 710 | 74016 | SENSE | 0.176 | 0.019 | 0.207 | 0.007 | 2.898 | 0.035 | 0.255 | 0.133 |
| 564 | 74072 | SENSE | 0.025 | 0.522 | 0.027 | 0.699 | 3.304 | 0.042 | 0.109 | 0.274 |
| 712 | 74479 | SENSE | 0.059 | 0.362 | 0.152 | 0.184 | 2.226 | 0.130 | 0.226 | 0.076 |
| 571 | 74490 | SENSE | 0.002 | 0.956 | 0.097 | 0.405 | 3.332 | 0.038 | 0.268 | 0.136 |
| 713 | 74549 | SENSE | 0.152 | 0.027 | 0.069 | 0.254 | 3.392 | 0.031 | 0.244 | 0.056 |
| 482 | 74707 | SENSE | 0.322 | 0.002 | 0.148 | 0.040 | 2.228 | 0.164 | 0.392 | 0.021 |
| 822 | 74718 | SENSE | 0.248 | 0.176 | 0.188 | 0.320 | 3.180 | 0.061 | 0.630 | 0.091 |
| 580 | 74733 | SENSE | 0.207 | 0.021 | 0.216 | 0.036 | 4.000 | 0.000 | 0.156 | 0.062 |
| 582 | 74752 | SENSE | −0.020 | 0.679 | −0.035 | 0.616 | 1.181 | 0.182 | 0.188 | 0.054 |
| 484 | 74755 | SENSE | 0.517 | 0.002 | 0.386 | 0.016 | 4.000 | 0.000 | 0.686 | 0.005 |
| 718 | 75380 | SENSE | 0.038 | 0.789 | −0.045 | 0.789 | 3.336 | 0.037 | 0.135 | 0.401 |
| 720 | 75765 | SENSE | 0.256 | 0.182 | 0.165 | 0.185 | 2.481 | 0.244 | 0.445 | 0.035 |
| 795 | 75867 | SENSE | −0.430 | 0.150 | −0.192 | 0.321 | 0.708 | 0.082 | −0.315 | 0.193 |
| 719 | 75560 | SENSE | 0.089 | 0.012 | 0.107 | 0.281 | 1.805 | 0.144 | 0.125 | 0.416 |
| 794 | 75752 | SENSE | 0.236 | 0.022 | 0.217 | 0.003 | 2.872 | 0.036 | 0.332 | 0.017 |
| 721 | 75977 | SENSE | 0.148 | 0.019 | 0.169 | 0.012 | 3.354 | 0.035 | 0.069 | 0.615 |
| 499 | 75984 | SENSE | 0.389 | 0.049 | 0.237 | 0.199 | 2.581 | 0.098 | 0.501 | 0.064 |
| 722 | 76052 | SENSE | 0.133 | 0.135 | 0.095 | 0.201 | 3.291 | 0.043 | 0.274 | 0.266 |
| 642 | 76061 | SENSE | 0.006 | 0.945 | 0.032 | 0.601 | 1.860 | 0.002 | 0.036 | 0.606 |
| 723 | 76109 | SENSE | 0.284 | 0.026 | 0.162 | 0.082 | 2.427 | 0.263 | 0.481 | 0.009 |
| 724 | 76116 | SENSE | 0.264 | 0.066 | 0.218 | 0.018 | 1.973 | 0.220 | 0.304 | 0.309 |
| 725 | 76158 | SENSE | 0.230 | 0.016 | 0.279 | 0.051 | 2.217 | 0.160 | −0.038 | 0.034 |
| 726 | 76232 | SENSE | 0.170 | 0.133 | 0.159 | 0.071 | 1.626 | 0.203 | 0.294 | 0.060 |
| 727 | 76269 | SENSE | 0.281 | 0.030 | 0.304 | 0.034 | 3.131 | 0.069 | 0.243 | 0.096 |
| 496 | 75907 | SENSE | 0.196 | 0.063 | 0.063 | 0.324 | 0.875 | 0.462 | 0.259 | 0.122 |
| 796 | 75910 | SENSE | 0.196 | 0.135 | 0.246 | 0.025 | 2.591 | 0.069 | 0.357 | 0.009 |
| 641 | 75975 | SENSE | 0.285 | 0.114 | 0.307 | 0.256 | 3.032 | 0.088 | 0.485 | 0.063 |
| 762 | 76293 | SENSE | 0.212 | 0.059 | −0.018 | 0.602 | 3.456 | 0.024 | 0.525 | 0.053 |
| 728 | 76303 | SENSE | −0.023 | 0.677 | 0.168 | 0.007 | 2.556 | 0.079 | 0.076 | 0.171 |
| 729 | 76474 | SENSE | 0.286 | 0.038 | 0.277 | 0.046 | 3.590 | 0.013 | 0.424 | 0.047 |
| 630 | 76403 | SENSE | 0.163 | 0.047 | 0.110 | 0.085 | 2.768 | 0.154 | 0.185 | 0.318 |
| 730 | 76529 | SENSE | 0.232 | 0.213 | 0.382 | 0.040 | 2.989 | 0.098 | −0.084 | 0.591 |
| 838 | 76557 | SENSE | 0.056 | 0.461 | 0.046 | 0.675 | 3.376 | 0.033 | 0.249 | 0.045 |
| 595 | 76513 | SENSE | 0.120 | 0.072 | 0.126 | 0.062 | 1.867 | 0.292 | 0.035 | 0.463 |
| 731 | 76625 | SENSE | 0.091 | 0.042 | 0.123 | 0.011 | 3.184 | 0.060 | 0.200 | 0.024 |
| 509 | 76741 | SENSE | −0.022 | 0.760 | 0.226 | 0.018 | 2.136 | 0.002 | −0.231 | 0.026 |
| 732 | 76759 | SENSE | −0.105 | 0.298 | −0.115 | 0.233 | 2.647 | 0.060 | −0.037 | 0.672 |
| 841 | 76764 | SENSE | 0.082 | 0.410 | −0.022 | 0.862 | 4.000 | 0.000 | 0.230 | 0.045 |
| 514 | 76917 | SENSE | 0.305 | 0.073 | 0.275 | 0.066 | 3.294 | 0.043 | 0.387 | 0.027 |
| 765 | 76804 | SENSE | 0.123 | 0.131 | 0.072 | 0.462 | 2.766 | 0.046 | 0.468 | 0.028 |
| 599 | 76891 | SENSE | 0.377 | 0.014 | 0.318 | 0.058 | 4.000 | 0.000 | 0.676 | 0.036 |
| 845 | 77014 | SENSE | 0.010 | 0.673 | 0.099 | 0.050 | 2.138 | 0.175 | −0.063 | 0.668 |
| 733 | 77026 | SENSE | 0.458 | 0.024 | 0.329 | 0.003 | 1.410 | 0.109 | 0.752 | 0.031 |

TABLE 7-continued

| PEP SEQ ID NO | Construct ID | Orientation | Root length at day 11 Delta mean | P-value | Root length at day 14 Delta mean | P-value | Growth stage at day 14 RS mean | P-value | Seedling weight at day 14 Delta mean | P-value |
|---|---|---|---|---|---|---|---|---|---|---|
| 685 | 77055 | SENSE | 0.636 | 0.026 | 0.512 | 0.016 | 4.000 | 0.000 | 0.536 | 0.061 |
| 522 | 77351 | SENSE | 0.137 | 0.055 | 0.116 | 0.023 | 2.509 | 0.096 | 0.738 | 0.009 |
| 767 | 77115 | SENSE | 0.301 | 0.032 | 0.234 | 0.062 | 4.000 | 0.000 | 0.855 | 0.005 |
| 734 | 77131 | SENSE | 0.251 | 0.081 | 0.211 | 0.005 | 1.240 | 0.394 | 0.169 | 0.340 |
| 769 | 77158 | SENSE | 0.258 | 0.149 | 0.223 | 0.193 | 4.000 | 0.000 | 0.519 | 0.045 |
| 770 | 77159 | SENSE | 0.054 | 0.713 | −0.101 | 0.107 | 3.028 | 0.089 | 0.481 | 0.112 |
| 521 | 77219 | SENSE | 0.187 | 0.242 | 0.207 | 0.103 | 1.728 | 0.268 | 0.419 | 0.022 |
| 849 | 77226 | SENSE | 0.353 | 0.033 | 0.373 | 0.016 | 4.000 | 0.000 | 0.542 | 0.022 |
| 621 | 77401 | SENSE | 0.264 | 0.045 | 0.174 | 0.196 | 3.288 | 0.044 | 0.404 | 0.003 |
| 850 | 77418 | SENSE | 0.210 | 0.089 | 0.132 | 0.222 | 3.024 | 0.090 | 0.440 | 0.027 |

If p<0.05 and delta or risk score mean>0, the transgenic plants showed statistically significant trait improvement as compared to the reference.

If p<0.2 and delta or risk score mean>0, the transgenic plants showed a trend of trait improvement as compared to the reference.

F. Cold Shock Tolerance Screen

This example set forth a screen to identify *Arabidopsis* plants transformed with the genes of interest that are more tolerant to cold stress subjected during day 8 to day 28 after seed planting. During these crucial early stages, seedling growth and leaf area increase were measured to assess tolerance when *Arabidopsis* seedlings were exposed to low temperatures. Using this screen, genetic alterations can be found that enable plants to germinate and grow better than wild type plants under sudden exposure to low temperatures.

Eleven seedlings from T2 seeds of each transgenic line plus one control line were plated together on a plate containing ½× Gamborg Salts with 0.8 Phytagel™, 1% Phytagel, and 0.3% Sucrose. Plates were then oriented horizontally and stratified for three days at 4° C. At day three, plates were removed from stratification and exposed to standard conditions (16 hr photoperiod, 22° C. at day and 20° C. at night) until day 8. At day eight, plates were removed from standard conditions and exposed to cold shock conditions (24 hr photoperiod, 8° C. at both day and night) until the final day of the assay, i.e., day 28. Rosette areas were measured at day 8 and day 28, which were analyzed as quantitative responses according to example 1M. Table 8 provides a list of recombinant nucleotides that improve cold shock stress tolerance in plants.

TABLE 8

| PEP SEQ ID NO | Construct ID | Nomination ID | Orientation | Rosette area at day 8 Delta mean | P-value | Rosette area at day 28 Risk score mean | P-value | Rosette area difference Delta mean | P-value |
|---|---|---|---|---|---|---|---|---|---|
| 426 | 10919 | CGPG699 | ANTI-SENSE | 0.437 | 0.036 | 0.247 | 0.108 | 0.265 | 0.013 |
| 428 | 11310 | CGPG267 | ANTI-SENSE | 0.224 | 0.560 | 0.497 | 0.218 | 0.832 | 0.055 |
| 429 | 11866 | CGPG1179 | ANTI-SENSE | 0.354 | 0.018 | 0.422 | 0.090 | 0.428 | 0.073 |
| 430 | 11937 | CGPG959 | ANTI-SENSE | −0.510 | 0.004 | −0.010 | 0.939 | 0.331 | 0.048 |
| 773 | 14836 | CGPG1072 | SENSE | 0.862 | 0.055 | 0.187 | 0.379 | 0.147 | 0.611 |
| 432 | 17410 | CGPG2446 | SENSE | 0.282 | 0.076 | 0.397 | 0.170 | 0.536 | 0.246 |
| 433 | 18401 | CGPG1862 | SENSE | 0.134 | 0.597 | 0.801 | 0.008 | 0.582 | 0.009 |
| 434 | 18665 | CGPG3014 | SENSE | 1.273 | 0.026 | 1.142 | 0.003 | 1.215 | 0.004 |
| 427 | 11142 | CGPG567 | SENSE | 0.916 | 0.053 | 0.255 | 0.234 | 0.048 | 0.792 |
| 431 | 16218 | CGPG2158 | SENSE | 0.443 | 0.278 | 0.475 | 0.081 | 0.501 | 0.074 |
| 435 | 19141 | CGPG1674 | SENSE | 0.901 | 0.002 | 0.935 | 0.000 | 0.956 | 0.000 |
| 436 | 19156 | CGPG2680 | SENSE | −0.483 | 0.002 | 0.610 | 0.002 | 0.576 | 0.052 |
| 437 | 19621 | CGPG3577 | SENSE | 0.231 | 0.388 | 1.265 | 0.058 | 1.486 | 0.059 |
| 438 | 19760 | CGPG4065 | SENSE | 0.759 | 0.043 | 0.833 | 0.029 | 0.983 | 0.021 |
| 439 | 19857 | CGPG3929 | SENSE | 0.060 | 0.931 | 0.766 | 0.090 | 0.853 | 0.097 |
| 440 | 70510 | CGPG2488 | SENSE | 0.591 | 0.010 | 0.146 | 0.520 | −0.009 | 0.978 |
| 441 | 70605 | CGPG3012 | SENSE | 0.442 | 0.088 | −0.167 | 0.612 | −0.624 | 0.107 |
| 442 | 70607 | CGPG3162 | SENSE | 0.747 | 0.209 | 1.688 | 0.001 | 1.929 | 0.001 |
| 443 | 70812 | CGPG607 | SENSE | 0.767 | 0.126 | 0.823 | 0.091 | 1.442 | 0.149 |
| 781 | 70821 | CGPG345 | SENSE | 0.523 | 0.039 | 0.380 | 0.019 | 0.584 | 0.070 |
| 444 | 70933 | CGPG4084 | SENSE | 0.506 | 0.071 | 1.352 | 0.009 | 1.660 | 0.012 |
| 445 | 70939 | CGPG3917 | SENSE | 0.310 | 0.057 | 1.473 | 0.012 | 1.787 | 0.014 |
| 779 | 70674 | CGPG4492 | SENSE | 0.060 | 0.625 | 1.600 | 0.013 | 1.904 | 0.012 |
| 446 | 71319 | CGPG4414 | SENSE | 0.292 | 0.299 | 0.516 | 0.089 | 0.494 | 0.090 |
| 447 | 71446 | CGPG185 | SENSE | 0.740 | 0.040 | 0.508 | 0.034 | 0.304 | 0.053 |
| 448 | 71609 | CGPG1679 | SENSE | 0.373 | 0.408 | 1.184 | 0.076 | 1.318 | 0.073 |
| 449 | 71649 | CGPG271 | SENSE | 0.652 | 0.037 | 0.656 | 0.157 | 1.012 | 0.060 |
| 450 | 71814 | CGPG4434 | SENSE | 0.311 | 0.066 | 0.548 | 0.006 | 0.498 | 0.008 |

TABLE 8-continued

| PEP SEQ ID NO | Construct ID | Nomination ID | Orientation | Rosette area at day 8 | | Rosette area at day 28 | | Rosette area difference | |
|---|---|---|---|---|---|---|---|---|---|
| | | | | Delta mean | P-value | Risk score mean | P-value | Delta mean | P-value |
| 451 | 71945 | CGPG2198 | SENSE | −0.140 | 0.232 | 0.603 | 0.013 | 0.755 | 0.011 |
| 452 | 72005 | CGPG5253 | SENSE | 0.369 | 0.180 | 1.152 | 0.012 | 1.410 | 0.015 |
| 782 | 72505 | CGPG4786 | SENSE | 0.487 | 0.021 | 0.632 | 0.086 | 0.714 | 0.077 |
| 454 | 72533 | CGPG4815 | SENSE | 0.099 | 0.817 | 0.286 | 0.087 | 0.158 | 0.077 |
| 455 | 72637 | CGPG4859 | SENSE | −0.231 | 0.461 | 0.641 | 0.034 | 0.698 | 0.025 |
| 456 | 72782 | CGPG1589 | SENSE | 1.087 | 0.013 | 0.655 | 0.050 | 0.274 | 0.208 |
| 457 | 72794 | CGPG1826 | SENSE | 0.375 | 0.150 | 0.648 | 0.076 | 0.528 | 0.074 |
| 458 | 72919 | CGPG3899 | SENSE | 0.628 | 0.039 | −0.151 | 0.385 | −0.346 | 0.155 |
| 459 | 72983 | CGPG5610 | SENSE | 0.760 | 0.006 | −0.077 | 0.605 | −0.453 | 0.195 |
| 463 | 73338 | CGPG4862 | SENSE | 0.473 | 0.301 | 0.600 | 0.053 | 0.833 | 0.039 |
| 464 | 73344 | CGPG4910 | SENSE | 0.350 | 0.074 | 0.394 | 0.170 | 0.280 | 0.453 |
| 466 | 73644 | CGPG1756 | SENSE | 0.637 | 0.050 | 0.893 | 0.069 | 0.968 | 0.007 |
| 467 | 73662 | CGPG4927 | SENSE | 0.402 | 0.133 | 1.524 | 0.005 | 1.791 | 0.002 |
| 468 | 73672 | CGPG5106 | SENSE | 0.943 | 0.012 | 0.901 | 0.038 | 0.991 | 0.033 |
| 453 | 72026 | CGPG5231 | SENSE | 0.447 | 0.104 | 0.699 | 0.124 | 0.705 | 0.084 |
| 469 | 73733 | CGPG5167 | SENSE | 0.308 | 0.336 | 0.295 | 0.015 | 0.197 | 0.108 |
| 460 | 73025 | CGPG5665 | SENSE | −0.139 | 0.244 | 0.441 | 0.012 | 0.585 | 0.004 |
| 462 | 73092 | CGPG5695 | SENSE | 0.183 | 0.396 | 1.011 | 0.035 | 0.986 | 0.069 |
| 465 | 73536 | CGPG6541 | SENSE | 0.767 | 0.043 | 0.731 | 0.024 | 0.826 | 0.024 |
| 473 | 74205 | CGPG5089 | SENSE | 0.443 | 0.198 | 0.824 | 0.078 | 0.728 | 0.159 |
| 474 | 74321 | CGPG5870 | SENSE | 0.132 | 0.257 | 0.715 | 0.002 | 0.789 | 0.000 |
| 475 | 74337 | CGPG5888 | SENSE | 1.176 | 0.010 | 0.981 | 0.003 | 0.987 | 0.001 |
| 476 | 74388 | CGPG1461 | SENSE | 0.489 | 0.116 | 0.480 | 0.092 | 0.297 | 0.287 |
| 792 | 74414 | CGPG6664 | SENSE | 1.118 | 0.037 | 0.557 | 0.021 | 0.388 | 0.040 |
| 479 | 74522 | CGPG82 | SENSE | 0.928 | 0.013 | 1.382 | 0.018 | 1.327 | 0.019 |
| 480 | 74526 | CGPG6761 | SENSE | 0.315 | 0.422 | 0.679 | 0.020 | 0.604 | 0.013 |
| 481 | 74576 | CGPG6781 | SENSE | 0.620 | 0.012 | −0.164 | 0.143 | −0.410 | 0.032 |
| 461 | 73050 | CGPG5697 | SENSE | 0.646 | 0.212 | 1.284 | 0.023 | 1.751 | 0.010 |
| 485 | 75202 | CGPG1743 | SENSE | 0.413 | 0.012 | 0.422 | 0.007 | 0.292 | 0.026 |
| 486 | 75220 | CGPG5434 | SENSE | 0.791 | 0.037 | 0.778 | 0.015 | 0.787 | 0.020 |
| 487 | 75226 | CGPG5824 | SENSE | 0.788 | 0.007 | 0.595 | 0.119 | 0.619 | 0.173 |
| 488 | 75231 | CGPG5879 | SENSE | 0.976 | 0.017 | 0.663 | 0.004 | 0.496 | 0.029 |
| 489 | 75239 | CGPG5949 | SENSE | 1.048 | 0.011 | 0.570 | 0.242 | 0.547 | 0.290 |
| 490 | 75258 | CGPG6096 | SENSE | 0.808 | 0.047 | 0.435 | 0.135 | 0.585 | 0.025 |
| 491 | 75270 | CGPG6218 | SENSE | 0.526 | 0.011 | 0.746 | 0.141 | 0.866 | 0.193 |
| 492 | 75271 | CGPG6226 | SENSE | 0.092 | 0.698 | 0.963 | 0.083 | 0.982 | 0.128 |
| 470 | 73846 | CGPG1924 | SENSE | 0.807 | 0.032 | 0.175 | 0.623 | 0.014 | 0.973 |
| 471 | 73863 | CGPG5201 | SENSE | 0.285 | 0.404 | 0.740 | 0.021 | 0.797 | 0.016 |
| 472 | 74059 | CGPG1884 | SENSE | 0.364 | 0.014 | 0.162 | 0.137 | −0.131 | 0.424 |
| 477 | 74412 | CGPG6743 | SENSE | 0.163 | 0.522 | 0.670 | 0.026 | 0.626 | 0.131 |
| 478 | 74445 | CGPG6722 | SENSE | 0.805 | 0.065 | 0.361 | 0.164 | 0.584 | 0.145 |
| 482 | 74707 | CGPG4914 | SENSE | 0.584 | 0.005 | 0.453 | 0.248 | 0.239 | 0.415 |
| 483 | 74743 | CGPG5840 | SENSE | 0.187 | 0.245 | 0.843 | 0.040 | 0.976 | 0.045 |
| 484 | 74755 | CGPG5980 | SENSE | 0.959 | 0.083 | 0.680 | 0.205 | 0.768 | 0.206 |
| 493 | 75355 | CGPG7518 | SENSE | 0.268 | 0.006 | 0.715 | 0.053 | 0.799 | 0.038 |
| 494 | 75460 | CGPG7654 | SENSE | 0.214 | 0.120 | 0.649 | 0.053 | 0.713 | 0.094 |
| 795 | 75867 | CGPG6965 | SENSE | 0.817 | 0.040 | 0.707 | 0.058 | 0.588 | 0.128 |
| 497 | 75927 | CGPG8229 | SENSE | 0.360 | 0.163 | 0.808 | 0.017 | 0.955 | 0.007 |
| 498 | 75962 | CGPG8224 | SENSE | −0.337 | 0.167 | 0.398 | 0.061 | 0.706 | 0.030 |
| 499 | 75984 | CGPG1927 | SENSE | 1.141 | 0.050 | 0.220 | 0.073 | 0.076 | 0.202 |
| 500 | 76119 | CGPG5962 | SENSE | 0.206 | 0.445 | 1.056 | 0.011 | 1.364 | 0.015 |
| 501 | 76209 | CGPG5375 | SENSE | 0.598 | 0.078 | 0.737 | 0.112 | 0.834 | 0.075 |
| 496 | 75907 | CGPG8259 | SENSE | 0.730 | 0.002 | 0.376 | 0.023 | 0.494 | 0.065 |
| 495 | 75847 | CGPG6875 | SENSE | 0.568 | 0.129 | 0.927 | 0.025 | 1.062 | 0.033 |
| 502 | 76323 | CGPG8949 | SENSE | 0.592 | 0.042 | 0.736 | 0.049 | 0.844 | 0.048 |
| 503 | 76346 | CGPG8943 | SENSE | 0.150 | 0.647 | 0.588 | 0.061 | 0.656 | 0.044 |
| 504 | 76352 | CGPG8896 | SENSE | 0.464 | 0.551 | 1.124 | 0.109 | 1.375 | 0.049 |
| 505 | 76360 | CGPG8960 | SENSE | 0.442 | 0.274 | 0.646 | 0.072 | 0.830 | 0.038 |
| 507 | 76575 | CGPG7260 | SENSE | 0.444 | 0.030 | 0.813 | 0.023 | 1.123 | 0.050 |
| 506 | 76512 | CGPG5891 | SENSE | −0.060 | 0.669 | 0.486 | 0.005 | 0.799 | 0.014 |
| 508 | 76733 | CGPG2647 | SENSE | 0.304 | 0.312 | 1.028 | 0.019 | 0.976 | 0.034 |
| 509 | 76741 | CGPG6995 | SENSE | 1.007 | 0.040 | 0.344 | 0.008 | 0.302 | 0.033 |
| 512 | 76902 | CGPG9083 | SENSE | 0.343 | 0.097 | 0.551 | 0.034 | 0.496 | 0.082 |
| 513 | 76913 | CGPG9076 | SENSE | 0.524 | 0.021 | 0.257 | 0.530 | 0.149 | 0.719 |
| 514 | 76917 | CGPG9108 | SENSE | 0.728 | 0.063 | 0.804 | 0.015 | 0.779 | 0.036 |
| 515 | 76929 | CGPG9109 | SENSE | 0.335 | 0.220 | 0.628 | 0.031 | 0.844 | 0.027 |
| 510 | 76845 | CGPG9046 | SENSE | 0.123 | 0.751 | 0.877 | 0.081 | 1.232 | 0.027 |
| 511 | 76857 | CGPG9047 | SENSE | 1.055 | 0.053 | 1.170 | 0.023 | 1.286 | 0.020 |
| 516 | 77009 | CGPG5933 | SENSE | 0.604 | 0.051 | 0.853 | 0.104 | 0.864 | 0.120 |
| 517 | 77022 | CGPG6335 | SENSE | 0.301 | 0.356 | 0.444 | 0.024 | 0.554 | 0.001 |
| 522 | 77351 | CGPG8087 | SENSE | 0.749 | 0.023 | 1.023 | 0.012 | 1.031 | 0.032 |
| 518 | 77108 | CGPG9174 | SENSE | 0.651 | 0.025 | 0.788 | 0.020 | 0.723 | 0.133 |
| 519 | 77125 | CGPG9120 | SENSE | 0.945 | 0.049 | 1.641 | 0.013 | 1.794 | 0.011 |

TABLE 8-continued

| PEP SEQ ID NO | Construct ID | Nomination ID | Orientation | Rosette area at day 8 | | Rosette area at day 28 | | Rosette area difference | |
|---|---|---|---|---|---|---|---|---|---|
| | | | | Delta mean | P-value | Risk score mean | P-value | Delta mean | P-value |
| 520 | 77135 | CGPG9200 | SENSE | 0.648 | 0.253 | 1.299 | 0.019 | 1.486 | 0.034 |
| 521 | 77219 | CGPG9263 | SENSE | 0.636 | 0.005 | 0.300 | 0.355 | 0.763 | 0.003 |

If p<0.05 and delta or risk score mean>0, the transgenic plants showed statistically significant trait improvement as compared to the reference (p value, of the delta of a quantitative response or of the risk score of a qualitative response, is the probability that the observed difference between the transgenic plants and the reference occur by chance) If p<0.2 and delta or risk score mean>0, the transgenic plants showed a trend of trait improvement as compared to the reference.

G. Cold Germination Tolerance Screen

This example sets forth a screen to identify *Arabidopsis* plants transformed with the genes of interests are resistant to cold stress based on their rate of development, root growth and chlorophyll accumulation under low temperature conditions.

T2 seeds were plated and all seedlings used in the experiment were grown at 8° C. Seeds were first surface disinfested using chlorine gas and then seeded on assay plates containing an aqueous solution of ½× Gamborg's B/5 Basal Salt Mixture (Sigma/Aldrich Corp., St. Louis, Mo., USA G/5788), 1% Phytagel™ (Sigma-Aldrich, P-8169), and 10 ug/ml glufosinate with the final pH adjusted to 5.8 using KOH. Test plates were held vertically for 28 days at a constant temperature of 8° C., a photoperiod of 16 hr, and average light intensity of approximately 100 umol/m²/s. At 28 days post plating, root length was measured, growth stage was observed, the visual color was assessed, and a whole plate photograph was taken.

The root length at day 28 was analyzed as a quantitative response according to example 1M. The growth stage at day 7 was analyzed as a qualitative response according to example 1L. Table 9 provides a list of recombinant DNA constructs that improve cold stress tolerance in transgenic plants.

TABLE 9

| PEP SEQ ID | Construct ID | Orientation | Root length at day 28 | | Growth stage at day 28 | |
|---|---|---|---|---|---|---|
| | | | Delta mean | P-value | Delta mean | P-value |
| 523 | 14810 | SENSE | 0.429 | 0.028 | 2.822 | 0.041 |
| 524 | 14835 | ANTI-SENSE | 0.307 | 0.114 | 2.658 | 0.058 |
| 525 | 15419 | ANTI-SENSE | / | / | 3.333 | 0.038 |
| 526 | 16223 | SENSE | 0.321 | 0.062 | 4.000 | 0.000 |
| 527 | 17903 | SENSE | / | / | 2.667 | 0.057 |
| 528 | 18279 | SENSE | 0.100 | 0.622 | 3.390 | 0.031 |
| 529 | 18284 | SENSE | 0.343 | 0.143 | 1.533 | 0.097 |
| 530 | 18332 | SENSE | 0.286 | 0.032 | 2.579 | 0.026 |
| 531 | 18349 | SENSE | 0.153 | 0.013 | 1.694 | 0.026 |
| 537 | 70125 | SENSE | 0.550 | 0.020 | 2.987 | 0.034 |
| 432 | 17410 | SENSE | 0.346 | 0.027 | 4.000 | 0.000 |
| 532 | 18623 | SENSE | 0.253 | 0.048 | 2.144 | 0.011 |
| 533 | 19551 | SENSE | 0.109 | 0.055 | 0.511 | 0.479 |
| 534 | 19627 | SENSE | 0.234 | 0.007 | 0.918 | 0.240 |
| 438 | 19760 | SENSE | 0.275 | 0.078 | 2.249 | 0.141 |
| 535 | 19785 | SENSE | 0.175 | 0.301 | 3.103 | 0.074 |
| 536 | 19944 | SENSE | 0.107 | 0.214 | 3.423 | 0.027 |
| 538 | 70504 | SENSE | −0.204 | 0.122 | 2.893 | 0.035 |
| 441 | 70605 | SENSE | −0.135 | 0.357 | 3.322 | 0.039 |
| 539 | 70830 | SENSE | 0.085 | 0.303 | 3.396 | 0.030 |
| 444 | 70933 | SENSE | 0.191 | 0.084 | 3.371 | 0.033 |
| 540 | 70943 | SENSE | 0.181 | 0.011 | 2.958 | 0.032 |
| 541 | 71711 | ANTI-SENSE | 0.086 | 0.492 | 3.345 | 0.036 |
| 542 | 71962 | SENSE | 0.251 | 0.096 | 3.025 | 0.090 |
| 543 | 72352 | SENSE | 0.267 | 0.200 | 3.358 | 0.035 |
| 544 | 72413 | SENSE | 0.316 | 0.087 | 4.000 | 0.000 |
| 545 | 72603 | SENSE | 0.703 | 0.015 | 3.298 | 0.011 |
| 546 | 72676 | SENSE | 0.164 | 0.097 | 2.360 | 0.012 |
| 547 | 72737 | SENSE | 0.153 | 0.127 | 2.900 | 0.035 |
| 548 | 72742 | SENSE | 0.320 | 0.038 | 2.868 | 0.127 |
| 549 | 72762 | SENSE | 0.904 | 0.015 | 2.647 | 0.087 |
| 552 | 73091 | SENSE | 0.357 | 0.027 | 2.858 | 0.038 |
| 554 | 73340 | SENSE | 0.305 | 0.015 | 1.663 | 0.346 |
| 453 | 72026 | SENSE | 0.365 | 0.027 | 3.359 | 0.035 |
| 557 | 73750 | SENSE | 0.353 | 0.032 | 4.000 | 0.000 |
| 558 | 73751 | SENSE | 0.668 | 0.008 | 4.000 | 0.000 |
| 551 | 73031 | SENSE | 0.265 | 0.005 | 4.000 | 0.000 |
| 555 | 73420 | SENSE | −0.007 | 0.910 | 2.116 | 0.031 |
| 556 | 73489 | SENSE | 0.266 | 0.069 | 3.297 | 0.043 |
| 567 | 74135 | SENSE | 0.092 | 0.134 | 1.544 | 0.014 |
| 550 | 72993 | SENSE | 0.305 | 0.085 | 2.926 | 0.032 |
| 562 | 73929 | SENSE | 0.260 | 0.018 | 4.000 | 0.000 |
| 568 | 74313 | SENSE | 0.157 | 0.026 | 3.280 | 0.045 |
| 569 | 74315 | SENSE | 0.158 | 0.012 | 4.000 | 0.000 |
| 790 | 74359 | SENSE | 0.341 | 0.080 | 2.062 | 0.101 |
| 570 | 74427 | SENSE | 0.132 | 0.097 | 1.952 | 0.051 |
| 573 | 74531 | SENSE | 0.242 | 0.018 | 4.000 | 0.000 |
| 574 | 74532 | SENSE | 0.288 | 0.079 | 3.361 | 0.034 |
| 575 | 74538 | SENSE | 0.250 | 0.226 | 3.737 | 0.005 |
| 576 | 74550 | SENSE | 0.245 | 0.043 | 4.000 | 0.000 |
| 577 | 74579 | SENSE | 0.255 | 0.002 | 3.346 | 0.036 |
| 578 | 74644 | SENSE | 0.105 | 0.492 | 2.711 | 0.052 |
| 584 | 74896 | SENSE | 0.381 | 0.036 | 4.000 | 0.000 |
| 585 | 74976 | SENSE | 0.134 | 0.038 | 2.342 | 0.293 |
| 586 | 74991 | SENSE | −0.132 | 0.117 | 1.739 | 0.090 |
| 488 | 75231 | SENSE | 0.042 | 0.074 | 4.000 | 0.000 |
| 587 | 75289 | SENSE | 0.173 | 0.053 | 4.000 | 0.000 |
| 553 | 73224 | SENSE | 0.245 | 0.077 | 1.439 | 0.015 |
| 785 | 73292 | SENSE | 0.169 | 0.363 | 2.790 | 0.055 |
| 559 | 73814 | SENSE | 0.305 | 0.075 | 1.976 | 0.058 |
| 560 | 73855 | SENSE | 0.637 | 0.034 | 3.222 | 0.015 |
| 561 | 73856 | SENSE | 0.650 | 0.011 | 2.895 | 0.056 |
| 471 | 73863 | SENSE | 0.132 | 0.134 | 3.385 | 0.032 |
| 572 | 74511 | SENSE | 0.265 | 0.011 | 0.667 | 0.423 |
| 563 | 74063 | SENSE | 0.244 | 0.005 | 4.000 | 0.000 |
| 564 | 74072 | SENSE | 0.245 | 0.005 | 2.536 | 0.225 |
| 565 | 74073 | SENSE | 0.352 | 0.065 | 3.019 | 0.091 |
| 566 | 74075 | SENSE | 0.240 | 0.026 | 4.000 | 0.000 |
| 478 | 74445 | SENSE | 0.223 | 0.073 | 2.618 | 0.064 |
| 571 | 74490 | SENSE | 0.143 | 0.016 | 4.000 | 0.000 |
| 579 | 74703 | SENSE | 0.468 | 0.024 | 3.125 | 0.070 |
| 580 | 74733 | SENSE | 0.487 | 0.020 | 2.504 | 0.088 |
| 581 | 74749 | SENSE | 0.501 | 0.026 | 3.406 | 0.029 |
| 582 | 74752 | SENSE | 0.276 | 0.097 | 3.389 | 0.031 |
| 484 | 74755 | SENSE | 0.136 | 0.392 | 2.821 | 0.045 |
| 583 | 74773 | SENSE | 0.376 | 0.004 | 4.000 | 0.000 |
| 795 | 75867 | SENSE | 0.401 | 0.061 | 4.000 | 0.000 |

TABLE 9-continued

| PEP SEQ ID | Construct ID | Orientation | Root length at day 28 Delta mean | P-value | Growth stage at day 28 Delta mean | P-value |
|---|---|---|---|---|---|---|
| 793 | 75530 | SENSE | −0.032 | 0.760 | 2.385 | 0.098 |
| 588 | 76003 | SENSE | 0.239 | 0.021 | 1.611 | 0.315 |
| 589 | 76074 | SENSE | 0.269 | 0.033 | 2.696 | 0.174 |
| 590 | 76137 | SENSE | 0.316 | 0.075 | 2.624 | 0.081 |
| 591 | 76220 | SENSE | 0.074 | 0.516 | 2.585 | 0.089 |
| 796 | 75910 | SENSE | 0.225 | 0.070 | 4.000 | 0.000 |
| 592 | 76301 | SENSE | 0.110 | 0.308 | 2.683 | 0.055 |
| 593 | 76318 | SENSE | 0.052 | 0.600 | 2.692 | 0.078 |
| 594 | 76347 | SENSE | 0.088 | 0.362 | 3.254 | 0.049 |
| 596 | 76566 | SENSE | 0.144 | 0.052 | 2.408 | 0.117 |
| 595 | 76513 | SENSE | 0.316 | 0.019 | 3.347 | 0.036 |
| 597 | 76719 | SENSE | 0.099 | 0.063 | 4.000 | |
| 598 | 76757 | SENSE | 0.251 | 0.037 | 3.042 | 0.086 |
| 514 | 76917 | SENSE | 0.165 | 0.055 | 1.834 | 0.254 |
| 599 | 76891 | SENSE | 0.382 | 0.070 | 0.000 | 1.000 |
| 600 | 77208 | SENSE | 0.408 | 0.034 | 2.835 | 0.051 |

If p<0.05 and delta or risk score mean>0, the transgenic plants showed statistically significant trait improvement as compared to the reference. If p<0.2 and delta or risk score mean>0, the transgenic plants showed a trend of trait improvement as compared to the reference.

H. Shade Tolerance Screen

Plants undergo a characteristic morphological response in shade that includes the elongation of the petiole, a change in the leaf angle, and a reduction in chlorophyll content. While these changes may confer a competitive advantage to individuals, in a monoculture the shade avoidance response is thought to reduce the overall biomass of the population. Thus, genetic alterations that prevent the shade avoidance response may be associated with higher yields. Genes that favor growth under low light conditions may also promote yield, as inadequate light levels frequently limit yield. This protocol describes a screen to look for *Arabidopsis* plants that show an attenuated shade avoidance response and/or grow better than control plants under low light intensity. Of particular interest, we were looking for plants that didn't extend their petiole length, had an increase in seedling weight relative to the reference and had leaves that were more close to parallel with the plate surface.

T2 seeds were plated on glufosinate selection plates with ½MS medium. Seeds were sown on ½×MS salts, 1% Phytagel, 10 ug/ml BASTA. Plants were grown on vertical plates at a temperature of 22° C. at day, 20° C. at night and under low light (approximately 30 uE/m$^2$/s, far/red ratio (655/665/725/735) ~0.35 using PLAQ lights with GAM color filter #680). Twenty-three days after seedlings were sown, measurements were recorded including seedling status, number of rosette leaves, status of flower bud, petiole leaf angle, petiole length, and pooled fresh weights. A digital image of the whole plate was taken on the measurement day. Seedling weight and petiole length were analyzed as quantitative responses according to example 1M. The number of rosette leaves, flowering bud formation and leaf angel were analyzed as qualitative responses according Lu example 1L.

Table 10 provides a list of recombinant DNA constructs that improve shade tolerance in plants

TABLE 10

| PEP SEQ ID NO | Construct ID | Orientation | Leaf angle at day 23 RS mean | P-value | Seedling weight at day 23 Delta mean | P-value | Petiole length at day 23 Delta mean | P-value |
|---|---|---|---|---|---|---|---|---|
| 441 | 70605 | SENSE | / | / | 0.424 | 0.061 | 0.352 | 0.038 |
| 632 | 72414 | SENSE | 0.000 | 1.000 | 0.396 | 0.067 | 0.222 | 0.047 |
| 464 | 73344 | SENSE | 2.667 | 0.057 | 0.179 | 0.444 | 0.289 | 0.058 |
| 744 | 73666 | SENSE | / | / | 0.838 | 0.008 | 0.142 | 0.445 |
| 453 | 72026 | SENSE | 0.000 | 1.000 | 0.469 | 0.042 | 0.313 | 0.073 |
| 634 | 73723 | SENSE | 1.333 | 0.423 | −0.103 | 0.677 | −0.406 | 0.089 |
| 635 | 73747 | SENSE | 2.000 | 0.225 | −0.605 | 0.002 | −0.565 | 0.050 |
| 633 | 73409 | SENSE | 2.667 | 0.057 | 0.365 | 0.052 | 0.283 | 0.010 |
| 636 | 74634 | SENSE | 0.667 | 0.423 | −0.636 | 0.109 | −0.869 | 0.017 |
| 615 | 74558 | SENSE | 1.333 | 0.184 | 0.486 | 0.018 | 0.231 | 0.108 |
| 824 | 74956 | SENSE | 1.333 | 0.423 | 0.154 | 0.076 | −0.052 | 0.289 |
| 486 | 75220 | SENSE | 0.000 | 1.000 | −0.644 | 0.230 | −0.716 | 0.099 |
| 487 | 75226 | SENSE | 0.000 | 1.000 | −0.601 | 0.067 | −1.142 | 0.086 |
| 488 | 75231 | SENSE | 0.667 | 0.423 | 0.455 | 0.039 | 0.258 | 0.072 |
| 638 | 75232 | SENSE | 1.333 | 0.423 | −1.931 | 0.077 | −1.992 | 0.038 |
| 489 | 75239 | SENSE | 0.667 | 0.423 | 0.149 | 0.075 | 0.060 | 0.444 |
| 560 | 73855 | SENSE | 3.333 | 0.038 | −0.261 | 0.121 | −0.361 | 0.215 |
| 472 | 74059 | SENSE | 0.000 | 1.000 | 0.409 | 0.066 | 0.331 | 0.062 |
| 482 | 74707 | SENSE | 3.333 | 0.038 | 0.269 | 0.071 | 0.136 | 0.016 |
| 754 | 74753 | SENSE | 0.000 | 1.000 | 0.365 | 0.079 | 0.267 | 0.057 |
| 637 | 74769 | SENSE | 1.333 | 0.184 | −0.141 | 0.346 | −0.221 | 0.029 |
| 493 | 75355 | SENSE | 1.333 | 0.423 | −0.735 | 0.069 | −0.581 | 0.058 |
| 639 | 75429 | SENSE | 2.667 | 0.057 | −0.453 | 0.151 | −1.319 | 0.032 |
| 640 | 75965 | SENSE | 0.667 | 0.423 | 0.092 | 0.086 | 0.109 | 0.122 |
| 642 | 76061 | SENSE | / | / | 0.373 | 0.075 | 0.110 | 0.330 |
| 643 | 76155 | SENSE | 0.667 | 0.423 | −0.473 | 0.021 | −0.608 | 0.004 |
| 761 | 76207 | SENSE | 2.667 | 0.057 | −0.374 | 0.060 | −0.369 | 0.088 |
| 641 | 75975 | SENSE | 2.000 | 0.225 | 0.405 | 0.056 | 0.223 | 0.044 |
| 762 | 76293 | SENSE | 2.667 | 0.184 | −0.412 | 0.052 | −0.717 | 0.018 |
| 644 | 76322 | SENSE | 0.667 | 0.423 | −0.533 | 0.044 | −0.559 | 0.045 |
| 645 | 76440 | SENSE | / | / | −0.405 | 0.141 | −0.525 | 0.045 |
| 509 | 76741 | SENSE | 0.667 | 0.423 | −0.793 | 0.027 | −0.803 | 0.018 |
| 513 | 76913 | SENSE | / | / | 0.313 | 0.073 | 0.336 | 0.129 |
| 646 | 76828 | SENSE | 0.667 | 0.423 | −0.185 | 0.141 | −1.189 | 0.001 |

TABLE 10-continued

| PEP SEQ ID NO | Construct ID | Orientation | Leaf angle at day 23 RS mean | P-value | Seedling weight at day 23 Delta mean | P-value | Petiole length at day 23 Delta mean | P-value |
|---|---|---|---|---|---|---|---|---|
| 517 | 77022 | SENSE | 0.000 | 1.000 | −0.495 | 0.282 | −0.475 | 0.079 |
| 648 | 77303 | SENSE | 2.000 | 0.225 | −0.296 | 0.117 | −0.176 | 0.038 |
| 649 | 77352 | SENSE | 1.333 | 0.423 | −0.298 | 0.127 | −0.377 | 0.036 |
| 631 | 77366 | SENSE | 0.667 | 0.423 | 0.611 | 0.015 | 0.327 | 0.044 |
| 647 | 77136 | SENSE | 1.333 | 0.423 | −0.824 | 0.076 | −0.566 | 0.089 |

For "seeding weight" and "leaf angle", if p<0.05 and delta or risk score mean>0, the transgenic plants showed statistically significant trait improvement as compared to the reference. If p<0.2 and delta or risk score mean>0, the transgenic plants showed a trend of trait improvement as compared to the reference with p<0.2.

For "petiole length", if p<0.05 and delta <0, the transgenic plants showed statistically significant trait improvement as compared to the reference. If p<0.2 and delta <0, the transgenic plants showed a trend of trait improvement as compared to the reference.

I. Early Plant Growth and Development Screen

This example sets forth a plate based phenotypic analysis platform for the rapid detection of phenotypes that are evident during the first two weeks of growth. In this screen, we were looking for genes that confer advantages in the processes of germination, seedling vigor, root growth and root morphology under non-stressed growth conditions to plants. The transgenic plants with advantages in seedling growth and development were determined by the seedling weight and root length at day 14 after seed planting.

T2 seeds were plated on glufosinate selection plates and grown under standard conditions (~100 uE/m$^2$/s, 16 h photoperiod, 22° C. at day, 20° C. at night). Seeds were stratified for 3 days at 4° C. Seedlings were grown vertically (at a temperature of 22° C. at day 20° C. at night). Observations were taken on day 10 and day 14. Both seedling weight and root length at day 14 were analyzed as quantitative responses according to example 1M.

Table 11 provides a list recombinant DNA constructs that improve early plant growth and development.

TABLE 11

| PEP SEQ ID NO | Construct ID | Orientation | Root length at day 10 Delta mean | P-value | Root length at day 14 Delta mean | P-value | Seedling weight at day 14 Delta mean | P-value |
|---|---|---|---|---|---|---|---|---|
| 523 | 14810 | SENSE | 0.175 | 0.027 | 0.049 | 0.231 | −0.089 | 0.337 |
| 773 | 14836 | SENSE | 0.105 | 0.007 | 0.089 | 0.029 | 0.162 | 0.217 |
| 735 | 14944 | SENSE | 0.205 | 0.207 | 0.175 | 0.046 | 0.259 | 0.221 |
| 525 | 15419 | ANTI-SENSE | 0.182 | 0.019 | 0.125 | 0.048 | 0.212 | 0.155 |
| 527 | 17903 | SENSE | 0.401 | 0.008 | 0.174 | 0.011 | 0.330 | 0.005 |
| 529 | 18284 | SENSE | 0.031 | 0.795 | 0.016 | 0.722 | 0.223 | 0.043 |
| 737 | 18536 | SENSE | 0.158 | 0.222 | 0.104 | 0.118 | 0.149 | 0.122 |
| 736 | 18410 | SENSE | 0.222 | 0.228 | 0.078 | 0.640 | 0.141 | 0.080 |
| 432 | 17410 | SENSE | 0.145 | 0.052 | 0.074 | 0.246 | 0.074 | 0.542 |
| 532 | 18623 | SENSE | 0.247 | 0.100 | 0.133 | 0.074 | 0.228 | 0.036 |
| 434 | 18665 | SENSE | 0.237 | 0.025 | 0.156 | 0.057 | 0.268 | 0.033 |
| 738 | 19540 | SENSE | 0.115 | 0.397 | 0.085 | 0.237 | 0.130 | 0.031 |
| 739 | 19624 | SENSE | 0.329 | 0.057 | 0.171 | 0.269 | 0.494 | 0.024 |
| 740 | 70353 | SENSE | 0.136 | 0.065 | 0.086 | 0.355 | 0.140 | 0.170 |
| 780 | 70804 | SENSE | 0.411 | 0.066 | 0.290 | 0.147 | 0.483 | 0.129 |
| 443 | 70812 | SENSE | 0.438 | 0.069 | 0.351 | 0.043 | 0.571 | 0.036 |
| 444 | 70933 | SENSE | 0.093 | 0.099 | 0.088 | 0.039 | 0.071 | 0.060 |
| 540 | 70943 | SENSE | 0.344 | 0.074 | 0.173 | 0.031 | 0.263 | 0.283 |
| 741 | 71215 | SENSE | 0.282 | 0.107 | 0.142 | 0.010 | 0.108 | 0.594 |
| 446 | 71319 | SENSE | 0.201 | 0.077 | 0.051 | 0.427 | 0.236 | 0.025 |
| 742 | 71320 | SENSE | 0.601 | 0.015 | 0.437 | 0.041 | 0.547 | 0.107 |
| 447 | 71446 | SENSE | 0.308 | 0.182 | 0.207 | 0.021 | 0.465 | 0.107 |
| 463 | 73338 | SENSE | 0.309 | 0.035 | 0.146 | 0.038 | 0.462 | 0.017 |
| 611 | 73619 | SENSE | 0.070 | 0.151 | 0.103 | 0.016 | 0.266 | 0.093 |
| 744 | 73666 | SENSE | 0.304 | 0.036 | 0.166 | 0.014 | 0.480 | 0.010 |
| 469 | 73733 | SENSE | 0.156 | 0.148 | −0.087 | 0.511 | 0.156 | 0.036 |
| 612 | 73737 | SENSE | 0.352 | 0.005 | 0.244 | 0.020 | 0.098 | 0.093 |
| 557 | 73750 | SENSE | 0.156 | 0.033 | 0.111 | 0.047 | 0.216 | 0.040 |
| 465 | 73536 | SENSE | 0.461 | 0.007 | 0.261 | 0.006 | 0.330 | 0.024 |
| 550 | 72993 | SENSE | 0.254 | 0.034 | 0.152 | 0.228 | 0.271 | 0.073 |
| 747 | 74211 | SENSE | 0.155 | 0.084 | 0.068 | 0.159 | 0.368 | 0.034 |
| 569 | 74315 | SENSE | 0.328 | 0.007 | 0.149 | 0.020 | 0.513 | 0.055 |
| 748 | 74510 | SENSE | 0.277 | 0.003 | 0.158 | 0.016 | 0.433 | 0.029 |
| 749 | 74527 | SENSE | 0.446 | 0.025 | 0.256 | 0.022 | 0.412 | 0.052 |
| 750 | 74539 | SENSE | 0.103 | 0.024 | 0.063 | 0.196 | 0.249 | 0.013 |
| 576 | 74550 | SENSE | 0.216 | 0.076 | 0.228 | 0.035 | 0.424 | 0.048 |
| 481 | 74576 | SENSE | 0.270 | 0.017 | 0.016 | 0.823 | 0.216 | 0.235 |
| 752 | 74577 | SENSE | 0.333 | 0.032 | 0.224 | 0.023 | 0.285 | 0.094 |

TABLE 11-continued

| PEP SEQ ID NO | Construct ID | Orientation | Root length at day 10 Delta mean | Root length at day 10 P-value | Root length at day 14 Delta mean | Root length at day 14 P-value | Seedling weight at day 14 Delta mean | Seedling weight at day 14 P-value |
|---|---|---|---|---|---|---|---|---|
| 743 | 73076 | SENSE | 0.129 | 0.459 | 0.063 | 0.513 | 0.244 | 0.055 |
| 756 | 74908 | SENSE | 0.237 | 0.006 | 0.184 | 0.014 | 0.253 | 0.094 |
| 751 | 74556 | SENSE | 0.147 | 0.111 | 0.076 | 0.025 | 0.377 | 0.035 |
| 489 | 75239 | SENSE | 0.180 | 0.145 | 0.085 | 0.019 | 0.236 | 0.162 |
| 758 | 75254 | SENSE | 0.144 | 0.233 | 0.031 | 0.502 | 0.363 | 0.054 |
| 553 | 73224 | SENSE | 0.384 | 0.035 | 0.257 | 0.022 | 0.616 | 0.029 |
| 745 | 73852 | SENSE | 0.029 | 0.760 | 0.031 | 0.617 | 0.031 | 0.019 |
| 572 | 74511 | SENSE | 0.345 | 0.003 | 0.107 | 0.069 | 0.487 | 0.043 |
| 565 | 74073 | SENSE | −0.003 | 0.969 | −0.023 | 0.646 | 0.225 | 0.096 |
| 746 | 74080 | SENSE | 0.252 | 0.031 | 0.102 | 0.152 | 0.296 | 0.074 |
| 753 | 74729 | SENSE | 0.065 | 0.082 | −0.031 | 0.642 | 0.080 | 0.068 |
| 581 | 74749 | SENSE | 0.160 | 0.161 | 0.104 | 0.120 | 0.243 | 0.322 |
| 754 | 74753 | SENSE | 0.136 | 0.127 | 0.061 | 0.224 | 0.422 | 0.002 |
| 755 | 74754 | SENSE | 0.216 | 0.004 | 0.133 | 0.040 | 0.188 | 0.055 |
| 484 | 74755 | SENSE | 0.397 | 0.071 | 0.243 | 0.084 | 0.499 | 0.037 |
| 757 | 75107 | SENSE | 0.352 | 0.014 | 0.212 | 0.044 | 0.342 | 0.086 |
| 759 | 75741 | SENSE | 0.160 | 0.098 | 0.062 | 0.399 | 0.123 | 0.320 |
| 760 | 75931 | SENSE | 0.162 | 0.037 | 0.134 | 0.012 | 0.225 | 0.061 |
| 797 | 76101 | SENSE | 0.142 | 0.445 | 0.109 | 0.361 | 0.372 | 0.051 |
| 761 | 76207 | SENSE | 0.397 | 0.015 | 0.235 | 0.100 | 0.151 | 0.149 |
| 762 | 76293 | SENSE | 0.160 | 0.172 | 0.178 | 0.042 | 0.491 | 0.000 |
| 495 | 75847 | SENSE | 0.262 | 0.003 | 0.005 | 0.928 | 0.246 | 0.159 |
| 763 | 76517 | SENSE | 0.220 | 0.080 | 0.162 | 0.021 | 0.210 | 0.017 |
| 764 | 76559 | SENSE | 0.283 | 0.130 | 0.211 | 0.123 | 0.266 | 0.093 |
| 765 | 76804 | SENSE | 0.219 | 0.061 | 0.130 | 0.066 | 0.419 | 0.003 |
| 766 | 77018 | SENSE | 0.338 | 0.002 | 0.137 | 0.095 | 0.469 | 0.059 |
| 522 | 77351 | SENSE | 0.052 | 0.566 | 0.060 | 0.290 | 0.343 | 0.091 |
| 518 | 77108 | SENSE | 0.000 | 0.998 | 0.095 | 0.080 | 0.067 | 0.085 |
| 767 | 77115 | SENSE | 0.339 | 0.102 | 0.173 | 0.044 | 0.788 | 0.056 |
| 768 | 77128 | SENSE | 0.360 | 0.075 | 0.174 | 0.170 | 0.304 | 0.125 |
| 769 | 77158 | SENSE | 0.290 | 0.052 | 0.033 | 0.484 | 0.365 | 0.010 |
| 770 | 77159 | SENSE | 0.303 | 0.019 | 0.177 | 0.166 | 0.408 | 0.033 |
| 771 | 77163 | SENSE | 0.497 | 0.007 | 0.434 | 0.002 | 1.047 | 0.038 |
| 600 | 77208 | SENSE | 0.206 | 0.011 | 0.103 | 0.077 | 0.388 | 0.009 |

If $p<0.05$ and delta or risk score mean>0, the transgenic plants showed statistically significant trait improvement as compared to the reference. If $p<0.2$ and delta or risk score mean>0, the transgenic plants showed a trend of trait improvement as compared to the reference.

J. Late Plant Growth and Development Screen

This example sets forth a soil based phenotypic platform to identify genes that confer advantages in the processes of leaf development, flowering production and seed maturity to plants.

*Arabidopsis* plants were grown on a commercial potting mixture (Metro Mix 360, Scotts Co., Marysville, Ohio) consisting of 30-40% medium grade horticultural vermiculite, 35-55% sphagnum peat moss, 10-20% processed bark ash, 1-15% pine bark and a starter nutrient charge. Soil was supplemented with Osmocote time-release fertilizer at a rate of 30 mg/ft³. T2 seeds were imbibed in 1% agarose solution for 3 days at 4° C. and then sown at a density of ~5 per 2½" pot. Thirty-two pots were ordered in a 4 by 8 grid in standard greenhouse flat. Plants were grown in environmentally controlled rooms under a 16 h day length with an average light intensity of ~200 μmoles/m²/s. Day and night temperature set points were 22° C. and 20° C., respectively. Humidity was maintained at 65%. Plants were watered by sub-irrigation every two days on average until mid-flowering, at which point the plants were watered daily until flowering was complete.

Application of the herbicide glufosinate was performed to select T2 individuals containing the target transgene. A single application of glufosinate was applied when the first true leaves were visible. Each pot was thinned to leave a single glufosinate-resistant seedling ~3 days after the selection was applied.

The rosette radius was measured at day 25. The silique length was measured at day 40. The plant parts were harvested at day 49 for dry weight measurements if flowering production was stopped. Otherwise, the dry weights of rosette and silique were carried out at day 53. The seeds were harvested at day 58. All measurements were analyzed as quantitative responses according to example 1M.

Table 12 provides a list of recombinant DNA constructs that improve late plant growth and development.

TABLE 12

| PEP SEQ ID NO | Orientation | Rosette dry weight at day 53 Delta mean | Rosette dry weight at day 53 P-value | Rosette radius at day 25 Delta mean | Rosette radius at day 25 P-value | Seed net dry weight at day 62 Delta mean | Seed net dry weight at day 62 P-value | Silique dry weight at day 53 Delta mean | Silique dry weight at day 53 P-value | Silique length at day 40 Delta mean | Silique length at day 40 P-value |
|---|---|---|---|---|---|---|---|---|---|---|---|
| 772 | ANTI-SENSE | 0.072 | 0.189 | / | / | 0.846 | 0.002 | 0.143 | 0.381 | −0.012 | 0.803 |

TABLE 12-continued

| PEP SEQ ID NO | Orientation | Rosette dry weight at day 53 | | Rosette radius at day 25 | | Seed net dry weight at day 62 | | Silique dry weight at day 53 | | Silique length at day 40 | |
|---|---|---|---|---|---|---|---|---|---|---|---|
| | | Delta mean | P-value | Delta mean | P-value | Delta mean | P-value | Delta mean | P-value | Delta mean | P-value |
| 773 | SENSE | 0.094 | 0.592 | −0.238 | 0.098 | 0.665 | 0.059 | 0.247 | 0.474 | −0.029 | 0.184 |
| 775 | SENSE | 0.134 | 0.019 | / | / | 0.675 | 0.061 | 0.540 | 0.010 | 0.093 | 0.008 |
| 774 | SENSE | −0.262 | 0.112 | −0.407 | 0.032 | −0.393 | 0.120 | 0.357 | 0.081 | 0.003 | 0.922 |
| 776 | SENSE | −1.027 | 0.044 | / | / | 2.216 | 0.004 | 0.351 | 0.355 | 0.135 | 0.001 |
| 780 | SENSE | 0.310 | 0.048 | / | / | −0.245 | 0.629 | 0.149 | 0.157 | 0.149 | 0.043 |
| 781 | SENSE | 0.219 | 0.069 | / | / | 0.779 | 0.001 | −0.174 | 0.108 | −0.015 | 0.595 |
| 777 | SENSE | 0.526 | 0.045 | / | / | −0.388 | 0.478 | 0.131 | 0.281 | −0.351 | 0.036 |
| 778 | SENSE | 0.402 | 0.004 | −0.158 | 0.126 | −2.159 | 0.036 | −0.410 | 0.016 | −0.195 | 0.043 |
| 779 | SENSE | 0.454 | 0.006 | −0.124 | 0.234 | −0.112 | 0.328 | 0.228 | 0.070 | 0.065 | 0.024 |
| 782 | SENSE | 0.195 | 0.205 | −0.153 | 0.019 | 0.352 | 0.005 | 0.488 | 0.031 | −0.063 | 0.473 |
| 783 | SENSE | −0.388 | 0.381 | / | / | 1.339 | 0.002 | −1.147 | 0.126 | 0.601 | 0.000 |
| 786 | SENSE | −0.107 | 0.280 | 0.091 | 0.148 | 0.563 | 0.058 | 0.166 | 0.165 | 0.042 | 0.084 |
| 787 | SENSE | −0.290 | 0.138 | −0.752 | 0.020 | 0.501 | 0.044 | −0.114 | 0.237 | 0.048 | 0.188 |
| 788 | SENSE | −0.064 | 0.709 | −0.060 | 0.302 | 0.346 | 0.027 | 0.198 | 0.082 | 0.062 | 0.115 |
| 789 | SENSE | −0.060 | 0.585 | −0.204 | 0.076 | 0.930 | 0.004 | −0.243 | 0.109 | 0.094 | 0.016 |
| 790 | SENSE | −0.299 | 0.076 | 0.208 | 0.181 | 0.683 | 0.008 | 0.140 | 0.652 | −0.047 | 0.070 |
| 792 | SENSE | 0.470 | 0.039 | / | / | 0.113 | 0.691 | −0.118 | 0.511 | −0.003 | 0.921 |
| 791 | SENSE | −0.037 | 0.754 | / | / | 0.484 | 0.084 | −0.163 | 0.366 | 0.024 | 0.328 |
| 784 | SENSE | −0.182 | 0.070 | −0.079 | 0.243 | 0.649 | 0.075 | 0.070 | 0.659 | −0.150 | 0.112 |
| 785 | SENSE | −0.057 | 0.216 | −0.086 | 0.016 | 1.645 | 0.008 | 0.278 | 0.036 | 0.015 | 0.364 |
| 795 | SENSE | 0.620 | 0.013 | / | / | 0.698 | 0.010 | −0.102 | 0.794 | 0.040 | 0.247 |
| 793 | SENSE | 0.492 | 0.045 | −0.232 | 0.029 | −0.505 | 0.030 | 0.025 | 0.881 | | |
| 794 | SENSE | −0.051 | 0.809 | / | / | 0.809 | 0.003 | −0.054 | 0.649 | −0.020 | 0.786 |
| 797 | SENSE | 0.121 | 0.107 | / | / | 0.915 | 0.017 | −0.287 | 0.054 | 0.054 | 0.120 |
| 796 | SENSE | 0.324 | 0.017 | / | / | −0.289 | 0.468 | 0.331 | 0.012 | 0.040 | 0.476 |
| 798 | SENSE | 0.411 | 0.038 | / | / | 0.809 | 0.018 | 0.231 | 0.286 | −0.048 | 0.279 |
| 799 | SENSE | −0.014 | 0.720 | / | / | 0.337 | 0.064 | −0.112 | 0.165 | 0.018 | 0.581 |

If p<0.05 and delta or risk score mean>0, the transgenic plants showed statistically significant trait improvement as compared to the reference. If p<0.2 and delta or risk score mean>0, the transgenic plants showed a trend of trait improvement as compared to the reference.

K. Limited Nitrogen Tolerance Screen

Under low nitrogen conditions, *Arabidopsis* seedlings become chlorotic and have less biomass. This example sets forth the limited nitrogen tolerance screen to identify *Arabidopsis* plants transformed with the gene of interest that are altered in their ability to accumulate biomass and/or retain chlorophyll under low nitrogen condition.

T2 seeds were plated on glufosinate selection plates containing 0.5×N-Free Hoagland's T 0.1 mM $NH_4NO_3$ T 0.1% sucrose T 1% phytagel media and grown under standard light and temperature conditions. At 12 days of growth, plants were scored for seedling status (i.e., viable or non-viable) and root length. After 21 days of growth, plants were scored for BASTA resistance, visual color, seedling weight, number of green leaves, number of rosette leaves, root length and formation of flowering buds. A photograph of each plant was also taken at this time point.

The seedling weight and root length were analyzed as quantitative responses according to example 1M. The number green leaves, the number of rosette leaves and the flowerbud formation were analyzed as qualitative responses according to example 1L. The leaf color raw data were collected on each plant as the percentages of five color elements (Green, DarkGreen, LightGreen, RedPurple, YellowChlorotic) using a computer imaging system. A statistical logistic regression model was developed to predict an overall value based on five colors for each plant.

Table 13 provides a list of recombinant DNA constructs that improve low nitrogen availability tolerance in plants.

TABLE 13

| PEP SEQ ID NO | Construct ID | Orientation | Root length | | Leaf color | | Rosette weight | |
|---|---|---|---|---|---|---|---|---|
| | | | Delta mean | P-value | Risk score mean | P-value | Delta mean | P-value |
| 650 | 10913 | ANTI-SENSE | −0.322 | 0.072 | 0.559 | 0.234 | −0.052 | 0.209 |
| 651 | 10925 | ANTI-SENSE | −0.407 | 0.047 | 5.828 | 0.342 | −0.064 | 0.416 |
| 652 | 11357 | SENSE | −0.436 | 0.016 | 0.996 | 0.047 | −0.093 | 0.233 |
| 653 | 11358 | SENSE | −0.521 | 0.000 | 1.297 | 0.012 | −0.003 | 0.945 |
| 654 | 11432 | ANTI-SENSE | −0.215 | 0.049 | 0.669 | 0.046 | 0.009 | 0.899 |
| 655 | 11927 | ANTI-SENSE | −0.416 | 0.028 | 0.581 | 0.021 | 0.028 | 0.293 |
| 430 | 11937 | ANTI-SENSE | −0.302 | 0.076 | 0.564 | 0.039 | −0.102 | 0.067 |
| 656 | 12050 | SENSE | −0.188 | 0.003 | 1.323 | 0.032 | −0.031 | 0.245 |
| 657 | 12358 | ANTI-SENSE | −0.179 | 0.050 | 0.278 | 0.065 | 0.024 | 0.818 |
| 658 | 13809 | SENSE | −0.126 | 0.024 | 0.796 | 0.303 | −0.099 | 0.073 |
| 603 | 14733 | SENSE | −0.161 | 0.131 | 2.267 | 0.085 | −0.055 | 0.676 |
| 525 | 15419 | ANTI-SENSE | −0.068 | 0.119 | 1.607 | 0.051 | 0.044 | 0.451 |
| 659 | 16877 | SENSE | −0.207 | 0.158 | 2.516 | 0.057 | 0.012 | 0.843 |
| 660 | 18117 | ANTI-SENSE | −0.221 | 0.004 | 0.906 | 0.004 | −0.146 | 0.067 |
| 805 | 70819 | SENSE | −0.258 | 0.057 | 2.275 | 0.088 | −0.103 | 0.231 |

TABLE 13-continued

| PEP SEQ ID NO | Construct ID | Orientation | Root length Delta mean | P-value | Leaf color Risk score mean | P-value | Rosette weight Delta mean | P-value |
|---|---|---|---|---|---|---|---|---|
| 777 | 70639 | SENSE | −0.276 | 0.071 | −1.184 | 0.099 | 0.132 | 0.052 |
| 778 | 70668 | SENSE | −0.126 | 0.010 | −0.521 | 0.156 | 0.067 | 0.520 |
| 661 | 71651 | SENSE | −0.037 | 0.599 | 0.485 | 0.042 | −0.020 | 0.682 |
| 662 | 72449 | SENSE | −0.019 | 0.645 | −0.738 | 0.043 | 0.324 | 0.024 |
| 454 | 72533 | SENSE | −0.011 | 0.866 | 1.131 | 0.017 | 0.068 | 0.237 |
| 663 | 72649 | SENSE | −0.154 | 0.309 | 0.181 | 0.093 | −0.046 | 0.350 |
| 610 | 72978 | SENSE | −0.304 | 0.184 | 0.367 | 0.125 | 0.144 | 0.008 |
| 464 | 73344 | SENSE | −0.068 | 0.002 | −0.547 | 0.400 | 0.040 | 0.612 |
| 744 | 73666 | SENSE | 0.239 | 0.137 | −2.192 | 0.089 | 0.125 | 0.064 |
| 635 | 73747 | SENSE | −0.031 | 0.568 | 0.671 | 0.010 | 0.002 | 0.974 |
| 664 | 73107 | SENSE | −0.236 | 0.039 | 0.196 | 0.057 | 0.050 | 0.554 |
| 567 | 74135 | SENSE | 0.173 | 0.081 | −2.988 | 0.061 | 0.117 | 0.090 |
| 636 | 74634 | SENSE | −1.049 | 0.019 | 0.805 | 0.083 | −0.084 | 0.034 |
| 578 | 74644 | SENSE | −0.224 | 0.027 | 0.247 | 0.353 | −0.054 | 0.256 |
| 665 | 74875 | SENSE | −0.297 | 0.201 | 1.084 | 0.089 | 0.201 | 0.106 |
| 666 | 75079 | SENSE | −0.303 | 0.277 | 0.583 | 0.071 | −0.122 | 0.329 |
| 485 | 75202 | SENSE | −0.277 | 0.093 | 0.463 | 0.049 | −0.020 | 0.570 |
| 668 | 75228 | SENSE | −0.838 | 0.036 | 1.239 | 0.033 | −0.091 | 0.503 |
| 669 | 75246 | SENSE | −1.192 | 0.009 | 1.314 | 0.039 | −0.136 | 0.205 |
| 809 | 73223 | SENSE | 0.060 | 0.764 | −0.249 | 0.442 | 0.066 | 0.084 |
| 784 | 73283 | SENSE | 0.200 | 0.242 | −2.819 | 0.046 | 0.198 | 0.051 |
| 637 | 74769 | SENSE | −0.135 | 0.090 | 0.642 | 0.024 | 0.102 | 0.064 |
| 667 | 75180 | SENSE | −0.266 | 0.031 | 0.602 | 0.021 | 0.006 | 0.281 |
| 670 | 75375 | SENSE | −0.647 | 0.012 | 1.618 | 0.001 | −0.156 | 0.043 |
| 671 | 75476 | SENSE | −0.563 | 0.011 | 1.101 | 0.003 | −0.091 | 0.162 |
| 673 | 75857 | SENSE | −0.256 | 0.067 | 2.472 | 0.006 | −0.125 | 0.041 |
| 672 | 75502 | SENSE | 0.101 | 0.209 | −0.147 | 0.482 | 0.156 | 0.066 |
| 675 | 75970 | SENSE | −0.125 | 0.191 | 0.963 | 0.036 | 0.046 | 0.391 |
| 676 | 76115 | SENSE | −0.499 | 0.113 | 0.619 | 0.092 | 0.018 | 0.752 |
| 833 | 76121 | SENSE | −0.707 | 0.012 | 1.695 | 0.007 | −0.199 | 0.049 |
| 643 | 76155 | SENSE | −0.059 | 0.454 | 0.779 | 0.022 | −0.033 | 0.742 |
| 677 | 76217 | SENSE | −0.312 | 0.120 | 0.750 | 0.001 | −0.010 | 0.864 |
| 678 | 76287 | SENSE | −0.504 | 0.035 | 1.326 | 0.003 | −0.147 | 0.018 |
| 679 | 76294 | SENSE | −0.492 | 0.002 | 1.096 | 0.006 | −0.134 | 0.013 |
| 762 | 76293 | SENSE | 0.102 | 0.330 | −2.184 | 0.008 | 0.358 | 0.049 |
| 674 | 75873 | SENSE | −0.191 | 0.071 | 3.070 | 0.093 | 0.109 | 0.197 |
| 680 | 76305 | SENSE | −0.643 | 0.001 | 2.319 | 0.000 | −0.110 | 0.018 |
| 644 | 76322 | SENSE | −0.568 | 0.019 | 1.259 | 0.091 | −0.205 | 0.019 |
| 837 | 76388 | SENSE | 0.078 | 0.155 | −0.032 | 0.862 | 0.130 | 0.017 |
| 681 | 76391 | SENSE | −0.259 | 0.114 | 1.043 | 0.046 | 0.036 | 0.806 |
| 798 | 76431 | SENSE | 0.143 | 0.134 | −0.383 | 0.554 | 0.196 | 0.034 |
| 682 | 76438 | SENSE | −0.183 | 0.029 | 0.790 | 0.057 | −0.062 | 0.291 |
| 683 | 76452 | SENSE | −0.284 | 0.112 | 0.928 | 0.017 | −0.002 | 0.969 |
| 684 | 76563 | SENSE | −0.032 | 0.100 | −0.047 | 0.203 | −0.095 | 0.153 |
| 839 | 76567 | SENSE | 0.228 | 0.057 | −0.403 | 0.418 | 0.180 | 0.024 |
| 646 | 76828 | SENSE | −0.163 | 0.051 | 0.666 | 0.018 | 0.156 | 0.078 |
| 685 | 77055 | SENSE | −0.261 | 0.180 | 0.926 | 0.079 | 0.054 | 0.516 |
| 686 | 77059 | SENSE | −0.380 | 0.005 | 1.188 | 0.021 | −0.138 | 0.012 |
| 687 | 77062 | SENSE | −0.494 | 0.020 | 1.284 | 0.033 | 0.010 | 0.759 |
| 688 | 77063 | SENSE | −0.290 | 0.018 | 0.814 | 0.019 | −0.082 | 0.116 |
| 691 | 77314 | SENSE | −0.500 | 0.046 | 0.369 | 0.008 | −0.185 | 0.029 |
| 692 | 77344 | SENSE | −0.163 | 0.029 | 0.199 | 0.016 | 0.067 | 0.350 |
| 693 | 77348 | SENSE | −0.218 | 0.003 | 0.313 | 0.000 | 0.002 | 0.960 |
| 846 | 77112 | SENSE | −0.025 | 0.839 | −0.057 | 0.919 | 0.142 | 0.059 |
| 689 | 77218 | SENSE | −0.072 | 0.687 | 0.679 | 0.008 | 0.054 | 0.336 |
| 521 | 77219 | SENSE | 0.183 | 0.071 | 0.134 | 0.290 | 0.319 | 0.038 |
| 690 | 77256 | SENSE | −0.339 | 0.015 | 0.216 | 0.205 | −0.058 | 0.302 |

For leaf color and rosette weight, if p<0.05 and delta or risk score mean>0, the transgenic plants showed statistically significant trait improvement as compared to the reference. If p<0.2 and delta or risk score mean>0, the transgenic plants showed a trend of trait improvement as compared to the reference with p<0.2. For root length, if p<0.05, the transgenic plants showed statistically significant trait improvement as compared to the reference. If p<0.2, the transgenic plants showed a trend of trait improvement as compared to the reference.

L. Statistic Analysis for Qualitative Responses

Table 14 provides a list of responses that were analyzed as qualitative responses

TABLE 14

| response | screen | categories (success vs. failure) |
|---|---|---|
| wilting response Risk Score | Soil drought tolerance screen | non-wilted vs. wilted |

TABLE 14-continued

| response | screen | categories (success vs. failure) |
|---|---|---|
| growth stage at day 14 | heat stress tolerance screen | 50% of plants reach stage1.03 vs. not |
| growth stage at day 14 | salt stress tolerance screen | 50% of plants reach stage1.03 vs. not |
| growth stage at day 14 | PEG induced osmotic stress tolerance screen | 50% of plants reach stage1.03 vs. not |
| growth stage at day 7 | cold germination tolerance screen | 50% of plants reach stage 0.5 vs. not |
| number of rosette leaves at day 23 | Shade tolerance screen | 5 leaves appeared vs. not |
| flower bud formation at day 23 | Shade tolerance screen | flower buds appear vs. not |
| leaf angle at day 23 | Shade tolerance screen | >60 degree vs. <60 degree |
| number of green leaves at day 21 | limited nitrogen tolerance screen | 6 or 7 leaves appeared vs. not |
| number of rosette leaves at day 21 | limited nitrogen tolerance screen | 6 or 7 leaves appeared vs. not |
| Flower bud formation at day 21 | limited nitrogen tolerance screen | flower buds appear vs. not |

Plants were grouped into transgenic and reference groups and were scored as success or failure according to Table 14. First, the risk (R) was calculated, which is the proportion of plants that were scored as of failure plants within the group. Then the relative risk (RR) was calculated as the ratio of R (transgenic) to R (reference). Risk score (RS) was calculated as $-\log_2^{RR}$. Subsequently the risk scores from multiple events for each transgene of interest were evaluated for statistical significance by t-test using SAS statistical software (SAS 9, SAS/STAT User's Guide, SAS Institute Inc, Cary, N.C., USA). RS with a value greater than 0 indicates that the transgenic plants perform better than the reference. RS with a value less than 0 indicates that the transgenic plants perform worse than the reference. The RS with a value equal to 0 indicates that the performance of the transgenic plants and the reference don't show any difference.

M. Statistic Analysis for Quantitative Responses

Table 15 provides a list of responses that were analyzed as quantitative responses.

TABLE 15

| response | screen |
|---|---|
| seed yield | Soil drought stress tolerance screen |
| seedling weight at day 14 | heat stress tolerance screen |
| root length at day 14 | heat stress tolerance screen |
| seedling weight at day 14 | salt stress tolerance screen |
| root length at day 14 | salt stress tolerance screen |
| root length at day 11 | salt stress tolerance screen |
| seedling weight at day 14 | PEG induced osmotic stress tolerance screen |
| root length at day 11 | PEG induced osmotic stress tolerance screen |
| root length at day 14 | PEG induced osmotic stress tolerance screen |
| rosette area at day 8 | cold shock tolerance screen |
| rosette area at day 28 | cold shock tolerance screen |
| difference in rosette area from day 8 to day 28 | cold shock tolerance screen |
| root length at day 28 | cold germination tolerance screen |
| seedling weight at day 23 | Shade tolerance screen |
| petiole length at day 23 | Shade tolerance screen |
| root length at day 14 | Early plant growth and development screen |
| Seedling weight at day 14 | Early plant growth and development screen |
| Rosette dry weight at day 53 | Late plant growth and development screen |
| rosette radius at day 25 | Late plant growth and development screen |

TABLE 15-continued

| response | screen |
|---|---|
| seed dry weight at day 58 | Late plant growth and development screen |
| silique dry weight at day 53 | Late plant growth and development screen |
| silique length at day 40 | Late plant growth and development screen |
| Seedling weight at day 21 | Limited nitrogen tolerance screen |
| Root length at day 21 | Limited nitrogen tolerance screen |

The measurements (M) of each plant were transformed by log 2 calculation. The Delta was calculated as $\log_2 M$(transgenic)$-\log 2M$(reference). Subsequently the mean delta from multiple events of the transgene of interest was evaluated for statistical significance by t-test using SAS statistical software (SAS 9, SAS/STAT User's Guide, SAS Institute Inc, Cary, N.C., USA). The Delta with a value greater than 0 indicates that the transgenic plants perform better than the reference. The Delta with a value less than 0 indicates that the transgenic plants perform worse than the reference. The Delta with a value equal to 0 indicates that the performance of the transgenic plants and the reference don't show any difference.

Example 2 Identification of Homologs

A BLAST searchable "All Protein Database" is constructed of known protein sequences using a proprietary sequence database and the National Center for Biotechnology Information (NCBI) non-redundant amino acid database (nr.aa). For each organism from which a DNA sequence provided herein was obtained, an "Organism Protein Database" is constructed of known protein sequences of the organism; the Organism Protein Database is a subset of the All Protein Database based on the NCBI taxonomy ID for the organism.

The All Protein Database is queried using amino acid sequence of cognate protein for gene DNA used in trait-improving recombinant DNA, i.e., sequences of SEQ ID NO: 426 through SEQ ID NO: 850 using "blastp" with E-value cutoff of 1e-8. Up to 1000 top hits were kept, and separated by organism names. For each organism other than that of the query sequence, a list is kept for hits from the query organism itself with a more significant E-value than the best hit of the organism. The list contains likely duplicated genes, and is referred to as the Core List. Another list was kept for all the hits from each organism, sorted by E-value, and referred to as the Hit List.

The Organism Protein Database is queried using amino acid sequences of SEQ ID NO: 426 through SEQ ID NO: 850 using "blastp" with E-value cutoff of 1e-4. Up to 1000 top hits are kept. A BLAST searchable database is constructed based on these hits, and is referred to as "SubDB". SubDB was queried with each sequence in the Hit List using "blastp" with E-value cutoff of 1e-8. The hit with the best E-value is compared with the Core List from the corresponding organism. The hit is deemed a likely ortholog if it belongs to the Core List, otherwise it is deemed not a likely ortholog and there is no further search of sequences in the Hit List for the same organism. Likely orthologs from a large number of distinct organisms were identified and are reported by amino acid sequences of SEQ ID NO: 851 to SEQ ID NO: 33634. These orthologs are reported in Tables 2 as homologs to the proteins cognate to genes used in trait-improving recombinant DNA.

Example 3 Consensus Sequence Build

ClustalW program is selected for multiple sequence alignments of an amino acid sequence of SEQ ID NO: 426 and its homologs, through SEQ ID NO: 850 and its homologs. Three major factors affecting the sequence alignments dramatically are (1) protein weight matrices; (2) gap open penalty; (3) gap extension penalty. Protein weight matrices available for ClustalW program include Blosum, Pam and Gonnet series. Those parameters with gap open penalty and gap extension penalty were extensively tested. On the basis of the test results, Blosum weight matrix, gap open penalty of 10 and gap extension penalty of 1 were chosen for multiple sequence alignment. The consensus sequence of SEQ ID NO: 601 and its 13 homologs was derived according to the procedure described above and is displayed in FIG. 1.

Example 4

This example illustrates the identification of amino acid domain by Pfam analysis.

The amino acid sequence of the expressed proteins that were shown to be associated with an enhanced trait were analyzed for Pfam protein family against the current Pfam collection of multiple sequence alignments and hidden Markov models using the HMMER software in the appended computer listing. The Pfam protein families for the proteins of SEQ ID NO: 425 through 850 are shown in Table 16. The Hidden Markov model databases for the identified patent families are also in the appended computer listing allowing identification of other homologous proteins and their cognate encoding DNA to enable the full breadth of the invention for a person of ordinary skill in the art. Certain proteins are identified by a single Pfam domain and others by multiple Pfam domains. For instance, the protein with amino acids of SEQ ID NO: 488 is characterized by two Pfam domains, i.e. "NAF" and "Pyr_redox_2". See also the protein with amino acids of SEQ ID NO: 441 which is characterized by three copies of the Pfam domain "zf-CCCH". In Table 16 "score" is the gathering score for the Hidden Markov Model of the domain which exceeds the gathering cutoff reported in Table 17.

TABLE 16

| PEP SEQ ID NO | GENE ID | Pfam domain name | begin | stop | score | E-value |
|---|---|---|---|---|---|---|
| 426 | CGPG699 | Histone | 27 | 100 | 99.6 | 8.80E−27 |
| 427 | CGPG567 | MIF | 2 | 115 | 69.4 | 1.00E−17 |
| 428 | CGPG267 | WD40 | 46 | 83 | 28.3 | 2.40E−05 |
| 428 | CGPG267 | WD40 | 136 | 173 | 36.3 | 9.60E−08 |
| 430 | CGPG959 | NPH3 | 209 | 444 | 429.9 | 3.20E−126 |
| 431 | CGPG2158 | LSM | 14 | 92 | 75.7 | 1.30E−19 |
| 432 | CGPG2446 | NUDIX | 63 | 210 | 94.9 | 2.20E−25 |
| 433 | CGPG1862 | Bromodomain | 421 | 510 | 97.4 | 4.00E−26 |
| 435 | CGPG1674 | efhand | 303 | 331 | 23.1 | 0.00089 |
| 435 | CGPG1674 | Na_Ca_ex | 441 | 575 | 58.5 | 1.90E−14 |
| 436 | CGPG2680 | Linker_histone | 23 | 93 | 101 | 3.30E−27 |
| 437 | CGPG3577 | Glyoxalase | 13 | 132 | 45.2 | 2.00E−10 |
| 438 | CGPG4065 | LRR_2 | 150 | 174 | 17.3 | 0.051 |
| 439 | CGPG3929 | Lung_7-TM_R | 134 | 419 | 130.2 | 5.20E−36 |
| 441 | CGPG3012 | zf-CCCH | 30 | 57 | 7.7 | 0.12 |
| 441 | CGPG3012 | zf-CCCH | 61 | 85 | 7.3 | 0.13 |
| 441 | CGPG3012 | zf-CCCH | 115 | 140 | 19.3 | 0.0034 |
| 442 | CGPG3162 | SBF | 128 | 313 | 239.7 | 5.60E−69 |
| 443 | CGPG607 | PurA | 28 | 275 | 44.4 | 5.80E−12 |
| 444 | CGPG4084 | PCI | 251 | 355 | 102 | 1.60E−27 |
| 445 | CGPG3917 | Pkinase | 13 | 268 | 341.6 | 1.20E−99 |
| 445 | CGPG3917 | NAF | 307 | 367 | 124.7 | 2.30E−34 |
| 446 | CGPG4414 | p450 | 32 | 502 | 364.5 | 1.50E−106 |
| 447 | CGPG185 | Cyclin_N | 62 | 187 | 117.7 | 3.00E−32 |
| 447 | CGPG185 | Cyclin_C | 189 | 312 | 83.3 | 7.00E−22 |
| 448 | CGPG1679 | Ferric_reduct | 183 | 304 | 126.7 | 6.00E−35 |
| 448 | CGPG1679 | FAD_binding_8 | 334 | 435 | 163.6 | 4.70E−46 |
| 448 | CGPG1679 | FAD_binding_6 | 336 | 435 | −7.5 | 0.0026 |
| 448 | CGPG1679 | NAD_binding_6 | 441 | 709 | 348.5 | 9.90E−102 |
| 449 | CGPG271 | PP2C | 269 | 629 | 56 | 1.10E−13 |
| 450 | CGPG4434 | p450 | 30 | 490 | 347.1 | 2.70E−101 |
| 452 | CGPG5253 | SBP56 | 20 | 487 | 1316.4 | 0 |
| 453 | CGPG5231 | Pkinase | 85 | 343 | 344.4 | 1.70E−100 |
| 453 | CGPG5231 | efhand | 390 | 418 | 35.6 | 1.50E−07 |
| 453 | CGPG5231 | efhand | 426 | 454 | 31.4 | 3.00E−06 |
| 453 | CGPG5231 | efhand | 462 | 490 | 28.3 | 2.50E−05 |
| 453 | CGPG5231 | efhand | 496 | 524 | 39.3 | 1.20E−08 |

TABLE 16-continued

| PEP SEQ ID NO | GENE ID | Pfam domain name | begin | stop | score | E-value |
|---|---|---|---|---|---|---|
| 455 | CGPG4859 | PSI_PsaF | 47 | 221 | 443.9 | 2.00E−130 |
| 456 | CGPG1589 | PLAC8 | 292 | 390 | 87.4 | 4.00E−23 |
| 458 | CGPG3899 | Pkinase | 132 | 417 | 294.1 | 2.40E−85 |
| 460 | CGPG5665 | Aminotran_3 | 27 | 362 | 550.2 | 2.00E−162 |
| 460 | CGPG5665 | Aminotran_1_2 | 42 | 417 | −49.4 | 5.40E−05 |
| 461 | CGPG5697 | Aminotran_3 | 25 | 360 | 503.2 | 2.70E−148 |
| 461 | CGPG5697 | Aminotran_1_2 | 40 | 415 | −51.6 | 7.00E−05 |
| 462 | CGPG5695 | Pyr_redox | 148 | 240 | 10.4 | 0.0019 |
| 462 | CGPG5695 | Pyr_redox_2 | 148 | 450 | 71.6 | 2.20E−18 |
| 463 | CGPG4862 | Glyco_hydro_1 | 40 | 520 | 611 | 9.40E−181 |
| 465 | CGPG6541 | PGK | 88 | 479 | 732.8 | 2.10E−217 |
| 466 | CGPG1756 | NOP5NT | 2 | 67 | 119.5 | 8.70E−33 |
| 466 | CGPG1756 | NOSIC | 160 | 212 | 127.9 | 2.70E−35 |
| 466 | CGPG1756 | Nop | 252 | 400 | 332.4 | 7.00E−97 |
| 467 | CGPG4927 | WD40 | 294 | 331 | 32.9 | 1.00E−06 |
| 467 | CGPG4927 | WD40 | 336 | 373 | 24.7 | 0.0003 |
| 467 | CGPG4927 | WD40 | 378 | 428 | 22.1 | 0.0018 |
| 468 | CGPG5106 | C2 | 17 | 96 | 91.7 | 2.10E−24 |
| 469 | CGPG5167 | p450 | 43 | 501 | 265.6 | 9.30E−77 |
| 470 | CGPG1924 | F-box | 21 | 68 | 39.6 | 9.80E−09 |
| 471 | CGPG5201 | Methyltransf_11 | 116 | 231 | 86.8 | 6.20E−23 |
| 471 | CGPG5201 | Methyltransf_12 | 116 | 229 | 31.3 | 3.10E−06 |
| 472 | CGPG1884 | Pkinase_Tyr | 88 | 365 | 137.7 | 2.90E−38 |
| 472 | CGPG1884 | Pkinase | 88 | 368 | 142.5 | 1.00E−39 |
| 473 | CGPG5089 | LRR_1 | 142 | 164 | 17.7 | 0.037 |
| 473 | CGPG5089 | LRR_1 | 166 | 188 | 8 | 8.2 |
| 473 | CGPG5089 | LRR_1 | 190 | 212 | 9.3 | 4.7 |
| 473 | CGPG5089 | LRR_1 | 214 | 233 | 10.7 | 2.6 |
| 473 | CGPG5089 | LRR_1 | 238 | 257 | 9.4 | 4.5 |
| 473 | CGPG5089 | Pkinase | 402 | 658 | −21.1 | 7.60E−07 |
| 474 | CGPG5870 | Pkinase | 47 | 314 | 77.2 | 4.60E−20 |
| 474 | CGPG5870 | Pkinase_Tyr | 48 | 314 | 67.5 | 8.20E−20 |
| 475 | CGPG5888 | Pkinase | 12 | 270 | 119.6 | 7.90E−33 |
| 476 | CGPG1461 | PGAM | 79 | 265 | 151.4 | 2.10E−42 |
| 477 | CGPG6743 | PGK | 88 | 483 | 573.5 | 1.80E−169 |
| 478 | CGPG6722 | Gln-synt_C | 208 | 468 | 370.2 | 2.90E−108 |
| 479 | CGPG82 | Pkinase | 43 | 329 | 324.8 | 1.40E−94 |
| 480 | CGPG6761 | Pyr_redox | 155 | 247 | 23.4 | 0.00017 |
| 480 | CGPG6761 | Pyr_redox_2 | 155 | 468 | 91.9 | 1.80E−24 |
| 481 | CGPG6781 | Aminotran_3 | 28 | 350 | 619.8 | 2.20E−183 |
| 482 | CGPG4914 | WD40 | 281 | 318 | 31 | 3.80E−06 |
| 483 | CGPG5840 | Pkinase | 5 | 274 | 146.1 | 8.30E−41 |
| 484 | CGPG5980 | Pkinase | 9 | 278 | 134.2 | 3.20E−37 |
| 485 | CGPG1743 | mTERF | 88 | 391 | 536.8 | 2.00E−158 |
| 486 | CGPG5434 | MtN3_slv | 9 | 98 | 76.7 | 6.50E−20 |
| 486 | CGPG5434 | MtN3_slv | 132 | 206 | 56.5 | 8.10E−14 |
| 487 | CGPG5824 | Pkinase | 121 | 407 | 304.3 | 2.00E−88 |
| 488 | CGPG5879 | Pkinase | 74 | 328 | 349 | 7.00E−102 |
| 488 | CGPG5879 | NAF | 383 | 441 | 95.5 | 1.50E−25 |
| 489 | CGPG5949 | Pyr_redox_2 | 6 | 302 | 154.8 | 2.00E−43 |
| 489 | CGPG5949 | Pyr_redox | 164 | 259 | 97 | 5.30E−26 |
| 490 | CGPG6096 | GSHPx | 79 | 187 | 229.1 | 8.70E−66 |
| 491 | CGPG6218 | MFS_1 | 27 | 449 | 95.1 | 2.00E−25 |
| 491 | CGPG6218 | Sugar_tr | 30 | 488 | 528.1 | 8.40E−156 |
| 492 | CGPG6226 | Sugar_tr | 101 | 556 | 315.4 | 9.20E−92 |
| 492 | CGPG6226 | MFS_1 | 105 | 515 | 81.2 | 2.90E−21 |
| 494 | CGPG7654 | HABP4_PAI-RBP1 | 159 | 272 | 149.9 | 6.00E−42 |
| 495 | CGPG6875 | zf-C3HC4 | 202 | 239 | 25.3 | 0.00019 |
| 496 | CGPG8259 | TIM | 4 | 245 | 454.3 | 1.40E−133 |
| 498 | CGPG8224 | NIR_SIR_ferr | 66 | 133 | 49.7 | 8.80E−12 |
| 498 | CGPG8224 | NIR_SIR | 166 | 347 | 199.3 | 8.30E−57 |
| 498 | CGPG8224 | NIR_SIR_ferr | 362 | 434 | 69.7 | 8.70E−18 |
| 498 | CGPG8224 | NIR_SIR | 443 | 591 | 0.4 | 0.0014 |
| 499 | CGPG1927 | F-box | 38 | 85 | 38.8 | 1.70E−08 |
| 499 | CGPG1927 | Arm | 418 | 458 | 27 | 5.90E−05 |
| 499 | CGPG1927 | Arm | 459 | 499 | 34.8 | 2.70E−07 |
| 499 | CGPG1927 | Arm | 500 | 543 | 39.2 | 1.30E−08 |
| 499 | CGPG1927 | Arm | 544 | 585 | 37.4 | 4.50E−08 |
| 499 | CGPG1927 | Arm | 589 | 630 | 45.7 | 1.40E−10 |
| 499 | CGPG1927 | Arm | 631 | 674 | 28.5 | 2.20E−05 |
| 499 | CGPG1927 | Arm | 675 | 715 | 45.8 | 1.30E−10 |
| 499 | CGPG1927 | Arm | 716 | 757 | 25 | 0.00025 |
| 500 | CGPG5962 | Glyco_hydro_14 | 95 | 523 | 269.8 | 5.00E−78 |
| 501 | CGPG5375 | IMPDH | 18 | 493 | 696.2 | 2.10E−206 |
| 503 | CGPG8943 | MGS | 123 | 238 | 189.9 | 5.50E−54 |
| 503 | CGPG8943 | AICARFT_IMPCHas | 243 | 568 | 635.4 | 4.30E−188 |
| 504 | CGPG8896 | Ferric_reduct | 122 | 279 | 184.5 | 2.40E−52 |

TABLE 16-continued

| PEP SEQ ID NO | GENE ID | Pfam domain name | begin | stop | score | E-value |
|---|---|---|---|---|---|---|
| 505 | CGPG8960 | DnaJ | 77 | 139 | 86.9 | 5.60E−23 |
| 505 | CGPG8960 | Fer4 | 162 | 185 | 12.6 | 0.0035 |
| 506 | CGPG5891 | Pkinase | 56 | 307 | −19.6 | 6.30E−07 |
| 507 | CGPG7260 | ATP-grasp_2 | 5 | 204 | −43.8 | 5.10E−08 |
| 508 | CGPG2647 | Fibrillarin | 79 | 310 | 599.4 | 2.90E−177 |
| 509 | CGPG6995 | F-box | 23 | 71 | 30.2 | 6.70E−06 |
| 510 | CGPG9046 | Pro_isomerase | 36 | 195 | 57.4 | 4.40E−14 |
| 511 | CGPG9047 | Pec_lyase_C | 108 | 274 | 124.5 | 2.80E−34 |
| 513 | CGPG9076 | Auxin_inducible | 7 | 106 | 26.3 | 5.50E−08 |
| 515 | CGPG9109 | CS | 19 | 93 | 91.2 | 2.80E−24 |
| 516 | CGPG5933 | Nodulin-like | 16 | 263 | 497.5 | 1.40E−146 |
| 517 | CGPG6335 | Sterol_desat | 35 | 246 | 238.8 | 1.10E−68 |
| 518 | CGPG9174 | YjeF_N | 28 | 205 | 146.4 | 7.10E−41 |
| 518 | CGPG9174 | Carb_kinase | 268 | 524 | 267.5 | 2.50E−77 |
| 519 | CGPG9120 | Glyoxal_oxid_N | 114 | 355 | 530.2 | 2.10E−156 |
| 522 | CGPG8087 | DUF1677 | 43 | 159 | 228.8 | 1.10E−65 |
| 523 | CGPG385 | RRM_1 | 13 | 76 | 71.4 | 2.70E−18 |
| 523 | CGPG385 | zf-CCHC | 99 | 116 | 34.1 | 4.40E−07 |
| 523 | CGPG385 | zf-CCHC | 121 | 138 | 28 | 1.90E−05 |
| 524 | CGPG1857 | FHA | 32 | 107 | 45.8 | 1.30E−10 |
| 525 | CGPG1788 | PB1 | 100 | 192 | 88.2 | 2.30E−23 |
| 526 | CGPG1966 | PHD | 66 | 114 | 57.6 | 3.70E−14 |
| 526 | CGPG1966 | SET | 238 | 373 | 99 | 1.30E−26 |
| 527 | CGPG1908 | F-box | 12 | 59 | 31 | 3.80E−06 |
| 527 | CGPG1908 | LRR_2 | 171 | 197 | 24.5 | 0.00035 |
| 529 | CGPG3557 | DnaJ | 4 | 67 | 139.6 | 7.80E−39 |
| 529 | CGPG3557 | DnaJ_C | 214 | 336 | 53.7 | 5.70E−13 |
| 530 | CGPG3340 | Dehydrin | 21 | 186 | 188.8 | 1.20E−53 |
| 531 | CGPG3431 | DUF914 | 3 | 330 | 829.1 | 2.20E−246 |
| 532 | CGPG3530 | DUF1644 | 29 | 181 | 359.3 | 5.80E−105 |
| 533 | CGPG3119 | DUF231 | 262 | 434 | 243.6 | 3.80E−70 |
| 534 | CGPG3594 | PRA-CH | 81 | 155 | 109.1 | 1.20E−29 |
| 534 | CGPG3594 | PRA-PH | 176 | 269 | 76 | 1.10E−19 |
| 535 | CGPG4031 | Pkinase_Tyr | 73 | 355 | 134.8 | 2.20E−37 |
| 535 | CGPG4031 | Pkinase | 73 | 355 | 173.8 | 4.10E−49 |
| 536 | CGPG4036 | Aa_trans | 31 | 467 | 546.7 | 2.20E−161 |
| 537 | CGPG2384 | Epimerase | 3 | 266 | 18.3 | 1.80E−07 |
| 537 | CGPG2384 | 3Beta_HSD | 4 | 292 | −95.6 | 5.50E−06 |
| 538 | CGPG1598 | Hist_deacetyl | 149 | 461 | 399.3 | 5.10E−117 |
| 539 | CGPG560 | zf-CCCH | 43 | 69 | 33.8 | 5.50E−07 |
| 539 | CGPG560 | zf-CCCH | 88 | 114 | 42 | 1.80E−09 |
| 539 | CGPG560 | zf-CCCH | 134 | 160 | 43.1 | 8.60E−10 |
| 539 | CGPG560 | zf-CCCH | 244 | 270 | 44.7 | 2.90E−10 |
| 539 | CGPG560 | zf-CCCH | 290 | 316 | 46.2 | 9.80E−11 |
| 540 | CGPG4002 | Aldo_ket_red | 15 | 319 | 258.8 | 1.00E−74 |
| 541 | CGPG1422 | ADH_N | 33 | 148 | 131.6 | 1.90E−36 |
| 541 | CGPG1422 | ADH_zinc_N | 179 | 314 | 106 | 9.80E−29 |
| 542 | CGPG4429 | p450 | 42 | 510 | 443 | 3.60E−130 |
| 544 | CGPG2251 | Abhydrolase_1 | 214 | 507 | 29.8 | 8.80E−06 |
| 545 | CGPG646 | 2-Hacid_dh | 31 | 357 | 64.1 | 4.10E−16 |
| 545 | CGPG646 | 2-Hacid_dh_C | 128 | 322 | 225.6 | 1.00E−64 |
| 546 | CGPG2569 | zf-CCCH | 146 | 171 | 27.5 | 4.30E−05 |
| 546 | CGPG2569 | WD40 | 178 | 215 | 25.9 | 0.00013 |
| 546 | CGPG2569 | WD40 | 302 | 338 | 31.9 | 2.00E−06 |
| 546 | CGPG2569 | WD40 | 343 | 378 | 26.4 | 9.40E−05 |
| 547 | CGPG5507 | zf-MYND | 74 | 111 | 47.9 | 3.10E−11 |
| 547 | CGPG5507 | UCH | 539 | 844 | 192.1 | 1.20E−54 |
| 548 | CGPG5547 | Hrf1 | 66 | 313 | 533.2 | 2.60E−157 |
| 548 | CGPG5547 | Yip1 | 108 | 286 | 1.7 | 0.00014 |
| 549 | CGPG5517 | HEAT | 178 | 214 | 14.2 | 0.44 |
| 549 | CGPG5517 | HEAT | 497 | 533 | 17.8 | 0.036 |
| 550 | CGPG5792 | AA_permease | 90 | 561 | 483.8 | 1.90E−142 |
| 551 | CGPG5766 | PHD | 282 | 329 | 54.3 | 3.70E−13 |
| 552 | CGPG5775 | SEP | 237 | 311 | 150.2 | 4.90E−42 |
| 552 | CGPG5775 | UBX | 343 | 422 | 105.7 | 1.20E−28 |
| 554 | CGPG4872 | WD40 | 310 | 347 | 31.9 | 2.00E−06 |
| 555 | CGPG6420 | ADH_N | 27 | 155 | 128.4 | 1.90E−35 |
| 555 | CGPG6420 | ADH_zinc_N | 186 | 327 | 138.2 | 2.10E−38 |
| 556 | CGPG6402 | PALP | 44 | 349 | −9.2 | 2.50E−07 |
| 557 | CGPG5073 | MatE | 49 | 209 | 124.5 | 2.70E−34 |
| 557 | CGPG5073 | MatE | 270 | 433 | 104.4 | 3.20E−28 |
| 558 | CGPG5091 | Lectin_C | 69 | 189 | 15.7 | 2.10E−05 |
| 558 | CGPG5091 | Pkinase | 257 | 542 | 64.3 | 3.60E−16 |
| 558 | CGPG5091 | Pkinase_Tyr | 283 | 542 | 69.1 | 6.30E−20 |
| 559 | CGPG3570 | TMEM14 | 4 | 107 | 204.8 | 1.90E−58 |
| 560 | CGPG4342 | Mito_carr | 114 | 210 | 119.3 | 1.00E−32 |
| 560 | CGPG4342 | Mito_carr | 214 | 301 | 100.5 | 4.60E−27 |

TABLE 16-continued

| PEP SEQ ID NO | GENE ID | Pfam domain name | begin | stop | score | E-value |
|---|---|---|---|---|---|---|
| 560 | CGPG4342 | Mito_carr | 304 | 392 | 100.7 | 4.10E−27 |
| 563 | CGPG4351 | ADH_N | 59 | 146 | 41.2 | 3.30E−09 |
| 563 | CGPG4351 | ADH_zinc_N | 177 | 323 | 66.6 | 7.40E−17 |
| 564 | CGPG4753 | FKBP_C | 43 | 137 | 190.9 | 2.80E−54 |
| 565 | CGPG4757 | DPBB_1 | 65 | 152 | 140.4 | 4.40E−39 |
| 565 | CGPG4757 | Pollen_allerg_1 | 163 | 240 | 133.5 | 5.20E−37 |
| 567 | CGPG6624 | YGGT | 92 | 174 | 111.5 | 2.20E−30 |
| 568 | CGPG3161 | ABC_tran | 92 | 280 | 155.8 | 1.00E−43 |
| 568 | CGPG3161 | ABC2_membrane | 384 | 590 | 180.6 | 3.60E−51 |
| 569 | CGPG3770 | ARID | 21 | 129 | 36.3 | 3.70E−08 |
| 569 | CGPG3770 | ELM2 | 372 | 427 | 33 | 9.50E−07 |
| 569 | CGPG3770 | Myb_DNA-binding | 472 | 518 | 19.4 | 0.011 |
| 571 | CGPG6702 | Aldedh | 103 | 564 | 794.5 | 5.60E−236 |
| 572 | CGPG21 | MIP | 30 | 265 | 447.2 | 2.00E−131 |
| 573 | CGPG6801 | PEPCK_ATP | 18 | 492 | 1215.7 | 0 |
| 574 | CGPG154 | Aa_trans | 29 | 428 | 516.5 | 2.80E−152 |
| 575 | CGPG6762 | Aldedh | 28 | 511 | 665.1 | 5.10E−197 |
| 576 | CGPG6763 | PK | 1 | 343 | 804.6 | 5.00E−239 |
| 576 | CGPG6763 | PK_C | 355 | 470 | 176.3 | 6.80E−50 |
| 576 | CGPG6763 | PEP-utilizers | 486 | 574 | 116.7 | 6.00E−32 |
| 577 | CGPG1467 | Auxin_inducible | 23 | 112 | 153 | 6.90E−43 |
| 578 | CGPG6160 | Miro | 11 | 126 | 66.4 | 8.20E−17 |
| 578 | CGPG6160 | Ras | 12 | 173 | 318 | 1.50E−92 |
| 579 | CGPG15 | p450 | 28 | 483 | 375.3 | 8.60E−110 |
| 580 | CGPG5825 | Pkinase | 138 | 425 | 297.9 | 1.80E−86 |
| 581 | CGPG5936 | MFS_1 | 48 | 421 | 141.9 | 1.60E−39 |
| 582 | CGPG5974 | FMO-like | 10 | 457 | −195.5 | 5.40E−15 |
| 582 | CGPG5974 | DAO | 12 | 288 | −14.4 | 7.70E−05 |
| 582 | CGPG5974 | Pyr_redox_2 | 12 | 308 | −16.4 | 0.0018 |
| 583 | CGPG1366 | Pkinase | 87 | 363 | 126.5 | 6.90E−35 |
| 583 | CGPG1366 | Pkinase_Tyr | 87 | 364 | 123.2 | 6.70E−34 |
| 584 | CGPG7390 | DapB_N | 51 | 180 | 68.3 | 2.20E−17 |
| 584 | CGPG7390 | DapB_C | 183 | 315 | 100.6 | 4.40E−27 |
| 585 | CGPG7421 | Ribul_P_3_epim | 91 | 291 | 411.7 | 9.30E−121 |
| 585 | CGPG7421 | OMPdecase | 94 | 300 | −46 | 0.0036 |
| 586 | CGPG7446 | TPR_1 | 123 | 156 | 26.4 | 9.10E−05 |
| 586 | CGPG7446 | TPR_2 | 123 | 156 | 24.4 | 0.00038 |
| 586 | CGPG7446 | TPR_1 | 160 | 193 | 37.1 | 5.70E−08 |
| 586 | CGPG7446 | TPR_2 | 160 | 193 | 32.9 | 9.90E−07 |
| 586 | CGPG7446 | TPR_1 | 194 | 241 | 14.4 | 0.093 |
| 587 | CGPG6295 | Pkinase | 67 | 345 | −14.9 | 3.40E−07 |
| 588 | CGPG1476 | RRM_1 | 26 | 97 | 63.9 | 4.80E−16 |
| 588 | CGPG1476 | RRM_1 | 114 | 184 | 98.1 | 2.40E−26 |
| 588 | CGPG1476 | RRM_1 | 203 | 273 | 88.2 | 2.30E−23 |
| 588 | CGPG1476 | RRM_1 | 306 | 376 | 94.6 | 2.80E−25 |
| 588 | CGPG1476 | PABP | 504 | 581 | 69.4 | 1.10E−17 |
| 589 | CGPG1821 | F-box | 10 | 57 | 37.4 | 4.50E−08 |
| 589 | CGPG1821 | LRR_2 | 166 | 190 | 16.6 | 0.077 |
| 589 | CGPG1821 | LRR_2 | 376 | 401 | 6.6 | 1.9 |
| 590 | CGPG6975 | Trp_syntA | 17 | 274 | 441.7 | 9.00E−130 |
| 591 | CGPG6189 | GDPD | 43 | 321 | 186.6 | 6.40E−53 |
| 592 | CGPG8868 | Pkinase | 49 | 318 | 114.4 | 2.90E−31 |
| 593 | CGPG8909 | Brix | 29 | 346 | 270.9 | 2.30E−78 |
| 594 | CGPG8951 | Lipase_3 | 102 | 222 | 8.9 | 9.40E−05 |
| 595 | CGPG5892 | Pkinase | 50 | 288 | −29.2 | 2.20E−06 |
| 597 | CGPG6142 | FAD_binding_4 | 123 | 258 | 118.8 | 1.40E−32 |
| 599 | CGPG9034 | Nicastrin | 249 | 458 | 357.9 | 1.50E−104 |
| 600 | CGPG9270 | Pkinase | 241 | 513 | 133.9 | 4.00E−37 |
| 600 | CGPG9270 | Pkinase_Tyr | 241 | 513 | 126.7 | 5.90E−35 |
| 602 | CGPG1284 | NAPRTase | 172 | 439 | 196.4 | 6.20E−56 |
| 603 | CGPG1640 | DUF1639 | 117 | 190 | 80.8 | 3.80E−21 |
| 604 | CGPG2136 | HMA | 13 | 73 | 52 | 1.80E−12 |
| 605 | CGPG3542 | Oxidored_FMN | 11 | 346 | 315.7 | 7.60E−92 |
| 606 | CGPG1691 | Mlo | 5 | 513 | 1236.3 | 0 |
| 607 | CGPG4067 | Glyco_transf_8 | 169 | 499 | 263 | 5.50E−76 |
| 608 | CGPG5335 | U-box | 256 | 329 | 93.1 | 7.90E−25 |
| 608 | CGPG5335 | Arm | 383 | 423 | 48.9 | 1.60E−11 |
| 608 | CGPG5335 | Arm | 424 | 464 | 22.1 | 0.0018 |
| 608 | CGPG5335 | Arm | 465 | 505 | 40.9 | 3.90E−09 |
| 608 | CGPG5335 | Arm | 506 | 546 | 18.7 | 0.019 |
| 608 | CGPG5335 | Arm | 547 | 587 | 34.1 | 4.30E−07 |
| 609 | CGPG27 | Ammonium_transp | 43 | 467 | 685.5 | 3.50E−203 |
| 611 | CGPG4375 | Anti-silence | 1 | 155 | 392.9 | 4.40E−115 |
| 612 | CGPG5176 | Pkinase | 334 | 602 | 135.4 | 1.40E−37 |
| 612 | CGPG5176 | Pkinase_Tyr | 334 | 606 | 124.9 | 2.00E−34 |
| 614 | CGPG661 | Flavodoxin_1 | 87 | 230 | 173.8 | 3.80E−49 |
| 614 | CGPG661 | FAD_binding_1 | 285 | 509 | 380.4 | 2.50E−111 |

TABLE 16-continued

| PEP SEQ ID NO | GENE ID | Pfam domain name | begin | stop | score | E-value |
|---|---|---|---|---|---|---|
| 614 | CGPG661 | NAD_binding_1 | 545 | 657 | 112 | 1.60E−30 |
| 615 | CGPG869 | ABC_tran | 110 | 312 | 147.5 | 3.20E−41 |
| 616 | CGPG6159 | Miro | 14 | 129 | 80.2 | 5.80E−21 |
| 616 | CGPG6159 | Ras | 15 | 176 | 332.9 | 5.10E−97 |
| 618 | CGPG6282 | Pkinase_Tyr | 86 | 365 | 140.5 | 4.10E−39 |
| 618 | CGPG6282 | Pkinase | 86 | 365 | 167.8 | 2.60E−47 |
| 619 | CGPG7671 | GATase_2 | 2 | 259 | 109.8 | 7.20E−30 |
| 619 | CGPG7671 | SIS | 356 | 490 | 123 | 7.60E−34 |
| 619 | CGPG7671 | SIS | 527 | 666 | 83.5 | 6.10E−22 |
| 620 | CGPG1574 | SPX | 1 | 293 | 370.2 | 2.90E−108 |
| 620 | CGPG1574 | EXS | 550 | 718 | 320.5 | 2.80E−93 |
| 621 | CGPG9294 | Pkinase | 22 | 281 | 169.6 | 7.20E−48 |
| 622 | CGPG2435 | Abhydrolase_3 | 92 | 307 | 250 | 4.50E−72 |
| 623 | CGPG3336 | GRP | 1 | 109 | 144.7 | 2.30E−40 |
| 625 | CGPG4168 | zf-A20 | 10 | 34 | 29.1 | 1.40E−05 |
| 625 | CGPG4168 | zf-AN1 | 99 | 139 | 61 | 3.50E−15 |
| 626 | CGPG6517 | Aldedh | 19 | 478 | 827.9 | 4.90E−246 |
| 627 | CGPG993 | p450 | 30 | 500 | 86.4 | 7.90E−23 |
| 629 | CGPG5393 | PALP | 20 | 309 | 439.2 | 5.10E−129 |
| 630 | CGPG1313 | Di19 | 10 | 218 | 482.6 | 4.40E−142 |
| 631 | CGPG8150 | DnaJ | 93 | 162 | 23.9 | 1.90E−05 |
| 631 | CGPG8150 | HSCB_C | 176 | 250 | 102.1 | 1.50E−27 |
| 632 | CGPG1661 | FAE_3-kCoA_syn1 | 14 | 340 | 776.2 | 1.80E−230 |
| 633 | CGPG6427 | ADH_N | 27 | 155 | 129.8 | 6.70E−36 |
| 633 | CGPG6427 | ADH_zinc_N | 186 | 332 | 129.4 | 9.40E−36 |
| 634 | CGPG4906 | WD40 | 46 | 83 | 39.2 | 1.30E−08 |
| 635 | CGPG5092 | Lectin_legB | 25 | 262 | 393.3 | 3.30E−115 |
| 635 | CGPG5092 | Pkinase | 353 | 611 | 45.8 | 1.30E−10 |
| 635 | CGPG5092 | Pkinase_Tyr | 353 | 611 | 65.9 | 1.10E−19 |
| 636 | CGPG6146 | DUF241 | 37 | 272 | 374.9 | 1.20E−109 |
| 637 | CGPG6022 | RRM_1 | 46 | 113 | 28.5 | 2.20E−05 |
| 637 | CGPG6022 | RRM_1 | 163 | 233 | 44.6 | 3.10E−10 |
| 638 | CGPG5883 | Pkinase | 129 | 411 | 125.5 | 1.40E−34 |
| 638 | CGPG5883 | Pkinase_Tyr | 129 | 411 | 86.8 | 6.00E−23 |
| 640 | CGPG8248 | NAD_binding_2 | 1 | 163 | 203 | 6.40E−58 |
| 640 | CGPG8248 | 6PGD | 167 | 301 | −145.6 | 3.60E−09 |
| 641 | CGPG8233 | Sedlin_N | 3 | 77 | 177.8 | 2.50E−50 |
| 645 | CGPG6337 | Sterol_desat | 38 | 246 | 218.1 | 1.80E−62 |
| 646 | CGPG9005 | CH | 14 | 115 | 54.8 | 2.60E−13 |
| 646 | CGPG9005 | EB1 | 200 | 247 | 76.6 | 7.30E−20 |
| 647 | CGPG9208 | CoA_trans | 5 | 242 | 104.7 | 2.50E−28 |
| 648 | CGPG4348 | Xan_ur_permease | 94 | 532 | −11.6 | 1.00E−07 |
| 650 | CGPG618 | ADK | 38 | 224 | 317.8 | 1.80E−92 |
| 650 | CGPG618 | ADK_lid | 160 | 195 | 83.4 | 6.40E−22 |
| 651 | CGPG251 | p450 | 37 | 459 | 223.1 | 5.80E−64 |
| 652 | CGPG636 | Ion_trans_2 | 81 | 163 | 75.3 | 1.80E−19 |
| 652 | CGPG636 | Ion_trans_2 | 202 | 277 | 59.5 | 9.80E−15 |
| 654 | CGPG287 | B56 | 71 | 484 | 1074.3 | 0 |
| 655 | CGPG893 | DUF231 | 210 | 368 | 324.8 | 1.30E−94 |
| 657 | CGPG657 | PI-PLC-X | 106 | 248 | 73.4 | 6.70E−19 |
| 657 | CGPG657 | C2 | 405 | 496 | 85.1 | 1.90E−22 |
| 658 | CGPG1489 | Enolase_N | 3 | 139 | 232.7 | 7.20E−67 |
| 658 | CGPG1489 | Enolase_C | 147 | 441 | 719.3 | 2.40E−213 |
| 660 | CGPG1683 | DUF568 | 89 | 227 | 302 | 9.90E−88 |
| 661 | CGPG4685 | MFS_1 | 40 | 446 | 143.1 | 6.60E−40 |
| 662 | CGPG4729 | Auxin_inducible | 37 | 146 | 217.2 | 3.40E−62 |
| 663 | CGPG4880 | Trehalose_PPase | 108 | 346 | 314.1 | 2.30E−91 |
| 664 | CGPG5680 | Aminotran_1_2 | 30 | 384 | 204.7 | 1.90E−58 |
| 665 | CGPG7317 | ADH_N | 27 | 155 | 123 | 7.60E−34 |
| 665 | CGPG7317 | ADH_zinc_N | 186 | 328 | 146.5 | 6.30E−41 |
| 666 | CGPG4902 | DUF260 | 15 | 116 | 240.1 | 4.30E−69 |
| 667 | CGPG6720 | Aldedh | 116 | 581 | 794.9 | 4.30E−236 |
| 668 | CGPG5850 | Pkinase | 75 | 349 | 170.9 | 2.80E−48 |
| 668 | CGPG5850 | Pkinase_Tyr | 75 | 349 | 128.3 | 2.00E−35 |
| 669 | CGPG6010 | RRM_1 | 130 | 200 | 60 | 7.30E−15 |
| 669 | CGPG6010 | RRM_1 | 229 | 299 | 62.6 | 1.20E−15 |
| 670 | CGPG7488 | OPT | 28 | 651 | 682.3 | 3.40E−202 |
| 672 | CGPG7672 | PTPA | 86 | 387 | 526.8 | 2.10E−155 |
| 674 | CGPG6988 | Sulfotransfer_1 | 79 | 340 | 296.6 | 4.10E−86 |
| 675 | CGPG1357 | DUF26 | 77 | 131 | 85.6 | 1.40E−22 |
| 675 | CGPG1357 | DUF26 | 190 | 241 | 81.6 | 2.20E−21 |
| 675 | CGPG1357 | Pkinase_Tyr | 326 | 598 | 144.7 | 2.30E−40 |
| 675 | CGPG1357 | Pkinase | 326 | 598 | 158.3 | 1.80E−44 |
| 676 | CGPG5918 | ADH_N | 35 | 150 | 102.7 | 1.00E−27 |
| 676 | CGPG5918 | ADH_zinc_N | 181 | 315 | 81.3 | 2.80E−21 |
| 677 | CGPG6020 | La | 107 | 166 | 135.1 | 1.70E−37 |
| 677 | CGPG6020 | RRM_1 | 195 | 278 | 39.7 | 9.50E−09 |

TABLE 16-continued

| PEP SEQ ID NO | GENE ID | Pfam domain name | begin | stop | score | E-value |
|---|---|---|---|---|---|---|
| 678 | CGPG7032 | Pkinase | 18 | 302 | 169.8 | 6.20E−48 |
| 678 | CGPG7032 | Pkinase_Tyr | 18 | 302 | 174.3 | 2.80E−49 |
| 679 | CGPG7069 | Na_Ca_ex | 115 | 249 | 118.5 | 1.80E−32 |
| 679 | CGPG7069 | Na_Ca_ex | 415 | 558 | 118.9 | 1.30E−32 |
| 680 | CGPG8900 | K_trans | 1 | 302 | 64.8 | 2.30E−23 |
| 681 | CGPG8923 | Pkinase | 134 | 418 | 303.1 | 4.80E−88 |
| 682 | CGPG6296 | Pkinase | 113 | 376 | 169.5 | 7.50E−48 |
| 682 | CGPG6296 | Pkinase_Tyr | 113 | 376 | 150.7 | 3.50E−42 |
| 685 | CGPG6951 | RNA_pol_Rpb8 | 9 | 145 | 314.2 | 2.10E−91 |
| 686 | CGPG6994 | Ion_trans_2 | 155 | 237 | 56.5 | 8.00E−14 |
| 686 | CGPG6994 | Ion_trans_2 | 279 | 354 | 44 | 4.80E−10 |
| 687 | CGPG7019 | Aldo_ket_red | 10 | 325 | −73.8 | 5.00E−05 |
| 689 | CGPG9255 | Pkinase | 97 | 417 | 246.9 | 3.90E−71 |
| 690 | CGPG9274 | CS | 73 | 150 | 66.2 | 9.80E−17 |
| 690 | CGPG9274 | SGS | 154 | 212 | 58.1 | 2.70E−14 |
| 691 | CGPG6130 | Miro | 107 | 222 | 145.6 | 1.20E−40 |
| 691 | CGPG6130 | Ras | 108 | 274 | −24.6 | 1.80E−07 |
| 692 | CGPG8074 | PMEI | 32 | 193 | 190.9 | 2.70E−54 |
| 694 | CGPG172 | WD40 | 187 | 222 | 23.4 | 0.00074 |
| 696 | CGPG3222 | zf-C3HC4 | 110 | 151 | 30.9 | 4.10E−06 |
| 697 | CGPG3259 | Asp | 86 | 507 | 507.1 | 1.90E−149 |
| 697 | CGPG3259 | SapB_2 | 319 | 353 | 56.5 | 8.10E−14 |
| 697 | CGPG3259 | SapB_1 | 379 | 417 | 57 | 5.70E−14 |
| 698 | CGPG1900 | F-box | 1 | 48 | 39.5 | 1.00E−08 |
| 700 | CGPG20 | MIP | 30 | 259 | 448.1 | 1.10E−131 |
| 701 | CGPG201 | PI-PLC-X | 113 | 257 | 137 | 4.80E−38 |
| 701 | CGPG201 | PI-PLC-Y | 299 | 417 | 97.2 | 4.40E−26 |
| 701 | CGPG201 | C2 | 439 | 531 | 80.2 | 5.70E−21 |
| 702 | CGPG3420 | WD40 | 573 | 612 | 26.9 | 6.50E−05 |
| 703 | CGPG4308 | NPH3 | 30 | 309 | 254 | 2.90E−73 |
| 704 | CGPG5244 | FH2 | 589 | 985 | 601.3 | 8.30E−178 |
| 705 | CGPG5538 | aPHC | 13 | 313 | 625.3 | 4.60E−185 |
| 706 | CGPG3738 | Glycolytic | 55 | 399 | 842.5 | 1.90E−250 |
| 707 | CGPG6454 | PGM_PMM_I | 103 | 249 | 157.3 | 3.70E−44 |
| 707 | CGPG6454 | PGM_PMM_II | 280 | 394 | 163.5 | 4.90E−46 |
| 707 | CGPG6454 | PGM_PMM_III | 396 | 518 | 150.6 | 3.70E−42 |
| 707 | CGPG6454 | PGM_PMM_IV | 539 | 647 | 96.5 | 7.50E−26 |
| 708 | CGPG6530 | Glutaminase | 121 | 412 | 609.3 | 3.10E−180 |
| 709 | CGPG5175 | p450 | 36 | 467 | 55.8 | 1.30E−13 |
| 710 | CGPG5756 | Pkinase | 504 | 838 | 165.3 | 1.40E−46 |
| 711 | CGPG5361 | U-box | 32 | 106 | 87.5 | 3.80E−23 |
| 712 | CGPG6709 | Aldedh | 103 | 562 | 699.5 | 2.10E−207 |
| 713 | CGPG6755 | Aminotran_3 | 123 | 449 | 313.4 | 3.80E−91 |
| 714 | CGPG6765 | Alpha-amylase | 16 | 418 | 541.6 | 7.40E−160 |
| 715 | CGPG6039 | LEA_2 | 2 | 151 | 358.6 | 8.90E−105 |
| 716 | CGPG6158 | Miro | 9 | 124 | 78.5 | 1.90E−20 |
| 716 | CGPG6158 | Ras | 10 | 171 | 357.2 | 2.40E−104 |
| 718 | CGPG7528 | Agenet | 3 | 68 | 34 | 4.80E−07 |
| 718 | CGPG7528 | Agenet | 141 | 206 | 93.6 | 5.50E−25 |
| 719 | CGPG7756 | BRAP2 | 51 | 161 | 137.8 | 2.70E−38 |
| 719 | CGPG7756 | zf-C3HC4 | 168 | 207 | 40.1 | 7.20E−09 |
| 719 | CGPG7756 | zf-UBP | 219 | 290 | 119.4 | 9.30E−33 |
| 721 | CGPG8249 | PfkB | 3 | 313 | 214 | 3.20E−61 |
| 722 | CGPG2232 | PCI | 293 | 397 | 103.9 | 4.20E−28 |
| 723 | CGPG5494 | FAE1_CUT1_RppA | 22 | 313 | 586 | 3.30E−173 |
| 723 | CGPG5494 | Chal_sti_synt_C | 287 | 426 | 0 | 0.0016 |
| 723 | CGPG5494 | ACP_syn_III_C | 333 | 424 | 31.3 | 7.50E−09 |
| 724 | CGPG5947 | Glyco_hydro_14 | 109 | 534 | 645.4 | 4.40E−191 |
| 726 | CGPG6262 | Pkinase | 68 | 304 | −46.3 | 2.00E−05 |
| 727 | CGPG6909 | 2OG-FeII_Oxy | 205 | 302 | 109.4 | 9.80E−30 |
| 729 | CGPG8965 | DnaJ | 6 | 68 | 116.2 | 8.30E−32 |
| 730 | CGPG5861 | Pkinase | 68 | 337 | 98.7 | 1.60E−26 |
| 730 | CGPG5861 | Pkinase_Tyr | 68 | 337 | 78.1 | 1.40E−20 |
| 732 | CGPG7246 | MIP | 75 | 285 | 170.5 | 3.80E−48 |
| 733 | CGPG5378 | WWE | 77 | 148 | 88.4 | 2.00E−23 |
| 734 | CGPG9168 | NTP_transferase | 5 | 286 | 481.1 | 1.20E−141 |
| 734 | CGPG9168 | MannoseP_isomer | 297 | 462 | 449.5 | 4.10E−132 |
| 734 | CGPG9168 | Cupin_2 | 377 | 447 | 52 | 1.80E−12 |
| 735 | CGPG1505 | PGI | 52 | 548 | 1050.2 | 0 |
| 737 | CGPG3220 | Methyltransf_6 | 2 | 159 | 181.8 | 1.60E−51 |
| 738 | CGPG3062 | Sugar_tr | 26 | 489 | 672.8 | 2.30E−199 |
| 738 | CGPG3062 | MFS_1 | 32 | 450 | 89.6 | 8.70E−24 |
| 739 | CGPG3580 | DUF588 | 27 | 169 | 202.1 | 1.20E−57 |
| 740 | CGPG3725 | DUF1325 | 8 | 269 | 487.8 | 1.20E−143 |
| 741 | CGPG592 | Spermine_synth | 50 | 295 | 493.4 | 2.40E−145 |
| 742 | CGPG4417 | p450 | 34 | 510 | 291.7 | 1.30E−84 |
| 743 | CGPG2276 | IF2_N | 419 | 470 | 46.9 | 6.20E−11 |

TABLE 16-continued

| PEP SEQ ID NO | GENE ID | Pfam domain name | begin | stop | score | E-value |
|---|---|---|---|---|---|---|
| 743 | CGPG2276 | GTP_EFTU | 499 | 670 | 157 | 4.40E−44 |
| 743 | CGPG2276 | Ras | 513 | 668 | −68.7 | 0.00036 |
| 743 | CGPG2276 | GTP_EFTU_D2 | 693 | 756 | 59 | 1.40E−14 |
| 744 | CGPG4975 | CK_II_beta | 96 | 270 | 447.9 | 1.20E−131 |
| 745 | CGPG2790 | Asp | 82 | 476 | −116.5 | 9.10E−07 |
| 746 | CGPG4972 | PP2C | 88 | 349 | 281 | 2.00E−81 |
| 747 | CGPG5140 | p450 | 27 | 502 | 87.5 | 3.70E−23 |
| 748 | CGPG19 | MIP | 11 | 232 | 391.4 | 1.20E−114 |
| 749 | CGPG6769 | iPGM_N | 12 | 367 | 828.1 | 4.30E−246 |
| 749 | CGPG6769 | Metalloenzyme | 377 | 493 | 184.1 | 3.00E−52 |
| 750 | CGPG6770 | Molybdop_Fe4S4 | 53 | 114 | 70.4 | 5.30E−18 |
| 750 | CGPG6770 | Molybdopterin | 117 | 670 | 82.9 | 8.90E−22 |
| 750 | CGPG6770 | Molydop_binding | 902 | 1021 | 63.2 | 7.60E−16 |
| 752 | CGPG6789 | Isoamylase_N | 12 | 98 | 134.2 | 3.20E−37 |
| 752 | CGPG6789 | Alpha-amylase | 138 | 574 | 49.2 | 1.10E−12 |
| 753 | CGPG5374 | CBS | 54 | 268 | 34 | 4.80E−07 |
| 753 | CGPG5374 | CBS | 291 | 426 | 80.3 | 5.60E−21 |
| 754 | CGPG5978 | Pkinase_Tyr | 74 | 349 | 229.9 | 5.00E−66 |
| 754 | CGPG5978 | Pkinase | 74 | 349 | 185.3 | 1.30E−52 |
| 755 | CGPG5979 | Pkinase | 108 | 369 | 219.6 | 6.40E−63 |
| 757 | CGPG948 | NPH3 | 165 | 407 | 469.9 | 2.90E−138 |
| 758 | CGPG6052 | DUF1723 | 61 | 110 | 92.8 | 9.50E−25 |
| 759 | CGPG7661 | HMA | 91 | 154 | 50.4 | 5.40E−12 |
| 759 | CGPG7661 | DAO | 188 | 525 | −20.6 | 0.0002 |
| 759 | CGPG7661 | Pyr_redox_2 | 188 | 497 | 237.8 | 2.10E−68 |
| 759 | CGPG7661 | Pyr_redox | 360 | 450 | 89 | 1.30E−23 |
| 759 | CGPG7661 | Pyr_redox_dim | 525 | 634 | 160.9 | 3.00E−45 |
| 760 | CGPG8261 | Aminotran_3 | 27 | 350 | 484.5 | 1.20E−142 |
| 761 | CGPG5447 | Cys_Met_Meta_PP | 176 | 561 | 752.1 | 3.20E−223 |
| 761 | CGPG5447 | Beta_elim_lyase | 215 | 461 | −106.2 | 0.0013 |
| 762 | CGPG7068 | DUF1005 | 249 | 432 | 467.9 | 1.10E−137 |
| 763 | CGPG5938 | MFS_1 | 45 | 420 | 78.2 | 2.30E−20 |
| 764 | CGPG7100 | BCNT | 149 | 228 | 153.6 | 4.90E−43 |
| 765 | CGPG9003 | SNARE | 37 | 99 | 66.1 | 1.00E−16 |
| 766 | CGPG6299 | Pkinase_Tyr | 73 | 349 | 136 | 9.50E−38 |
| 766 | CGPG6299 | Pkinase | 73 | 349 | 139.1 | 1.10E−38 |
| 767 | CGPG9135 | Acyl-CoA_dh_N | 51 | 162 | 83.6 | 5.80E−22 |
| 767 | CGPG9135 | Acyl-CoA_dh_M | 166 | 218 | 85.2 | 1.80E−22 |
| 767 | CGPG9135 | Acyl-CoA_dh_1 | 272 | 418 | 95.2 | 1.80E−25 |
| 767 | CGPG9135 | Acyl-CoA_dh_2 | 284 | 407 | −9.9 | 0.0016 |
| 771 | CGPG9139 | TB2_DP1_HVA22 | 2 | 98 | 38.6 | 6.60E−09 |
| 772 | CGPG414 | Pkinase | 80 | 338 | 353.1 | 4.00E−103 |
| 774 | CGPG1986 | Sulfotransfer_1 | 71 | 332 | 273.5 | 3.80E−79 |
| 775 | CGPG2916 | PC4 | 68 | 158 | 190.2 | 4.70E−54 |
| 776 | CGPG111 | PBP | 20 | 165 | 256.9 | 3.80E−74 |
| 777 | CGPG4317 | zf-AN1 | 102 | 142 | 70.1 | 6.60E−18 |
| 778 | CGPG4387 | zf-A20 | 31 | 55 | 40.6 | 4.90E−09 |
| 778 | CGPG4387 | zf-AN1 | 124 | 164 | 64.7 | 2.80E−16 |
| 779 | CGPG4492 | Oleosin | 27 | 145 | 87.2 | 4.70E−23 |
| 780 | CGPG597 | Glyco_hydro_28 | 98 | 437 | 482.9 | 3.60E−142 |
| 781 | CGPG345 | TPR_2 | 491 | 524 | 25 | 0.00024 |
| 781 | CGPG345 | TPR_1 | 491 | 524 | 18.8 | 0.018 |
| 781 | CGPG345 | TPR_2 | 590 | 623 | 25.4 | 0.00018 |
| 781 | CGPG345 | TPR_1 | 590 | 623 | 32.3 | 1.60E−06 |
| 781 | CGPG345 | TPR_1 | 624 | 657 | 24 | 0.00048 |
| 781 | CGPG345 | TPR_2 | 658 | 691 | 32.6 | 1.30E−06 |
| 781 | CGPG345 | TPR_1 | 658 | 691 | 36.6 | 8.00E−08 |
| 783 | CGPG4998 | LRRNT_2 | 27 | 67 | 57.2 | 5.00E−14 |
| 783 | CGPG4998 | LRR_1 | 71 | 93 | 9.9 | 3.6 |
| 783 | CGPG4998 | LRR_1 | 95 | 117 | 17.8 | 0.035 |
| 783 | CGPG4998 | LRR_1 | 119 | 141 | 17.2 | 0.056 |
| 783 | CGPG4998 | LRR_1 | 143 | 165 | 12.8 | 1 |
| 785 | CGPG5104 | C2 | 8 | 87 | 94.8 | 2.30E−25 |
| 786 | CGPG6502 | Pribosyltran | 95 | 241 | 137.3 | 3.90E−38 |
| 787 | CGPG6630 | Lactamase_B | 113 | 278 | 42.4 | 1.40E−09 |
| 788 | CGPG5484 | PP2C | 100 | 340 | 253.9 | 3.10E−73 |
| 789 | CGPG5394 | PDT | 101 | 278 | 281.4 | 1.60E−81 |
| 789 | CGPG5394 | ACT | 288 | 371 | 26.6 | 8.30E−05 |
| 791 | CGPG2090 | DUF786 | 5 | 107 | 220.1 | 4.60E−63 |
| 792 | CGPG6664 | FeThRed_A | 91 | 157 | 166.5 | 6.10E−47 |
| 793 | CGPG7706 | Acetyltransf_1 | 58 | 149 | 71.2 | 3.10E−18 |
| 794 | CGPG7884 | Aldedh | 72 | 516 | 216.4 | 5.70E−62 |
| 795 | CGPG6965 | COX5C | 2 | 63 | 162.4 | 1.10E−45 |
| 797 | CGPG2297 | TCTP | 1 | 165 | 320.9 | 2.00E−93 |
| 798 | CGPG6246 | Pkinase | 24 | 278 | 334.9 | 1.30E−97 |
| 798 | CGPG6246 | NAF | 311 | 373 | 119.5 | 8.90E−33 |
| 799 | CGPG9037 | Ribophorin_I | 40 | 472 | 658 | 6.90E−195 |

TABLE 16-continued

| PEP SEQ ID NO | GENE ID | Pfam domain name | begin | stop | score | E-value |
|---|---|---|---|---|---|---|
| 800 | CGPG1941 | TBC | 271 | 503 | −52.5 | 0.00069 |
| 801 | CGPG2055 | Terpene_synth | 1 | 105 | −37 | 7.70E−05 |
| 803 | CGPG386 | Ank | 57 | 89 | 46.8 | 6.50E−11 |
| 803 | CGPG386 | Ank | 91 | 123 | 22.6 | 0.0013 |
| 803 | CGPG386 | RCC1 | 259 | 307 | 29 | 1.50E−05 |
| 803 | CGPG386 | RCC1 | 311 | 361 | 25.7 | 0.00015 |
| 804 | CGPG393 | CDI | 155 | 208 | 92.1 | 1.50E−24 |
| 805 | CGPG609 | Smr | 428 | 502 | 81.8 | 2.00E−21 |
| 806 | CGPG4022 | Aa_trans | 41 | 435 | 323.9 | 2.60E−94 |
| 807 | CGPG942 | AMP-binding | 32 | 441 | 405 | 9.70E−119 |
| 808 | CGPG1800 | PHD | 605 | 653 | 48.3 | 2.30E−11 |
| 810 | CGPG3257 | LRRNT_2 | 26 | 63 | 39.9 | 7.80E−09 |
| 810 | CGPG3257 | LRR_1 | 91 | 113 | 18.9 | 0.016 |
| 810 | CGPG3257 | LRR_1 | 115 | 137 | 12.2 | 1.4 |
| 810 | CGPG3257 | LRR_1 | 163 | 183 | 9.6 | 4.1 |
| 810 | CGPG3257 | Pkinase_Tyr | 344 | 612 | 68.3 | 7.20E−20 |
| 810 | CGPG3257 | Pkinase | 345 | 612 | 63.9 | 4.90E−16 |
| 811 | CGPG1696 | MtN3_slv | 6 | 93 | 133.5 | 5.40E−37 |
| 811 | CGPG1696 | MtN3_slv | 128 | 214 | 96.2 | 8.80E−26 |
| 813 | CGPG3780 | Response_reg | 78 | 194 | 79.9 | 7.10E−21 |
| 813 | CGPG3780 | CCT | 675 | 713 | 71.5 | 2.40E−18 |
| 814 | CGPG6602 | RuBisCO_large_N | 104 | 229 | 293.3 | 4.30E−85 |
| 814 | CGPG6602 | RuBisCO_large | 237 | 545 | 816.5 | 1.30E−242 |
| 815 | CGPG6621 | GIDA | 128 | 453 | −213 | 0.0004 |
| 815 | CGPG6621 | Pyr_redox_2 | 128 | 437 | 209.4 | 7.80E−60 |
| 815 | CGPG6621 | Pyr_redox | 296 | 391 | 126.7 | 6.00E−35 |
| 815 | CGPG6621 | Pyr_redox_dim | 470 | 579 | 158.4 | 1.70E−44 |
| 816 | CGPG5493 | FAE1_CUT1_RppA | 113 | 402 | 727.7 | 7.00E−216 |
| 816 | CGPG5493 | Chal_sti_synt_C | 384 | 528 | −2.9 | 0.0028 |
| 816 | CGPG5493 | ACP_syn_III_C | 442 | 526 | 23.2 | 5.20E−08 |
| 817 | CGPG5811 | Pkinase | 107 | 381 | 198.8 | 1.20E−56 |
| 817 | CGPG5811 | Pkinase_Tyr | 107 | 381 | 253.2 | 4.80E−73 |
| 818 | CGPG5902 | ADH_N | 27 | 108 | 66.2 | 9.80E−17 |
| 818 | CGPG5902 | ADH_zinc_N | 139 | 281 | 165.3 | 1.50E−46 |
| 819 | CGPG6791 | PGI | 25 | 480 | 184.8 | 2.00E−52 |
| 820 | CGPG6778 | Alpha-amylase | 13 | 420 | 442.8 | 4.00E−130 |
| 821 | CGPG6166 | Miro | 7 | 121 | 52.9 | 1.00E−12 |
| 821 | CGPG6166 | Ras | 8 | 177 | 266.5 | 4.90E−77 |
| 822 | CGPG3735 | LisH | 47 | 73 | 43.8 | 5.40E−10 |
| 823 | CGPG5854 | Pkinase | 2 | 275 | 97.2 | 4.60E−26 |
| 825 | CGPG5024 | adh_short | 30 | 212 | 15.2 | 3.60E−07 |
| 826 | CGPG6054 | Miro | 6 | 120 | 63.4 | 6.90E−16 |
| 826 | CGPG6054 | Ras | 7 | 178 | 255.3 | 1.20E−73 |
| 827 | CGPG6207 | Sugar_tr | 34 | 479 | 468.3 | 8.90E−138 |
| 827 | CGPG6207 | MFS_1 | 38 | 438 | 121.3 | 2.50E−33 |
| 828 | CGPG7620 | Arginase | 69 | 349 | 375.5 | 7.30E−110 |
| 831 | CGPG73 | Dicty_CAR | 10 | 314 | −6.3 | 2.80E−06 |
| 832 | CGPG2100 | PLAC8 | 17 | 116 | 142.7 | 9.00E−40 |
| 833 | CGPG6026 | RRM_1 | 8 | 62 | 43.4 | 7.20E−10 |
| 834 | CGPG7269 | Tim17 | 18 | 146 | 146.8 | 5.20E−41 |
| 836 | CGPG6993 | Peptidase_C12 | 12 | 219 | 381.6 | 1.10E−111 |
| 838 | CGPG6926 | Yip1 | 93 | 240 | 161.1 | 2.70E−45 |
| 839 | CGPG7172 | Pkinase | 3 | 269 | 192.5 | 9.30E−55 |
| 840 | CGPG7129 | DUF1070 | 9 | 63 | 115.5 | 1.40E−31 |
| 842 | CGPG9031 | MFAP1_C | 141 | 423 | 511 | 1.20E−150 |
| 843 | CGPG9105 | ARD | 14 | 168 | 329.7 | 4.50E−96 |
| 843 | CGPG9105 | Cupin_2 | 88 | 162 | 28.3 | 2.50E−05 |
| 844 | CGPG9082 | DUF662 | 7 | 169 | 236.3 | 6.00E−68 |
| 845 | CGPG6212 | Sugar_tr | 20 | 490 | 52.4 | 1.40E−12 |
| 845 | CGPG6212 | MFS_1 | 29 | 451 | 98.9 | 1.40E−26 |
| 846 | CGPG9206 | Carboxyl_trans | 34 | 535 | 1022.5 | 1.30E−304 |
| 847 | CGPG9151 | Aminotran_3 | 82 | 421 | 269 | 8.90E−78 |
| 848 | CGPG9129 | HATPase_c | 228 | 356 | 83.7 | 5.20E−22 |
| 850 | CGPG9358 | TPR_1 | 551 | 584 | 10.5 | 0.28 |
| 850 | CGPG9358 | TPR_1 | 585 | 618 | 15.5 | 0.068 |
| 850 | CGPG9358 | TPR_1 | 655 | 688 | 16.1 | 0.059 |

TABLE 17

| Pfam domain name | accession number | gathering cutoff | domain description |
|---|---|---|---|
| zf-MYND | PF01753.8 | 11 | MYND finger |
| UCH | PF00443.18 | −8.6 | Ubiquitin carboxyl-terminal hydrolase |

TABLE 17-continued

| Pfam domain name | accession number | gathering cutoff | domain description |
|---|---|---|---|
| MIF | PF01187.7 | −17.6 | Macrophage migration inhibitory factor (MIF) |
| PurA | PF04845.3 | 25 | PurA ssDNA and RNA-binding protein |
| Gln-synt_C | PF00120.14 | −124 | Glutamine synthetase, catalytic domain |
| WD40 | PF00400.20 | 21.5 | WD domain, G-beta repeat |
| Pkinase | PF00069.14 | −70.8 | Protein kinase domain |
| Pkinase | PF00069.14 | −70.8 | Protein kinase domain |
| NAF | PF03822.4 | 4.5 | NAF domain |
| Sterol_desat | PF01598.7 | −13 | Sterol desaturase |
| Pkinase | PF00069.14 | −70.8 | Protein kinase domain |
| Asp | PF00026.13 | −186.1 | Eukaryotic aspartyl protease |
| Glyco_hydro_1 | PF00232.9 | −301.8 | Glycosyl hydrolase family 1 |
| Oleosin | PF01277.7 | −27 | Oleosin |
| Sugar_tr | PF00083.13 | −85 | Sugar (and other) transporter |
| MFS_1 | PF07690.5 | 23.5 | Major Facilitator Superfamily |
| ATP-grasp_2 | PF08442.1 | −118.8 | ATP-grasp domain |
| PLAC8 | PF04749.6 | −1.1 | PLAC8 family |
| Ferric_reduct | PF01794.8 | −7 | Ferric reductase like transmembrane component |
| FAD_binding_8 | PF08022.1 | −10.4 | FAD-binding domain |
| FAD_binding_6 | PF00970.13 | −11.4 | Oxidoreductase FAD-binding domain |
| NAD_binding_6 | PF08030.1 | −23.6 | Ferric reductase NAD binding domain |
| LSM | PF01423.12 | 13.7 | LSM domain |
| Fibrillarin | PF01269.7 | −86.6 | Fibrillarin |
| WD40 | PF00400.20 | 21.5 | WD domain, G-beta repeat |
| WD40 | PF00400.20 | 21.5 | WD domain, G-beta repeat |
| Linker_histone | PF00538.8 | −8 | linker histone H1 and H5 family |
| PP2C | PF00481.11 | −44 | Protein phosphatase 2C |
| Sugar_tr | PF00083.13 | −85 | Sugar (and other) transporter |
| MFS_1 | PF07690.5 | 23.5 | Major Facilitator Superfamily |
| SBF | PF01758.6 | −27.8 | Sodium Bile acid symporter family |
| Glyoxalase | PF00903.14 | 12.1 | Glyoxalase/Bleomycin resistance protein/Dioxygenase superfamily |
| Pkinase | PF00069.14 | −70.8 | Protein kinase domain |
| NAF | PF03822.4 | 4.5 | NAF domain |
| LRR_2 | PF07723.2 | 6 | Leucine Rich Repeat |
| p450 | PF00067.11 | −105 | Cytochrome P450 |
| WD40 | PF00400.20 | 21.5 | WD domain, G-beta repeat |
| WD40 | PF00400.20 | 21.5 | WD domain, G-beta repeat |
| WD40 | PF00400.20 | 21.5 | WD domain, G-beta repeat |
| LRR_1 | PF00560.21 | 7.7 | Leucine Rich Repeat |
| LRR_1 | PF00560.21 | 7.7 | Leucine Rich Repeat |
| LRR_1 | PF00560.21 | 7.7 | Leucine Rich Repeat |
| LRR_1 | PF00560.21 | 7.7 | Leucine Rich Repeat |
| LRR_1 | PF00560.21 | 7.7 | Leucine Rich Repeat |
| Pkinase | PF00069.14 | −70.8 | Protein kinase domain |
| C2 | PF00168.18 | 3.7 | C2 domain |
| SBP56 | PF05694.1 | 25 | 56 kDa selenium binding protein (SBP56) |
| IMPDH | PF00478.13 | −190.6 | IMP dehydrogenase/GMP reductase domain |
| MtN3_slv | PF03083.5 | −0.8 | MtN3/saliva family |
| MtN3_slv | PF03083.5 | −0.8 | MtN3/saliva family |
| Aminotran_3 | PF00202.10 | −207.6 | Aminotransferase class-III |
| Aminotran_1_2 | PF00155.10 | −57.5 | Aminotransferase class I and II |
| Aminotran_3 | PF00202.10 | −207.6 | Aminotransferase class-III |
| Aminotran_1_2 | PF00155.10 | −57.5 | Aminotransferase class I and II |
| Pkinase | PF00069.14 | −70.8 | Protein kinase domain |
| Pkinase | PF00069.14 | −70.8 | Protein kinase domain |
| Pkinase | PF00069.14 | −70.8 | Protein kinase domain |
| Pkinase_Tyr | PF07714.5 | 65 | Protein tyrosine kinase |
| Pkinase | PF00069.14 | −70.8 | Protein kinase domain |
| NAF | PF03822.4 | 4.5 | NAF domain |
| Pkinase | PF00069.14 | −70.8 | Protein kinase domain |
| Pkinase | PF00069.14 | −70.8 | Protein kinase domain |
| Nodulin-like | PF06813.3 | −57.8 | Nodulin-like |
| Glyco_hydro_14 | PF01373.7 | −231.4 | Glycosyl hydrolase family 14 |
| GSHPx | PF00255.10 | −16 | Glutathione peroxidase |
| MFS_1 | PF07690.5 | 23.5 | Major Facilitator Superfamily |
| Sugar_tr | PF00083.13 | −85 | Sugar (and other) transporter |
| PGK | PF00162.9 | −39.9 | Phosphoglycerate kinase |
| PGK | PF00162.9 | −39.9 | Phosphoglycerate kinase |
| Pyr_redox | PF00070.17 | 5 | Pyridine nucleotide-disulphide oxidoreductase |
| Pyr_redox_2 | PF07992.3 | −20 | Pyridine nucleotide-disulphide oxidoreductase |
| zf-C3HC4 | PF00097.13 | 16.9 | Zinc finger, C3HC4 type (RING finger) |
| MIP | PF00230.9 | −62 | Major intrinsic protein |
| Tim17 | PF02466.8 | 2.7 | Tim17/Tim22/Tim23 family |
| HABP4_PAI-RBP1 | PF04774.4 | 17.1 | Hyaluronan/mRNA binding family |
| DUF1677 | PF07911.4 | 25 | Protein of unknown function (DUF1677) |

TABLE 17-continued

| Pfam domain name | accession number | gathering cutoff | domain description |
|---|---|---|---|
| NIR_SIR_ferr | PF03460.6 | 2.4 | Nitrite/Sulfite reductase ferredoxin-like half domain |
| NIR_SIR | PF01077.11 | −25 | Nitrite and sulphite reductase 4Fe—4S domain |
| NIR_SIR_ferr | PF03460.6 | 2.4 | Nitrite/Sulfite reductase ferredoxin-like half domain |
| NIR_SIR | PF01077.11 | −25 | Nitrite and sulphite reductase 4Fe—4S domain |
| TIM | PF00121.8 | −97 | Triosephosphate isomerase |
| DnaJ | PF00226.19 | −8 | DnaJ domain |
| Fer4 | PF00037.15 | 9.3 | 4Fe—4S binding domain |
| Pro_isomerase | PF00160.10 | −37 | Cyclophilin type peptidyl-prolyl cis-trans isomerase/CLD |
| Pec_lyase_C | PF00544.8 | −45 | Pectate lyase |
| CS | PF04969.5 | 8.6 | CS domain |
| Glyoxal_oxid_N | PF07250.1 | 25 | Glyoxal oxidase N-terminus |
| YjeF_N | PF03853.4 | 25 | YjeF-related protein N-terminus |
| Carb_kinase | PF01256.7 | −66.3 | Carbohydrate kinase |
| TPR_1 | PF00515.16 | 7.7 | Tetratricopeptide repeat |
| TPR_1 | PF00515.16 | 7.7 | Tetratricopeptide repeat |
| TPR_1 | PF00515.16 | 7.7 | Tetratricopeptide repeat |
| DUF1644 | PF07800.2 | 25 | Protein of unknown function (DUF1644) |
| TMEM14 | PF03647.3 | −1 | Transmembrane proteins 14C |
| Aldo_ket_red | PF00248.10 | −97 | Aldo/keto reductase family |
| Pkinase | PF00069.14 | −70.8 | Protein kinase domain |
| BCNT | PF07572.2 | 25 | Bucentaur or craniofacial development |
| Mito_carr | PF00153.15 | 0 | Mitochondrial carrier protein |
| Mito_carr | PF00153.15 | 0 | Mitochondrial carrier protein |
| Mito_carr | PF00153.15 | 0 | Mitochondrial carrier protein |
| NUDIX | PF00293.17 | 0 | NUDIX domain |
| PRA-CH | PF01502.9 | 25 | Phosphoribosyl-AMP cyclohydrolase |
| PRA-PH | PF01503.8 | 6 | Phosphoribosyl-ATP pyrophosphohydrolase |
| Pkinase | PF00069.14 | −70.8 | Protein kinase domain |
| Pkinase_Tyr | PF07714.5 | 65 | Protein tyrosine kinase |
| zf-CCCH | PF00642.14 | 0 | Zinc finger C-x8-C-x5-C-x3-H type (and similar) |
| WD40 | PF00400.20 | 21.5 | WD domain, G-beta repeat |
| WD40 | PF00400.20 | 21.5 | WD domain, G-beta repeat |
| WD40 | PF00400.20 | 21.5 | WD domain, G-beta repeat |
| CK_II_beta | PF01214.9 | −106 | Casein kinase II regulatory subunit |
| MFS_1 | PF07690.5 | 23.5 | Major Facilitator Superfamily |
| Yip1 | PF04893.6 | −6.4 | Yip1 domain |
| ARID | PF01388.11 | −8 | ARID/BRIGHT DNA binding domain |
| ELM2 | PF01448.12 | 12 | ELM2 domain |
| Myb_DNA-binding | PF00249.19 | 2.8 | Myb-like DNA-binding domain |
| PP2C | PF00481.11 | −44 | Protein phosphatase 2C |
| MatE | PF01554.8 | 59.6 | MatE |
| MatE | PF01554.8 | 59.6 | MatE |
| Methyltransf_11 | PF08241.1 | 17.1 | Methyltransferase domain |
| Methyltransf_12 | PF08242.1 | 21.4 | Methyltransferase domain |
| FMO-like | PF00743.9 | −381.6 | Flavin-binding monooxygenase-like |
| DAO | PF01266.12 | −35.9 | FAD dependent oxidoreductase |
| Pyr_redox_2 | PF07992.3 | −20 | Pyridine nucleotide-disulphide oxidoreductase |
| Auxin_inducible | PF02519.4 | −15 | Auxin responsive protein |
| Response_reg | PF00072.12 | 4 | Response regulator receiver domain |
| CCT | PF06203.4 | 25 | CCT motif |
| Pkinase | PF00069.14 | −70.8 | Protein kinase domain |
| Pkinase | PF00069.14 | −70.8 | Protein kinase domain |
| Pkinase_Tyr | PF07714.5 | 65 | Protein tyrosine kinase |
| RRM_1 | PF00076.11 | 20.7 | RNA recognition motif. (a.k.a. RRM, RBD, or RNP domain) |
| RRM_1 | PF00076.11 | 20.7 | RNA recognition motif. (a.k.a. RRM, RBD, or RNP domain) |
| RRM_1 | PF00076.11 | 20.7 | RNA recognition motif. (a.k.a. RRM, RBD, or RNP domain) |
| RRM_1 | PF00076.11 | 20.7 | RNA recognition motif. (a.k.a. RRM, RBD, or RNP domain) |
| PABP | PF00658.8 | 25 | Poly-adenylate binding protein, unique domain |
| p450 | PF00067.11 | −105 | Cytochrome P450 |
| Aa_trans | PF01490.7 | −128.4 | Transmembrane amino acid transporter protein |
| F-box | PF00646.21 | 13.6 | F-box domain |
| LRR_2 | PF07723.2 | 6 | Leucine Rich Repeat |
| LRR_2 | PF07723.2 | 6 | Leucine Rich Repeat |
| FHA | PF00498.14 | 25 | FHA domain |
| Bromodomain | PF00439.14 | 8.9 | Bromodomain |
| PHD | PF00628.17 | 25.9 | PHD-finger |
| SET | PF00856.17 | 23.5 | SET domain |

TABLE 17-continued

| Pfam domain name | accession number | gathering cutoff | domain description |
|---|---|---|---|
| Abhydrolase_1 | PF00561.10 | 10.3 | alpha/beta hydrolase fold |
| Epimerase | PF01370.11 | −46.3 | NAD dependent epimerase/dehydratase family |
| 3Beta_HSD | PF01073.8 | −135.9 | 3-beta hydroxysteroid dehydrogenase/isomerase family |
| DUF231 | PF03005.5 | −58 | Arabidopsis proteins of unknown function |
| ABC_tran | PF00005.15 | 9.5 | ABC transporter |
| ABC2_membrane | PF01061.12 | −17.9 | ABC-2 type transporter |
| Dehydrin | PF00257.9 | −4.4 | Dehydrin |
| DnaJ | PF00226.19 | −8 | DnaJ domain |
| DnaJ_C | PF01556.9 | −24 | DnaJ C terminal region |
| Ank | PF00023.18 | 0 | Ankyrin repeat |
| Ank | PF00023.18 | 0 | Ankyrin repeat |
| RCC1 | PF00415.8 | 19 | Regulator of chromosome condensation (RCC1) |
| RCC1 | PF00415.8 | 19 | Regulator of chromosome condensation (RCC1) |
| Pkinase | PF00069.14 | −70.8 | Protein kinase domain |
| Lung_7-TM_R | PF06814.3 | 25 | Lung seven transmembrane receptor |
| Pkinase_Tyr | PF07714.5 | 65 | Protein tyrosine kinase |
| Pkinase | PF00069.14 | −70.8 | Protein kinase domain |
| Aa_trans | PF01490.7 | −128.4 | Transmembrane amino acid transporter protein |
| PCI | PF01399.15 | 25 | PCI domain |
| ADH_N | PF08240.2 | −14.5 | Alcohol dehydrogenase GroES-like domain |
| ADH_zinc_N | PF00107.16 | 23.8 | Zinc-binding dehydrogenase |
| p450 | PF00067.11 | −105 | Cytochrome P450 |
| FKBP_C | PF00254.17 | −7.6 | FKBP-type peptidyl-prolyl cis-trans isomerase |
| WD40 | PF00400.20 | 21.5 | WD domain, G-beta repeat |
| Lectin_C | PF00059.10 | −10.4 | Lectin C-type domain |
| Pkinase | PF00069.14 | −70.8 | Protein kinase domain |
| Pkinase_Tyr | PF07714.5 | 65 | Protein tyrosine kinase |
| HEAT | PF02985.10 | 9.9 | HEAT repeat |
| HEAT | PF02985.10 | 9.9 | HEAT repeat |
| zf-CCCH | PF00642.14 | 0 | Zinc finger C-x8-C-x5-C-x3-H type (and similar) |
| zf-CCCH | PF00642.14 | 0 | Zinc finger C-x8-C-x5-C-x3-H type (and similar) |
| zf-CCCH | PF00642.14 | 0 | Zinc finger C-x8-C-x5-C-x3-H type (and similar) |
| zf-CCCH | PF00642.14 | 0 | Zinc finger C-x8-C-x5-C-x3-H type (and similar) |
| zf-CCCH | PF00642.14 | 0 | Zinc finger C-x8-C-x5-C-x3-H type (and similar) |
| PHD | PF00628.17 | 25.9 | PHD-finger |
| SEP | PF08059.2 | 25 | SEP domain |
| UBX | PF00789.10 | 10 | UBX domain |
| AA_permease | PF00324.10 | −120.8 | Amino acid permease |
| Pkinase_Tyr | PF07714.5 | 65 | Protein tyrosine kinase |
| Pkinase | PF00069.14 | −70.8 | Protein kinase domain |
| FAD_binding_4 | PF01565.12 | −8.1 | FAD binding domain |
| PALP | PF00291.14 | −70 | Pyridoxal-phosphate dependent enzyme |
| GIDA | PF01134.11 | −226.7 | Glucose inhibited division protein A |
| Pyr_redox_2 | PF07992.3 | −20 | Pyridine nucleotide-disulphide oxidoreductase |
| Pyr_redox | PF00070.17 | 5 | Pyridine nucleotide-disulphide oxidoreductase |
| Pyr_redox_dim | PF02852.12 | −13 | Pyridine nucleotide-disulphide oxidoreductase, dimerisation domain |
| YGGT | PF02325.7 | 0 | YGGT family |
| Aldedh | PF00171.11 | −209.3 | Aldehyde dehydrogenase family |
| PEPCK_ATP | PF01293.10 | −327 | Phosphoenolpyruvate carboxykinase |
| Trp_syntA | PF00290.11 | −149.8 | Tryptophan synthase alpha chain |
| DapB_N | PF01113.10 | −20.7 | Dihydrodipicolinate reductase, N-terminus |
| DapB_C | PF05173.3 | 0.5 | Dihydrodipicolinate reductase, C-terminus |
| Ribul_P_3_epim | PF00834.8 | −97.3 | Ribulose-phosphate 3 epimerase family |
| OMPdecase | PF00215.13 | −47.3 | Orotidine 5'-phosphate decarboxylase/HUMPS family |
| Arginase | PF00491.11 | −120 | Arginase family |
| Pkinase | PF00069.14 | −70.8 | Protein kinase domain |
| Ferric_reduct | PF01794.8 | −7 | Ferric reductase like transmembrane component |
| Lipase_3 | PF01764.14 | −8 | Lipase (class 3) |
| Auxin_inducible | PF02519.4 | −15 | Auxin responsive protein |
| TPR_2 | PF07719.5 | 20.1 | Tetratricopeptide repeat |
| TPR_1 | PF00515.16 | 7.7 | Tetratricopeptide repeat |
| TPR_2 | PF07719.5 | 20.1 | Tetratricopeptide repeat |
| TPR_1 | PF00515.16 | 7.7 | Tetratricopeptide repeat |
| TPR_1 | PF00515.16 | 7.7 | Tetratricopeptide repeat |

TABLE 17-continued

| Pfam domain name | accession number | gathering cutoff | domain description |
|---|---|---|---|
| TPR_2 | PF07719.5 | 20.1 | Tetratricopeptide repeat |
| TPR_1 | PF00515.16 | 7.7 | Tetratricopeptide repeat |
| Anti-silence | PF04729.4 | 25 | Anti-silencing protein, ASF1-like |
| p450 | PF00067.11 | −105 | Cytochrome P450 |
| Pkinase | PF00069.14 | −70.8 | Protein kinase domain |
| Pkinase_Tyr | PF07714.5 | 65 | Protein tyrosine kinase |
| TCTP | PF00838.7 | −70.7 | Translationally controlled tumour protein |
| NAPRTase | PF04095.5 | −88.5 | Nicotinate phosphoribosyltransferase (NAPRTase) family |
| SPX | PF03105.9 | −20 | SPX domain |
| EXS | PF03124.4 | 20 | EXS family |
| DUF1639 | PF07797.3 | 25 | Protein of unknown function (DUF1639) |
| Mlo | PF03094.5 | −263 | Mlo family |
| Sulfotransfer_1 | PF00685.16 | −53.1 | Sulfotransferase domain |
| PI-PLC-X | PF00388.8 | 18.8 | Phosphatidylinositol-specific phospholipase C, X domain |
| PI-PLC-Y | PF00387.8 | −11 | Phosphatidylinositol-specific phospholipase C, Y domain |
| C2 | PF00168.18 | 3.7 | C2 domain |
| HMA | PF00403.14 | 17.4 | Heavy-metal-associated domain |
| Ammonium_transp | PF00909.10 | −144 | Ammonium Transporter Family |
| Asp | PF00026.13 | −186.1 | Eukaryotic aspartyl protease |
| SapB_2 | PF03489.6 | 10.7 | Saposin-like type B, region 2 |
| SapB_1 | PF05184.4 | 3 | Saposin-like type B, region 1 |
| Oxidored_FMN | PF00724.9 | −147.7 | NADH: flavin oxidoreductase/NADH oxidase family |
| Pyr_redox | PF00070.17 | 5 | Pyridine nucleotide-disulphide oxidoreductase |
| Pyr_redox_2 | PF07992.3 | −20 | Pyridine nucleotide-disulphide oxidoreductase |
| Pkinase | PF00069.14 | −70.8 | Protein kinase domain |
| Miro | PF08477.1 | 28 | Miro-like protein |
| Ras | PF00071.11 | −69.9 | Ras family |
| Miro | PF08477.1 | 28 | Miro-like protein |
| Ras | PF00071.11 | −69.9 | Ras family |
| Pkinase_Tyr | PF07714.5 | 65 | Protein tyrosine kinase |
| Pkinase | PF00069.14 | −70.8 | Protein kinase domain |
| Sterol_desat | PF01598.7 | −13 | Sterol desaturase |
| ADH_N | PF08240.2 | −14.5 | Alcohol dehydrogenase GroES-like domain |
| ADH_zinc_N | PF00107.16 | 23.8 | Zinc-binding dehydrogenase |
| Sulfotransfer_1 | PF00685.16 | −53.1 | Sulfotransferase domain |
| TPR_1 | PF00515.16 | 7.7 | Tetratricopeptide repeat |
| TPR_2 | PF07719.5 | 20.1 | Tetratricopeptide repeat |
| TPR_1 | PF00515.16 | 7.7 | Tetratricopeptide repeat |
| TPR_2 | PF07719.5 | 20.1 | Tetratricopeptide repeat |
| TPR_1 | PF00515.16 | 7.7 | Tetratricopeptide repeat |
| GATase_2 | PF00310.10 | −106.2 | Glutamine amidotransferases class-II |
| SIS | PF01380.11 | 0 | SIS domain |
| SIS | PF01380.11 | 0 | SIS domain |
| Acetyltransf_1 | PF00583.13 | 18.6 | Acetyltransferase (GNAT) family |
| DUF1005 | PF06219.2 | 25 | Protein of unknown function (DUF1005) |
| DUF231 | PF03005.5 | −58 | Arabidopsis proteins of unknown function |
| TB2_DP1_HVA22 | PF03134.9 | −25.1 | TB2/DP1, HVA22 family |
| Di19 | PF05605.2 | 25 | Drought induced 19 protein (Di19) |
| MtN3_slv | PF03083.5 | −0.8 | MtN3/saliva family |
| MtN3_slv | PF03083.5 | −0.8 | MtN3/saliva family |
| Pkinase | PF00069.14 | −70.8 | Protein kinase domain |
| p450 | PF00067.11 | −105 | Cytochrome P450 |
| PGI | PF00342.8 | −168.9 | Phosphoglucose isomerase |
| Glyco_hydro_28 | PF00295.7 | −97 | Glycosyl hydrolases family 28 |
| Pkinase | PF00069.14 | −70.8 | Protein kinase domain |
| Isoamylase_N | PF02922.7 | −6.5 | Isoamylase N-terminal domain |
| Alpha-amylase | PF00128.12 | −93 | Alpha amylase, catalytic domain |
| PBP | PF01161.9 | −20.6 | Phosphatidylethanolamine-binding protein |
| zf-CCCH | PF00642.14 | 0 | Zinc finger C-x8-C-x5-C-x3-H type (and similar) |
| zf-CCCH | PF00642.14 | 0 | Zinc finger C-x8-C-x5-C-x3-H type (and similar) |
| zf-CCCH | PF00642.14 | 0 | Zinc finger C-x8-C-x5-C-x3-H type (and similar) |
| Aa_trans | PF01490.7 | −128.4 | Transmembrane amino acid transporter protein |
| Smr | PF01713.11 | 10 | Smr domain |
| 2-Hacid_dh | PF00389.19 | 11.2 | D-isomer specific 2-hydroxyacid dehydrogenase, catalytic domain |
| 2-Hacid_dh_C | PF02826.7 | −82.2 | D-isomer specific 2-hydroxyacid dehydrogenase, NAD binding domain |
| DUF1070 | PF06376.2 | 25 | Protein of unknown function (DUF1070) |
| AMP-binding | PF00501.16 | 0 | AMP-binding enzyme |

TABLE 17-continued

| Pfam domain name | accession number | gathering cutoff | domain description |
|---|---|---|---|
| Enolase_N | PF03952.6 | −3.3 | Enolase, N-terminal domain |
| Enolase_C | PF00113.12 | −34 | Enolase, C-terminal TIM barrel domain |
| FAE_3-kCoA_syn1 | PF07168.2 | 25 | Fatty acid elongase 3-ketoacyl-CoA synthase 1 |
| efhand | PF00036.20 | 17.5 | EF hand |
| Na_Ca_ex | PF01699.12 | 25 | Sodium/calcium exchanger protein |
| NOP5NT | PF08156.5 | 25 | NOP5NT (NUC127) domain |
| NOSIC | PF08060.2 | 25 | NOSIC (NUC001) domain |
| Nop | PF01798.6 | 25 | Putative snoRNA binding domain |
| Terpene_synth | PF01397.10 | −86 | Terpene synthase, N-terminal domain |
| PCI | PF01399.15 | 25 | PCI domain |
| Abhydrolase_3 | PF07859.2 | 25.8 | alpha/beta hydrolase fold |
| GRP | PF07172.1 | 16.8 | Glycine rich protein family |
| DUF914 | PF06027.2 | −193 | Eukaryotic protein of unknown function (DUF914) |
| DUF1325 | PF07039.1 | 25 | Protein of unknown function (DUF1325) |
| zf-A20 | PF01754.6 | 25 | A20-like zinc finger |
| zf-AN1 | PF01428.6 | 0 | AN1-like Zinc finger |
| PALP | PF00291.14 | −70 | Pyridoxal-phosphate dependent enzyme |
| MFS_1 | PF07690.5 | 23.5 | Major Facilitator Superfamily |
| DUF1723 | PF08330.1 | 17 | Protein of unknown function (DUF1723) |
| GDPD | PF03009.7 | −18 | Glycerophosphoryl diester phosphodiesterase family |
| Pkinase | PF00069.14 | −70.8 | Protein kinase domain |
| Pkinase_Tyr | PF07714.5 | 65 | Protein tyrosine kinase |
| Pkinase | PF00069.14 | −70.8 | Protein kinase domain |
| ADH_N | PF08240.2 | −14.5 | Alcohol dehydrogenase GroES-like domain |
| ADH_zinc_N | PF00107.16 | 23.8 | Zinc-binding dehydrogenase |
| Pribosyltran | PF00156.15 | 2 | Phosphoribosyl transferase domain |
| Aldedh | PF00171.11 | −209.3 | Aldehyde dehydrogenase family |
| BRAP2 | PF07576.1 | 25 | BRCA1-associated protein 2 |
| zf-C3HC4 | PF00097.13 | 16.9 | Zinc finger, C3HC4 type (RING finger) |
| zf-UBP | PF02148.8 | 25 | Zn-finger in ubiquitin-hydrolases and other protein |
| DnaJ | PF00226.19 | −8 | DnaJ domain |
| HSCB_C | PF07743.4 | −7 | HSCB C-terminal oligomerisation domain |
| ABC_tran | PF00005.15 | 9.5 | ABC transporter |
| Acyl-CoA_dh_N | PF02771.7 | 10.9 | Acyl-CoA dehydrogenase, N-terminal domain |
| Acyl-CoA_dh_M | PF02770.9 | 25 | Acyl-CoA dehydrogenase, middle domain |
| Acyl-CoA_dh_1 | PF00441.13 | −15.6 | Acyl-CoA dehydrogenase, C-terminal domain |
| Acyl-CoA_dh_2 | PF08028.1 | −16.9 | Acyl-CoA dehydrogenase, C-terminal domain |
| NTP_transferase | PF00483.12 | −90.5 | Nucleotidyl transferase |
| MannoseP_isomer | PF01050.8 | −70 | Mannose-6-phosphate isomerase |
| Cupin_2 | PF07883.1 | 16.6 | Cupin domain |
| Lectin_legB | PF00139.10 | −110.1 | Legume lectin domain |
| Pkinase | PF00069.14 | −70.8 | Protein kinase domain |
| Pkinase_Tyr | PF07714.5 | 65 | Protein tyrosine kinase |
| Pkinase_Tyr | PF07714.5 | 65 | Protein tyrosine kinase |
| Pkinase | PF00069.14 | −70.8 | Protein kinase domain |
| PGAM | PF00300.12 | −3 | Phosphoglycerate mutase family |
| WD40 | PF00400.20 | 21.5 | WD domain, G-beta repeat |
| Alpha-amylase | PF00128.12 | −93 | Alpha amylase, catalytic domain |
| PTPA | PF03095.4 | −106 | Phosphotyrosyl phosphate activator (PTPA) protein |
| Sedlin_N | PF04628.2 | 25 | Sedlin, N-terminal conserved region |
| NAD_binding_2 | PF03446.4 | −63.5 | NAD binding domain of 6-phosphogluconate dehydrogenase |
| 6PGD | PF00393.8 | −232.3 | 6-phosphogluconate dehydrogenase, C-terminal domain |
| ADK | PF00406.11 | 24.2 | Adenylate kinase |
| ADK_lid | PF05191.3 | 25 | Adenylate kinase, active site lid |
| DUF26 | PF01657.7 | 0 | Domain of unknown function DUF26 |
| DUF26 | PF01657.7 | 0 | Domain of unknown function DUF26 |
| Pkinase_Tyr | PF07714.5 | 65 | Protein tyrosine kinase |
| Pkinase | PF00069.14 | −70.8 | Protein kinase domain |
| mTERF | PF02536.4 | −60 | mTERF |
| B56 | PF01603.9 | −210 | Protein phosphatase 2A regulatory B subunit (B56 family) |
| zf-AN1 | PF01428.6 | 0 | AN1-like Zinc finger |
| Xan_ur_permease | PF00860.10 | −151.2 | Permease family |
| MFS_1 | PF07690.5 | 23.5 | Major Facilitator Superfamily |
| Auxin_inducible | PF02519.4 | −15 | Auxin responsive protein |
| Trehalose_PPase | PF02358.6 | −49.4 | Trehalose-phosphatase |
| DUF260 | PF03195.4 | 0.8 | Protein of unknown function DUF260 |
| Aminotran_1_2 | PF00155.10 | −57.5 | Aminotransferase class I and II |
| Pkinase | PF00069.14 | −70.8 | Protein kinase domain |
| Pkinase_Tyr | PF07714.5 | 65 | Protein tyrosine kinase |
| Pkinase | PF00069.14 | −70.8 | Protein kinase domain |

TABLE 17-continued

| Pfam domain name | accession number | gathering cutoff | domain description |
|---|---|---|---|
| Pkinase_Tyr | PF07714.5 | 65 | Protein tyrosine kinase |
| ADH_N | PF08240.2 | −14.5 | Alcohol dehydrogenase GroES-like domain |
| ADH_zinc_N | PF00107.16 | 23.8 | Zinc-binding dehydrogenase |
| RRM_1 | PF00076.11 | 20.7 | RNA recognition motif. (a.k.a. RRM, RBD, or RNP domain) |
| RRM_1 | PF00076.11 | 20.7 | RNA recognition motif. (a.k.a. RRM, RBD, or RNP domain) |
| La | PF05383.5 | 25 | La domain |
| RRM_1 | PF00076.11 | 20.7 | RNA recognition motif. (a.k.a. RRM, RBD, or RNP domain) |
| RRM_1 | PF00076.11 | 20.7 | RNA recognition motif. (a.k.a. RRM, RBD, or RNP domain) |
| RRM_1 | PF00076.11 | 20.7 | RNA recognition motif. (a.k.a. RRM, RBD, or RNP domain) |
| RRM_1 | PF00076.11 | 20.7 | RNA recognition motif. (a.k.a. RRM, RBD, or RNP domain) |
| LEA_2 | PF03168.3 | 25 | Late embryogenesis abundant protein |
| Miro | PF08477.1 | 28 | Miro-like protein |
| Ras | PF00071.11 | −69.9 | Ras family |
| DUF241 | PF03087.4 | −53.6 | Arabidopsis protein of unknown function |
| Sugar_tr | PF00083.13 | −85 | Sugar (and other) transporter |
| MFS_1 | PF07690.5 | 23.5 | Major Facilitator Superfamily |
| Ion_trans_2 | PF07885.4 | 24.9 | Ion channel |
| Ion_trans_2 | PF07885.4 | 24.9 | Ion channel |
| PI-PLC-X | PF00388.8 | 18.8 | Phosphatidylinositol-specific phospholipase C, X domain |
| C2 | PF00168.18 | 3.7 | C2 domain |
| Aldedh | PF00171.11 | −209.3 | Aldehyde dehydrogenase family |
| RNA_pol_Rpb8 | PF03870.5 | −31.2 | RNA polymerase Rpb8 |
| COX5C | PF05799.1 | 25 | Cytochrome c oxidase subunit Vc (COX5C) |
| Ion_trans_2 | PF07885.4 | 24.9 | Ion channel |
| Ion_trans_2 | PF07885.4 | 24.9 | Ion channel |
| Aldo_ket_red | PF00248.10 | −97 | Aldo/keto reductase family |
| Pkinase | PF00069.14 | −70.8 | Protein kinase domain |
| Pkinase_Tyr | PF07714.5 | 65 | Protein tyrosine kinase |
| Na_Ca_ex | PF01699.12 | 25 | Sodium/calcium exchanger protein |
| Na_Ca_ex | PF01699.12 | 25 | Sodium/calcium exchanger protein |
| Pkinase | PF00069.14 | −70.8 | Protein kinase domain |
| ADH_N | PF08240.2 | −14.5 | Alcohol dehydrogenase GroES-like domain |
| ADH_zinc_N | PF00107.16 | 23.8 | Zinc-binding dehydrogenase |
| OPT | PF03169.6 | −238.6 | OPT oligopeptide transporter protein |
| PMEI | PF04043.5 | 25 | Plant invertase/pectin methylesterase inhibitor |
| K_trans | PF02705.6 | −482 | K+ potassium transporter |
| Pkinase | PF00069.14 | −70.8 | Protein kinase domain |
| CH | PF00307.19 | 22.5 | Calponin homology (CH) domain |
| EB1 | PF03271.6 | 25 | EB1-like C-terminal motif |
| Carboxyl_trans | PF01039.11 | −262.3 | Carboxyl transferase domain |
| CoA_trans | PF01144.12 | 25 | Coenzyme A transferase |
| Pkinase | PF00069.14 | −70.8 | Protein kinase domain |
| CS | PF04969.5 | 8.6 | CS domain |
| SGS | PF05002.5 | 5.2 | SGS domain |
| NPH3 | PF03000.4 | 25 | NPH3 family |
| WD40 | PF00400.20 | 21.5 | WD domain, G-beta repeat |
| Spermine_synth | PF01564.6 | −93.8 | Spermine/spermidine synthase |
| FeThRed_A | PF02941.5 | 25 | Ferredoxin thioredoxin reductase variable alpha chain |
| Alpha-amylase | PF00128.12 | −93 | Alpha amylase, catalytic domain |
| Cyclin_N | PF00134.13 | −14.7 | Cyclin, N-terminal domain |
| Cyclin_C | PF02984.8 | −13 | Cyclin, C-terminal domain |
| F-box | PF00646.21 | 13.6 | F-box domain |
| F-box | PF00646.21 | 13.6 | F-box domain |
| Arm | PF00514.11 | 17 | Armadillo/beta-catenin-like repeat |
| Arm | PF00514.11 | 17 | Armadillo/beta-catenin-like repeat |
| Arm | PF00514.11 | 17 | Armadillo/beta-catenin-like repeat |
| Arm | PF00514.11 | 17 | Armadillo/beta-catenin-like repeat |
| Arm | PF00514.11 | 17 | Armadillo/beta-catenin-like repeat |
| Arm | PF00514.11 | 17 | Armadillo/beta-catenin-like repeat |
| Arm | PF00514.11 | 17 | Armadillo/beta-catenin-like repeat |
| Arm | PF00514.11 | 17 | Armadillo/beta-catenin-like repeat |
| MIP | PF00230.9 | −62 | Major intrinsic protein |
| LRRNT_2 | PF08263.2 | 18.6 | Leucine rich repeat N-terminal domain |
| LRR_1 | PF00560.21 | 7.7 | Leucine Rich Repeat |
| LRR_1 | PF00560.21 | 7.7 | Leucine Rich Repeat |
| LRR_1 | PF00560.21 | 7.7 | Leucine Rich Repeat |
| Pkinase_Tyr | PF07714.5 | 65 | Protein tyrosine kinase |
| Pkinase | PF00069.14 | −70.8 | Protein kinase domain |

TABLE 17-continued

| Pfam domain name | accession number | gathering cutoff | domain description |
|---|---|---|---|
| WD40 | PF00400.20 | 21.5 | WD domain, G-beta repeat |
| Glycolytic | PF00274.9 | −174.5 | Fructose-bisphosphate aldolase class-I |
| PSI_PsaF | PF02507.5 | 25 | Photosystem I reaction centre subunit III |
| LRRNT_2 | PF08263.2 | 18.6 | Leucine rich repeat N-terminal domain |
| LRR_1 | PF00560.21 | 7.7 | Leucine Rich Repeat |
| LRR_1 | PF00560.21 | 7.7 | Leucine Rich Repeat |
| LRR_1 | PF00560.21 | 7.7 | Leucine Rich Repeat |
| LRR_1 | PF00560.21 | 7.7 | Leucine Rich Repeat |
| C2 | PF00168.18 | 3.7 | C2 domain |
| p450 | PF00067.11 | −105 | Cytochrome P450 |
| FH2 | PF02181.13 | −98.3 | Formin Homology 2 Domain |
| U-box | PF04564.5 | 10.5 | U-box domain |
| FAE1_CUT1_RppA | PF08392.1 | −192.7 | FAE1/Type III polyketide synthase-like protein |
| Chal_sti_synt_C | PF02797.5 | −6.1 | Chalcone and stilbene synthases, C-terminal domain |
| ACP_syn_III_C | PF08541.1 | −24.4 | 3-Oxoacyl-[acyl-carrier-protein (ACP)] synthase III C terminal |
| aPHC | PF05875.2 | 25 | Alkaline phytoceramidase (aPHC) |
| Pkinase | PF00069.14 | −70.8 | Protein kinase domain |
| Pkinase | PF00069.14 | −70.8 | Protein kinase domain |
| Pkinase_Tyr | PF07714.5 | 65 | Protein tyrosine kinase |
| Glyco_hydro_14 | PF01373.7 | −231.4 | Glycosyl hydrolase family 14 |
| Miro | PF08477.1 | 28 | Miro-like protein |
| Ras | PF00071.11 | −69.9 | Ras family |
| PGM_PMM_I | PF02878.5 | −37.5 | Phosphoglucomutase/phosphomannomutase, alpha/beta/alpha domain I |
| PGM_PMM_II | PF02879.5 | −20 | Phosphoglucomutase/phosphomannomutase, alpha/beta/alpha domain II |
| PGM_PMM_III | PF02880.5 | −7.8 | Phosphoglucomutase/phosphomannomutase, alpha/beta/alpha domain III |
| PGM_PMM_IV | PF00408.9 | −6 | Phosphoglucomutase/phosphomannomutase, C-terminal domain |
| Glutaminase | PF04960.5 | −143.6 | Glutaminase |
| Aldedh | PF00171.11 | −209.3 | Aldehyde dehydrogenase family |
| Aminotran_3 | PF00202.10 | −207.6 | Aminotransferase class-III |
| 2OG-FeII_Oxy | PF03171.9 | 11.5 | 2OG-Fe(II) oxygenase superfamily |
| Histone | PF00125.13 | 17.4 | Core histone H2A/H2B/H3/H4 |
| F-box | PF00646.21 | 13.6 | F-box domain |
| Agenet | PF05641.2 | 6.6 | Agenet domain |
| Agenet | PF05641.2 | 6.6 | Agenet domain |
| DnaJ | PF00226.19 | −8 | DnaJ domain |
| SNARE | PF05739.8 | 20.8 | SNARE domain |
| adh_short | PF00106.19 | −17 | short chain dehydrogenase |
| Pyr_redox_2 | PF07992.3 | −20 | Pyridine nucleotide-disulphide oxidoreductase |
| Pyr_redox | PF00070.17 | 5 | Pyridine nucleotide-disulphide oxidoreductase |
| NPH3 | PF03000.4 | 25 | NPH3 family |
| PB1 | PF00564.13 | 12.3 | PB1 domain |
| MIP | PF00230.9 | −62 | Major intrinsic protein |
| F-box | PF00646.21 | 13.6 | F-box domain |
| LRR_2 | PF07723.2 | 6 | Leucine Rich Repeat |
| F-box | PF00646.21 | 13.6 | F-box domain |
| MIP | PF00230.9 | −62 | Major intrinsic protein |
| Methyltransf_6 | PF03737.5 | 25 | Demethylmenaquinone methyltransferase |
| zf-C3HC4 | PF00097.13 | 16.9 | Zinc finger, C3HC4 type (RING finger) |
| RRM_1 | PF00076.11 | 20.7 | RNA recognition motif. (a.k.a. RRM, RBD, or RNP domain) |
| zf-CCHC | PF00098.12 | 17.9 | Zinc knuckle |
| zf-CCHC | PF00098.12 | 17.9 | Zinc knuckle |
| NPH3 | PF03000.4 | 25 | NPH3 family |
| p450 | PF00067.11 | −105 | Cytochrome P450 |
| p450 | PF00067.11 | −105 | Cytochrome P450 |
| DPBB_1 | PF03330.7 | 5.3 | Rare lipoprotein A (RlpA)-like double-psi beta-barrel |
| Pollen_allerg_1 | PF01357.10 | 17.2 | Pollen allergen |
| p450 | PF00067.11 | −105 | Cytochrome P450 |
| p450 | PF00067.11 | −105 | Cytochrome P450 |
| CBS | PF00571.16 | 17.5 | CBS domain pair |
| CBS | PF00571.16 | 17.5 | CBS domain pair |
| Cys_Met_Meta_PP | PF01053.9 | −278.4 | Cys/Met metabolism PLP-dependent enzyme |
| Beta_elim_lyase | PF01212.10 | −114.4 | Beta-eliminating lyase |
| Aldedh | PF00171.11 | −209.3 | Aldehyde dehydrogenase family |
| PK | PF00224.10 | −244 | Pyruvate kinase, barrel domain |
| PK_C | PF02887.5 | −44 | Pyruvate kinase, alpha/beta domain |
| PEP-utilizers | PF00391.12 | 10 | PEP-utilising enzyme, mobile domain |
| iPGM_N | PF06415.3 | −263.4 | BPG-independent PGAM N-terminus (iPGM_N) |

TABLE 17-continued

| Pfam domain name | accession number | gathering cutoff | domain description |
|---|---|---|---|
| Metalloenzyme | PF01676.7 | −14.4 | Metalloenzyme superfamily |
| Molybdop_Fe4S4 | PF04879.5 | 13.6 | Molybdopterin oxidoreductase Fe4S4 domain |
| Molybdopterin | PF00384.11 | −50 | Molybdopterin oxidoreductase |
| Molydop_binding | PF01568.10 | 1.1 | Molydopterin dinucleotide binding domain |
| Aminotran_3 | PF00202.10 | −207.6 | Aminotransferase class-III |
| HMA | PF00403.14 | 17.4 | Heavy-metal-associated domain |
| DAO | PF01266.12 | −35.9 | FAD dependent oxidoreductase |
| Pyr_redox_2 | PF07992.3 | −20 | Pyridine nucleotide-disulphide oxidoreductase |
| Pyr_redox | PF00070.17 | 5 | Pyridine nucleotide-disulphide oxidoreductase |
| Pyr_redox_dim | PF02852.12 | −13 | Pyridine nucleotide-disulphide oxidoreductase, dimerisation domain |
| Aminotran_3 | PF00202.10 | −207.6 | Aminotransferase class-III |
| ADH_N | PF08240.2 | −14.5 | Alcohol dehydrogenase GroES-like domain |
| ADH_zinc_N | PF00107.16 | 23.8 | Zinc-binding dehydrogenase |
| Hist_deacetyl | PF00850.9 | −71 | Histone deacetylase domain |
| zf-A20 | PF01754.6 | 25 | A20-like zinc finger |
| zf-AN1 | PF01428.6 | 0 | AN1-like Zinc finger |
| U-box | PF04564.5 | 10.5 | U-box domain |
| Arm | PF00514.11 | 17 | Armadillo/beta-catenin-like repeat |
| Arm | PF00514.11 | 17 | Armadillo/beta-catenin-like repeat |
| Arm | PF00514.11 | 17 | Armadillo/beta-catenin-like repeat |
| Arm | PF00514.11 | 17 | Armadillo/beta-catenin-like repeat |
| Arm | PF00514.11 | 17 | Armadillo/beta-catenin-like repeat |
| PDT | PF00800.8 | 25 | Prephenate dehydratase |
| ACT | PF01842.13 | 0 | ACT domain |
| PP2C | PF00481.11 | −44 | Protein phosphatase 2C |
| Aminotran_3 | PF00202.10 | −207.6 | Aminotransferase class-III |
| DUF568 | PF04526.3 | 25 | Protein of unknown function (DUF568) |
| PHD | PF00628.17 | 25.9 | PHD-finger |
| TBC | PF00566.8 | −58 | TBC domain |
| DUF786 | PF05646.3 | −31.3 | Protein of unknown function (DUF786) |
| PLAC8 | PF04749.6 | −1.1 | PLAC8 family |
| IF2_N | PF04760.6 | 25 | Translation initiation factor IF-2, N-terminal region |
| GTP_EFTU | PF00009.15 | 8 | Elongation factor Tu GTP binding domain |
| Ras | PF00071.11 | −69.9 | Ras family |
| GTP_EFTU_D2 | PF03144.14 | 25 | Elongation factor Tu domain 2 |
| PC4 | PF02229.5 | 4 | Transcriptional Coactivator p15 (PC4) |
| DUF588 | PF04535.2 | 25 | Domain of unknown function (DUF588) |
| LisH | PF08513.1 | 20.7 | LisH |
| CDI | PF02234.8 | 17 | Cyclin-dependent kinase inhibitor |
| Glyco_transf_8 | PF01501.9 | −43.2 | Glycosyl transferase family 8 |
| Pkinase | PF00069.14 | −70.8 | Protein kinase domain |
| efhand | PF00036.20 | 17.5 | EF hand |
| efhand | PF00036.20 | 17.5 | EF hand |
| efhand | PF00036.20 | 17.5 | EF hand |
| efhand | PF00036.20 | 17.5 | EF hand |
| WWE | PF02825.9 | 25 | WWE domain |
| FAE1_CUT1_RppA | PF08392.1 | −192.7 | FAE1/Type III polyketide synthase-like protein |
| Chal_sti_synt_C | PF02797.5 | −6.1 | Chalcone and stilbene synthases, C-terminal domain |
| ACP_syn_III_C | PF08541.1 | −24.4 | 3-Oxoacyl-[acyl-carrier-protein (ACP)] synthase III C terminal |
| Hrf1 | PF03878.5 | −81.2 | Hrf1 family |
| Yip1 | PF04893.6 | −6.4 | Yip1 domain |
| Pkinase | PF00069.14 | −70.8 | Protein kinase domain |
| Pkinase_Tyr | PF07714.5 | 65 | Protein tyrosine kinase |
| Pkinase | PF00069.14 | −70.8 | Protein kinase domain |
| ADH_N | PF08240.2 | −14.5 | Alcohol dehydrogenase GroES-like domain |
| ADH_zinc_N | PF00107.16 | 23.8 | Zinc-binding dehydrogenase |
| Miro | PF08477.1 | 28 | Miro-like protein |
| Ras | PF00071.11 | −69.9 | Ras family |
| Miro | PF08477.1 | 28 | Miro-like protein |
| Ras | PF00071.11 | −69.9 | Ras family |
| Sugar_tr | PF00083.13 | −85 | Sugar (and other) transporter |
| MFS_1 | PF07690.5 | 23.5 | Major Facilitator Superfamily |
| RuBisCO_large_N | PF02788.5 | 25 | Ribulose bisphosphate carboxylase large chain, N-terminal domain |
| RuBisCO_large | PF00016.9 | −76 | Ribulose bisphosphate carboxylase large chain, catalytic domain |
| Flavodoxin_1 | PF00258.14 | 6.3 | Flavodoxin |
| FAD_binding_1 | PF00667.9 | −79 | FAD binding domain |
| NAD_binding_1 | PF00175.10 | −3.9 | Oxidoreductase NAD-binding domain |
| Lactamase_B | PF00753.16 | 24.6 | Metallo-beta-lactamase superfamily |
| PGI | PF00342.8 | −168.9 | Phosphoglucose isomerase |
| Peptidase_C12 | PF01088.10 | −91.4 | Ubiquitin carboxyl-terminal hydrolase, family 1 |

TABLE 17-continued

| Pfam domain name | accession number | gathering cutoff | domain description |
| --- | --- | --- | --- |
| Dicty_CAR | PF05462.2 | −39.7 | Slime mold cyclic AMP receptor |
| Aldedh | PF00171.11 | −209.3 | Aldehyde dehydrogenase family |
| PfkB | PF00294.13 | −67.8 | pfkB family carbohydrate kinase |
| Brix | PF04427.7 | 11.4 | Brix domain |
| MGS | PF02142.11 | 3 | MGS-like domain |
| AICARFT_IMPCHas | PF01808.8 | −98 | AICARFT/IMPCHase bienzyme |
| MFAP1_C | PF06991.1 | 25 | Micro-fibrillar-associated protein 1 C-terminus |
| Nicastrin | PF05450.4 | −85.8 | Nicastrin |
| Ribophorin_I | PF04597.4 | −217 | Ribophorin I |
| DUF662 | PF04949.2 | 25 | Family of unknown function (DUF662) |
| ARD | PF03079.4 | 25 | ARD/ARD' family |
| Cupin_2 | PF07883.1 | 16.6 | Cupin domain |
| HATPase_c | PF02518.14 | 22.4 | Histidine kinase-, DNA gyrase B-, and HSP90-like ATPase |
| Pkinase | PF00069.14 | −70.8 | Protein kinase domain |
| Pkinase_Tyr | PF07714.5 | 65 | Protein tyrosine kinase |
| Pkinase | PF00069.14 | −70.8 | Protein kinase domain |

Example 5 A

This example illustrates the construction of plasmids for transferring recombinant DNA into the nucleus of a plant cell which can be regenerated into a transgenic crop plant of this invention. Primers for PCR amplification of protein coding nucleotides of recombinant DNA are designed at or near the start and stop codons of the coding sequence, in order to eliminate most of the 5' and 3' untranslated regions. DNA of interest, i.e. each DNA identified in Table 1 and the DNA for the identified homologous genes, are cloned and amplified by PCR prior to insertion into the insertion site the base vector.

Elements of an exemplary common expression vector, pMON82060 are illustrated in Table 18. The exemplary base vector which is especially useful for corn transformation is illustrated in FIG. 2 and assembled using technology known in the art. The DNA of interest are inserted in a expression vector at the insertion site between the intron1 of rice act 1 gene and the termination sequence of PinII gene.

TABLE 18 pMON82060

| function | name | annotation | Coordinates of SEQ ID NO: 33636 |
| --- | --- | --- | --- |
| Agro transformation | B-AGRtu.right border | Agro right border sequence, essential for transfer of T-DNA. | 5235-5591 |
| Gene of interest plant expression cassette | P-Os.Act1 | Promoter from the rice actin gene act1. | 5609-7009 |
| | L-Os.Act1 | Leader (first exon) from the rice actin 1 gene. | |
| | I-Os.Act1 | First intron and flanking UTR exon sequences from the rice actin 1 gene | |
| | insertion site | | |
| | T-St.Pis4 | The 3' non-translated region of the potato proteinase inhibitor II gene which functions to direct polyadenylation of the mRNA | 7084-8026 |
| Plant selectable marker expression cassette | P-CaMV.35S | CaMV 35S promoter | 8075-8398 |
| | L-CaMV.35S | 5' UTR from the 35S RNA of CaMV | |
| | CR-Ec.nptII-Tn5 | nptII selectable marker that confers resistance to neomycin and kanamycin | 8432-9226 |
| | T-AGRtu.nos | A 3' non-translated region of the nopaline synthase gene of Agrobacterium tumefaciens Ti plasmid which functions to direct polyadenylation of the mRNA. | 9255-9507 |
| Agro transformation | B-AGRtu.left border | Agro left border sequence, essential for transfer of T-DNA. | 39-480 |
| Maintenance in E. coli | OR-Ec.oriV-RK2 | The vegetative origin of replication from plasmid RK2. | 567-963 |
| | CR-Ec.rop | Coding region for repressor of primer from the ColE1 plasmid. Expression of this gene product interferes with primer binding at the origin of replication, keeping plasmid copy number low. | 2472-2663 |
| | OR-Ec.ori-ColE1 | The minimal origin of replication from the E. coli plasmid ColE1. | 3091-3679 |
| | P-Ec.aadA-SPC/STR | promoter for Tn7 adenylyltransferase (AAD(3")) | 4210-4251 |

TABLE 18-continued pMON82060

| function | name | annotation | Coordinates of SEQ ID NO: 33636 |
|---|---|---|---|
| | CR-Ec.aadA-SPC/STR | Coding region for Tn7 adenylyltransferase (AAD(3")) conferring spectinomycin and streptomycin resistance. | 4252-5040 |
| | T-Ec.aadA-SPC/STR | 3' UTR from the Tn7 adenylyltransferase (AAD(3")) gene of E. coli. | 5041-5098 |

Figure 3:
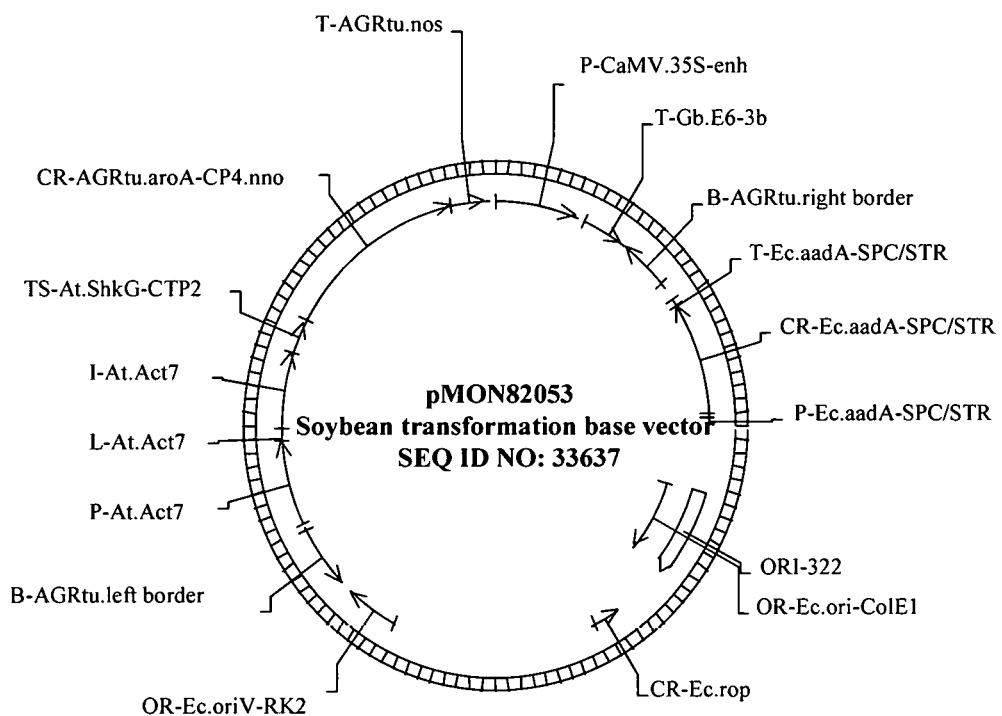

Plasmids for use in transformation of soybean are also prepared. Elements of an exemplary common expression vector plasmid pMON82053 are shown in Table 19 below. This exemplary soybean transformation base vector illustrated in FIG. 3 was assembled using the technology known in the art. DNA of interest, i.e. each DNA identified in Table 1 and the DNA for the identified homologous genes, are cloned and amplified by PCR prior to insertion into the insertion site the base vector at the insertion site between the enhanced 35S CaMV promoter and the termination sequence of cotton E6 gene.

TABLE 19 pMON82053

| function | name | annotation | Coordinates of SEQ ID NO: 33637 |
|---|---|---|---|
| Agro transforamtion | B-AGRtu.left border | Agro left border sequence, essential for transfer of T-DNA. | 6144-6585 |
| Plant selectable marker expression cassette | P-At.Act7 | Promoter from the arabidopsis actin 7 gene | 6624-7861 |
| | L-At.Act7 | 5'UTR of *Arabidopsis* Act7 gene | |
| | I-At.Act7 | Intron from the *Arabidopsis* actin7 gene | |
| | TS-At.ShkG-CTP2 | Transit peptide region of *Arabidopsis* EPSPS | 7864-8091 |
| | CR-AGRtu.aroA-CP4.nno__At | Synthetic CP4 coding region with dicot preferred codon usage. | 8092-9459 |
| | T-AGRtu.nos | A 3' non-translated region of the nopaline synthase gene of *Agrobacterium tumefaciens* Ti plasmid which functions to direct polyadenylation of the mRNA. | 9466-9718 |
| Gene of interest expression cassette | P-CaMV.35S-enh insertion site | Promoter for 35S RNA from CaMV containing a duplication of the −90 to −350 region. | 1-613 |
| | T-Gb.E6-3b | 3' untranslated region from the fiber protein E6 gene of sea-island cotton; | 688-1002 |
| Agro transformation | B-AGRtu.right border | Agro right border sequence, essential for transfer of T-DNA. | 1033-1389 |
| Maintenance in *E. coli* | OR-Ec.oriV-RK2 | The vegetative origin of replication from plasmid RK2. | 5661-6057 |
| | CR-Ec.rop | Coding region for repressor of primer from the ColE1 plasmid. Expression of this gene product interferes with primer binding at the origin of replication, keeping plasmid copy number low. | 3961-4152 |
| | OR-Ec.ori-ColE1 | The minimal origin of replication from the *E. coli* plasmid ColE1. | 2945-3533 |

TABLE 19-continued pMON82053

| function | name | annotation | Coordinates of SEQ ID NO: 33637 |
|---|---|---|---|
| | P-Ec.aadA-SPC/STR | romoter for Tn7 adenylyltransferase (AAD(3")) | 2373-2414 |
| | CR-Ec.aadA-SPC/STR | Coding region for Tn7 adenylyltransferase (AAD(3")) conferring spectinomycin and streptomycin resistance. | 1584-2372 |
| | T-Ec.aadA-SPC/STR | 3' UTR from the Tn7 adenylyltransferase (AAD(3")) gene of E. coli. | 1526-1583 |

Example 5 B

This example illustrates monocot plant transformation to produce nuclei of this invention in cells of a transgenic plant by transformation of corn callus. Corn plants of a readily transformable line are grown in the greenhouse and ears harvested when the embryos are 1.5 to 2.0 mm in length. Ears are surface sterilized by spraying or soaking the ears in 80% ethanol, followed by air drying. Immature embryos are isolated from individual kernels on surface sterilized ears. Prior to inoculation of *maize* cells, *Agrobacterium* cells are grown overnight at room temperature. Immature *maize* embryos are inoculated with *Agrobacterium* shortly after excision, and incubated at room temperature with *Agrobacterium* for 5-20 minutes. Immature embryos are then co-cultured with *Agrobacterium* for 1 to 3 days at 23° C. in the dark. Co-cultured embryos are transferred to selection media and cultured for approximately two weeks to allow embryogenic callus to develop. Embryogenic callus is transferred to culture medium containing 100 mg/L paromomycin and subcultured at about two week intervals. Transformants are recovered 6 to 8 weeks after initiation of selection.

Plasmid vectors are prepared essentially as described in Example 5 for transforming into corn callus each of DNA identified in Table 1 and the corresponding DNA for the identified homologous genes identified in Table 2, by *Agrobacterium*-mediated transformation.

For *Agrobacterium*-mediated transformation of corn callus, immature embryos are cultured for approximately 8-21 days after excision to allow callus to develop. Callus is then incubated for about 30 minutes at room temperature with the *Agrobacterium* suspension, followed by removal of the liquid by aspiration. The callus and *Agrobacterium* are co-cultured without selection for 3-6 days followed by selection on paromomycin for approximately 6 weeks, with biweekly transfers to fresh media, and paromomycin resistant callus identified as containing the recombinant DNA in an expression cassette.

Transgenic corn plants are regenerated from transgenic callus resulting from transformation on media to initiate shoot development in plantlets which are transferred to potting soil for initial growth in a growth chamber at 26 degrees C. followed by a mist bench before transplanting to 5 inch pots where plants are grown to maturity. The plants are self fertilized and seed is harvested for screening as seed, seedlings or progeny R2 plants or hybrids, e.g. for yield trials in the screens indicated above. Populations of transgenic plants and seeds produced form transgenic plant cells from each transgenic event are screened as described in Example 7 below to identify the members of the population having the enhanced trait.

Example 6

This example illustrates dicot plant transformation to produce nuclei of this transgenic in cells of transgenic plants by transformation of soybean tissue. For *Agrobacterium*-mediated transformation, soybean seeds are germinated overnight and the meristem explants excised. The meristems and the explants are placed in a wounding vessel. Soybean explants and induced *Agrobacterium* cells from a strain containing plasmid DNA with the gene of interest cassette and a plant selectable marker cassette are mixed no later than 14 hours from the time of initiation of seed germination and wounded using sonication. Following wounding, explants are placed in co-culture for 2-5 days at which point they are transferred to selection media for 6-8 weeks to allow selection and growth of transgenic shoots. Trait positive shoots are harvested approximately 6-8 weeks post bombardment and placed into selective rooting media for 2-3 weeks. Shoots producing roots are transferred to the greenhouse and potted in soil. Shoots that remain healthy on selection, but do not produce roots are transferred to non-selective rooting media for an additional two weeks. Roots from any shoots that produce roots off selection are tested for expression of the plant selectable marker before they are transferred to the greenhouse and potted in soil. Populations of transgenic plants and seeds produced form transgenic plant cells from each transgenic event are screened as described in Example 7 below to identify the members of the population having the enhanced trait.

Example 7

This example illustrates identification of nuclei of the invention by screening derived plants and seeds for an enhanced trait identified below.

Many transgenic events which survive to fertile transgenic plants that produce seeds and progeny plants will not exhibit an enhanced agronomic trait. Populations of transgenic seed and plants prepared in Examples 5 and 6 are screened to identify those transgenic events providing transgenic plant cells with a nucleus having recombinant DNA imparting an enhanced trait. Each population is screened for enhanced nitrogen use efficiency, increased yield, enhanced water use efficiency, enhanced tolerance to cold and heat, increased level of oil and protein in seed using assays described below. Plant cell nuclei having recombinant DNA with each of the genes identified in Table 1 and the identified homologs are identified in plants and seeds with at least one of the enhanced traits.

Selection for Enhanced Nitrogen Use Efficiency

Transgenic corn plants with nuclei of the invention are planted in fields with three levels of nitrogen (N) fertilizer being applied, i.e. low level (0 pounds per acre N), medium level (80 pounds per acre N) and high level (180 pounds per acre N). Liquid 28% or 32% UAN (Urea, Ammonium Nitrogen) are used as the N source and apply by broadcast boom and incorporate with a field cultivator with rear rolling basket in the same direction as intended crop rows. Although there is no N applied in the low level treatment, the soil should still be disturbed in the same fashion as the treated area. Transgenic plants and control plants can be grouped by genotype and construct with controls arranged randomly within genotype blocks. For improved statistical analysis each type of transgenic plant can be tested by 3 replications and across 4 locations. Nitrogen levels in the fields are analyzed before planting by collecting sample soil cores from 0-24" and 24 to 48" soil layer. Soil samples are analyzed for nitrate-nitrogen, phosphorus (P), potassium (K), organic matter and pH to provide baseline values. P, K and micronutrients are applied based upon soil test recommendations.

Transgenic corn plants prepared in Example 5 and which exhibit a 2 to 5% yield increase as compared to control plants when grown in the high nitrogen field are selected as having nuclei of the invention. Transgenic corn plants which have at least the same or higher yield as compared to control plants when grown in the medium nitrogen field are selected as having nuclei of the invention. Transgenic corn plants having a nucleus with DNA identified in Table 3 as imparting nitrogen use efficiency (LN) and homologous DNA are selected from a nitrogen use efficiency screen as having a nucleus of this invention.

Selection for Increased Yield

Many transgenic plants of this invention exhibit improved yield as compared to a control plant. Improved yield can result from enhanced seed sink potential, i.e. the number and size of endosperm cells or kernels and/or enhanced sink strength, i.e. the rate of starch biosynthesis. Sink potential can be established very early during kernel development, as endosperm cell number and size are determined within the first few days after pollination.

Much of the increase in corn yield of the past several decades has resulted from an increase in planting density. During that period, corn yield has been increasing at a rate of 2.1 bushels/acre/year, but the planting density has increased at a rate of 250 plants/acre/year. A characteristic of modern hybrid corn is the ability of these varieties to be planted at high density. Many studies have shown that a higher than current planting density should result in more biomass production, but current germplasm does not perform. well at these higher densities. One approach to increasing yield is to increase harvest index (HI), the proportion of biomass that is allocated to the kernel compared to total biomass, in high density plantings.

Effective yield selection of enhanced yielding transgenic corn events uses hybrid progeny of the transgenic event over multiple locations with plants grown under optimal production management practices, and maximum pest control. A useful target for improved yield is a 5% to 10% increase in yield as compared to yield produced by plants grown from seed for a control plant. Selection methods may be applied in multiple and diverse geographic locations, for example up to 16 or more locations, over one or more planting seasons, for example at least two planting seasons to statistically distinguish yield improvement from natural environmental effects. It is to plant multiple transgenic plants, positive and negative control plants, and pollinator plants in standard plots, for example 2 row plots, 20 feet long by 5 feet wide with 30 inches distance between rows and a 3 foot alley between ranges. Transgenic events can be grouped by recombinant DNA constructs with groups randomly placed in the field. A pollinator plot of a high quality corn line is planted for every two plots to allow open pollination when using male sterile transgenic events. A useful planting density is about 30,000 plants/acre. High planting density is greater than 30,000 plants/acre, preferably about 40,000 plants/acre, more preferably about 42,000 plants/acre, most preferably about 45,000 plants/acre.

Each of the transgenic corn plants and soybean plants with a nucleus of the invention prepared in Examples 5 and 6 are screened for yield enhancement. At least one event from each of the corn and soybean plants is selected as having at least between 3 and 5% increase in yield as compared to a control plant as having a nucleus of this invention.

Selection for Enhanced Water Use Efficiency (WUE)

The following is a high-throughput method for screening for water use efficiency in a greenhouse to identify the transgenic corn plants with a nucleus of this invention. This selection process imposes 3 drought/re-water cycles on plants over a total period of 15 days after an initial stress free growth period of 11 days. Each cycle consists of 5 days, with no water being applied for the first four days and a water quenching on the 5th day of the cycle. The primary phenotypes analyzed by the selection method are the changes in plant growth rate as determined by height and biomass during a vegetative drought treatment. The hydration status of the shoot tissues following the drought is also measured. The plant height are measured at three time points. The first is taken just prior to the onset drought when the plant is 11 days old, which is the shoot initial height (SIFT). The plant height is also measured halfway throughout the drought/re-water regimen, on day 18 after planting, to give rise to the shoot mid-drought height (SMH). Upon the completion of the final drought cycle on day 26 after planting, the shoot portion of the plant is harvested and measured for a final height, which is the shoot wilt height (SWH) and also measured for shoot wilted biomass (SWM). The shoot is placed in water at 40 degree Celsius in the dark. Three days later, the shoot is weighted to give rise to the shoot turgid weight (STM). After drying in an oven for four days, the shoots are weighted for shoot dry biomass (SDM). The shoot average height (SAH) is the mean plant height across the 3 height measurements. The procedure described above may be adjusted for +/--one day for each step given the situation.

To correct for slight differences between plants, a size corrected growth value is derived from SIH and SWH. This is the Relative Growth Rate (RGR). Relative Growth Rate (RGR) is calculated for each shoot using the formula [RGR %=(SWH−SIH)/((SWH+SIH)/2)×100]. Relative water content (RWC) is a measurement of how much (%) of the plant was water at harvest. Water Content (RWC) is calculated for each shoot using the formula [RWC %=(SWM−SDM)/(STM−SDM)×100]. Fully watered corn plants of this age run around 98% RWC.

Transgenic corn plants and soybean plants prepared in Examples 5 and 6 are screened for water use efficiency. Transgenic plants having at least a 1% increase in GRG and RWC as compared to control plants are identified as having enhanced water used efficiency and are selected as having a nucleus of this invention. Transgenic corn and soybean plants having in their nucleus DNA identified in Table 3 as imparting drought tolerance improvement (DS) and homologous DNA are identified as showing increased water use efficiency as compared to control plants and are selected as having a nucleus of this invention.

Selection for Growth Under Cold Stress

Cold germination assay—Three sets of seeds are used for the assay. The first set consists of positive transgenic events (F1 hybrid) where the genes of the present invention are expressed in the seed. The second seed set is nontransgenic, wild-type negative control made from the same genotype as the transgenic events. The third set consisted of two cold tolerant and one cold sensitive commercial check lines of corn. All seeds are treated with a fungicide "Captan" (MAESTRO® 80DF Fungicide, Arvesta Corporation, San Francisco, Calif., USA). 0.43 mL Captan is applied per 45 g of corn seeds by mixing it well and drying the fungicide prior to the experiment.

Corn kernels are placed embryo side down on blotter paper within an individual cell (8.9×8.9 cm) of a germination tray (54×36 cm). Ten seeds from an event are placed into one cell of the germination tray. Each tray can hold 21 transgenic events and 3 replicates of wildtype (LH244SDms+LH59), which is randomized in a complete block design. For every event there are five replications (five trays). The trays are placed at 9.7 C for 24 days (no light) in a Convrion® growth chamber (Conviron Model PGV36, Controlled Environments, Winnipeg, Canada). Two hundred and fifty millilters of deionized water are added to each germination tray. Germination counts are taken 10th, 11th, 12th, 13th, 14th, 17th, 19th, 21st, and 24th day after start date of the experiment. Seeds are considered germinated if the emerged radicle size is 1 cm. From the germination counts germination index is calculated.

The germination index is calculated as per:

$$\text{Germination index} = (\Sigma([T+1-n_i]*[P_i-P_{i-1}]))/T$$

where T is the total number of days for which the germination assay is performed. The number of days after planting is defined by n. "i" indicated the number of times the germination had been counted, including the current day. P is the percentage of seeds germinated during any given rating. Statistical differences are calculated between transgenic events and wild type control. After statistical analysis, the events that show a statistical significance at the p level of less than 0.1 relative to wild-type controls will advance to a secondary cold selection. The secondary cold screen is conducted in the same manner of the primary selection only increasing the number of repetitions to ten. Statistical analysis of the data from the secondary selection is conducted to identify the events that show a statistical significance at the p level of less than 0.05 relative to wild-type controls.

Transgenic corn plants and soybean plants prepared in Examples 5 and 6 are screened for water use efficiency. Transgenic plants having at least a 5% increase in germination index as compared to control plants are identified as having enhanced cold stress tolerance and are selected as having a nucleus of this invention. Transgenic corn and soybean plants having in their nucleus DNA identified in Table 3 as imparting cold tolerance improvement (CK or CS) and homologous DNA are identified as showing increased cold stress tolerance as compared to control plants and are selected as having a nucleus of this invention.

Screens for Transgenic Plant Seeds with Increased Protein and/or Oil Levels

The following is a high-throughput selection method for identifying plant seeds with improvement in seed composition using the Infratec® 1200 series Grain Analyzer, which is a near-infrared transmittance spectrometer used to determine the composition of a bulk seed sample. Near infrared analysis is a non-destructive, high-throughput method that can analyze multiple traits in a single sample scan. An NIR calibration for the analytes of interest is used to predict the values of an unknown sample. The NIR spectrum is obtained for the sample and compared to the calibration using a complex chemometric software package that provides a predicted values as well as information on how well the sample fits in the calibration.

Infratec® Model 1221, 1225, or 1227 analyzer with transport module by Foss North America is used with cuvette, item #1000-4033, Foss North America or for small samples with small cell cuvette, Foss standard cuvette modified by Leon Girard Co. Corn and soy check samples of varying composition maintained in check cell cuvettes are supplied by Leon Girard Co. NIT collection software is provided by Maximum Consulting Inc. Calculations are performed automatically by the software. Seed samples are received in packets or containers with barcode labels from the customer. The seed is poured into the cuvettes and analyzed as received.

TABLE 21

| | |
|---|---|
| Typical sample(s): | Whole grain corn and soybean seeds |
| Analytical time to run method: | Less than 0.75 min per sample |
| Total elapsed time per run: | 1.5 minute per sample |
| Typical and minimum sample size: | Corn typical: 50 cc; minimum 30 cc Soybean typical: 50 cc; minimum 5 cc |
| Typical analytical range: | Determined in part by the specific calibration. Corn - moisture 5-15%, oil 5-20%, protein 5-30%, starch 50-75%, and density 1.0-1.3%. Soybean - moisture 5-15%, oil 15-25%, and protein 35-50%. |

Transgenic corn plants and soybean plants prepared in Examples 5 and 6 are screened for increased protein and oil in seed. Transgenic inbred corn and soybean plants having an increase of at least 1 percentage point in the total percent seed protein or at least 0.3 percentage point in total seed oil and transgenic hybrid corn plants having an increase of at least 0.4 percentage point in the total percent seed protein as compared to control plants are identified as having enhanced seed protein or enhanced seed oil and are selected as having a nucleus of this invention.

Example 8

This example illustrates monocot and dicot plant transformation to produce nuclei of this invention in cells of a transgenic plant by transformation where the recombinant DNA suppresses the expression of an endogenous protein identified by Pfam, Histone, WD40, NPH3, FHA, PB1, ADH_zinc_N, NAPRTase, ADK_lid, p450, B56, DUF231, C2, DUF568, WD40, F-box, Pkinase, or Terpene_synth. Corn callus and soybean tissue are transformed as describe in Examples 5 and 6 using recombinant DNA in the nucleus with DNA that transcribes to RNA that forms double-stranded RNA targeted to an endogenous gene with DNA encoding the protein. The genes for which the double-stranded RNAs are targeted are the native gene in corn and soybean that are homolog of the genes encoding the protein with an amino acid sequence of SEQ ID NO: 426, 428, 429, 430, 524, 525, 541, 601, 602, 650, 651, 654, 655, 657, 660, 694, 698, 772, 801.

Populations of transgenic corn plants and soybean plants prepared in Examples 5 and 6 with DNA for suppressing a gene identified in Table 3 as providing an enhanced trait by gene suppression are screened to identify an event from those plants with a nucleus of the invention by selecting the trait identified in this specification.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10538781B2). An electronic copy of the "Sequence Listing" will also be available from the USPTO upon request and payment of the fee set forth in 37 CFR 1.19(b)(3).

We claim:

1. A method for manufacturing transgenic seed that can be used to produce a crop of transgenic plants with an enhanced trait resulting from expression of stably-integrated, recombinant DNA in a plant cell nucleus comprising the recombinant DNA comprising a promoter that is functional in a plant cell and that is operably linked to a DNA segment encoding a protein comprising an amino acid sequence having at least 90% amino acid sequence identity to SEQ ID NO: 557 and having the activity of a protein comprising SEQ ID NO:557, said method for manufacturing said transgenic seed comprising:
    (a) screening a population of plants for said enhanced trait and said recombinant DNA, wherein individual plants in said population can exhibit said trait at a level less than, essentially the same as or greater than the level that said trait is exhibited in control plants which do not express the recombinant DNA, wherein said enhanced trait is enhanced cold tolerance, enhanced resistance to salt exposure, or increased yield,
    (b) selecting from said population one or more plants that exhibit said trait at a level greater than the level that said trait is exhibited in control plants,
    (c) verifying that said recombinant DNA is stably integrated in said selected plants,
    (d) analyzing tissue of said selected plant to determine the production a protein having the function of a protein comprising SEQ ID NO:557; and
    (e) collecting seed from said selected plant.

2. The method of claim 1 wherein plants in said population further comprise DNA expressing a protein that provides tolerance to exposure to an herbicide applied at levels that are lethal to wild type plant cells, and wherein said selecting is effected by treating said population with said herbicide.

3. The method of claim 2 wherein said herbicide comprises a glyphosate, dicamba, or glufosinate compound.

4. The method of claim 1 wherein said selecting is effected by identifying plants with said enhanced trait.

5. The method of claim 2 wherein said seed is corn, soybean, cotton, alfalfa, wheat or rice seed.

6. The method of claim 1 wherein said protein has an amino acid sequence with at least 99% identity to SEQ ID NO: 557.

7. The method of claim 1 wherein the plant cell or plant cell nucleus is homozygous for said recombinant DNA.

8. The method of claim 1 wherein the seed can produce corn plants that are resistant to disease from the Mal de Rio Cuarto virus or the *Puccina sorghi* fungus or both.

* * * * *